US006767991B1

(12) United States Patent
Llinas-Brunet et al.

(10) Patent No.: US 6,767,991 B1
(45) Date of Patent: Jul. 27, 2004

(54) HEPATITIS C INHIBITOR PEPTIDES

(75) Inventors: Montse Llinas-Brunet, D. D. O. (CA); Murray D. Bailey, Pierrefonds (CA); Dale Cameron, Rosemère (CA); Elise Ghiro, Laval (CA); Nathalie Goudreau, Mont-Royal (CA); Marc-André Poupart, Vimont (CA); Jean Rancourt, Laval (CA); Youla S. Tsantrizos, Saint-Laurent (CA); Bruno Simoneau, Laval (CA); Dominik M. Wernic, Laval (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/368,670

(22) Filed: Aug. 5, 1999

Related U.S. Application Data

(63) Continuation of application No. 09/219,939, filed on Dec. 23, 1998, now abandoned, which is a continuation-in-part of application No. 09/131,758, filed on Aug. 10, 1998, now abandoned.
(60) Provisional application No. 60/095,945, filed on Aug. 10, 1998, and provisional application No. 60/055,186, filed on Aug. 11, 1997.

(51) Int. Cl.$^7$ .............................................. C07K 7/00
(52) U.S. Cl. ..................... 530/329; 530/330; 530/331; 514/17; 514/18
(58) Field of Search ............................ 530/329, 330, 530/331; 514/17, 18

(56) References Cited

U.S. PATENT DOCUMENTS

| 5,633,388 A | 5/1997 | Diana et al. ............. 548/305.7 |
| 5,962,638 A | * 10/1999 | Naumann et al. ............ 530/329 |
| 5,994,311 A | * 11/1999 | Eichner et al. ................ 514/18 |
| 6,323,180 B1 | 11/2001 | Llinas-Brunet et al. ....... 514/18 |

FOREIGN PATENT DOCUMENTS

| CA | 2271288 | 5/1999 |
| WO | WO 95/33763 | 12/1995 |
| WO | WO 97/06804 | 2/1997 |
| WO | WO 98/17679 | 5/1998 |
| WO | WO 98/22496 | 5/1998 |
| WO | WO 98/46597 | 10/1998 |
| WO | WO 98/46630 | 10/1998 |

OTHER PUBLICATIONS

Llinas–Brunet, Montse, "Peptide–based Inhibitors of the Hepatitis Virus Serine Protease;" Bioorganic & Medicinal Chemistry Letters, vol. 8, No. 13, Jul. 7, 1998, pp. 1713–1718.
Ingallinella, Paolo; "Potent Peptide Inhibitors of Human Heptatis C Virus NS3 Protease Are Obtained by Optimizing the Cleavage Products"; Biochemistry 1998, 37, 8906–8914.
Landro, James A..; "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping"; Biochemistry 1997, 36, 9340–9348.
Mori, E.A.; "The N–terminal region of NS3 serine protease of HCV is important to maintain its enzymatic integrity", Biochem. Biophys. Res. Comm., vol. 231, No. 3., Feb. 24, 1997, pp. 738–742.
Chu, et al; Tetrahedron Letters, 1996 vol. 37, pp. 7229–7232.
Matsumoto, et al; Antiviral Research, vol. 30, No. 1, p. A23 (abstract 19) 1996.
Steinkuhler, et al; Biochemistry, vol. 37, pp. 8899–8905–1998.
Abstract of Patents Preview, 1997, Derwent Information Ltd. for Japanese Patent Application JP 1029815–A published Nov. 10, 1998 (Japanese Energy Corp.).
Llinas–Brunet, Montse, et al. "Studies on the C–Terminal of Hexapeptide Inhibitors of the Hepatitis C Virus Serine Protease", Bio. & Med. Chem. Letters, vol. 8, pp. 2719–2724, 1998.

* cited by examiner

*Primary Examiner*—Robert A. Wax
*Assistant Examiner*—David Lukton
(74) *Attorney, Agent, or Firm*—Robert P. Raymond; Michael Morris; Philip I. Datlow

(57) ABSTRACT

Disclosed herein are hepatitis C viral protease inhibitors of formula (I):

(I)

[chemical structure with positions P6 P5 P4 P3 P2 P1]

wherein a is 0 or 1; b is 0 or 1; Y is H or $C_{1-6}$ alkyl;
B is H, an acyl derivative or a sulfonyl derivative;
$R_6$, when present, is $C_{1-6}$ alkyl substituted with carboxyl;
$R_5$, when present, is $C_{1-6}$ alkyl optionally substituted with carboxyl;
$R_4$ is $C_{1-10}$ alkyl, $C_{3-7}$ cycloalkyl or $C_{4-10}$ (alkylcycloalkyl);
$R_3$ is $C_{1-10}$ alkyl optionally substituted with carboxyl, $C_{3-7}$ cycloalkyl or $C_{4-10}$ (alkylcycloalkyl);
$R_2$ is $CH_2$—$R_{20}$, NH—$R_{20}$, O—$R_{20}$ or S—$R_{20}$; wherein $R_{20}$ is a saturated or unsaturated $C_{3-7}$ cycloalkyl or $C_{4-10}$ (alkyl cycloalkyl) being optionally mono-, di- or tri-substituted with
$R_{21}$, or $R_{20}$ is a $C_6$ or $C_{10}$aryl, $C_{7-16}$ aralkyl, Het or (lower alkyl)-Het, all optionally mono-, di- or tri-substituted with $R_{21}$, wherein $R_{21}$ is as defined herein;
$R_1$ is $C_{1-6}$ alkyl, $C_{2-6}$ alkenyl or $C_{2-6}$ alkynyl, all optionally substituted with halogen; and
W is hydroxy or a N-substituted amino: or W taken together with the carbonyl group to which it is bonded represents an ester group, or a pharmaceutically acceptable salt thereof.

104 Claims, No Drawings

SEQUENCE LISTING

<160> NUMBER OF SEQ ID NOS: 53

<210> SEQ ID NO 1
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is capped with Ac

<400> SEQUENCE: 1

Asp Asp Ile Val Pro Cys
 1               5

<210> SEQ ID NO 2
<211> LENGTH: 12
<212> TYPE: PRT
<213> ORGANISM: Hepatitis C

<400> SEQUENCE: 2

Asp Asp Ile Val Pro Cys Ser Met Ser Tyr Thr Trp
 1               5                  10

<210> SEQ ID NO 3
<211> LENGTH: 12
<212> TYPE: PRT
<213> ORGANISM: Hepatitis C
<220> FEATURE:
<221> NAME/KEY: VARIANT
<222> LOCATION: 1
<223> OTHER INFORMATION: Asp is capped with biotin
<220> FEATURE:
<221> NAME/KEY: VARIANT
<222> LOCATION: 10
<223> OTHER INFORMATION: Tyr is iodinated

<400> SEQUENCE: 3

Asp Asp Ile Val Pro Cys Ser Met Ser Tyr Thr Trp
 1               5                  10

<210> SEQ ID NO 4
<211> LENGTH: 6
<212> TYPE: PRT
<213> ORGANISM: Hepatitis C
<220> FEATURE:
<221> NAME/KEY: VARIANT
<222> LOCATION: 4
<223> OTHER INFORMATION: Tyr is iodinated

<400> SEQUENCE: 4

Ser Met Ser Tyr Thr Trp
 1               5

<210> SEQ ID NO 5
<211> LENGTH: 17
<212> TYPE: PRT
<213> ORGANISM: Hepatitis C

<400> SEQUENCE: 5

Lys Lys Gly Ser Val Val Ile Val Gly Arg Ile Ile Leu Ser Gly Arg
 1               5                  10                  15

Lys

<210> SEQ ID NO 6

-continued

```
<211> LENGTH: 11
<212> TYPE: PRT
<213> ORGANISM: Hepatitis C
<220> FEATURE:
<221> NAME/KEY: VARIANT
<222> LOCATION: 1
<223> OTHER INFORMATION: Asp is derivatized with anthranilyl
<220> FEATURE:
<221> NAME/KEY: VARIANT
<222> LOCATION: 6
<223> OTHER INFORMATION: Xaa=Abu
<220> FEATURE:
<221> NAME/KEY: VARIANT
<222> LOCATION: (6)...(7)
<223> OTHER INFORMATION: Abu-A between 6 and 7 is C(O)-O
<220> FEATURE:
<221> NAME/KEY: VARIANT
<222> LOCATION: 9
<223> OTHER INFORMATION: Tyr is derivatized with 3-NO2

<400> SEQUENCE: 6

Asp Asp Ile Val Pro Xaa Ala Met Tyr Thr Trp
 1               5                  10

<210> SEQ ID NO 7
<211> LENGTH: 4
<212> TYPE: PRT
<213> ORGANISM: Hepatitis C
<220> FEATURE:
<221> NAME/KEY: VARIANT
<222> LOCATION: 1
<223> OTHER INFORMATION: Ala is succinylated
<220> FEATURE:
<221> NAME/KEY: VARIANT
<222> LOCATION: 4
<223> OTHER INFORMATION: Phe is derivatized with para-nitro-aniline

<400> SEQUENCE: 7

Ala Ala Pro Phe
 1

<210> SEQ ID NO 8
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 8

Asp Asp Ile Val Pro Cys
 1               5

<210> SEQ ID NO 9
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Glu is acetylated

<400> SEQUENCE: 9

Glu Asp Ile Val Pro Cys
 1               5

<210> SEQ ID NO 10
<211> LENGTH: 5
<212> TYPE: PRT
<213> ORGANISM: Hepatitis C
```

```
<220> FEATURE:
<221> NAME/KEY: VARIANT
<222> LOCATION: 1
<223> OTHER INFORMATION: Asp is capped with DAD

<400> SEQUENCE: 10

Asp Ile Val Pro Cys
 1               5

<210> SEQ ID NO 11
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 11

Asp Glu Ile Val Pro Cys
 1               5

<210> SEQ ID NO 12
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 12

Asp Val Ile Val Pro Cys
 1               5

<210> SEQ ID NO 13
<211> LENGTH: 6
<212> TYPE: PRT
<213> ORGANISM: Hepatitis C
<220> FEATURE:
<221> NAME/KEY: VARIANT
<222> LOCATION: 2
<223> OTHER INFORMATION: Xaa=Tbg
<220> FEATURE:
<221> NAME/KEY: VARIANT
<222> LOCATION: 1
<223> OTHER INFORMATION: Asp is acetylated

<400> SEQUENCE: 13

Asp Xaa Ile Val Pro Cys
 1               5

<210> SEQ ID NO 14
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 14

Asp Asp Val Val Pro Cys
 1               5

<210> SEQ ID NO 15
<211> LENGTH: 6
<212> TYPE: PRT
<213> ORGANISM: Hepatitis C
```

```
<220> FEATURE:
<221> NAME/KEY: VARIANT
<222> LOCATION: 3
<223> OTHER INFORMATION: Xaa=Chg
<220> FEATURE:
<221> NAME/KEY: VARIANT
<222> LOCATION: 1
<223> OTHER INFORMATION: Asp is acetylated

<400> SEQUENCE: 15

Asp Asp Xaa Val Pro Cys
 1               5

<210> SEQ ID NO 16
<211> LENGTH: 6
<212> TYPE: PRT
<213> ORGANISM: Hepatitis C
<220> FEATURE:
<221> NAME/KEY: VARIANT
<222> LOCATION: 3
<223> OTHER INFORMATION: Xaa=Tbg
<220> FEATURE:
<221> NAME/KEY: VARIANT
<222> LOCATION: 1
<223> OTHER INFORMATION: Asp is acetylated

<400> SEQUENCE: 16

Asp Asp Xaa Val Pro Cys
 1               5

<210> SEQ ID NO 17
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 17

Asp Asp Leu Val Pro Cys
 1               5

<210> SEQ ID NO 18
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 18

Asp Asp Ile Ile Pro Cys
 1               5

<210> SEQ ID NO 19
<211> LENGTH: 6
<212> TYPE: PRT
<213> ORGANISM: Hepatitis C
<220> FEATURE:
<221> NAME/KEY: VARIANT
<222> LOCATION: 4
<223> OTHER INFORMATION: Xaa=Chg
<220> FEATURE:
<221> NAME/KEY: VARIANT
<222> LOCATION: 1
<223> OTHER INFORMATION: Asp is acetylated

<400> SEQUENCE: 19
```

```
Asp Asp Ile Xaa Pro Cys
 1               5

<210> SEQ ID NO 20
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=Abu
<220> FEATURE:
<221> NAME/KEY: VARIANT
<222> LOCATION: 1
<223> OTHER INFORMATION: Asp is acetylated

<400> SEQUENCE: 20

Asp Asp Ile Val Xaa Cys
 1               5

<210> SEQ ID NO 21
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 21

Asp Asp Ile Val Leu Cys
 1               5

<210> SEQ ID NO 22
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 22

Asp Asp Ile Val Phe Cys
 1               5

<210> SEQ ID NO 23
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 23

Asp Asp Ile Val Val Cys
 1               5

<210> SEQ ID NO 24
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 24
```

-continued

```
Asp Asp Ile Val Ile Cys
1               5

<210> SEQ ID NO 25
<211> LENGTH: 6
<212> TYPE: PRT
<213> ORGANISM: Hepatitis C
<220> FEATURE:
<221> NAME/KEY: VARIANT
<222> LOCATION: 1
<223> OTHER INFORMATION: Asp is acetylated

<400> SEQUENCE: 25

Asp Asp Ile Val Ala Cys
1               5

<210> SEQ ID NO 26
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 1
<223> OTHER INFORMATION: Asp is acetylated

<400> SEQUENCE: 26

Asp Asp Ile Val Xaa Cys
1               5

<210> SEQ ID NO 27
<211> LENGTH: 6
<212> TYPE: PRT
<213> ORGANISM: Hepatitis C
<220> FEATURE:
<221> NAME/KEY: VARIANT
<222> LOCATION: 6
<223> OTHER INFORMATION: Xaa=Abu
<220> FEATURE:
<221> NAME/KEY: VARIANT
<222> LOCATION: 1
<223> OTHER INFORMATION: Asp is acetylated

<400> SEQUENCE: 27

Asp Asp Ile Val Pro Xaa
1               5

<210> SEQ ID NO 28
<211> LENGTH: 6
<212> TYPE: PRT
<213> ORGANISM: Hepatitis C
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 28

Asp Asp Ile Val Pro Xaa
1               5

<210> SEQ ID NO 29
<211> LENGTH: 6
<212> TYPE: PRT
```

```
<213> ORGANISM: Hepatitis C
<220> FEATURE:
<221> NAME/KEY: VARIANT
<222> LOCATION: 6
<223> OTHER INFORMATION: Xaa=AlGly
<220> FEATURE:
<221> NAME/KEY: VARIANT
<222> LOCATION: 1
<223> OTHER INFORMATION: Asp is acetylated

<400> SEQUENCE: 29

Asp Asp Ile Val Pro Xaa
 1               5

<210> SEQ ID NO 30
<211> LENGTH: 6
<212> TYPE: PRT
<213> ORGANISM: Hepatitis C
<220> FEATURE:
<221> NAME/KEY: VARIANT
<222> LOCATION: 6
<223> OTHER INFORMATION: Xaa=Acpe
<220> FEATURE:
<221> NAME/KEY: VARIANT
<222> LOCATION: 1
<223> OTHER INFORMATION: Asp is acetylated

<400> SEQUENCE: 30

Asp Asp Ile Val Pro Xaa
 1               5

<210> SEQ ID NO 31
<211> LENGTH: 6
<212> TYPE: PRT
<213> ORGANISM: Hepatitis C
<220> FEATURE:
<221> NAME/KEY: VARIANT
<222> LOCATION: 6
<223> OTHER INFORMATION: Xaa=Acca
<220> FEATURE:
<221> NAME/KEY: VARIANT
<222> LOCATION: 1
<223> OTHER INFORMATION: Asp is acetylated

<400> SEQUENCE: 31

Asp Asp Ile Val Pro Xaa
 1               5

<210> SEQ ID NO 32
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=Pip
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 32

Asp Asp Ile Val Xaa Xaa
 1               5

<210> SEQ ID NO 33
<211> LENGTH: 6
```

```
<212> TYPE: PRT
<213> ORGANISM: Hepatitis C
<220> FEATURE:
<221> NAME/KEY: VARIANT
<222> LOCATION: 2
<223> OTHER INFORMATION: Xaa=Tbg
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 33

Asp Xaa Ile Val Pro Xaa
 1               5

<210> SEQ ID NO 34
<211> LENGTH: 5
<212> TYPE: PRT
<213> ORGANISM: Hepatitis C
<220> FEATURE:
<221> NAME/KEY: VARIANT
<222> LOCATION: 5
<223> OTHER INFORMATION: Xaa=Nva
<220> FEATURE:
<221> NAME/KEY: VARIANT
<222> LOCATION: 1
<223> OTHER INFORMATION: Asp is capped with DAD

<400> SEQUENCE: 34

Asp Ile Val Pro Xaa
 1               5

<210> SEQ ID NO 35
<211> LENGTH: 6
<212> TYPE: PRT
<213> ORGANISM: Hepatitis C
<220> FEATURE:
<221> NAME/KEY: VARIANT
<222> LOCATION: 3
<223> OTHER INFORMATION: Xaa=Chg
<220> FEATURE:
<221> NAME/KEY: VARIANT
<222> LOCATION: 1
<223> OTHER INFORMATION: Asp is acetylated

<400> SEQUENCE: 35

Asp Glu Xaa Glu Glu Cys
 1               5

<210> SEQ ID NO 36
<211> LENGTH: 6
<212> TYPE: PRT
<213> ORGANISM: Hepatitis C
<220> FEATURE:
<221> NAME/KEY: VARIANT
<222> LOCATION: 3
<223> OTHER INFORMATION: Xaa=Chg
<220> FEATURE:
<221> NAME/KEY: VARIANT
<222> LOCATION: 5
<223> OTHER INFORMATION: Xaa=Glu(OBn)
<220> FEATURE:
<221> NAME/KEY: VARIANT
<222> LOCATION: 6
<223> OTHER INFORMATION: Xaa=Acca
<220> FEATURE:
<221> NAME/KEY: VARIANT
<222> LOCATION: 1
<223> OTHER INFORMATION: Asp is acetylated
```

```
<400> SEQUENCE: 36

Asp Glu Xaa Val Xaa Xaa
1               5

<210> SEQ ID NO 37
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 37

Asp Asp Ile Val Xaa Xaa
1               5

<210> SEQ ID NO 38
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 38

Asp Asp Ile Val Xaa Xaa
1               5

<210> SEQ ID NO 39
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 39

Asp Asp Ile Val Xaa Xaa
1               5

<210> SEQ ID NO 40
<211> LENGTH: 6
<212> TYPE: PRT
```

```
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 40

Asp Asp Ile Val Xaa Xaa
1               5

<210> SEQ ID NO 41
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 41

Asp Asp Ile Val Xaa Xaa
1               5

<210> SEQ ID NO 42
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 42

Asp Asp Ile Val Xaa Xaa
1               5

<210> SEQ ID NO 43
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
```

```
<221> NAME/KEY: VARIANT
<222> LOCATION: 1
<223> OTHER INFORMATION: Asp is acetylated

<400> SEQUENCE: 43

Asp Asp Ile Val Xaa Xaa
 1               5

<210> SEQ ID NO 44
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 44

Asp Asp Ile Val Xaa Xaa
 1               5

<210> SEQ ID NO 45
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 45

Asp Asp Ile Val Xaa Xaa
 1               5

<210> SEQ ID NO 46
<211> LENGTH: 5
<212> TYPE: PRT
<213> ORGANISM: Hepatitis C
<220> FEATURE:
<221> NAME/KEY: VARIANT
<222> LOCATION: 4
<223> OTHER INFORMATION: Xaa=derivatized Hyp
<220> FEATURE:
<221> NAME/KEY: VARIANT
<222> LOCATION: 5
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 46

Asp Ile Val Xaa Xaa
 1               5
```

```
<210> SEQ ID NO 47
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 47

Asp Asp Ile Val Xaa Xaa
 1               5

<210> SEQ ID NO 48
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Acca
<220> FEATURE:
<221> NAME/KEY: VARIANT
<222> LOCATION: 1
<223> OTHER INFORMATION: Asp is acetylated

<400> SEQUENCE: 48

Asp Glu Ile Val Xaa Xaa
 1               5

<210> SEQ ID NO 49
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 49

Asp Asp Ile Val Xaa Xaa
 1               5

<210> SEQ ID NO 50
<211> LENGTH: 6
<212> TYPE: PRT
<213> ORGANISM: Hepatitis C
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
```

```
<222> LOCATION: 1
<223> OTHER INFORMATION: Asp is acetylated

<400> SEQUENCE: 50

Asp Asp Ile Val Pro Xaa
 1               5

<210> SEQ ID NO 51
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 51

Asp Asp Ile Val Xaa Xaa
 1               5

<210> SEQ ID NO 52
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 52

Asp Asp Ile Val Xaa Xaa
 1               5

<210> SEQ ID NO 53
<211> LENGTH: 6
<212> TYPE: PRT
<213> ORGANISM: Hepatitis C
<220> FEATURE:
<221> NAME/KEY: VARIANT
<222> LOCATION: 5
<223> OTHER INFORMATION: Xaa=derivatized Hyp
<220> FEATURE:
<221> NAME/KEY: VARIANT
<222> LOCATION: 6
<223> OTHER INFORMATION: Xaa=Nva
<220> FEATURE:
<221> NAME/KEY: VARIANT
<222> LOCATION: 1
<223> OTHER INFORMATION: Asp is acetylated

<400> SEQUENCE: 53

Asp Asp Ile Val Xaa Xaa
 1               5
```

HEPATITIS C INHIBITOR PEPTIDES

This application is a continuation of Ser. No. 09/219,939 filed Dec. 23, 1998 now abandoned, and a C.I.P. of U.S. patent Ser. No. 09/131,758 filed on Aug. 10, 1998, now abandoned, that claimed benefit of U.S. provisional application No. 60/055,186 filed on Aug. 11, 1997. The present c-i-p application further claims benefit of U.S. provisional application serial No. 60/095,945 filed on Aug. 10, 1998.

FIELD OF THE INVENTION

The present invention relates to compounds, compositions and methods for the treatment of hepatitis C virus (HCV) infection. In particular, the present invention provides novel peptides and analogs thereof, pharmaceutical compositions containing such peptides and methods for using these peptides in the treatment of HCV infection. This invention further relates to method for the synthesis of these peptide analogs and intermediates therefor.

BACKGROUND OF THE INVENTION

Hepatitis C virus (HCV) is the major etiological agent of post-transfusion and community-acquired non-A non-B hepatitis worldwide. It is estimated that over 150 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis. However, the Center for Disease Control does not presently recommend immunoglobulins for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events enhancing the proteolytic efficiency at all of the sites. The NS3 protein also exhibits nucleoside triphosphatase and RNA helicase activities. NS5B is a RNA-dependent RNA polymerase that is involved in the replication of HCV. A general strategy for the development of antiviral agents is to inactivate virally encoded enzymes that are essential for the replication of the virus. In this vein, patent application WO 97/06804 describes the (−) enantiomer of the nucleoside analogue cytosine-1,3-oxathiolane (also known as 3TC) as active against HCV. This compound, although reported as safe in previous clinical trials against HIV and HBV has yet to be clinically proven active against HCV and its mechanism of action against the virus has yet to be reported.

Intense efforts to discover compounds which inhibit the NS3 protease or RNA helicase of HCV have led to the following disclosures:

U.S. Pat. No. 5,633,388 describes heterocyclic-substituted carboxamides and analogues as being active against HCV. These compounds are directed against the helicase activity of the NS3 protein of the virus but clinical tests have not yet been reported.

A phenanthrenequinone has been reported by Chu et al (Tet. Lett., (1996), 7229–7232) to have activity against the HCV NS3 protease in vitro. No further development on this compound has been reported.

A paper presented at the Ninth International Conference on Antiviral Research, Urabandai, Fukyshima, Japan (1996) (Antiviral Research, 30, 1, 1996; A23 (abstract 19)) reports thiazolidine derivatives to be inhibitory to the HCV protease.

Several studies have reported compounds inhibitory to other serine proteases, such as human leukocyte elastase. One family of these compounds is reported in WO 95/33764 (Hoechst Marion Roussel, 1995). The peptides disclosed in that application are morpholinylcarbonyl-benzoyl-peptide analogues that are structurally different from the peptides of the present invention.

WO 98/17679 from Vertex Pharmaceuticals Inc. discloses inhibitors of serine protease, particularly, Hepatitis C virus NS3 protease. These inhibitors are peptide analogues based on the NS5A/5B natural substrate that contain C-terminal activated carbonyl function as an essential feature. These peptides were also reported to be active against other serine protease and are therefore not specific for HCV NS3 protease.

Hoffman LaRoche has also reported hexapeptides that are proteinase inhibitors useful as antiviral agents for the treatment of HCV infection. These peptides contain an aldehyde or a boronic acid at the C-terminus.

Steinkühler et al. and Ingallinella et al. have published on NS4A-4B product inhibition (Biochemistry (1998), 37, 8899–8905 and 8906–8914). However, the peptides and peptide analogues presented do not include nor do they lead to the design of the peptides of the present invention.

WO 98/46597 from Emory University discloses serine proteace inhibitors. particularly Hepatitis C virus protease. All of the compounds disclosed are structurally different from the peptides of the present invention.

WO 98/46630 from Peptide Therapeutics Ltd. discloses hepatitis C NS3 protease inhibitors. However, none of the peptides disclosed are related to the peptides of the invention.

JP10298151 from Japan Energy Corp. discloses N-(2,3-dihydroxybenzoyl)-substituted serine derivatives as serine protease inhibitors, specifically as hepatitis C viral protease inhibitors. These compounds do not contain any structural similarity to the peptide analogs of the present invention.

One advantage of the present invention is that it provides peptides that are inhibitory to the NS3 protease of the hepatitis C virus.

A further advantage of one aspect of the present invention resides in the fact that these peptides specifically inhibit the NS3 protease and do not show significant inhibitory activity at concentrations up to 300 $\mu$M against other serine proteases such as human leukocyte elastase (HLE). porcine pancreatic elastase (PPE). or bovine pancreatic chymotrypsin, or cysteine proteases such as human liver cathepsin B (Cat B).

SUMMARY OF THE INVENTION

We investigated peptides potentially inhibitory to the NS3 protease. The discovery that the N-terminal cleavage product (Ac-D-D-I-V-P-C-OH) [SEQ. ID NO. 1] of an analog of a natural substrate of the NS3 protease was inhibitory led us to the peptide analogs of the present invention.

Included in the scope of the invention are racemates, diastereoisomers and optical isomers of compounds of formula (I):

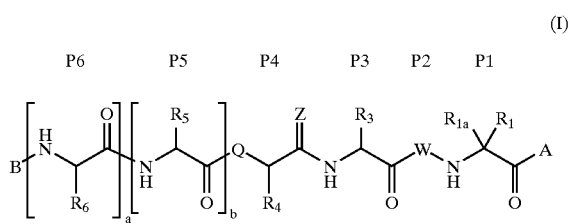

(I)

wherein Q is $CH_2$ or N—Y wherein Y is H or $C_{1-6}$ alkyl;

a) when Q is $CH_2$, a is 0, b is 0, then B is an amide derivative of formula $R_{11a}N(R_{11b})$—C(O)— wherein $R_{11a}$, is H; $C_{1-10}$ alkyl; $C_6$ aryl; $C_{7-10}$ alkylaryl; $C_{3-7}$ cycloalkyl or $C_{4-8}$ (alkylcycloalkyl) optionally substituted with carboxyl; or heterocycle-$C_{1-6}$ alkyl such as

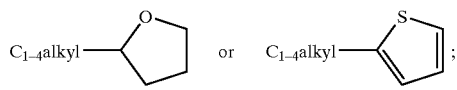

and $R_{11b}$ is $C_{1-6}$ alkyl substituted with carboxyl, ($C_{1-6}$ alkoxy)carbonyl or phenylmethoxycarbonyl; or $C_{7-16}$ aralkyl substituted on the aromatic portion with carboxyl, ($C_{1-6}$ alkoxy)carbonyl or phenylmethoxycarbonyl;

or $R_{11a}$ and $R_{11b}$ are joined to form a 3 to 7-membered nitrogen-containing ring optionally substituted with carboxyl or ($C_{1-6}$ alkoxy) carbonyl; or b) when Q is N—Y, a is 0 or 1, b is 0 or 1, then B is H, an acyl derivative of formula $R_{11}$—C(O)— or a sulfonyl of formula $R_{11}$—$SO_2$ wherein $R_{11}$ is (i) $C_{1-10}$ alkyl optionally substituted with carboxyl, $C_{1-6}$ alkanoyloxy (e.g.

AcOCH$_2$—), $C_{1-6}$ alkoxy (e.g. Boc), or carboxyl substituted with 1 to 3 $C_{1-6}$ alkyl substituents:

(ii) $C_{3-7}$ cycloalkyl or $C_{4-10}$ alkylcycloalkyl, both optionally substituted with carboxyl

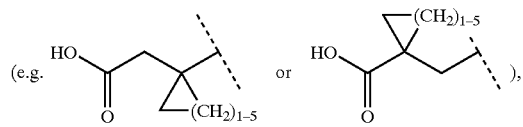

($C_{1-6}$ alkoxy)carbonyl or phenylmethoxycarbonyl;

(iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or (iv) Het optionally substituted with $C_{1-6}$ alkyl, hydroxy, amino optionally substituted with $C_{1-6}$ alkyl, or amido optionally substituted with $C_{1-6}$ alkyl, or

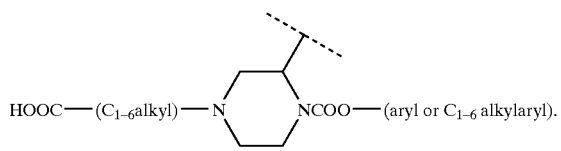

$R_6$ when present, is
$C_{1-6}$ alkyl substituted with carboxyl;
$R_5$, when present, is $C_{1-6}$ alkyl optionally substituted with carboxyl: or c) when Q is either $CH_2$ or N—Y, then
$R_4$ is $C_{1-10}$ alkyl, $C_{3-7}$ cycloalkyl or $C_{4-10}$ (alkylcycloalkyl);
Z is oxo or thioxo;
$R_3$ is $C_{1-10}$ alkyl optionally substituted with carboxyl, $C_{3-7}$ cycloalkyl or $C_{4-10}$ (alkylcycloalkyl);
W is a group of formula II:

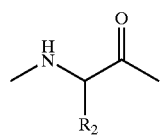

Formula II wherein $R_2$ is $C_{1-10}$ alkyl or $C_{3-10}$ cycloalkyl optionally substituted with carboxyl or an ester or amide thereof; $C_6$ or $C_{10}$ aryl or $C_{7-16}$ aralkyl; or W is a group of formula IIa:

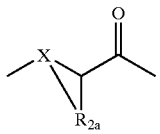

Formula IIa wherein X is CH or N; and

R$_{2a}$ is divalent C$_{3-4}$ alkylene which together with X and the carbon atom to which X and R$_{2a}$ are attached form a 5- or 6-membered ring, said ring optionally substituted with OH; SH; NH$_2$; carboxyl; R$_{12}$; CH$_2$—R$_{12}$, OR$_{12}$, C(O)OR$_{12}$, SR$_{12}$, NHR$_{12}$ or NR$_{12}$R$_{12a}$:

wherein R$_{12}$ and R$_{12a}$ are independently a saturated or unsaturated C$_{3-7}$ cycloalkyl or C$_{4-10}$ (alkyl cycloalkyl) being optionally mono-, di- or tri-substituted with R$_{15}$, or R$_{12}$ and R$_{12a}$ is a C$_6$ or C$_{10}$ aryl or C$_{7-16}$aralkyl optionally mono-, di- or tri-substituted with R$_{15}$, or R$_{12}$ and R$_{12a}$ is Het or (lower alkyl)-Het optionally mono-, di- or tri-substituted with R$_{15}$, wherein each R$_{15}$ is independently C$_{1-6}$ alkyl; C$_{1-6}$ alkoxy: amino optionally mono- or di-substituted with C$_{1-6}$ alkyl; sulfonyl; NO$_2$; OH; SH; halo; haloalkyl; amido optionally mono-substituted with C$_{1-6}$ alkyl, C$_6$ or C$_{10}$ aryl, C$_{7-16}$ aralkyl, Het or (lower alkyl)-Het; carboxyli, carboxy(lower alkyl): C$_6$ or C$_{10}$ aryl, C$_{7-16}$ aralkyl, or Het, said aryl aralkyl or Het being optionally substituted with R$_{16}$:

wherein R$_{16}$ is C$_{1-6}$ alkyl; C$_{1-6}$ alkoxy; amino optionally mono- or di-substituted with C$_{1-6}$ alkyl; sulfonyl: NO$_2$; OH; SH; halo; haloalkyl; carboxyl; amide; or (lower alkyl)amide;

or X is CH or N; and R$_{2a}$, is a divalent C$_{3-4}$ alkylene which together with X and the carbon atom to which X and R$_{2a}$ are attached form a 5- or 6-membered ring which in turn is fused with a second 5-, 6- or 7-membered ring to form a bicyclic system wherein the second ring is substituted with OR$_{12a}$ wherein R$_{12a}$ is C$_{7-16}$ aralkyl; R$_{1a}$ is hydrogen, and R$_1$ is C$_{1-6}$ alkyl optionally substituted with thiol or halo; or R$_1$ is C$_{2-6}$ alkenyl; or R$_{1a}$ and R$_1$ together form a 3- to 6-membered ring optionally substituted with R$_{14}$ wherein R$_{14}$ is C$_{1-6}$ alkyl, C$_{3-5}$ cycloalkyl, C$_{2-6}$ alkenyl, C$_{2-6}$ alkynyl, C$_6$ aryl or C$_{7-10}$ aralkyl all optionally substituted with halo; and A is hydroxy or a N-substituted amino;

or a pharmaceutically acceptable salt or ester thereof.

Included within the scope of this invention is a pharmaceutical composition comprising an anti-hepatitis C virally effective amount of a compound of formula I, or a therapeutically acceptable salt or ester thereof, in admixture with a pharmaceutically acceptable carrier medium or auxiliary agent.

An important aspect of the invention involves a method of treating a hepatitis C viral infection in a mammal by administering to the mammal an anti-hepatitis C virally effective amount of the compound of formula I, or a therapeutically acceptable salt or ester thereof or a composition as described above.

Another important aspect involves a method of inhibiting the replication of hepatitis C virus by exposing the virus to a hepatitis C viral NS3 protease inhibiting amount of the compound of formula I, or a therapeutically acceptable salt or ester thereof or a composition as described above.

Still another aspect involves a method of treating a hepatitis C viral infection in a mammal by administering thereto an anti-hepatitis C virally effective amount of a combination of the compound of formula I, or a therapeutically acceptable salt or ester thereof, and an interferon. A pharmaceutical composition comprising the combination in admixture with a pharmaceutically acceptable carrier medium or auxiliary agent is also within the scope of this invention.

DETAILED DESCRIPTION OF THE INVENTION

Definitions

As used herein, the following definitions apply unless otherwise noted: With reference to the instances where (R) or (S) is used to designate the configuration of a radical, e.g. R$_4$ of the compound of formula I, the designation is done in the context of the compound and not in the context of the radical alone. The natural amino acids, with exception of glycine, contain a chiral carbon atom. Unless otherwise specifically indicated, the compounds containing natural amino acids with the L-configuration are preferred. However, applicants contemplate that when specified, some amino acids of the formula I can be of either D- or L-configuration or can be mixtures of D- and L-isomers, including racemic mixtures.

The designation "P1, P2, P3 et." as used herein refer to the position of the amino acid residues starting from the C-terminus end of the peptide analogues and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

The abbreviations for the at-amino acids are set forth in Table A.

TABLE A

| AMINO ACID | SYMBOL |
|---|---|
| Allylglycine | AlGly |
| Aminobutyric acid | Abu |
| 1-aminocyclopertyl-carboxylic acid | Acpe |
| 1-aminocyclopropyl-carboxylic acid | Acca |
| Alanine | Ala |
| Allo-isoleucine | Allo-Ile |
| Aspartic acid | Asp |
| Cysteine | Cys |
| Cyclohexylalanine | Cha |
| Cyclohexylglycine (also named: 2-amino-2-cyclohexyl-acetic acid) | Chg |
| Glutamic acid | Glu |
| Isoleucine | Ile |
| Leucine | Leu |
| Norvaline | Nva |
| Phenylalanine | Phe |
| Pipecolic acid | Pip |
| Proline | Pro |
| 4(R)-Hydroxyproline | Hyp |
| 4(R)-Benzyloxyproline | Hyp(4-Bn) |
| Valine | Val |
| tert-Butylglycine | Tbg |

As used herein the term "aminobutyric acid" refers to a compound of formula:

As used herein the term "allylglycine" refers to a compound of formula:

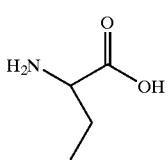

As used herein the term "1-aminocyclopropyl-carboxylic acid" (Acca) refers to a compound of formula:

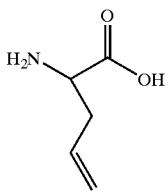

As used herein the term "tert-butylglycine" refers to a compound of formula:

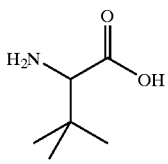

The term "residue" with reference to an amino acid or amino acid derivative means a radical derived from the corresponding α-amino acid by eliminating the hydroxyl of the carboxy group and one hydrogen of the α-amino group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "$C_{1-10}$ alkyl" or "(tower)alkyl" as used herein, either alone or in combination with another radical, means acyclic, straight chain or branched alkyl radicals containing up to ten carbon atoms and includes, for example, methyl, ethyl, propyl, butyl, hexyl, 1-methylethyl, 1-methylpropyl, 2-methylpropyl, 1,1-dimethylethyl. Likewise, the terms "$C_{1-3}$ alkyl" "$C_{1-4}$ alkyl", "$C_{1-10}$ alkyl" and $C_{1-16}$ alkyl are used to denote alkyl radicals containing up to three, four, ten and sixteen carbon atoms, respectively.

The term "halo" as used herein means a halogen radical selected from bromo, chloro, fluoro or iodo.

The term "$C_{1-6}$ haloalkyl" as used herein means a $C_{1-6}$ alkyl as defined hereinabove wherein one or more of the hydrogen atom of the alkyl radical is replaced by a halogen atom. Such a haloalkyl is, for example, trifluoromethyl e.g. $CF_3$.

The term "$C_{3-7}$ cycloalkyl" as used herein, either alone or in combination with another radical, means a cycloalkyl radical containing from three to seven carbon atoms and includes cyclopropyl, cyclobutyl, cyclopentyl, cyclohexyl and cycloheptyl.

The term "$C_{4-10}$ (alkylcycloalkyl)" as used herein means a cycloalkyl radical containing from three to seven carbon atoms linked to an alkyl radical, the linked radicals containing up to ten carbon atoms; for example, cyclopropylmethyl, cyclopentylethyl, cyclohexylmeihyl, cyclohexylethyl or cycloheptylethyl. The term alkylcycloalkyl also refers a substituent such as:

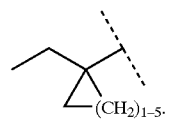

The term "$C_{2-6}$ alkenyl" as used herein, either alone or in combination with another radical, means an alkyl radical as defined above containing from 2 to 6 carbon atoms, and further containing at least one double bond. For example alkenyl includes allyl or vinyl.

The term "$C_{2-6}$ alkynyl" as used herein, either alone or in combination with another radical, means an alkyl radical as defined above containing from 2 to 6 carbon atoms, and further containing at least one triple bond.

The term "$C_{2-4}$ alkylene" as used herein means a divalent alkyl radical derived by the removal of two hydrogen atoms from a straight or branched chain aliphatic hydrocarbon containing from three to four carbon atoms and includes, for example, —$CH_2CH_2CH_2$—, $CH(CH_3)CH_2CH_2$—, —$CH_2C(CH_3)_2$— and —$CH_2CH_2CH_2CH_2$—.

The term "$C_{1-6}$ alkanoyl" as used herein, either alone or in combination with another radical, means straight or branched 1-oxoalkyl radicals containing one to six carbon atoms and includes formyl, acetyl, 1-oxopropyl(propionyl), 2-methyl-1-oxopropyl, 1-oxohexyl and the like.

The term "$C_{1-6}$ alkoxy" as used herein, either alone or in combination with another radical, means the radical —O—$C_{1-6}$ alkyl wherein alkyl is as defined above containing up to six carbon atoms. Alkoxy includes methoxy, ethoxy, propoxy, 1-methylethoxy, butoxy and 1,1-dimethylethoxy. The latter radical is known commonly as tert-butoxy.

The term "$C_{3-7}$ cycloalkoxy" as used herein, either alone or in combination with another radical, means a $C_{3-7}$ cycloalkyl group linked to an oxygen atom, such as, for example:

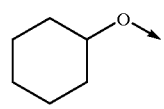

The term "$C_6$ or $C_{10}$ aryl" as used herein, either alone or in combination with another radical, means either an aromatic monocyclic system containing 6 carbon atoms or an aromatic bicyclic system containing 10 carbon atoms. For example, aryl includes phenyl or naphthyl.

The term "$C_{7-16}$ aralkyl" as used herein, either alone or in combination with another radical, means an aryl as defined above linked through an alkyl group, wherein alkyl is as defined above containing from 1 to 6 carbon atoms. Aralkyl includes for example benzyl, and butylphenyl.

The term "amino aralkyl" as used herein, either alone or in combination with another radical, means an amino group substituted with a $C_{7-16}$ aralkyl group, such as, for example, the amino aralkyl:

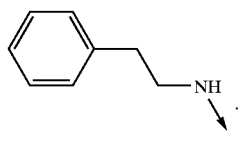

The term "carboxy(lower)alkyl" as used herein, either alone or in combination with another radical, means a carboxyl group (COOH) linked through a (lower)alkyl group as defined above and includes for example butyric acid or the groups:

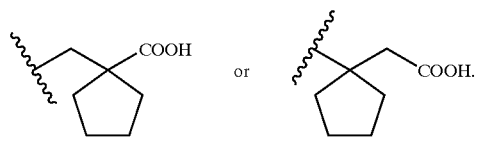

The term "cyclic" as used herein, either alone or in combination with another radical, means a monovalent radical derived by removal of a hydrogen from a saturated or unsaturated cyclic hydrocarbon, containing from three to seven carbon atoms, unless otherwise indicated and optionally containing one or more heteroatom. The term cycle or cyclic, for example, cyclopropyl, cyclopentyl, cyclohexyl, cyclohexenyl, The term "bicyclic" as used herein, either alone or in combination with another radical, means a monovalent radical derived from the fusion of two cycles as defined hereinabove. The term bicycle or bicyclic includes, for example, decalinyl, indenyl, and naphthyl.

The term "unsaturated cycloalkyl" includes, for example, the cyclohexenyl:

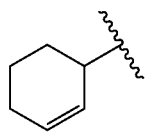

The term "heterocycle" or "Het" as used herein, either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "Het" as used herein, means a heterocycle as defined above fused to one or more other cycle be it a heterocycle or any other cycle. Examples of suitable heterocycles include: pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

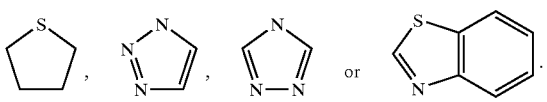

The term "(lower alkyl)-Het" as used herein, means a heterocyclic radical as defined above linked through a chain or branched alkyl group, wherein alkyl is as defined above containing from 1 to 6 carbon atoms. Examples of (lower alkyl)-Het include:

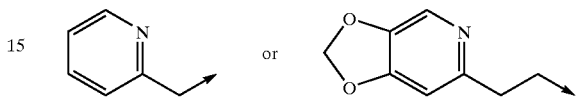

The term "pharmaceutically acceptable ester" as used herein, either alone or in combination with another radical, means esters of the compound of formula I in which any of the carboxyl functions of the molecule, but preferably the carboxy terminus, is replaced by an alkoxycarbonyl function:

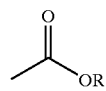

in which the R moiety of the ester is selected from alkyl (e.g. methyl, ethyl, n-propyl, t-butyl, nbutyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters can be found in Design of prodrugs, Bundgaard, H. Ed. Elsevier (1985) incorporated herewith by reference, Such pharmaceutically acceptable esters are usually hydrolyzed in vivo when injected in a mammal and transformed into the acid form of the compound of formula I.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et at., J. Pharm. Sci. (1977), 66, 1–19, incorporated herein by reference).

Preferred Embodiments

Included specifically within the scope of the compounds of formula I are racemates, diastereoisomers and optical isomers of compounds represented by formula IA:

(IA)

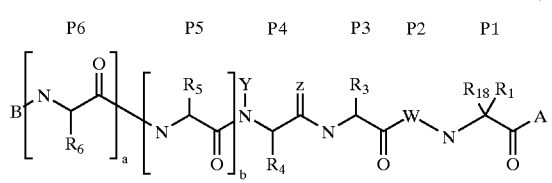

wherein Y is H or $C_{1-6}$ alkyl; a is 0 or 1; b is 0 or 1; and

B is preferably an acyl derivative of formula $R_{11}C(O)$— wherein $R_{11}$ is preferably $C_{1-6}$ alkyl optionally substituted with carboxyl, $C_{1-6}$ alkanoyloxy or $C_{1-6}$ alkoxy;, $C_{3-7}$ cycloalkyl optionally substituted with carboxyl, MeOC(O), EtOC(O) or BnOC(O);

3-carboxypropionyl (DAD); 4-carboxybutyryl (DAE); or

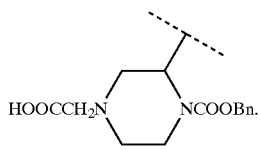

More preferably, B is acetyl, 3-carboxypropionyl (DAD), 4-carboxylbutyryl (DAE),

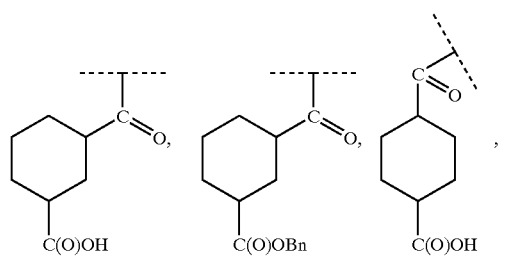

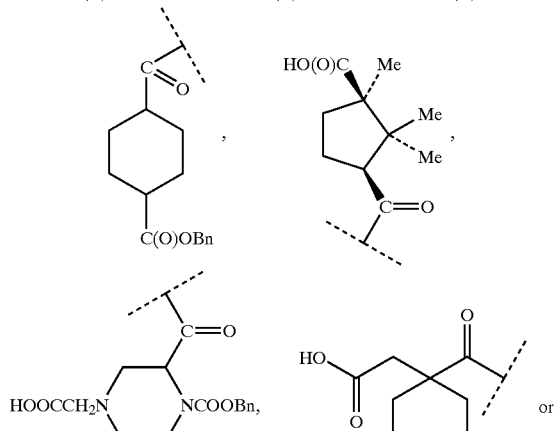

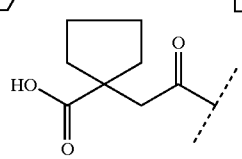

Still, more preferably, B is acetyl, DAD, DAE,

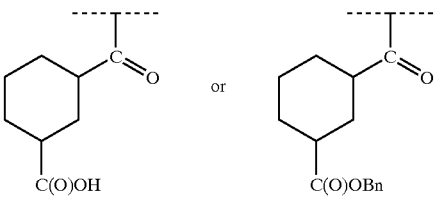

Most preferably, B is acetyl.

The present invention comprises compounds of formula I or IA wherein preferably, $R_6$, when present, is the side chain of Asp or Glu.

Most preferably, $R_6$, when present, is the side chain of Asp.

Alternatively, preferably, a is 0 and then $R_6$ is absent.

The present invention comprises compounds of formula I or IA wherein preferably, $R_5$, when present, is the side chain of an amino acid selected from the group consisting of: D-Asp, L-Asp, D-Glu, L-Glu, D-Val, L-Val, D-tert-butylglycine (Tbg), and L-Tbg.

More preferably, $R_5$, when present, is the side chain of D-Asp, D-Val, or D-Glu.

Most preferably, $R_5$, when present, is the side chain of D-Glu.

Alternatively, preferably a is 0 and b is 0, and then both $R_6$ and $R_5$ are absent.

The present invention comprises compounds of formula I or IA wherein preferably, $R_4$ is isopropyl, cyclohexyl, 1-methytpropyl, 2-methylpropyl or tert-butyl, More preferably; $R_4$ is cyclohexyl or 1-methylpropyl.

Most preferably, $R_4$ is cyclohexyl.

The present invention comprises compounds of formula I or IA wherein Z is preferably oxo.

The present invention comprises compounds of formula I or IA wherein preferably, $R_3$ is the side chain of an amino acid selected from the group consisting of: Ile, allo-Ile, Chg, cyclohexylalanine (Cha), Val, Tbg or Glu More preferably, $R_3$ is the side chain of Val, Tbg or Chg.

Most preferably, $R_3$ is the side chain of Val.

The present invention comprises compounds of formula I or IA wherein preferably, W is a group of formula II:

II

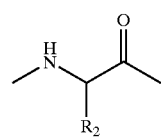

wherein $R_2$ is $C_{1-8}$ alkyl; $C_{1-8}$ alkyl substituted with carboxyl, $C_{1-6}$ alkoxycarbonyl, benzyloxycarbonyl or benzylaminocarbonyl; $C_{3-7}$ cyctoalkyl or benzyl.

Preferably, $R_2$ is the side of chain of aminobutyric acid (Abu), Leu, Phe, Cha, Val, Ala, Asp, Glu, Glu(OBn), or Glu(NHBn).

Most preferably, $R_2$ is the side chain of Asp, Abu or Val.

Still, more preferably, the invention comprises compounds of formula I wnerein W is a group of formula IIa:

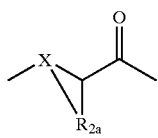

(IIa)

wherein preferably, X is CH or N.

Preferably $R_{2a}$ is a $C_3$ or $C_4$ alkylene (shown in bold) that joins X to form a 5- or 6-membered ring of formula III:

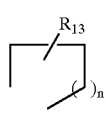

(III)

$R_{2a}$ being optionally substituted at any position with $R_{13}$, wherein X is CH or N; n is 1 or 2, and $R_{13}$ is as defined below.

Most preferably, X is N. For example, preferably $R_{2a}$ is propyl joined to X wherein X is nitrogen to form a proline substituted with $R_{13}$.

Most preferably $R_2$ is the side chain of proline substituted at the 3-, 4-, or 5-position with $R_{13}$, wherein $R_{13}$ is as defined below.

Still, most preferably $R_{2a}$ is the side chain of proline (as shown in bold) substituted with $R_{13}$ at the 4-position with the stereochemistry shown in formula IIIa:

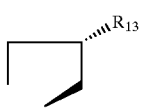

(IIIa)

wherein $R_{13}$ is S—$R_{12}$ or O—$R_{12}$ wherein $R_{12}$ is preferably a $C_6$ or $C_{10}$ aryl, $C_{7-15}$ aralkyl, Het or —$CH_2$—Het, all optionally mono-, di- or tri-substituted with $R_{15}$.

Preferably, $R_{15}$ is $C_{1-6}$ alkyl; $C_{1-6}$ alkoxy; amino; mono- or di-(lower alkyl)amino; amido optionally mono-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{16}$. More preferably, $R_{15}$ is $C_{1-6}$ alkyl; $C_{1-6}$ alkoxy; amino; di(lower alkyl)amino; (lower alkyl)amide; $C_6$ or $C_{10}$ aryl, or Het, said aryl or Het being optionally substituted with $R_{16}$.

Preferably, $R_{16}$ is $C_{1-6}$ alkyl; $C_{1-6}$ alkoxy; amino; mono- or di-(lower alkyl)amino; (lower alkyl)amide; $NO_2$; OH; halo; trifluoromethyl; or carboxyl. More preferably, $R_{16}$ is $C_{1-6}$ alkoxy; amino; di(lower alkyl)amino; (lower alkyl) amide; halo; or trifluoromethyl.

Preferably, $R_{13}$ is o-tolylmethoxy; m-tolylmethoxy; p-tolylmethoxy; (4-tert-butyl)methoxy; (3I—Ph)$CH_2$O; (4Br—Ph)O; (2Br—Ph)O; (3Br—Ph)O; (4I—Ph)O; (3Br—Ph)$CH_2$O; (3,5-$Br_2$—Ph)$CH_2$O; or $R_{13}$ is $OR_{12}$ or $SR_{12}$ wherein $R_{12}$ is $C_6$ or $C_{10}$ aryl, $C_{7-16}$ aralkyl or Het, all optionally substituted with $C_{1-6}$ alkyl, $C_{3-7}$ cycloalkyl, $C_{1-6}$ alkoxy, acetylamido, nitro, $CF_3$, $NH_2$, OH, SH, halo, carboxyl, carboxy(lower)alkyl or a second aryl or aralkyl;

For example, $R_{13}$ is preferably 1-naphthyloxy; 2-naphthyloxy; 1-naphthylmethoxy; 2-naphthylmethoxy;

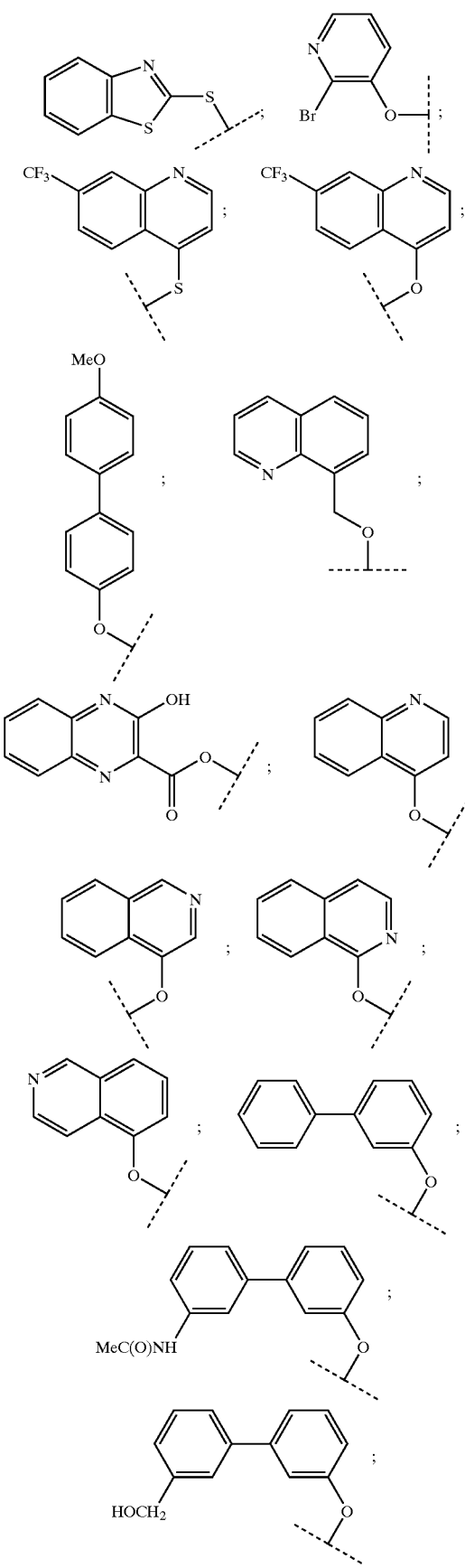

-continued

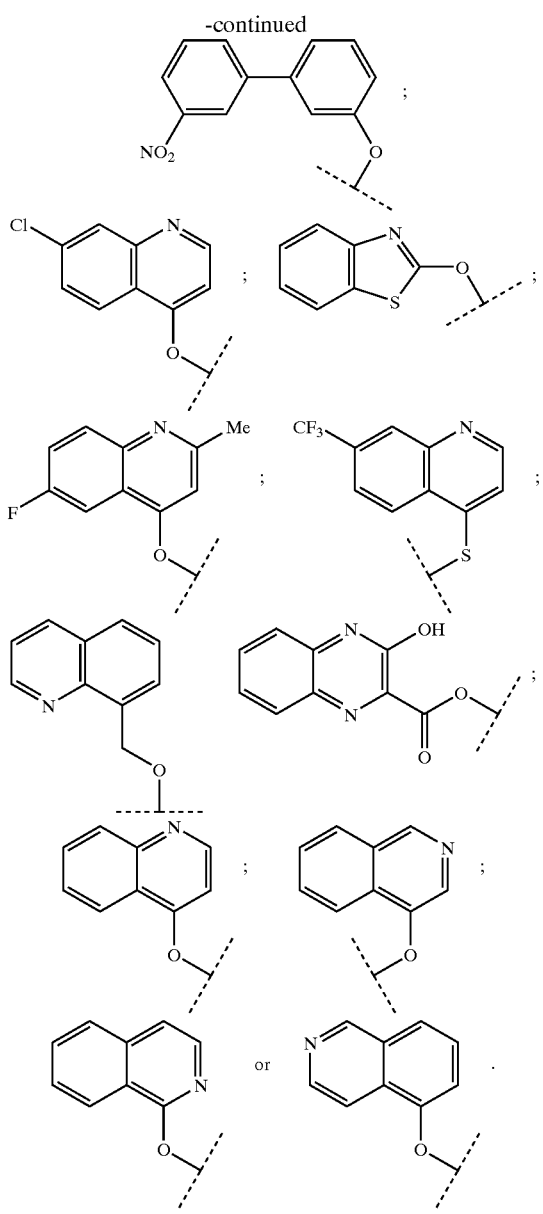

Further comprised within the invention are compounds of formula I or IA wherein $R_{1a}$ is preferably hydrogen and $R_1$ is $C_{1-6}$ alkyl optionally substituted with thiol. For example, $R_1$ is preferably the side chain of the amino acid selected from the group consisting of: cysteine (Cys) aminobutyric acid (Abu), norvaline (Nva), or allylglycine (AlGly).

More preferably, $R_{1a}$ is H and $R_1$ is propyl. For example, $R_1$ is more preferably the side chain of the amino acid Nva.

Alternatively, preferably $R_{1a}$ and $R_1$ together form a 3 to 6-membered ring said ring being optionally substituted with $R_{14}$. For example, $R_{1a}$ and $R_1$ together form preferably a cyclopropyl optionally substituted with $R_{14}$. For example, $R_{1a}$ and $R_1$ together can be the side chain (shown in bold) of the following amino acid:

referred to as 1-aminocyclopropylcarboxylic acid (Acca).

Preferably, $R_{14}$ is methyl, ethyl, propyl, vinyl, allyl, benzyl, phenylethyl or phenylpropyl, all of which optionally substituted with halo. More preferably, $R_{14}$ is ethyl, propyl, vinyl, bromovinyl or allyl. Most preferably, $R_{14}$ is ethyl, vinyl or bromovinyl.

Further comprised in the present invention are compounds of formula I or IA wherein A is preferably hydroxy or a pharmaceutically acceptable salt or ester thereof; or $C_{1-6}$ alkylamino, di($C_{1-6}$ alkyl)amino or phenyl-$C_{1-6}$ alkylamino.

More preferably, A is hydroxy, or $N(R_{17a})R_{17b}$ wherein $R_{17a}$ and $R_{17b}$ are independently H, aryl or $C_{1-6}$ alkyl optionally substituted with hydroxy or aryl.

Most preferably, A is OH, NH-benzyl or NH—CH(Me)Ph.

Still most preferably, A is OH or NH—CH(Me)-phenyl.

Specifically included within the scope of compounds of formula I or IA are racemates, diastereoisomers and optical isomers of compounds represented by formula IB:

(IB)

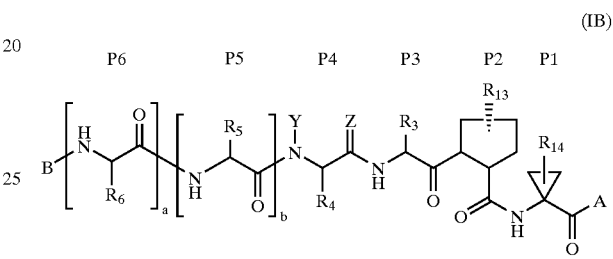

wherein
a, b, $R_6$, $R_5$, Y, $R_4$, Z, $R_3$, $R_{14}$ and A are as defined above.

B is preferably $R_{11}$—$SO_2$ wherein $R_{11}$ is preferably $C_6$ or $C_{10}$ aryl, a $C_{7-16}$ aralkyl or Het all optionally substituted with $C_{1-6}$ alkyl.

Alternatively, B is preferably H or an acyl derivative of formula $R_{11}C(O)$— wherein $R_{11}$ is preferably $C_{1-6}$ alkyl; $C_{1-6}$ alkoxy, $C_{3-7}$ cycloalkyl optionally substituted with hydroxy; amido optionally substituted with $C_{1-6}$ alkyl or Het; $C_6$ or $C_{10}$ aryl, $C_{7-16}$ aralkyl or Het all optionally substituted with $C_{1-6}$ alkyl or hydroxy. More preferably, B is H or $R_{11}C(O)$— wherein $R_{11}$ is more preferably $C_{1-6}$ alkyl or Heterocycles such as:

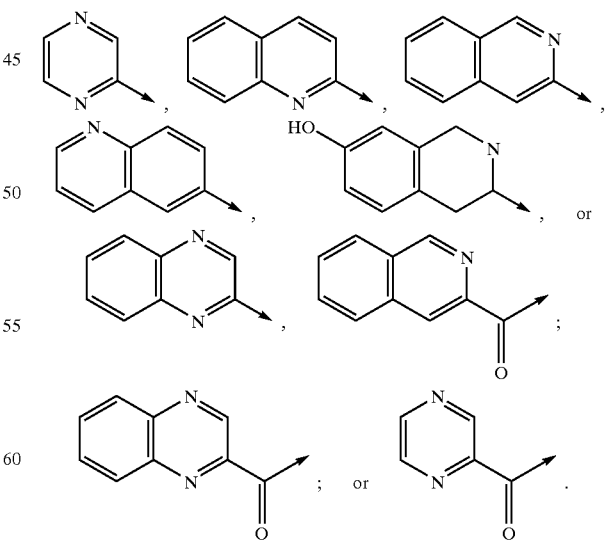

Most preferably, B is H; acetyl;
Included within the scope of the invention are compounds of formula IB wherein $R_{13}$ is preferably o-tolylmethoxy;

m-tolylmethoxy; p-tolyl methoxy; (4-tert-butyl)methoxy; (3I—Ph)CH$_2$O; (4Br—Ph)O; (2Br—Ph)O; (3Br—Ph)O; (4I—Ph)O; (3Br—Ph)CH$_2$O; (3,5-Br—Ph)CH$_2$O; or R$_{13}$ is OR$_{12}$ or SR$_{12}$ wherein R$_{12}$ is C$_6$ or C$_{10}$ aryl, C$_{7-16}$ aralkyl or Het, all optionally substituted with C$_{1-6}$ alkyl, C$_{3-7}$ cycloalkyl, C$_{1-6}$ alkoxy, acetylamido, nitro, CF$_3$, NH$_2$, OH, SH, halo, carboxyl, carboxy(lower)alkyl or a second aryl or aralkyl:

More preferably, R$_{13}$ is preferably 1-naphthyloxy; 2-naphthyloxy; 1-naphthylmethoxy; 2-naphthylmethoxy; 2-, 3-, 4-, or 6-quinolinoxy, all optionally substituted.

Most preferably R$_{13}$ is 1-naphthyloxy; 2-naphthyloxy; 1-naphthylmethoxy; 2-naphthylmethoxy; or substituted 4-quinolinoxy.

Even most preferably, R$_{13}$ is 1-naphthylmethoxy; 2-naphthylmethoxy; benzyloxy, 1-naphthyloxy; 2-naphthyloxy; or quinolinoxy unsubstituted, mono- or di-substituted: with R$_{15}$ as defined above. Most preferably, R$_{13}$ is 1-naphthylmethoxy; or quinolinoxy unsubstituted, mono- or di-substituted with R$_{15}$ as defined above.

Still, most preferably, R$_{13}$ is:

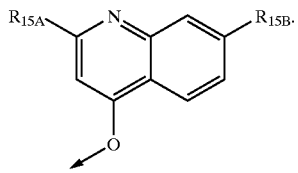

More preferably, R$_{15A}$ is amido optionally mono-substituted with C$_{1-6}$ alkyl, C$_6$ or C$_{10}$ aryl, C$_{7-16}$ aralkyl or Het; or C$_6$ or C$_{10}$ aryl or Het optionally substituted with R$_{16}$. Most preferably, R$_{15A}$ is C$_6$ or C$_{10}$ aryl or Het, all optionally substituted with R$_{16}$. Most preferably, R$_{16}$ is amino; di(lower alkyl)amino; or (lower alkyl)amide. Even most preferably, R$_{16}$ is amino; dimethylamino; or acetamido.

Even most preferably. R$_{15A}$ is C$_6$ or C$_{10}$ aryl or Het, all unsubstitulted.

Preferably, R$_{15B}$ is C$_{1-6}$ alkyl; C$_{1-6}$ alkoxy; amino; di(lower alkyl)amino; (lower alkyl)amide; NO$_2$; OH; halo; trifluoromethyl; or carboxyl. More preferably, R$_{15B}$ is C$_{1-6}$ alkoxy; or di(lower alkyl)amino. Most preferably, R$_{15B}$ is methoxy.

As described hereinabove the P1 segment of the compounds of formula IB is a cyclopropyl ring system of formula:

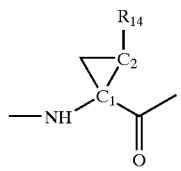

wherein C$_1$ and C$_2$ each represent an asymmetric carbon atom at positions 1 and 2 of the cyclopropyl ring. Notwithstanding other possible asymmetric centers at other segments of the compounds of formula I, the presence of these two asymmetric centers means that the compound of formula I can exist as racemic mixtures of diastereoisomers. As illustrated in the examples hereinafter the racemic mixtures can be prepared and thereafter separated into individual optical isomers, or these optical isomers can be prepared by chiral synthesis.

Hence, the compound of formula I can exist as a racemic mixture of diastereoisomers wherein R$_{14}$ at position 2 is orientated syn to the carbonyl at position 1, represented by the radical:

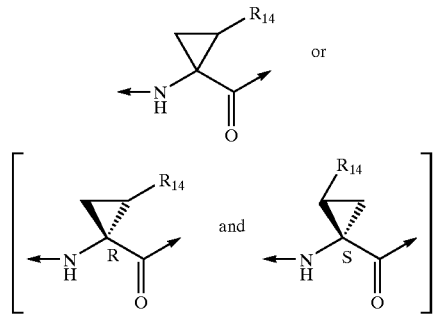

or the compound of formula I can exist as a racemic mixture of diastereoisomers wherein R$_{14}$ at position 2 is orientated anti to the carbonyl at position 1, represented by the radical:

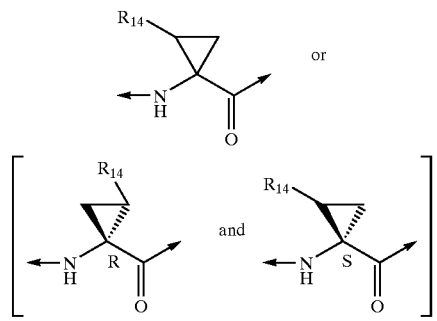

In turn the racemic mixtures can be separated into individual optical isomers. A most interesting finding of this invention pertains to the spatial orientation of the P1 segment. The finding concerns the configuration of the asymmetric carbon at position 1. A preferred embodiment is one wherein asymmetric carbon at position 1 has the R configuration.

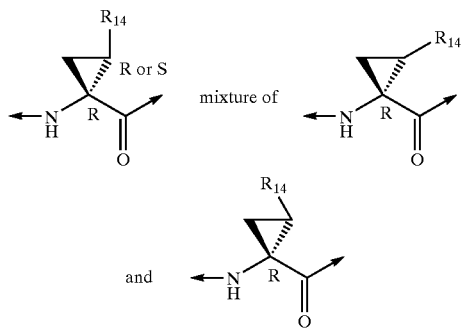

More explicitly, when carbon 1 has the R configuration, HCV NS3 protease inhibition is further enhanced by the position of the substituent R$_{14}$ (e.g. alkyl or alkylene) at carbon 2 of the cyclopropyl ring. A most preferred compound is an optical isomer having the R$_{14}$ substituent and the carbonyl in a syn orientation in the following absolute configuration:

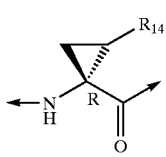

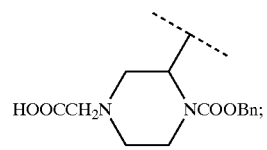

(v)

In the case where $R_{14}$ is ethyl, for example, the asymmetric carbon atoms at positions 1 and 2 have the R,R configuration.

By way of illustrating the role of the absolute configuration of the substituent on the level of potency of the compound, compound 513 (Table 5) having the absolute configuration as 1R,2R, has an $IC_{50}$ of 1.6 $\mu$M whereas the corresponding 1S,2S isomer (compound 514) has an $IC_{50}$ of 27.5 $\mu$M. Therefore, the 1R,2R isomer is 25 fold more potent than the corresponding 1S,2S isomer.

Further specifically included within the scope of compounds of formula I are racemates, diastereoisomers and optical isomers of compounds represented by formula IC:

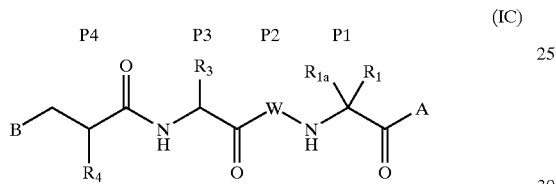

(IC)

wherein $R_4$, $R_3$, W, $R_{1a}$, $R_1$ and A are as defined above, and

B is preferably an amide of formula $R_{11a}N(R_{11b})C(O)$— wherein $R_{11a}$ is preferably $C_{1-6}$ alkyl; $C_{3-6}$ cycloalkyl; $C_{3-7}$ (alkylcycloalkyl) optionally substituted with carboxy; $C_{1-3}$ carboxyalkyl; $C_6$ aryl; $C_{7-10}$ arylalkyl; 2-tetrahydrofuranylmethyl; or 2-thiazolidylmethyl;

and $R_{11b}$ is preferably $C_{1-4}$ alkyl substituted with carboxyl.

More preferably, B is $R_{11a}N(R_{11b})$—C(O)— wherein $R_{11a}$ is preferably cyclopropylmethyl, isopropyl, carboxyethyl, benzylmethyl, benzyl, or 2-tetrahydrofuranylmethyl. More preferably $R_{11b}$ is $C_{1-4}$ alkyl substituted with carboxyl.

Most preferably, $R_{11b}$ is ethyl carboxyl.

Specific Embodiments

Specifically comprised in the scope of the invention are compounds of formula I wherein Q is $CH_2$, a is 0, b is 0, and B is an amide of formula $R_{11a}N(R_{11b})$—C(O)— wherein $R_{11a}$ is $C_{1-6}$ alkyl, $C_{3-6}$ cycloalkyl, $C_{3-7}$ (alkylcycloalkyl) optionally substituted with carboxy, $C_{1-3}$ carboxyalkyl, phenyl, $C_{7-10}$ arylalkyl, 2-tetrahydrofuranylmethyl, or 2-thiazolidylmethyl;

and $R_{11b}$ is phenyl; or $C_{1-6}$ alkyl substituted with carboxyl or $C_{1-4}$ carboxyalkyl; or Q is N—Y wherein Y is H or $C_{1-6}$ alkyl; a is 0 or 1; b is 0 or 1; and B is an acyl derivative of formula $R_{11}$—C(O)— wherein $R_{11}$ is (i) $C_{1-6}$ alkyl, $C_{1-6}$ alkyl substituted with carboxyl, MeC(O)O—, MeO—, EtO—, MeCH$_2$CH$_2$O— or Me$_3$C—O—, (ii) cyclopentyl or cyclohexyl optionally substituted with carboxyl; (iv) $C_{4-10}$ (alkylcycloalkyl) optionally substituted on the cycloalkyl portion with carboxyl;

or (vi) phenyl, benzyl or phenylethyl;

$R_5$, when present, is $CH_2COOH$ or $CH_2CH_2COOH$;

$R_5$, when present, is $C_{1-6}$ alkyl or $CH_2COOH$ or $CH_2CH_2COOH$;

and when Q is either $CH_2$ or N—Y, $R_4$ is $C_{1-6}$ alkyl, $C_{3-7}$ cycloalkyl or $C_{4-10}$ (alkylcycloalkyl);

Z is oxo or thio;

$R_3$ is $C_{1-6}$ alkyl; $C_{3-7}$ cycloalkyl or $C_{4-10}$ (alkylcycloalkyl);

W is a group of formula II wherein $R_2$ is $C_{1-10}$ alkyl, $C_{3-10}$ cycloalkyl, $C_{7-11}$ aralkyl; $CH_2COOH$ or $CH_2CH_2COOH$; or W is a group of formula II' wherein X is N or CH and $R_2$ is the divalent radical —$CH_2CH_2CH_2$— or —$CH_2CH_2CH_2CH_2$— which together with X and the carbon atom to which X and $R_2$ are attached form a 5- or 6-membered ring, said ring optionally substituted with $R_{13}$ wherein $R_{13}$ is S—$R_{12}$ or O—$R_{12}$ wherein $R_{12}$ is a $C_6$ or $C_{10}$ aryl, $C_{7-16}$ aralkyl, Het or —$CH_2$—Het, all optionally mono-, di- or tri-substituted with $R_{15}$, wherein $R_{15}$ is $C_{1-6}$ alkyl; $C_{1-6}$ alkoxy; amino; mono- or di-(lower alkyl)amino; amido optionally mono-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{16}$, and wherein $R_{16}$ is $C_{1-6}$ alkyl; $C_{1-6}$ alkoxy; amino; mono- or di-(lower alkyl)amino; (lower alkyl)amide; $NO_2$; OH; halo; trifluoromethyl; or carboxyl.

$R_{1a}$ is hydrogen and $R_1$ is methyl, thiomethyl, 1-methylethyl, propyl, 1-methylpropyl, 2-(methylthio) ethyl or 2-propylene; or $R_{1a}$ and $R_1$ together with the carbon atom to which they are attached form a cyclopropyl which may optionally be substituted with $C_{1-8}$ alkyl; and A is hydroxy or a pharmaceutically acceptable salt thereof; $C_{1-6}$ alkoxy, or (aryl $C_{1-6}$-alkoxy).

Also comprised within the scope of the present invention are compounds of formula I:

wherein B is an acyl derivative of formula $R_{11}$—C(O)— wherein $R_{11}$ is $C_{1-10}$ alkyl optionally substituted with carboxyl; $C_{3-7}$ cycloalkyl optionally substituted with carboxyl; or a $C_{4-10}$ (alkylcycloalkyl) optionally substituted on the cycloalkyl portion with carboxyl; or $R_{11}$ is $C_6$ or $C_{10}$ aryl or $C_{7-16}$ aralkyl optionally substituted with a $C_{1-6}$ alkyl:

a is 0 or 1;

$R_6$, when present, is $C_{1-6}$ alkyl optionally substituted with carboxyl;

b is 0 or 1;

$R_5$, when present, is $C_{1-6}$ alkyl optionally substituted with carboxyl;

Q is N—Y wherein Y is H or $C_{1-6}$ alkyl;

$R_4$ is $C_{1-10}$ alkyl, $C_{3-7}$ cycloalkyl or $C_{4-10}$ (alkylcycloalkyl);

Z is oxo;

$R_3$ is $C_{1-10}$ alkyl, $C_{3-7}$ cycloalkyl or $C_{4-10}$ (alkylcycloalkyl);

W is a group of formula II:

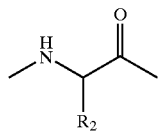

(II)

wherein $R_2$ is $C_{1-6}$ alkyl; $C_{1-6}$ alkyl optionally substituted with carboxyl; $C_6$ or $C_{10}$ aryl; or $C_{7-16}$ aralkyl;

W is a group of formula IIa:

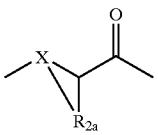

(IIa)

wherein X is CH or N; and $R_{2a}$ is $C_{3-4}$ alkyl that joins X to form a 5- or 6-membered ring, said ring optionally substituted with $R_{13}$ OH; SH; $NH_2$; carboxyl; $R_{12}$; $CH_2$—$R_{12}$, $OR_{12}$, $SR_{12}$, $NHR_{12}$ or $NR_{12}R_{12a}$ wherein $R_{12}$ and $R_{12a}$ are independently:

a saturated or unsaturated $C_{3-7}$ cycloalkyl or $C_{4-10}$ (alkyl cycloalkyl) being optionally mono-, di- or tri-substituted with $R_{15}$, or $R_{12}$ or $R_{12a}$ is a $C_6$ or $C_{10}$ aryl or $C_{7-16}$ aralkyl optionally mono-, di- or tri-substituted with $R_{15}$, or $R_{12}$ or $R_{12a}$ is Het or (lower alkyl)-Het optionally mono-, di- or tri-substituted with $R_{15}$, wherein each $R_{15}$ is independently $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{16}$;

wherein $R_{16}$ is $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; carboxyl; amide; or (lower alkyl)amide; and $R_{1a}$ is hydrogen, and $R_1$ is $C_{1-6}$ alkyl optionally substituted with thiol, or $C_{2-6}$ alkenyl; or $R_{1a}$ and $R_1$ together form a 3- to 6-membered ring optionally substituted with $C_{1-6}$ alkyl; and A is OH or a pharmaceutically acceptable salt or ester thereof.

Further comprised in the scope of the invention are compounds of formula IA, wherein B is an acyl derivative of formula $R_{11}$—C(O)— wherein $R_{11}$ is $C_{1-6}$ alkoxy, $C_{1-10}$ alkyl optionally substituted with carboxyl; $C_{3-7}$ cycloalkyl optionally substituted with carboxyl or benzylcarboxy; or

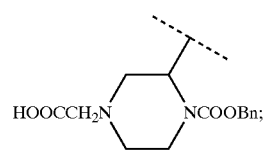

$R_6$ is absent;

$R_5$ is absent;

Y is H;

$R_4$ is $C_{1-10}$ alkyl, $C_{3-7}$ cycloalkyl or $C_{4-10}$ (alkylcycloalkyl);

Z is oxo;

$R_3$ is $C_{1-10}$ alkyl, $C_{3-7}$ cycloalkyl or $C_{4-10}$ (alkylcycloalkyl);

W is a group of formula II:

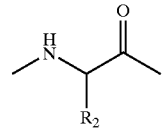

(II)

wherein $R_2$ is $C_{1-6}$ alkyl; $C_{3-6}$ cycloalkyl; $C_{1-6}$ alkyl substituted with carboxyl; $C_6$ or $C_{10}$ aryl; or $C_{7-11}$ aralkyl; or W is a group of formula IIa:

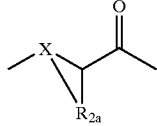

(IIa)

wherein X is N; and $R_{2a}$ is $C_{3-4}$ alkyl that joins X to form a 5- or 6-membered ring, said ring optionally substituted with OH; SH; $NH_2$; carboxyl; $R_{12}$; $CH_2$—$R_{12}$, $OR_{12}$, $SR_{12}$, $NHR_{12}$ or $NR_{12}R_{12a}$ wherein $R_{12}$ and $R_{12a}$ are independently:

a saturated or unsaturated $C_{3-7}$ cycloalkyl or $C_{4-10}$ (alkyl cycloalkyl) being optionally mono-, di- or tri-substituted with $R_{15}$, or $R_{12}$ or $R_{12a}$ is a $C_6$ or $C_{10}$ aryl or $C_{7-16}$ aralkyl optionally mono-, di- or tri-substituted with $R_{15}$, or $R_{12}$ or $R_{12a}$ is Het or (lower alkyl)-Het optionally mono-, di- or tri-substituted with $R_{15}$, wherein each $R_{15}$ is independently $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{16}$;

wherein $R_{16}$ is $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; carboxyl; amide: or (lower alkyl)amide;

$R_{1a}$ is H and $R_1$ is the side chain of Cys, Abu, Nva or allylglycine; or $R_{1a}$ and $R_1$ together with the carbon atom to which they are attached form a cyclopropyl; and A is or a pharmaceutically acceptable salt thereof; methoxy, ethoxy, phenoxy, or benzyloxy.

Also comprised in the scope of the invention are compounds of formula IA, wherein B is acetyl, 3-carboxypropionyl, 4-carboxylbutyryl, $AcOCH_2C(O)$, $Me_3COC(O)$.

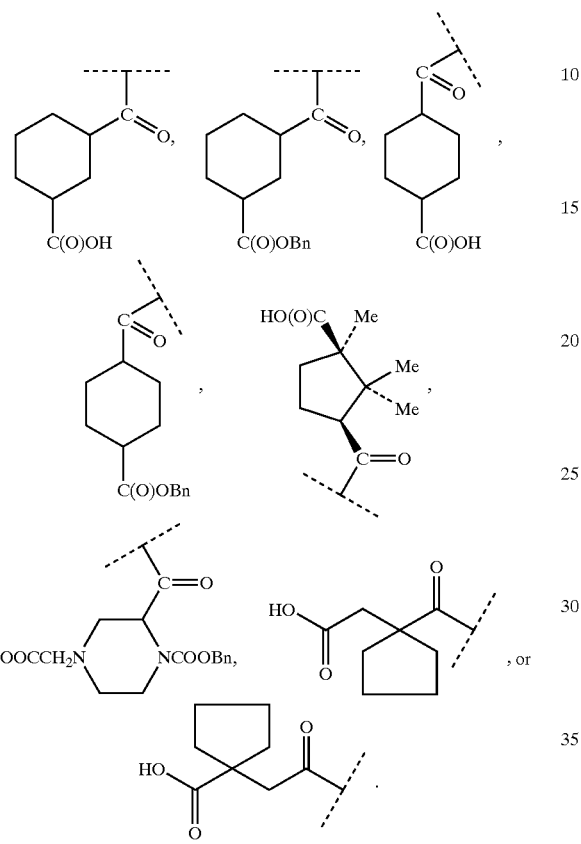

Y is H or Me, a is 0 or 1, b is 0 or 1,
$R_6$, when present, is the side chain of Asp or Glu,
$R_5$, when present, is the side chain of Asp, D-Asp, Glu, D-Glu, Val, D-Val or Tbg,
$R_4$ is the side chain of Val, Chg, Tbg, Ile or Leu,:
Z is oxo or thioxo,
$R_3$ is hydrogen or the side chain of Ile, Chg, Val, Glu;
W is Abu, Leu, Phe, Val, Ala, Glu, Glu(OBn); or
W is group of formula IIIa:

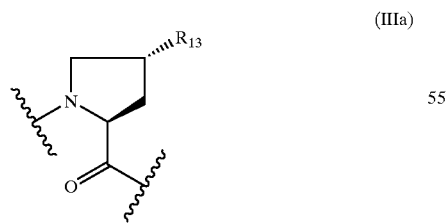

(IIIa)

wherein $R_{13}$ is Bn, $PhCH_2CH_2$, $PhCH_2CH_2CH_2$, O—Bn, o-tolylmethoxy, m-tolylmethoxy, p-tolylmethoxy, 1-naphthylmethoxy, 2-naphthylmethoxy, (4-tert-butyl)benzyloxy, (3I—Ph)$CH_2$O, (4Br—Ph)O, (2Br—Ph)O, (3Br—Ph)O, (4I—Ph)O, (3Br—Ph)$CH_2$O, (3,5-$Br_2$—Ph)$CH_2$O,

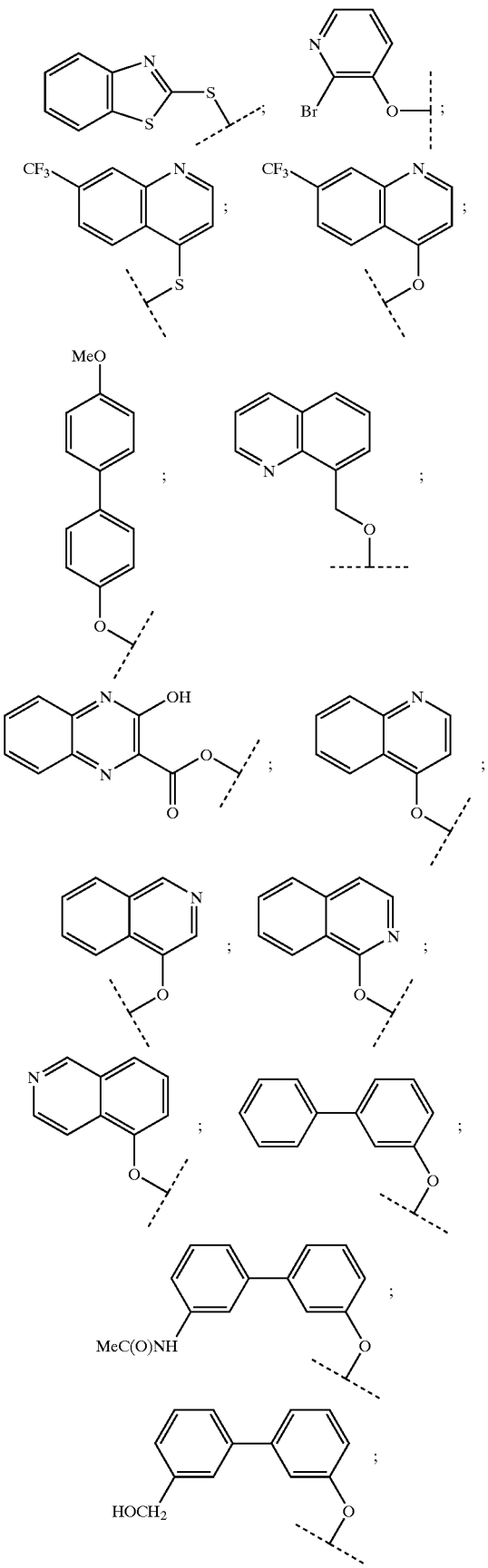

$R_{1a}$ is H and $R_1$ is the side chain of Cys, Abu, Nva or allylglycine; or $R_{1a}$ and $R_1$ together with the carbon atom to which they are attached form a cyclopropyl; and A is hydroxyl, or a pharmaceutically acceptable salt or ester thereof.

A further preferred embodiment of the invention comprises compounds of formula IB:

(IB)

wherein a is 0 or 1; b is 0 or 1; Y is H or $C_{1-6}$ alkyl; and z is oxo;

B is H, an acyl derivative of formula $R_{11}$—C(O)— or a sulfonyl of formula $R_{11}$—$SO_2$ wherein $R_{11}$ is (i) $C_{1-10}$ alkyl optionally substituted with carboxyl, $C_{1-6}$ alkanoyloxy or $C_{1-6}$ alkoxy;

(ii) $C_{3-7}$ cycloalkyl optionally substituted with carboxyl, ($C_{1-6}$ alkoxy)carbonyl or phenylmethoxycarbonyl;

(iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or (iv) Het optionally substituted with $C_{1-6}$ alkyl, hydroxy, amino optionally substituted with $C_{1-6}$ alkyl, or amido optionally substituted with $C_{1-6}$ alkyl;

$R_6$, when present, is $C_{1-6}$ alkyl substituted with carboxyl;

$R_5$, when present, is $C_{1-6}$ alkyl optionally substituted with carboxyl;

$R_4$ is $C_{1-10}$ alkyl, $C_{3-7}$ cycloalkyl or $C_{4-10}$ (alkylcycloalkyl);

$R_3$ is $C_{1-10}$ alkyl, $C_{3-7}$ cycloalkyl or $C_{4-10}$ (alkylcycloalkyl);

$R_{13}$ is $CH_2$—$R_{12}$, NH—$R_{12}$, O—$R_{12}$ or S—$R_{12}$, wherein $R_{12}$ is a saturated or unsaturated $C_{3-7}$ cycloalkyl or $C_{4-10}$ (alkyl cycloalkyl) being optionally mono-, di- or tri-substituted with $R_{15}$, or $R_{12}$ is a $C_6$ or $C_{10}$ aryl or $C_{7-16}$ aralkyl optionally mono-, di- or tri-substituted with $R_{15}$, or $R_{12}$ is Het or (lower alkyl)-Het optionally mono-, di- or tri-substituted with $R_{15}$, wherein each $R_{15}$ is independently $C_{1-6}$ alkyl, $C_{1-6}$ alkoxy; amino optionally mono- or di-substituted with $C_{1-6}$ alkyl; sulfony; $NO_2$; OH; SH; halo; haloalkyl: amido optionally mono-substituted with $C_{1-6}$ alkyl, $C_6$ or $C_{10}$ aryl, $C_{7-16}$ aralkyl, Het or (lower alkyl)-Het; carboxyl; carboxy (lower alkyl); $C_6$ or $C_{10}$ aryl, $C_{7-16}$ aralkyl or Het, said aryl, aralkyl or Het being optionally substituted with $R_{16}$;

wherein $R_{16}$ is $C_{1-6}$ alkyl; $C_{1-6}$ alkoxy: amino optionally mono- or di-substituted with $C_{1-6}$ alkyl; sulfonyl; $NO_2$; OH; SH; halo; haloalkyl; carboxyl; amide; or (lower alkyl)amide;

$R_{14}$ is $C_{1-6}$ alkyl or $C_{2-6}$ alkenyl optionally substituted with halogen; and A is hydroxy or a N-substituted amino, or a pharmaceutically acceptable salt or ester thereof.

Further included in the scope of the invention are compounds of formula IB, wherein.

B is H, lower alkyl-C(O)— or Het—C(O)—;

$R_6$, when present, is the side chain of Asp or Glu;

$R_5$, when present, is the side chain of D- or L-: Asp, Glu, Val, or Tbg;

Y is H or methyl;

$R_4$ is the side chain of Val, Chg, Tbg, Ile or Leu;

$R_3$ is the side chain of Ile, Chg, Val or Tbg;

$R_{13}$ is Bn, $PhCH_2CH_2$, $PhCH_2CH_2CH_2$, O—Bn, o-tolylmethoxy, m-tolylmethoxy, p-tolylmethoxy, 1-naphthylmethoxy, 2-naphthylmethoxy, (4-tert-butyl)benzyloxy, (3I—Ph)$CH_2$O, (4Br—Ph)O, (2Br—Ph)O, (3Br—Ph)O, (4I—Ph)O, (3Br—Ph)$CH_2$O, (3,5-$Br_2$—Ph)$CH_2$O.

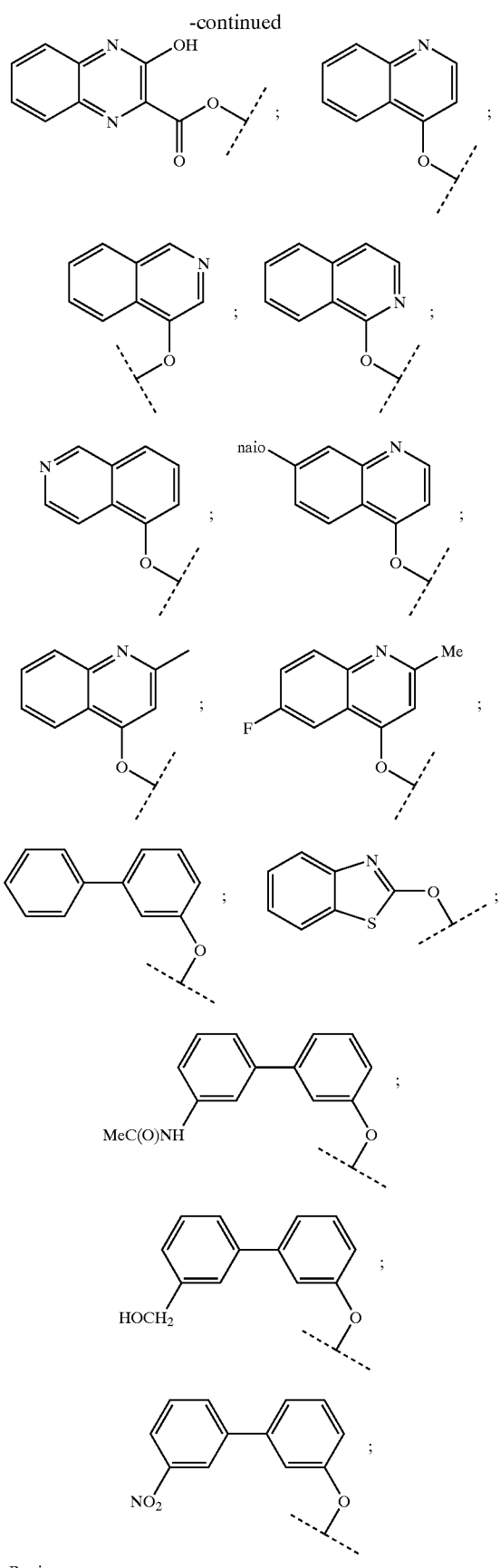

or $R_{13}$ is:

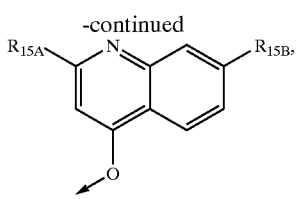

wherein $R_{15A}$ is amido optionally monosubstituted with $C_{1-6}$ alkyl $C_6$ or $C_{10}$ aryl, $C_{7-16}$ aralkyl or Het; or $C_6$ or $C_{10}$ aryl or Het optionally substituted with $R_{16}$, and $R_{16}$ is amino; di(lower alkyl)amino; or (lower alkyl)amide.

P1 is a cyclopropyl ring system of formula

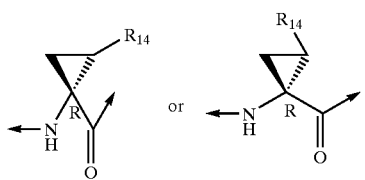

wherein $R_{14}$ is ethyl, vinyl or bromovinyl; and

A is hydroxy or $N(R_{17a})R_{17b}$ wherein $R_{17a}$ and $R_{17b}$ are independently H, aryl or $C_{1-6}$ alkyl optionally substituted with hydroxy or phenyl; or a pharmaceutically acceptable salt or ester thereof.

A further preferred group of compounds is represented by formula IB wherein B is H, acetyl or Het—C(O)—; $R_6$, when present, is the side chain of Asp; $R_5$, when present, is the side chain of D-Asp, D-Glu or D-Val; Y is H; $R_4$ is the side chain of Chg or Ile; $R_3$ is the side chain of Val, Chg or Tbg; $R_{13}$ is 1-naphthylmethoxy, benzyloxy, 4-quinolinoxy, or

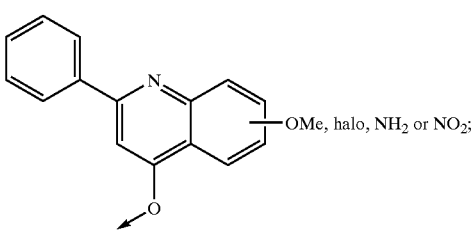

P1 is a cyclopropyl ring system of formula

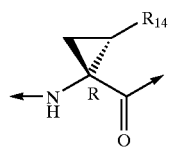

wherein $R_{14}$ is Et or —CH=CH$_2$ or —CH=CHBr; and

A is hydroxy or —NH—(S)CH(Me)Ph, or a pharmaceutically acceptable salt or ester thereof.

An even further preferred group of compounds is represented by formula IB wherein B is acetyl; $R_6$, when present, is the side chain of Asp: $R_5$, when present is the side chain of D-Glu; Y is H; $R_4$ is the side chain of Chg; $R_3$ is the side chain of Val or Tbg;

$R_{13}$ is:

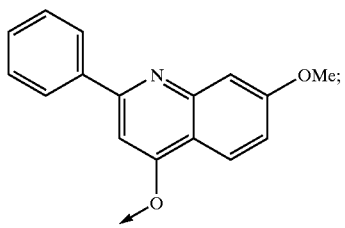

P1 is:

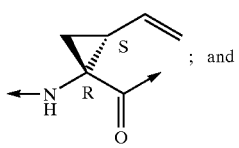
; and

A is hydroxy, or a pharmaceutically acceptable salt or ester thereof.

Further comprised in the scope of the invention are compounds of formula IC. wherein B is an amide of formula $R_{11a}N(R_{11b})$—C(O)— wherein $I_{11a}$ is $C_{1-6}$ alkyl, $C_{3-6}$ cycloalkyl, $C_{3-7}$ (alkylcycloalkyl) optionally substituted with carboxy, $C_{1-3}$ carboxyalkyl, phenyl, $C_{7-10}$ arylalkyl, 2-tetrahydrofuranyimethyl, or 2-thiazolidylmethyl; and $R_{11b}$ is phenyl; or $C_{1-6}$ alkyl substituted with carboxyl or $C_{1-4}$ carboxyalkyl;

$R_4$ is cyclohexyl:

Z is oxo;

$R_3$ is hydrogen or the side chain of Ile, Chg, Val, Glu;

W is Abu, Leu, Phe, Val, Ala, Glu, Glu(OBn); or

W is group of formula IIIa:

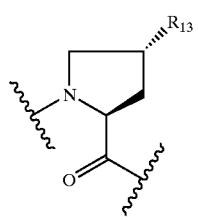
(IIIa)

wherein $R_{13}$ is Bn, PhCH$_2$CH$_2$, PhCH$_2$CH$_2$CH$_2$, O—Bn, o-tolylmethoxy, m-tolylmethoxy, p-tolylmethoxy, 1-naphthylmethoxy, 2-naphthylmethoxy, (4-tert-butyl)methoxy, (3I—Ph)CH$_2$O, (4Br—Ph)O, (2Br—Ph)O, (3Br—Ph)O, (4I—Ph)O, (3Br—Ph)CH$_2$O, (3.5-Br2—Ph)CH$_2$O,

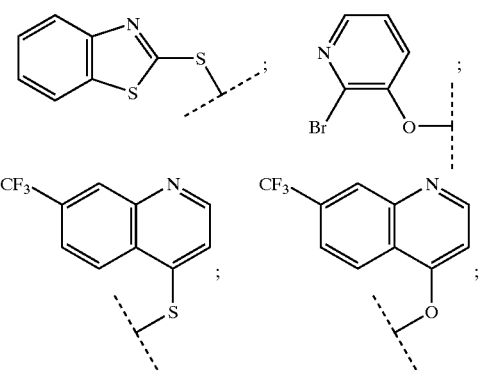

-continued

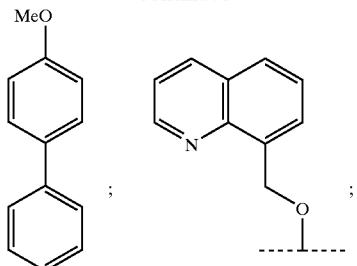

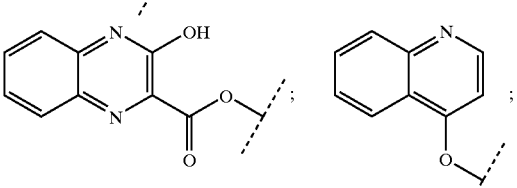

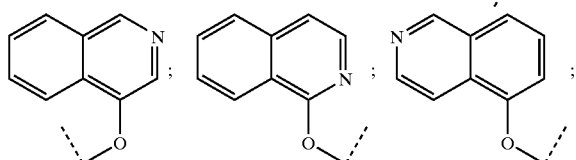

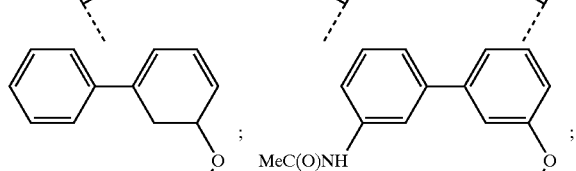

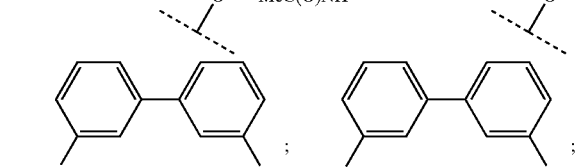

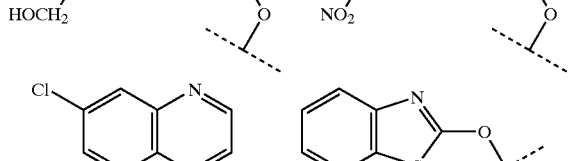

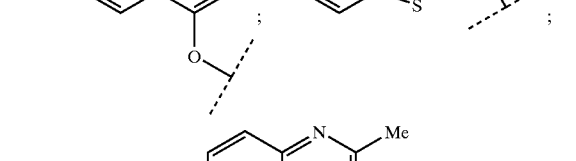

$R_{1a}$ is H and $R_1$ is the side chain of Cys, Abu, Nva or allylglycine; or $R_{1a}$ and $R_1$ together with the carbon atom to which they are attached form a cyclopropyl; and A is hydroxy, or a pharmaceutically acceptable salt or ester thereof.

Finally, specifically included in the scope of the invention are all compounds of formula I presented in Tables 1 to 10.

According to an alternate embodiment, the pharmaceutical compositions of this invention may additionally comprise another anti-HCV agent. Examples of anti-HCV agents include α- or β-interferon, ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, including but not limited to, such as helicase, polymerase, metalloprotease or internal ribosome entry site (IRES).

The pharmaceutical compositions of this invention may be administered orally, parenterally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents.

The pharmaceutical compositions of this invention may be orally administered in any orally acceptable dosage form including, but not limited to, capsules, tablets, and aqueous suspensions and solutions in the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Penn., (1995).

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of HCV mediated disease. Typically, the pharmaceutical compositions of this invention will be administered from about 1 to about 5 times per day, as a continuous infusion, or alternatively, as a once-a-week slow release formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen or as combination therapy as described below When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection. Such treatment may also be achieved using the compounds of this invention in combination with agents which include, but are not limited to: immunomodulatory agents such as α-, β-, or γ-interferons; other antiviral agents such as ribavirin, amantadine; other inhibitors of HCV NS3 protease; inhibitors of other targets in the HCV life cycle such as helicase, polymerase, metalloprotease, or internal ribosome entry; or combinations thereof. The additional agents may be combined with the compounds of this invention to create a single dosage form. Alternatively these additional agents may be separately administered to a mammal as part of a multiple dosage form.

Accordingly, another embodiment of this invention provides methods of inhibiting HCV NS3 protease activity in mammals by administering a compound of the formula I, wherein the substituents are as defined above.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, metalloprotease or IRES. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing HCV disease. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

The compounds set forth herein may also be used as research reagents. The compounds of this invention maybe used as positive control to validate surrogate cell-based assays or in vitro or in vivo viral replication assays.

PROCESS

The compounds of the present invention were synthesized according to the process as illustrated in scheme I (wherein CPG is a carboxyl protecting group. APG is an amino protecting group and a is an amine)

nation of both processes, or by solid phase peptide synthesis according to the method originally described in Merrifield, J. Am. Chem. Soc. (1963), 85, 2149–2154, the disclosure of which is hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

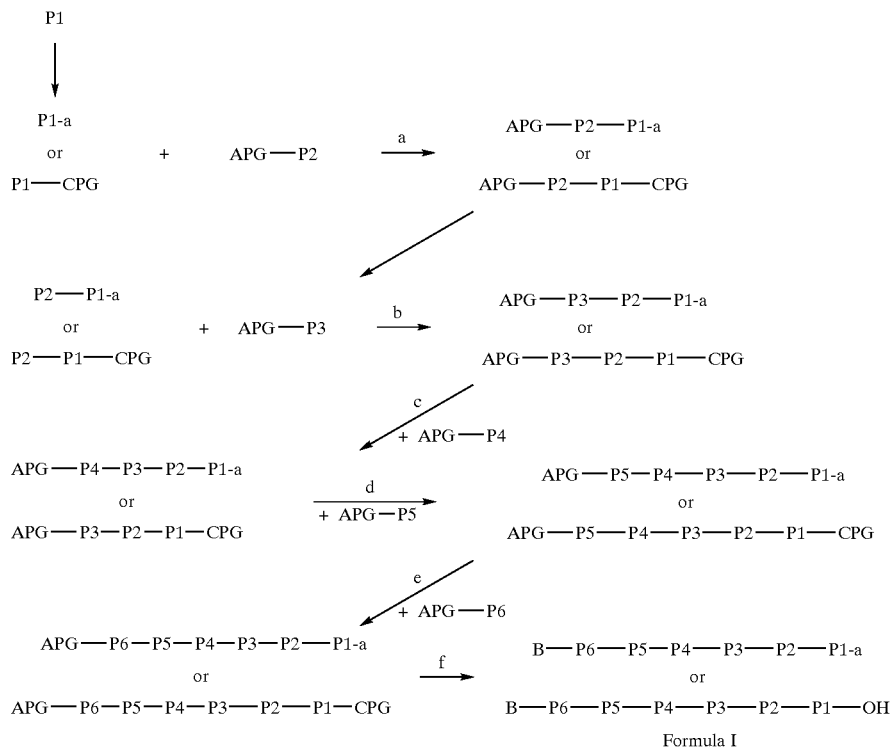

Formula I

Briefly, the P1, P2, P3, P4, and optionally P5 and P6 can be linked by well known peptide coupling techniques. The P1, P2, P3, P4, and P5 and P6 groups may be linked together in any order as long as the final compound corresponds to peptides of formula 1. For example, P6 can be linked to P5 to give P5-P6 that is linked to P4-P3-P2-P1; or P6 linked to P5-P4-P3-P2 then linked to an appropriately C-terminal protected P1.

Generally, peptides are elongated by deprotecting the (α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I, or by condensation of fragments (two or several amino acids), or combi- More explicitly, the coupling step involves the dehydrative coupling of a free carboxyl of one reactant with the free amino group of the other reactant in the presence of a coupling agent to form a linking amide bond. Descriptions of such coupling agents are found in general textbooks on peptide chemistry for example. M. Bodanszky, "Peptide Chemistry", 2nd rev ed., Springer-Verlag, Berlin, Germany, (1993). Examples of suitable coupling agents are N,N'dicyclohexylcarbodiimide, 1-hydroxybenzotriazole in the presence of N,N'-dicyclohexylcarbodiimide or N-pethyl-N'[(3-dimethylamino)propyl]carbodiimide. A very practical and useful coupling agent is the commercially available (benzotriazol-1-yloxy)tris-(dimethylamino)phosphonium hexafluorophosphate, either by itself or in the presence of 1-hydroxybenzotriazole. Another very practical and useful coupling agent is commercially available 2-(1H-benzotriazol-1-yl)-N, N, N', N'-tetramethyluronium tetrafluoroborate. Still another very practical and useful coupling agent is commercially available O-(7-azabenzotriazol-1-yl)-N,N,N'N'-tetramethyiuronium hexafluorophosphate.

The coupling reaction is conducted in an inert solvent, e.g. dichloromethane, acetonitrile or dimethylformamide. An excess of a tertiary amine, e.g. diisopropylethylamine. N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated. Alternatively, the amino acid can be incorporated on the solid support by known methods Wang, S.-S., J. Am. Chem. Soc., (1973), 95, 1328; Atherton, E.; Shepard, R. C. "Solid-phase peptide synthesis; a practical approach" IRL Press: Oxford, (1989); 131–148. In addition to the foregoing, other methods of peptide synthesis are described in Stewart and Young, "Solid Phase Peptide Synthesis", $2^{nd}$ ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980–1987); Bodansky et al., "The Practice of Peptide Synthesis" Springer-Verlag, New-York (1984), the disclosures of which are hereby incorporated by reference.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (PG1) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The α-amino group of each amino acid to be coupled to the growing peptide chain must be protected (PG2). Any protecting group known in the art can be used. Examples of such groups include: 1) acyl groups such as formyl trifluoroacetyl, phthalyl, and prtoluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropyl-methoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT), usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting groups are suitable: ptoluenesulfonyl (tosyl) moieties can be used to protect the amino side chain of amino acids such as Lys and Arg; acetamidomethyl, benzyl (Bn), or t-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the a-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

When A is an amide, P1 is coupled to an appropriate amine (a) prior to the coupling to P2. Such amination will be readily recognized by persons skilled in the art. Once the elongation of the peptide is completed all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin simultaneously with the removal of the protecting groups. When the Boc protection method is used in the synthesis, treatment with anhydrous HF containing additives such as dimethyl sulfide, anisole, thioanisole, or pcresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection method is used, the N-terminal Fmoc group is cleaved with reagents described earlier. The other protecting groups and the peptide are cleaved from the resin using solution of trifluoroacetic acid and various additives such as anisole, etc.

When Q is $CH_2$, a is 0, b is 0 and B is $R_{11a}N(R_{11b})C(O)$, the compounds were prepared according to a method analogous to the general method described for the peptides in Scheme I using a readily available succinyl intermediate, t-BuO-C(O)$CH_2$CH($R_4$)—CO-PG1 (e.g. PG 1=2-oxo-4-substituted-oxazolidin-3-yl). This succinyl intermediate can easily be prepared according to the method of Evans' et al (J. Am. Chem. Soc. (1982), 104, 1737) using the appropriate 4-substituted-3-acyl-2-oxazolidinone in the presence of a strong base such as lithium diisopropylamide or sodium bis(trimethylsilyl)amide and t-butyl bromoacetate. After cleavage of the 2-oxazolidinone moiety with LiOOH (Evans' et al., Tetrahedron Lett. (1987), 28, 6141), the resulting acid was coupled to the P3-P2-P1-PG1 segment to give t-BuO-C(O)—CH$_2$CH(R$_4$)—CO-P3-P2-P1-PG1. The latter was treated with hydrogen chloride to selectively convert the terminal t-butyl ester into the corresponding acid that was finally coupled to R$_{11a}$NH(R$_{11b}$) to give, after removal of the protective group(s), the desired peptide derivative. The amines R$_{11a}$NH(R$_{11b}$) are commercially available or the synthesis is well known in the art. A specific embodiment of this process is presented in Example 23.

Alternatively, starting with the same succinyl intermediate (t-BuO-C(O)CH$_2$CH(R$_4$)—CO-PG1), the sequence of reactions can be inverted to introduce first R$_{11a}$NH(R$_{11b}$) and then P3-P2-P1-PG1 to give the desired peptide derivative.

Synthesis of capping group B and P6, P5, P4, and P3 moieties Different capping groups B are introduced to protected P6, P5, P4, the whole peptide or to any peptide segment with an appropriate acyl chloride or sultonyl chloride that is either available commercially or for which the synthesis is well known in the art.

Different P6 to P3 moieties are available commercially or the synthesis is well known in the art.

1. Synthesis of P2 Moieties
1.1 Synthesis of Orecursors:

A) Synthesis of haloarylmethane derivatives.

The preparation of halomethyl-8-quinoline IId was done according to the procedure of K. N. Campbell et al., J. Amer. Chem. Soc., (1946), 68, 1844.

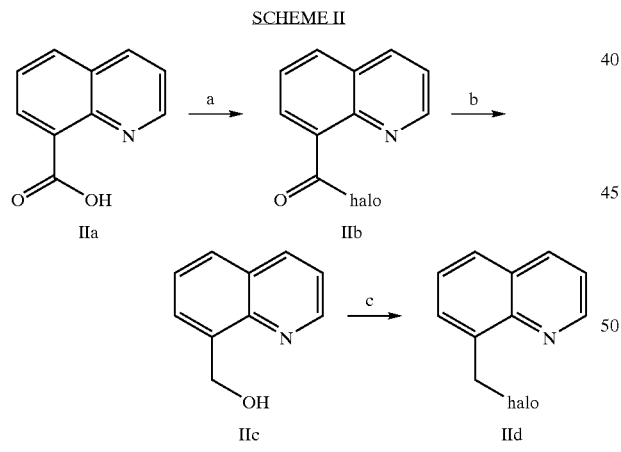

Briefly, 8-quinoline carboxylic acid IIa was converted to the corresponding alcohol IIc by reduction of the corresponding acyl halide IIb with a reducing agent such as lithium aluminium hydride. Treatment of alcohol IIb with the appropriate hydrohaloacid gives the desired halo derivative IId. A specific embodiments of this process is presented in Example 1A.

B) Synthesis of aryl alcohols derivatives:

2-phenyl-4-hydroxyquinoline derivatives IIIc were prepared according to Giardina et al. (J. Med. Chem., (1997), 40, 1794–1807).

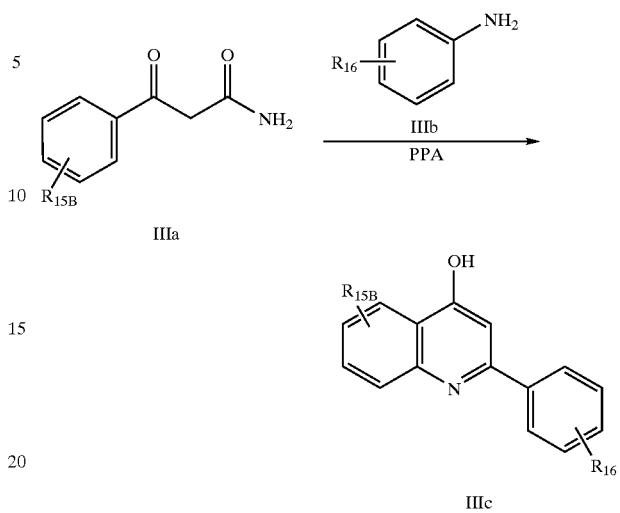

R$_{16}$ & R$_{15B}$=alkyl, OH, SH, halo, NH$_2$, NO$_2$.

Benzoylacetamide (IIIa) was condensed with the appropriate aniline (IIIb) and the imine obtained was cyclized with polyphosphoric acid to give the corresponding 2-phenyl-4-hydroxyquinoline (IIIc). A specific embodiment of this process is presented in Example 1B and 1C.

1.2 Synthesis of P2:

A) The synthesis of 4-substituted proline (wherein R$^{13}$ is attached to the ring via a carbon atom) (with the stereochemistry as shown).

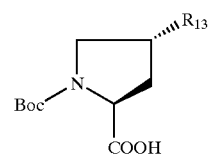

is done as shown in Scheme IV according to the procedures described by J. Ezquerra et al. (Tetrahedron, (1993), 38, 8665–8678) and C. Pedregal et al. (Tetrahedron Lett., (1994), 35, 2053–2056). A specific embodiment of this process is presented in Example 2.

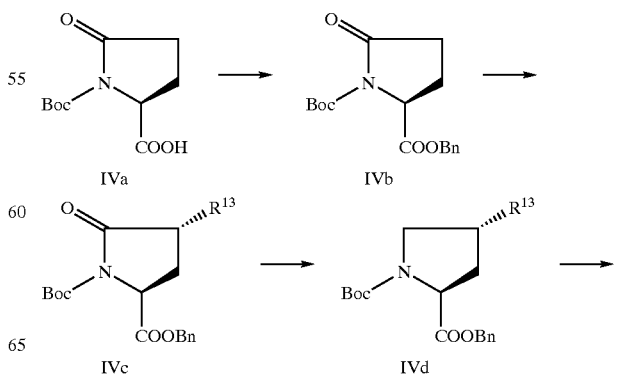

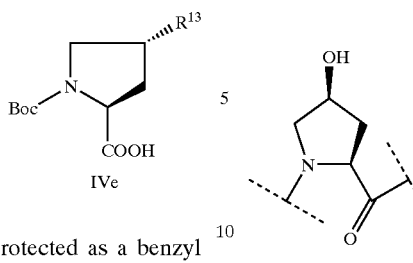

IVe

Briefly, Boc-pyroglutamic acid is protected as a benzyl ester. Treatment with a strong base such as lithium diisopropylamide followed by addition of an alkylating agent (Br—$R^{12}$ or I—$R^{12}$) gives the desired compounds IVe after reduction of the amide and deprotection of the ester.

B) The synthesis of O-substituted 4-(R)-hydroxyproline:

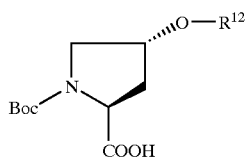

may be carried out using the different processes described below.

When $R^{12}$ is aryl, Het, aralkyl, or (lower alkyl)-Het, the process can be carried out according to the procedure described by E. M. Smith et al. (J. Med. Chem. (1988), 31, 875–885). Briefly, commercially available Boc-4(R) hydroxyproline is treated with a base such as sodium hydride or K-tBuO and the resulting alkoxide reacted with an halo-$R^{12}$ (Br—$R^{12}$, I—$R^{12}$, etc.,) to give the desired compounds. Specific embodiments of this process are presented in Examples 3, 4A and 4B C) Alternatively, when $R^{12}$ is aryl or Het, the compounds can also be prepared via a Mitsunobu reaction (Mitsunobu (1981), Synthesis, January, 1–28; Rano etal., (1995), Tet. Lett. 36(22), 3779–3792; Krchnak et al., (1995), Tet. Lett. 36(5), 62193–6196; Richter et al., (1994), Tet. Lett. 35(27), 4705–4706). Briefly, commercially available Boc-4(S)-hydroxyproline methyl ester is treated with the appropriate aryl alcohol or thiol in the presence of triphenylphosphine and diethylazodicarboxylate (DEAD) and the resulting ester is hydrolyzed to the acid. Specific embodiment of this process is presented in Example 5.

SCHEME V

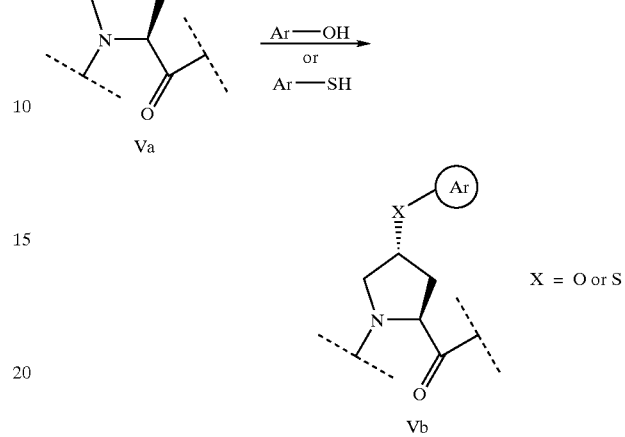

X = O or S

Alternatively, the Mitsunobu reaction can be produced in solid phase (as shown in Scheme V). The 96-well block of the Model 396 synthesizer (advanced ChemTech) is provided with aliquots of resin-bound compound (Va) and a variety of aryl alcohols or thiols and appropriate reagents are added. After incubation, each resin-bound product (Vb) is washed, dried, and cleaved from the resin.

Furthermore, a Suzuki reaction (Miyaura et al., (1981), Synth. Comm. 11, 513; Sato et al., (1989), Chem. Lett., 1405; Watanabe et al., (1992), Synlett., 207; Takayuki et al., (1993), J. Org. Chem. 58, 2201; Frenette et al., (1994), Tet. Lett. 35(49), 9177–9180; Guiles et al., (1996), J. Org. Chem. 61, 5169–5171) can also be used to further functionalize the aryl substituent.

2. Synthesis of the 4 Possible Isomers of P1 Moieties (2-substituted 1-aminocyclopropyl Carboxylic Acid)

2.1 The synthesis was done according to scheme VI.

SCHEME VI

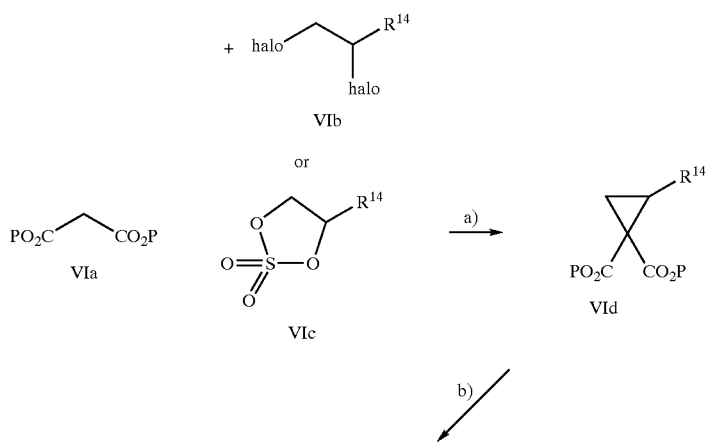

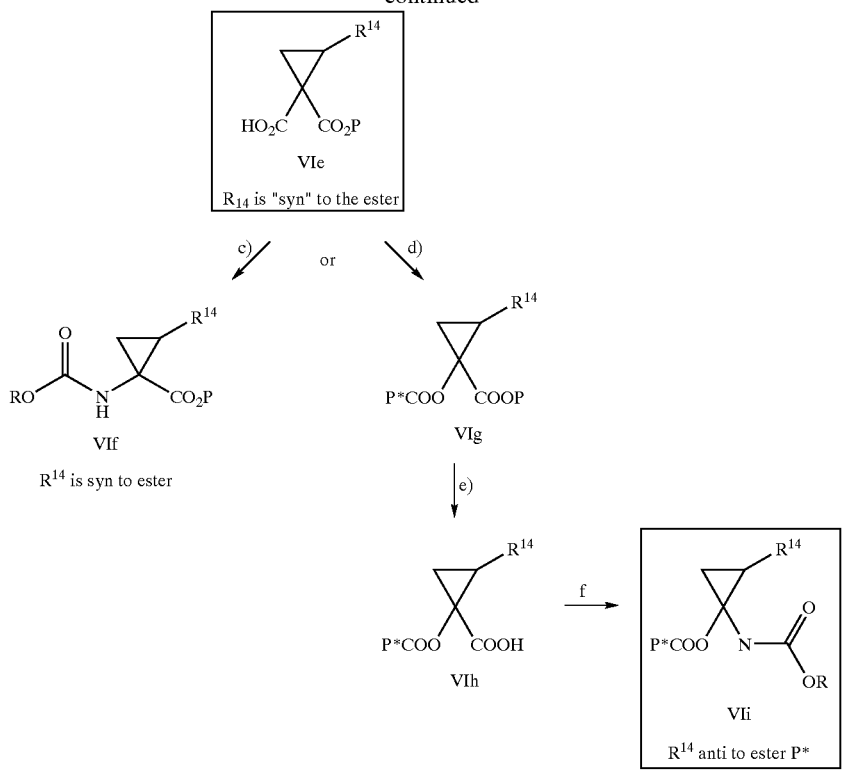

a) Briefly, di-protected malonate VIa and 1,2-dihaloalkane VIb or cyclic sulfate VIc, (synthesized according to K. Burgess and Chun-Yen KE (Synthesis, (1996), 1463–1467) are reacted under basic conditions to give the diester VId.

b) A regioselective hydrolysis of the less hindered ester is performed to give the acid VIe.

c) This acid VIe is subjected to a Curtius rearrangement to give a racemic mixture of 1-aminocyclopropylcarboxylic acid derivatives VIf with $R^{14}$ being syn to the carboxyl group. A specific embodiment for this synthesis is presented in Example 6.

d, e) Alternatively, selective ester formation from the acid VIe with an appropriate halide (P*Cl) or alcohol (P*OH) forms diester VIg in which the P* ester is compatible with the selective hydrolysis of the P ester. Hydrolysis of P ester provides acid VIh.

f) A Curtius rearrangement on VIh gives a racemic mixture of 1-aminocyclopropylcarboxylic acid derivatives VIi with $R^{14}$ group being anti to the carboxyl group. A specific embodiment for this synthesis is presented in Example 11.

2.2 An alternative synthesis for the preparation of derivatives VIf (when $R^{14}$ i vinil, syn to the carboxyl group) is described below.

SCHEME VII

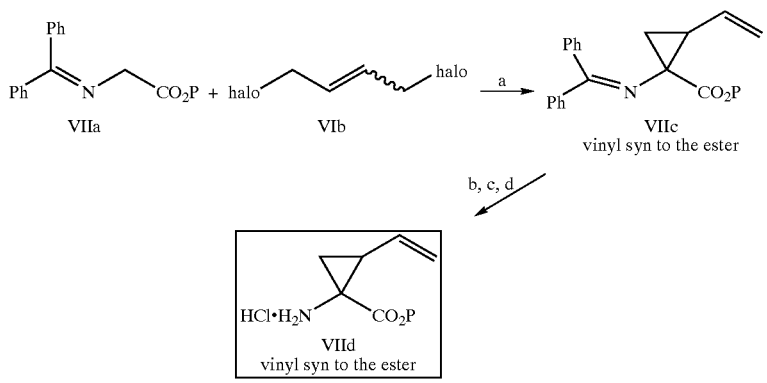

Treatment of commercially available imine VIIa with 1,4-dihalobutene VIIb in presence of a base produces, after hydrolysis of the resulting imine VIIc, VIId having the allyl substituent syn to the carboxyl group. This process is presented in Example 12.

Resolution of all of the above enantiomeric mixtures at carbon 1 (VIe and VIId) can be carried out via:

1) enzymatic separation (Examples 10 and 14);
2) crystallization with a chiral acid (Example 15); or
3) chemical derivatization (Example 7).

Following resolution, determination of the absolute stereochemistry can be carried out as presented in Example 8.

Resolution and stereochemistry determination can be carried out in the same manner for the enantiomeric mixtures at carbon 1 wherein the substituent at C2 is anti to the carboxyl group (VIi).

Accordingly, the invention further comprises a process for the preparation of a peptide analog of formula I, IA, IB or IC, wherein P1 is a substituted aminocyclopropyl carboxylic acid residue, comprising the step of: coupling a peptide selected from the group consisting of: APG-P6-P5-P4-P3-P2; APG-P5-P4-P3-P2; APG-P4-P3-P2; APG-P3-P2; and APG-P2; with a P1 intermediate of formula:

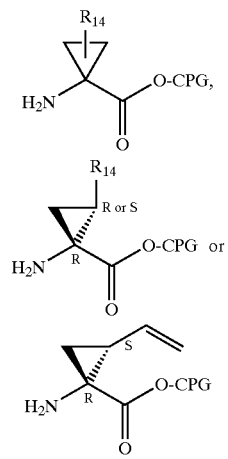

wherein $R_{14}$ is $C_{1-6}$ alkyl or $C_{2-6}$ alkenyl optionally substituted with halogen, CPG is a carboxyl protecting group and APG is an amino protecting group, and P6 to P2 are as defined above.

Finally, the invention also comprises the use of an intermediate of formula:

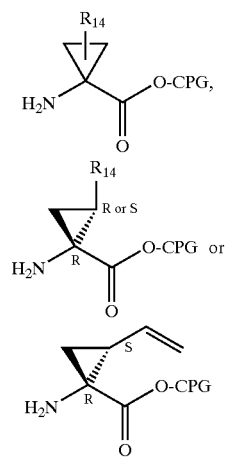

wherein $R_{14}$ is $C_{1-6}$ alkyl or $C_{2-6}$ alkenyl optionally substituted with halogen, CPG is a carboxyl protecting group and APG is an amino protecting group, for the preparation of a compound of formula I, IA, IB, or IC as defined above

EXAMPLES

The present invention is illustrated in further detail by the following non-limiting examples.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem. (1978), 43, 2923).

Abbreviations used in the examples include Bn: benzyl; Boc: tert-butyloxycarbonyl $\{Me_3COC(O)\}$; BSA: bovine serum albumin; CHAPS: 3-[(3-cholamidopropyl)-dimethylammonio]-1-propanesulfonate; DBU: 1,8-diazabicyclo[5.4.0]undec-7-ene; $CH_2Cl_2$=DCM: methylene chloride; DEAD: diethylazodicarboxylate; DIAD: diisopropylazodicarboxylate; DIPEA: diisopropylethylamine; DMAP: dimethylaminopyridine; DCC: 1,3-dicyclohexylcarbodiimide; DME: 1,2-dimethyoxyethane; DMF: dimethylformamide; DMSO: dimethylsulfoxide; DTT: dithiothreitol or threo-1,4-dimercapto-2,3-butanediol; DPPA: diphenylphosphoryl azide; EDTA: ethylenediaminetetraacetic acid; Et: ethyl; EtOH: ethanol; EtOAc: ethyl acetate; $Et_2O$: diethyl ether; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Disorption Ionization-Time of Flight, FAB: Fast Atom Bombardment); LAH: lithium aluminum hydride; Me: methyl; MeOH: methanol; MES: (2-{N-morpholino}ethane-sulfonic acid); NaHMDS: sodium bis(trimethylsilyl)amide; NMM: N-methylmorpholine; NMP: N-methylpyrrolidine; Pr: propyl; Succ: 3-carboxypropanoyl; PNA: 4-nitrophenylamino or p-nitroaniline; TBAF: tetra-n-butylammonium fluoride; TBTU: 2-(1H-benzotriazole-1-yl)-1,1,3,3-tetramethyluronium tetrafluoroborate; TCEP: tris(2-carboxyethyl)phosphine hydrochloride; TFA: trifluoroacetic acid; THF: tetrahydrofuran; TIS: triisopropylsilane; TLC: thin layer chromatography; TMSE: trimethylsilylethyl; Tris/HCl: tris(hydroxymethyl)aminomethane hydrochloride.

GENERAL PROCEDURES

Example A

General Procedure for Mitsunobu Reaction in Solid Phase (Scheme V)

The polymer-bound peptide of general structure Va (0.327 mmols of peptide per gram of Wang resin) was dried under high vacuum in a dessicator over $P_2O_5$. The 96-well block of the Advanced ChemTech Model 396 synthesizer was furnished with aliquots of Va (120 mg, 0.04 mmol peptide per well) and each sample was washed for 5 min with anhydrous $CH_2Cl_2$ (5×1200 μL) and then with anhydrous THF (5×1500 μL). Anhydrous THF (200 μL) was added to each sample and the synthesizer was temporarily stopped to allow the manual addition of reagents. $Ph_3P$ (5 eq. in 400 μL of anhydrous THF) and diethylazodicarboxylate (DIAD, 5 eq. in 250 μL of anhydrous THF)) were added to each sample before the addition of a phenol or thiophenol reagent (5 eq, 0.2 mmol, dissolved in 500 μL of anhydrous THF); a library of reagents was used to produce the library of HCV protease inhibitors described in this patent application. After the addition of all reagents, the mixtures were shaken for a total of 4 h with a 10 min delay after each hour. Each resin-bound product was washed with THF (2×1500 μL), DMF (4×1500 μL), isopropanol (4×1500 μL), CH$_2$Cl$_2$ (4×1500 μL) and finally methanol (2×1500 μL). The sample was dried under vacuum and then treated with 40% TFA in CH$_2$Cl$_2$ for 1 h in order to cleave the peptide product (general structure Vb) from the resin. All products were purified by preparative HPLC on a reversed phase C18 column using a linear solvent gradient from 5% aqueous CH$_3$CN to 100% CH$_3$CN.

The preparation of a library of Ac-Chg-Val-Hyp(aryl)-Acca-OH was carried out according to this protocol where appropriate peptides were used.

Example B
Suzuki Library of Reactions in Solid Phase Synthesis

All reactions were carried out in 16×100 mm, high pressure screw-cap test tubes with Teflon caps, equipped with small magnetic stirring bars. For each reaction, a degassed suspension of the polymer-bound peptide (100 mg of Wang resin with 0.033 mmol of bound peptide) was first added to the test tube, followed by the addition of DME (2 mL), Pd(Ph$_3$P)$_3$ (~3 mg, 0.05 eq.), Na$_2$CO$_3$ (70 μL of a 2M solution in H$_2$O, 2.5 eq.) and one of the phenyl boronic acid reagents from our library. The test tubes were flashed with nitrogen gas, sealed and placed in an oil bath at 80° C. All of the reactions were stirred gently and allowed to proceed for 15–18 h. Each resin bound peptide product was subsequently transferred into a plastic filtration tube, washed with DME:H$_2$O (1:1, 5×2 mL), DME (5×2 mL), methanol (5×2 mL), CH$_3$CN (5×2 mL), CH$_2$Cl$_2$ (5×2 mL) and dried under high vacuum. Each product was cleaved from the resin by treating the sample with 45% TFA in CH$_2$Cl$_2$ (1 mL) for 1 hour. All products were purified by preparative HPLC on a reversed phase C18 column using a solvent linear gradient from 5% aqueous CH$_3$CN to 100% CH$_3$CN.

Example C
General Procedure for Coupling Reactions Done in Solution
{See also R. Knorr et al., Tetrahedron Letters, 30, 1927, (1989).}

The reactants, i.e. a free amine (1 eq.) (or its hydrochloride salt) and the free carboxylic acid (1 eq.) were dissolved in CH$_2$Cl$_2$, CH$_3$CN or DMF. Under a nitrogen atmosphere, four equivalents of N-methylmorpholine and 1.05 equivalents of the coupling agent were added to the stirred solution. After 20 min, one equivalent of the second reactant, i.e. a free carboxylic acid was added. (Practical and efficient coupling reagents for this purpose are (benzotriazol-1-yloxy)tris-(dimethylamino)phosphonium hexafluorophosphate (HOBT) or preferably 2-(1H-benzotriazol-1-yl)-N,N,N',N'-tetramethyluronium tetrafluoroborate (TBTU) or O-(7-azabenzotriazol-1-yl)-N,N,N',N'-tetramethyluronium tetrafluoroborate (HATU). The reaction was monitored by TLC. After completion of the reaction, the solvent was evaporated under reduced pressure. The residue was dissolved in EtOAc. The solution was washed successively with 10% aqueous citric acid, saturated aqueous NaHCO$_3$ and brine. The organic phase was dried (MgSO$_4$), filtered and concentrated under reduced pressure. When the residue was purified, it was done by flash chromatography as defined above.

Example D
General Procedure for Coupling Reactions Done on Solid Support.

The synthesis was done on a parallel synthesizer model ACT396 from Advanced ChemTech with the 96 well block: Typically, 24 peptides were synthesized in parallel using standard solid-phase techniques. The starting Fmoc-Nva-Wang resin and the 1-(Fmoc-amino)cyclopropane carboxylic acid-Wang resin were prepared by the DCC/DMAP coupling method (Atherton, E; Scheppard, R. C. *Solid Phase Peptide Synthesis, a Practical Approach*; IRL Press: Oxford (1989); pp 131–148). Other amino acid-Wang resins were obtained from commercial sources. Each well was loaded with 100 mg of the starting resin (approximately 0.05 mmol).

The resins were washed successively with 1.5 mL portions of NMP (1×) and DMF (3×). The Fmoc protecting group was removed by treatment with 1.5 mL of a 25% v/v solution of piperidine in DMF for 20 min. The resins were washed with 1.5 mL portions of DMF (4×), MeOH (3×) and DMF (3×). The coupling was done in DMF (350 μL), using 400 μL (0.2 mmol) of a 0.5M solution of Fmoc-amino acid/HOBt hydrate in DMF, 400 μL (0.4 mmol) of a 0.5M solution of DIPEA in DMF and 400 μL (0.2 mmol) of a 0.5M solution of TBTU in DMF. After shaking for 1 h, the wells were drained, the resins were washed with 1.5 mL of DMF and the coupling was repeated once more under the same conditions. The resins were then washed as described above and the cycle was repeated with the next amino acid.

The capping groups were introduced in two ways:
1. In the form of a carboxylic acid using the protocol described above (for example acetic acid) or,
2. As an acylating agent such as an anhydride or an acid chloride. The following example illustrates the capping with succinic anhydride: After the Fmoc deprotection and subsequent washing protocol, DMF was added (350 μL), followed by 400 μL each of a DMF solution of succinic anhydride (0.5 M, 0.2 mmol) and DIPEA (1.0 M, 0.4 mmol). The resins were stirred for 2 h and a recoupling step was performed.

At the end of the synthesis the resin was washed with 1.5 mL portions of DCM (3×), MeOH (3×), DCM (3×), and were dried under vacuum for 2 h.

The cleavage from the resin and concomitant side chain deprotection was effected by the addition of 1.5 mL of a mixture of TFA, H$_2$O, DTT and TIS (92.5: 2.5: 2.5: 2.5). After shaking for 2.5 h, the resin was filtered and washed with 1.5 mL of DCM. The filtrates were combined and concentrated by vacuum centrifugation.

Each compound was purified by preparative reversed phase HPLC using a C18 column (22 mm by 500 mm). The product-containing fractions were identified by MALDI-TOF mass spectrometry, combined and lyophilized.

P2 BUILDING BLOCKS

Example 1A
Synthesis of bromomethyl-8-quinoline (1A):

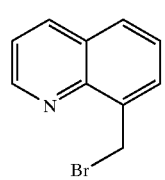
(1A)

To commercially available 8-quinoline carboxylic acid (2.5 g, 14.4 mmol) was added neat thionyl chloride (10 ml, 144 mmol). This mixture was heated at 80° C. for 1 h before the excess thionyl chloride was distilled off under reduced pressure. To the resulting brownish solid was added absolute EtOH (15 mL) which was heated at 80° C. for 1 h before being concentrated in vacuo. The residue was partitioned between EtOAc and saturated aqueous NaHCO$_3$, and the organic phase dried (MgSO$_4$), filtered and concentrated to give a brownish oil (2.8 g). This material (ca. 14.4 mmol) was added dropwise over 35 min to a LAH (0.76 g, 20.2 mmol)/Et$_2$O suspension which was cooled to −60° C. The reaction mixture was slowly warmed to −35° C. over 1.5 h before the reaction was complete. The reaction was quenched with MgSO$_4$.10H$_2$O slowly over 30 min and then wet THF. The mixture was partitioned between Et$_2$O and 10% aqueous NaHCO$_3$. The organic phase was dried (MgSO$_4$), filtered and concentrated to give a yellowish solid (2.31 g, 80% over 2 steps) corresponding to the alcohol. The alcohol (2.3 g, 11.44 mmol) was dissolved in AcOH/HBr (20 mL, 30% solution from Aldrich) and heated at 70° C. for 2.5 h. The mixture was concentrated in vacuo to dryness, partitioned between EtOAc (100 mL) and saturated aqueous NaHCO$_3$ before being dried (MgSO$_4$), filtered and concentrated to give the desired compound (1) as a brownish solid (2.54 g, 100%).

silica gel, eluting with EtOAc:hexane (3:7), to give the corresponding amide as a white solid, 1.60 g, 31% yield.

This amide (250 mg, 1.53 mmol) was refluxed using a Dean-Stark apparatus with aniline (143 mg, 1.53 mmol) and aniline.HCl (10 mg, 0.08 mmol) in toluene (10 mL) for 16 h. The solution was concentrated to afford a brown oil that was mixed with polyphosphoric acid (2 g) and heated at 135° C. for 20 min. The reaction mixture was poured into water and adjusted to pH 8 with 5 M NaOH. The aqueous suspension was extracted twice with ethyl acetate. The organic layers were combined, washed with brine, dried over MgSO$_4$, filtered and concentrated. The residue was flash chromatographed on silica gel, eluting with 3% MeOH in ethyl acetate, to give 2-phenyl-4-hydroxyquinoline (2), 67 mg, 20% yield.

$^1$H NMR (DMSO-d$_6$) δ 8.11 (d, J=7 Hz, 1H), 7.86–7.83 (m, 2H), 7.77 (d, J=8 Hz, 1H), 7.68 (dd, J=8, 7 Hz, 1H), 7.61–7.58 (m, 3H), 7.35 (dd, J=8, 7 Hz, 1H), 6.34 (s, 1H).

Example 1C

Synthesis of 4-hydroxy-2-phenyl-7-methoxyquinoline (1C)

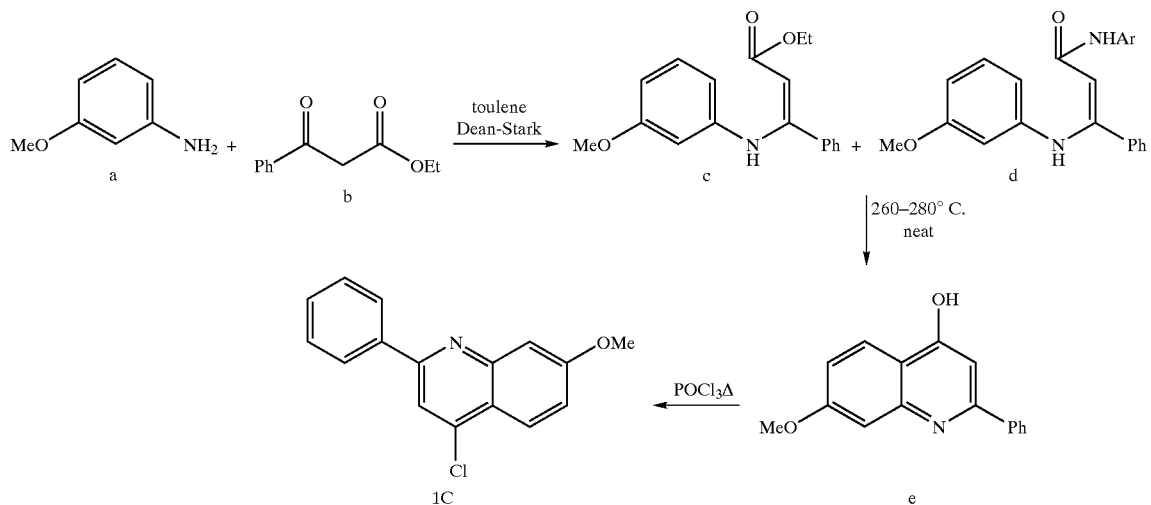

Example 1B
Synthesis of 2-phenyl-4-hydroxyquinoline (1b):

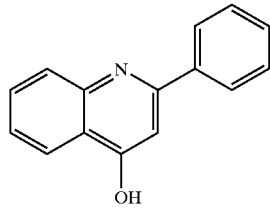

(1B)

Commercially available ethyl benzoylacetate (6.00 g, 31.2 mmol) was heated at 85° C. (sealed tube) in 75 mL of 30% NH$_4$OH for 2 hours. The solid formed upon cooling was filtered and refluxed in water for 2 hours. The solution was extracted three times with CH$_2$Cl$_2$. The organic layers were combined, dried over MgSO$_4$, filtered and concentrated. The yellow residue was flash chromatographed on 4-hydroxy-2-phenyl-7-methoxyquinoline (e):
A solution of ethyl benzoylacetate (b) (100.0 g, 0.52 mol), m-anisidine (a) (128.1 g, 1.04 mol) and 4 N HCl/dioxane (5.2 mL) in toluene (1.0 L) was refluxed for 6.25 h in a Dean-Stark apparatus. The cooled toluene solution was successively washed with aqueous 10% HCl (2×300 mL), 1 N NaOH (2×300 mL), H$_2$O (300 mL) and brine (150 mL). The toluene phase was dried (MgSO$_4$), filtered and concentrated under reduced pressure to give a 1.2:1.0 mixture of ester c and amide d (144.6 g, 45%/38% crude yield) as a dark brown oil. The crude oil was heated to 280° C. for 80 min while distilling generated EtOH. The cooled dark solid obtained was triturated with CH$_2$Cl$_2$ (200 mL). The suspension was filtered and the resulting solid washed with CH$_2$Cl$_2$ to give e (22.6 g, 17% from a) as a beige solid: $^1$H NMR (DMSO-d$_6$) δ 8.00 (d, J=9.0 Hz, 1H), 7.81–7.82 (m, 2H), 7.57–7.59 (m, 3H), 7.20 (d, J=2.2 Hz, 1H), 6.94 (dd, J=9.0, 2.2 Hz, 1H), 6.26 (s, 1H), 3.87 (s, 3H).

4-Chloro-2-phenyl-7-methoxyquinoline (1C):
A suspension of e (8.31 g, 33.1 mmol) in POCl$_3$ (90 mL) was heated to reflux for 2 h (clear solution obtained upon heating). The reaction mixture was concentrated under reduced pressure. The residue was partitioned between 1 N NaOH (exothermic, 10 N NaOH added to maintain high pH) and EtOAc (500 mL). The organic layer was washed with H₂O (100 mL) and brine (100 mL) then was dried (MgSO₄), filtered and concentrated under reduced pressure to give 1C (8.60 g, 96%) as a pale yellow solid: $^1$H NMR (DMSO-$d_6$) δ 8.28–8.30 (m, 2H), 8.20 (s, 1H), 8.10 (d, J=9.1 Hz, 1H), 7.54–7.58 (m, 3H), 752 (d, J=2.5 Hz, 1H), 7.38 (dd, J=9.1, 2.5 Hz, 1H), 3.98 (s, 3H). This reaction was repeated three times and gave always 96–98% yield which is significantly higher that the 68% yield reported in J. Med. Chem. 1997, 40, 1794.

Example 2
Synthesis of Boc-4(R)-(3-phenylpropyl)proline (2d).

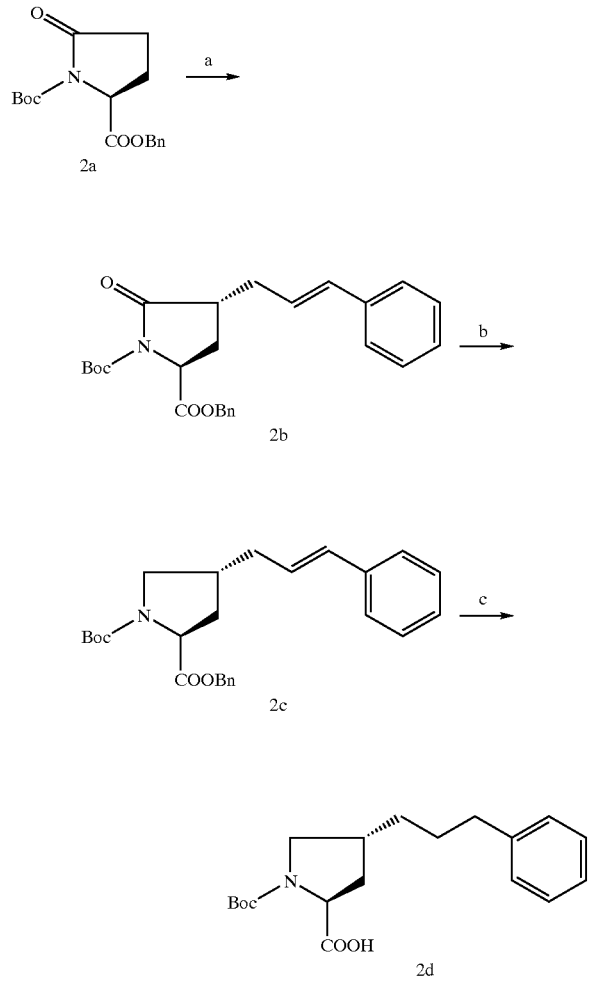

a) Synthesis of Compound 2b:

To a solution of Boc-pyroglutamic acid benzyl ester (2a) (prepared as described by A. L Johnson et al., J. Med. Chem. (1985), 28, 1596–1602) (500 mg, 1.57 mmol) in THF (10 mL) at −78° C., was slowly added lithium hexamethydisilylazide (1.72 mL, 1M solution in THF). After stirring for 1 h at −78° C., cinnamyl bromide (278 μL, 1.88 mmol) was added and the stirring continued for an additional 2 h. The reaction mixture was quenched with saturated ammonium chloride solution and extracted with ethyl ether (3×20 mL). The combined organic extracts were dried (MgSO₄), filtered and concentrated. The residue was purified by flash column chromatography (8:2 hexane:ethyl acetate) to give compound 2b as an off-white solid (367 mg, 54% yield). $^1$H NMR (CDCl₃): δ 7.35–7.19 (m, 10H), 6.43 (d, J=15 Hz, 1H), 6.11 (ddd, J=15, J'=J"=8 Hz, 1H), 5.26 (d, J=16 Hz, 1H), 5.17 (d, J=16 Hz, 1H), 4.59 (dd, J=9.5, J'=2 Hz, 1H), 2.83–2.70 (m, 2H), 2.41–2.34 (m, 1H), 2.22–2.16 (m, 1H), 2.10–2.02 (m, 1H) 1.42 (s, 9H).

b) Synthesis of Compound 2c:

At −78° C., lithium triethylborohydride (1M solution in THF, 1.01 mL, 1.01 mmol) was added to a solution of compound 2b (367 mg, 0.843 mmol) in THF (5 mL), under a nitrogen atmosphere. After 30 min, the reaction mixture was quenched with saturated aqueous NaHCO₃ (2 mL) and warmed to 0° C. 30% H₂O₂ (5 drops) was added and the mixture was stirred at 0° C. for 20 min. The organic volatiles were removed in vacuo, and the aqueous layer was extracted with CH₂Cl₂ (3×10 mL). The combined organic extracts were dried (MgSO₄), filtered and concentrated. To a cold (−78° C.) solution of the residue and triethylsilane (134 μL, 0.843 mmol) in CH₂Cl₂ (3 mL) boron trifluoride etherate (118 μL, 0.927 mmol) was added dropwise under an atmosphere of nitrogen. After 30 min, additional triethylsilane (134 μL) and boron trifluoride etherate (118 μL) were added. After stirring for 2 h at −78° C., the reaction mixture was quenched with saturated aqueous NaHCO₃ (2 mL) and extracted with DCM (3×10 mL). The combined organic extracts were dried (MgSO₄), filtered and concentrated. The crude product was purified by flash column chromatography (8:2 hexane:ethyl acetate) to give compound 2c as a colorless oil (140 mg, 40% yield). $^1$H NMR (CDCl₃) indicated the presence of two rotamers: δ 7.34–7.22 (m, 10H), 6.38 (d, J=15.5 Hz, 1H), 6.15–6.08 (m, 1H), 5.29–5.07 (m, 2H), 4.44 (d, J=7 Hz, 1/3H), 4.33 (d, J=7 Hz, 2/3H), 3.76 (dd, J=10.5, J'=8.5 Hz, 2/3H), 3.69 (dd, J=10.5, J'=8.5 Hz, 1/3H), 3.13 (dd, J=9, J'=8.5 Hz, 2/3H), 3.05 (dd, J=9, J'=8.5 Hz, 1/3H), 2.47–2.40 (m, 1H), 2.35–2.22 (m, 2H) 2.15–1.85 (m, 2H), 1.45 (s, (3/9) 9H), 1.33 (s, (6/9) 9H).

c) Synthesis of Compound 2d:

To a solution of compound 2c (140 mg, 0.332 mmol) in ethanol (4 mL) was added 10% palladium on charcoal (30 mg). The mixture was stirred under an atmosphere of hydrogen for 2 h. The catalyst was removed by passing the mixture through a Millipore: Millex-HV 0.45 μm filter. The clear solution was concentrated to give the desired compound 2d as a colorless oil (115 mg, quant. yield). $^1$H NMR (DMSO-$d_6$) indicated the presence of two rotamers: δ 7.28–7.14 (m, 5H), 4.33 (br, s, 1H), 4.06–4.10, (m, 1H), 3.56–3.42 (m, 3H), 2.89–2.79 (m, 1H),), 2.53–2.49 (m, 1H, under DMSO-$d_6$), 2.24–2.10 (m, 1H), 2.03–1.93 (m, 1H), 1.87–1.75 (m, 1H), 1.62–1.45 (m, 2H), 1.38 (s, (3/9) 9H), 1.33 (s, (6/9) 9H).

Example 3
Synthesis of Boc-4(R)-(naphthalen-1-ylmethoxy)proline (3):

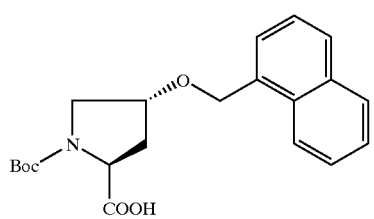

(3)

Commercially available Boc-4(R)-hydroxyproline (5.00 g, 21.6 mmol) was dissolved in THF (100 mL) and cooled to 0° C. Sodium hydride (60% dispersion in oil, 1.85 g, 45.4 mmol) was added portionwise over 10 minutes and the suspension was stirred at RT for 1 h. Then, 1-(bromomethyl) naphthalene (8.00 g, 36.2 mmol) (prepared as described in E. A. Dixon et al. Can. J. Chem., (1981), 59, 2629–2641) was added and the mixture was heated at reflux for 18 h. The mixture was poured into water (300 mL) and washed with hexane. The aqueous layer was acidified with 10% aqueous HCl and extracted twice with ethyl acetate. The organic layers were combined and washed with brine, dried (MgSO$_4$), filtered and concentrated. The residue was purified by flash chromatography (49:49:2 hexane:ethyl acetate:acetic acid) to give the title compound as a colorless oil (4.51 g, 56% yield). $^1$H NMR (DMSO-d$_6$) indicated the presence of two rotamers: δ 8.05 (m, 1H), 7.94 (m, 1H), 7.29 (d, J=14 Hz, 1H), 7.55–7.45 (m, 4H), 4.96 (m, 2H), 4.26 (br, s, 1H), 4.12 (dd, J=J=8 Hz, 1H), 3.54–3,42 (m, 2H), 2.45–234 (m, 1H), 2.07–1.98 (m, 1H) 1.36 (s, (3/9) 9H), 1.34 (s, (6/9) 9H).

Example 4A

Synthesis of Boc-4(R)(8-quinoline-methyloxy)proline (4A):

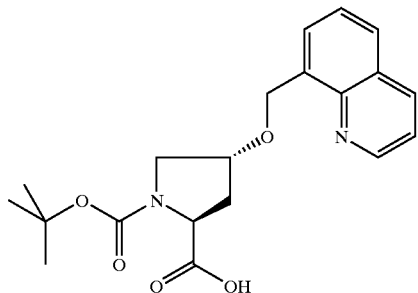

(4A)

Boc-4(R)-hydroxyproline (1.96 g, 8.5 mmol) in anhydrous THF (20 mL) was added to a suspension of NaH (1.4 g, 60% in oil, 34 mmol) in THF (100 mL). This mixture was stirred 30 min before bromomethyl-8-quinoline from Example 1a (2.54 g, 11.44 mmol) was added in THF (30 mL). The reaction mixture was heated at 70° C. (5 h) before the excess NaH was destroyed carefully with wet THF. The reaction was concentrated in vacuo and the resulting material was dissolved in EtOAc and H$_2$O. The basic aqueous phase was separated and acidified with 10% aqueous HCl to pH~5 before being extracted with EtOAc (150 mL). The organic phase was dried (MgSO$_4$), filtered and concentrated to give a brown oil. Purification by flash chromatography (eluent: 10% MeOH/CHCl$_3$) gave the desired compound as a pale yellow solid (2.73 g, 86%). HPLC (97.5%); $^1$H-NMR (DMSO-d$_6$) shows rotamer populations in a 6:4 ratio, δ 12–11.4 (bs, 1H), 8.92 (2×d, J=4.14 and 4.14 Hz, 1H), 8.38 (2×d, J=8.27 and 8.27 Hz, 1H), 7.91 (d, J=7.94 Hz, 1H), 7.77 (d, J=7.0 Hz, 1H), 7.63–7.54 (m, 2H), 5.14 (2×s, 2H), 4.32–4.29 (m, 1H), 4.14–4.07 (m, 1H), 3.52–3.44 (m, 2H), 2.43–2.27 (m, 1H), 2.13–2.04 (m, 1H), 1.36 and 1.34 (2×s, 9H).

Example 4B

Synthesis of Boc-4(R)-(2-phenyl-7-methoxyquinoline-4-oxo)proline (4B):

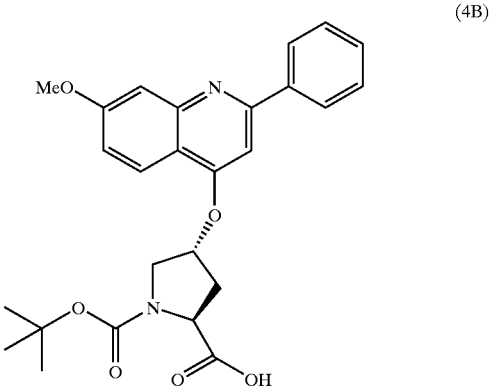

(4B)

Potassium tert-butoxide (8.16 g, 72.7 mmol) was added in small portions, over 15 min, to a solution of commercially available 4-(S)-hydroxyproline (6.73 g, 29.1 mmol) in DMSO (83 mL) maintained at 25° C. The mixture was stirred at 25° C. for 1.5 h. Chloro-2-phenyl-7-methoxyquinoline 1C (8.61 g, 32.0 mmol) was added in 4 portions over 15 min to the reaction mixture. The reaction mixture was stirred at 25° C. for 19 h. The resulting suspension was poured in H$_2$O (650 mL) and the mixture was washed with Et$_2$O (3×150 mL) to remove excess chloroquinoline (EtOAc was later found to be more efficient). The aqueous layer was acidified with aqueous 1 N HCl (38 mL of calculated 1.5 equiv. required, 43.6 mL) to pH 4–5. The white solid that precipitated was recovered by filtration. The moist solid was dried under reduced pressure over P$_2$O$_5$ to give the proline derivative 4B (12.6 g, 91%, contains 2.3% w/w of DMSO) as a beige solid:

$^1$H NMR (DMSO-d$_6$) δ (2:1 mixture of rotamers) 8.27 (d, J=7.0 Hz, 2H), 8.00, 7.98 (2d, J=9.2, ~9.2 Hz, 1H), 7.48–7.56 (m, 3H), 7.45, 7.43 (2s, 1H), 7.39 (d, J=2.5 Hz, 1H), 7.17 (dd, J=9.2, 2.5 Hz, 1H), 5.53–5.59 (m, 1H), 4.34–4.41 (m, 1H), 3.93 (s, 3H), 3.76 (broad s, 2H), 2.63–2.73 (m, 1H), 2.32–2.43 (m, 1H), 1.36, 1.33 (2s, 9H).

Example 5

Preparation of Boc-4(R(7-chloroquinoline4-oxo)proline (5):

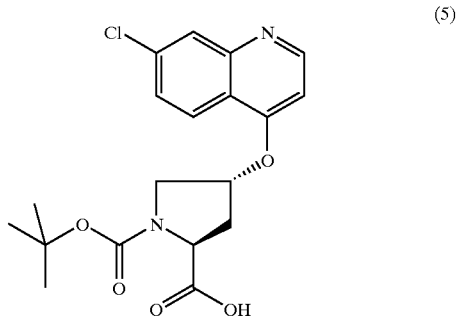

(5)

Commercially available Boc-4(S)-hydroxyproline methyl ester (500 mg, 2.04 mmol) and 7-chloro-4-hydroxyquinoline (440 mg, 2.45 mmol) were placed in dry THF (10 mL) at 0°

C. Triphenylphosphine (641 mg, 2.95 mmol) was added, followed by slow addition of DIAD (426 mg, 2.45 mmol). The mixture was stirred at RT for 20 h. The reaction mixture was then concentrated, taken up in ethyl acetate and extracted three times with HCl 1N. The aqueous phase was basified with Na$_2$CO$_3$ and extracted twice with ethyl acetate. The organic layers were combined, dried over MgSO$_4$, filtered and concentrated to give a yellow oil. The oil was purified by flash chromatography to give compound (5) methyl ester as a white solid, 498 mg, 58% yield.

This methyl ester (400 mg, 0.986 mmol) was hydrolyzed with 1M aqueous sodium hydroxide (1.7 mL, 1.7 mmol) in methanol (4 mL), at 0° C., for 3 h. The solution was concentrated to remove the methanol and neutralized with 1M aqueous HCl. The suspension was concentrated to dryness and taken up in methanol (20 mL), the salts were filtered off and the filtrate concentrated to give the desired compound (5) as a white solid, 387 mg, quant. yield.

$^1$H NMR (DMSO-d$_6$) (ca. 1:1 mixture of rotamers) δ 8.74 (d, J=5 Hz, 1H), 8.13–8.09 (m, 1H), 7.99 and 7.98 (s, 1H), 7.58 (d, J=9 Hz, 1H), 7.02 (d, J=5 Hz, 1H), 5.26–5.20 (m, 1H), 4.10–4.01 (m, 1H), 3.81–3.72 (m, 1H), 3.59 (dd, J=12, 10 Hz, 1H), 2.41–2.31 (m, 2H), 1.34 and 1.31 (s, 9H).

P1 BUILDING BLOCKS

Example 6

A) Synthesis of Mixture of (1R,2R)/(1S,2R) 1-amino-2-ethylcyclopropyl carboxylic acid

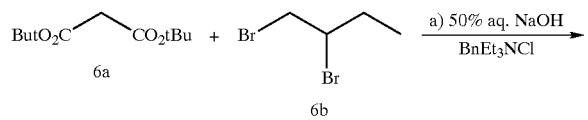
6a   6b   a) 50% aq. NaOH / BnEt$_3$NCl

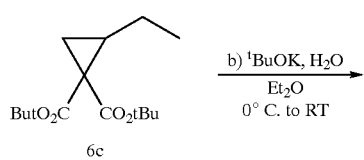
6c   b) $^t$BuOK, H$_2$O / Et$_2$O / 0° C. to RT

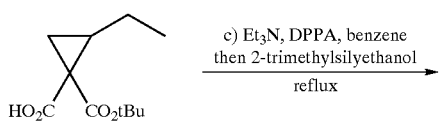
6d
ethyl syn to the ester
c) Et$_3$N, DPPA, benzene then 2-trimethylsilyethanol reflux

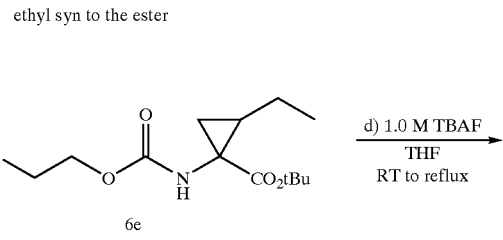
6e   d) 1.0 M TBAF / THF / RT to reflux

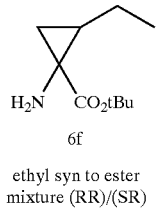
6f
ethyl syn to ester
mixture (RR)/(SR)

a) To a suspension of benzyltriethylammonium chloride (21.0 g, 92.19 mmol) in a 50% aqueous NaOH solution (92.4 g in 185 mL H$_2$O) were successively added di tert-butylmalonate (20.0 g, 92.47 mmol) and 1,2-dibromobutane (30.0 g, 138.93 mmol). The reaction mixture was vigorously stirred overnight at RT, a mixture of ice and water was then added. The crude product was extracted with CH$_2$Cl$_2$ (3×) and sequentially washed with water (3×) and brine. The organic layer was dried (MgSO$_4$), filtered and concentrated. The residue was flash chromatographed (7 cm, 2 to 4% Et$_2$O in hexane) to afford the desired cyclopropane derivative 5c (19.1 g, 70.7 mmol, 76% yield). $^1$H NMR (CDCl$_3$) δ 1.78–1.70 (m, 1H), 1.47 (s, 9H), 1.46 (s, 9H), 1.44–1.39 (m, 1H), 1.26–1.64 (m, 3H), 1.02 (t, 3H, J=7.6 Hz).

b) To a suspension of potassium tert-butoxide (6.71 g, 59.79 mmol, 4.4 eq.) in dry ether (100 mL) at 0° C. was added H$_2$O (270 µL, 15.00 mmol, 1.1 eq.). After 5 min diester 6c (3.675 g, 13.59 mmol) in ether (10 mL) was added to the suspension. The reaction mixture was stirred overnight at RT, then poured in a mixture of ice and water and washed with ether (3×). The aqueous layer was acidified with a 10% aq. citric acid solution at 0° C. and extracted with AcOEt (3×). The combined organic layer was successively washed with water (2×) and brine. After the usual treatment (Na$_2$SO$_4$, filtration, concentration), the desired acid 6d was isolated as a pale yellow oil (1.869, 8.68 mmol, 64% yield). $^1$H NMR (CDCl$_3$) δ 2.09–2.01 (m, 1H), 1.98 (dd, J=3.8, 9.2 Hz, 1H), 1.81–1.70 (m, 1H), 1.66 (dd, J=3.0, J=8.2 Hz, 1H), 1.63–1.56 (m, 1H), 1.51 (s, 9H), 1.0 (t, J=7.3 Hz, 3H).

c) To the acid 6d (2.017 g, 9.414 mmol) in dry benzene (32 mL) were successively added Et$_3$N (1.50 mL, 10.76 mmol, 1.14 eq.) and DPPA (2.20 mL, 10.21 mmol, 1.08 eq.). The reaction mixture was refluxed for 3.5 h then 2-trimethylsilylethanol (2.70 mL, 18.84 mmol, 2.0 eq.) was added. The reflux was maintained overnight then the reaction mixture was diluted with Et$_2$O and successively washed with a 10% aqueous citric acid solution, water, saturated aqueous NaHCO$_3$, water (2×) and brine. After the usual treatment (MgSO$_4$, filtration, concentration) the residue was purified by flash chromatography (5 cm, 10% AcOEt-hexane) to afford the desired carbamate 6e (2.60 g, 7.88 mmol, 84% yield) as a pale yellow oil. MS (FAB) 330 (MH$^+$); $^1$H NMR (CDCl$_3$) δ 5.1 (bs, 1H), 4.18–4.13 (m, 2H), 1.68–1.38 (m, 4H), 1.45 (s, 9H), 1.24–1.18 (m, 1H), 1.00–0.96 (m, 5H), 0.03 (s, 9H).

d) To carbamate 6e (258 mg, 0.783 mmol) was added a 1.0 M TBAF solution in THF (940 µL, 0.94 mmol, 1.2 eq.). After 4.5 h an additional amount of 1.0 M TBAF was added (626 µL, 0.63 mmol, 0.8 eq.). The reaction mixture was stirred overnight at RT, refluxed for 30 min and then diluted with AcOEt. The solution was successively washed with water (2×) and brine. After the usual treatment (MgSO$_4$, filtration and concentration) the desired amine 6f was isolated (84 mg, 0.453 mmol, 58% yield) as a pale yellow liquid. $^1$H NMR (CDCl$_3$) δ 1.96 (bs, 2H), 1.60–1.40 (m, 2H), 1.47 (s, 9H), 1.31–1.20 (m, 1H), 1.14 (dd, J=4.1, 7.3 Hz, 1H), 1.02 (dd, J=4.1, 9.2 Hz, 1H), 0.94 (t, J=7.3 Hz, 3H).

Example 7
Chemical Resolution of t-butyl-(1R,2R)/(1S,2R) 1-amino-2-ethylcyclopropyl carboxylate (From Example 6):

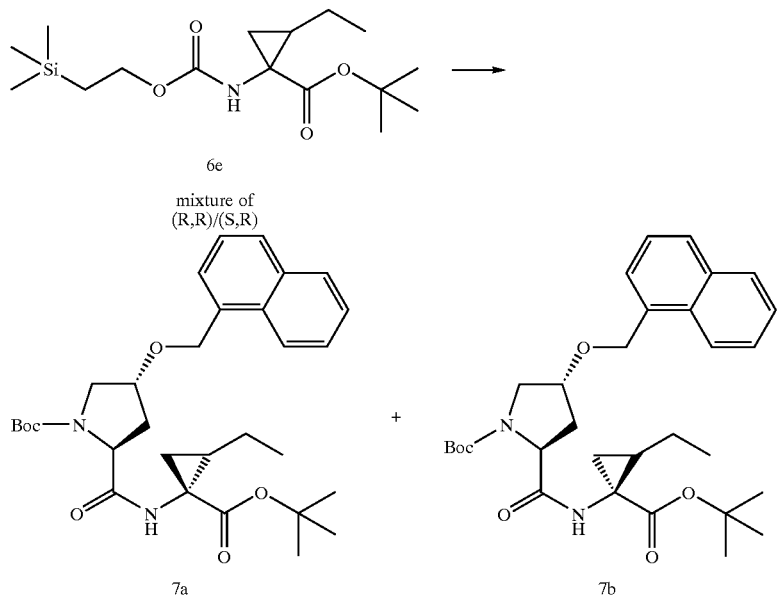

Isomers separated by column chromatography.

RR Isomer           SR Isomer

Compound 6e from Example 6 (8.50 g, 25.86 mmol) was treated with 1M TBAF/THF (26 mL) at reflux for 45 min. The cooled reaction mixture was diluted with EtOAc, washed with water (3×) and brine (1×), then, dried ($MgSO_4$), filtered and evaporated to provide the free amine as a light yellow oil. The free amine was dissolved in anhydrous $CH_2Cl_2$ (120 mL), NMM (8.5 mL, 77.57 mmol), compound 3 (Example 3) (10.08 g, 27.15 mmol) and HATU (11.79 g, 31.03 mmol) were added successively. The reaction mixture was stirred at RT overnight, then worked up as described previously. The crude diastereomeric mixture was separated by flash chromatography (eluent-hexane:$Et_2O$; 25:75) to provide the dipeptide 7a (the less polar eluting spot) as a white foam (4.42 g; 64% of the theoretical yield) and 7b (the more polar eluting spot) as an ivory foam (4 g., 57% of theoretical yield). At this time both isomers were separated but the absolute stereochemistry was still not known.

Example 6
Determination of the Absolute Stereochemistry of Compounds 7a and 7b by Correlation With Known t-butyl (1R-amino-2R-ethylcyclopropyl carboxylate

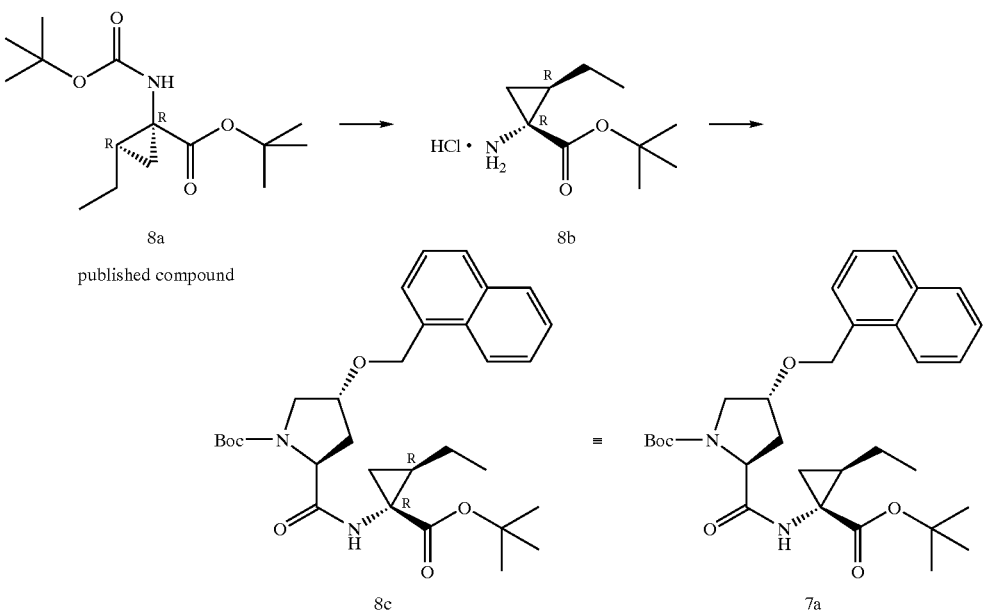

Direct comparison by TLC, HPLC and NMR

Prof. A. Charette, from the University of Montreal, provided compound 8a having the absolute stereochemistry as shown, which was determined by X-ray crystallography (J. Am. Chem. Soc., 1995, 117, 12721). Compound 8a (13.2 mg, 0.046 mmol) was dissolved in 1M HCl/EtOAc (240 μL) and stirred approximately 48 hours. The mixture was evaporated to dryness to provide compound 8b as a light yellow paste and was coupled to compound 3 (18 mg, 0.049 mmol) as described in Example 7, using NMM (20.3 μL, 0.185 mmol) and HATU (21.1 mg, 0.056 mmol) in $CH_2Cl_2$. The crude material was purified by flash chromatography (eluent-hexane:$Et_2O$; 50:50) to provide the dipeptide 8c as an oil (7.7 mg; 31%). By TLC, HPLC and NMR comparison, dipeptide 8c, was found to be identical to the less polar compound 7a obtained in Example 7, thus identifying the absolute stereochemistry of 7a as (1R,2R).

Example 9
Preparation of (1R,2R)/(1S,2R) 1-Boc-amino-2-ethylcyclopropylcarboxylic acid (9a):

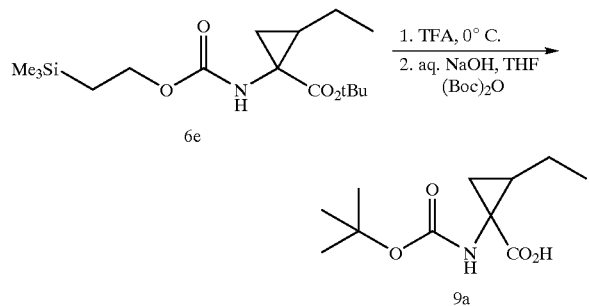

The carbamate 6e from Example 6 (2.6 g, 7.88 mmol) was stirred for 40 min in TFA at 0° C. The mixture was then concentrated and diluted with THF (10 mL). An aqueous NaOH solution (700 mg, 17.5 mmol in 8.8 mL of $H_2O$) was added followed by a THF (13 mL) solution of $(Boc)_2O$ (2.06 g, 9.44 mmol, 1.2 eq.). The reaction mixture was stirred overnight at RT(the pH was maintained at 8 by adding a 10% aqueous NaOH solution when needed), then diluted with $H_2O$, washed with $Et_2O$ (3×) and acidified at 0° C. with a 10% aq. citric acid solution. The aqueous layer was extracted with EtOAc (3×) and successively washed with $H_2O$ (2×) and brine. After the usual treatment ($MgSO_4$, filtration and concentration) the desired Boc-protected amino acid (9a) (788 mg, 3.44 mmol, 44% yield) was isolated. 1H NMR ($CDCl_3$) δ 5.18 (bs, 1H), 1.64–1.58 (m, 2H), 1.55–1.42 (m, 2H), 1.45 (s, 9H), 1.32–1.25 (m, 1H), 0.99 (t, 3H, J=7.3 Hz).

Preparation of (1R,2R)/(1S,2R)-1-Boc-amino-2-ethylcyclopropylcarboxylic acid methyl ester (9b):

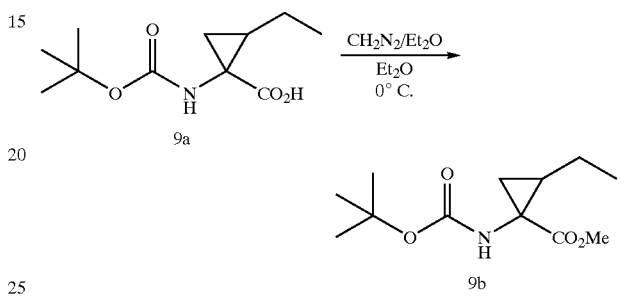

The Boc derivative 9a (0.30 g, 1.31 mmol) was dissolved in $Et_2O$ (10 mL) and treated with freshly prepared diazomethane in $Et_2O$ at 0° C. until the yellow color of a slight excess of diazomethane remained. After stirring for 20 min at RT the reaction mixture was concentrated to dryness to give 9b as a clear colorless oil (0.32 g, 100%). $^1$H NMR ($CDCl_3$) δ 5.1 (bs, 1H), 3.71 (s, 3H), 1.62–1.57 (m, 2H), 1.55 (s, 9H), 1.53–1.43 (m, 1H), 1.28–1.21 (m, 2H), 0.95 (t, J=7.3 Hz, 3H).

Example 10
Enzymatic Resolution of methyl (1R,2R)/(1S,2R) Boc-1-amino-2-ethylcyclopropyl carboxylate:

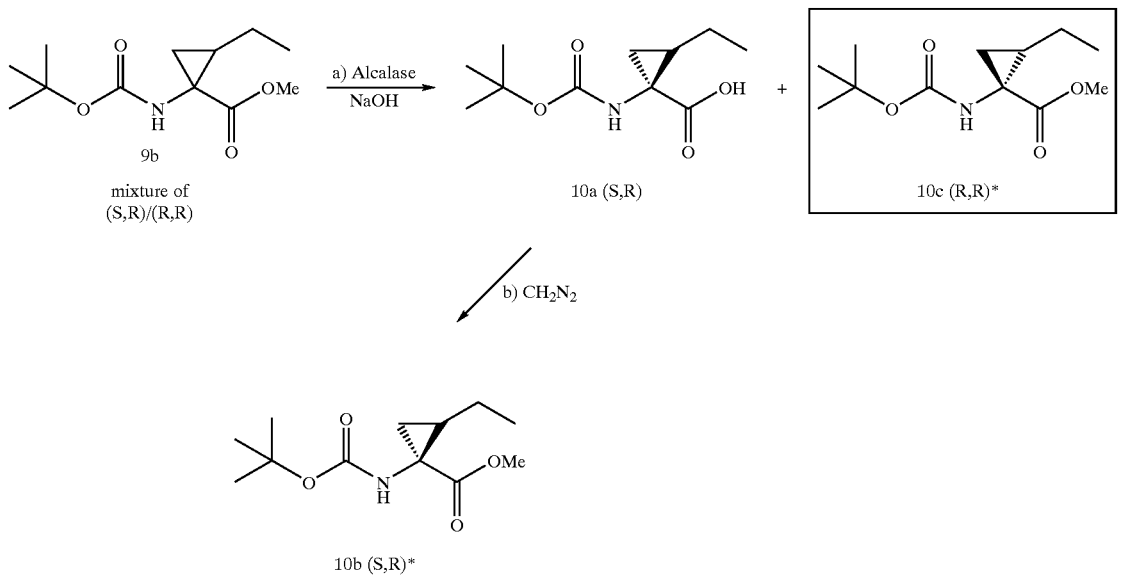

*Analysis by HPLC using Chiracle® OD-H column
**Other esters also acceptable (eg. Et)

a) The enantiomeric mixture of (1S,2R)/(1R,2R) 1-Boc-amino-2-ethylcarboxylic acid methyl ester of Example 9 (0.31 g, 1.27 mmol) was dissolved in acetone (3 mL) and then diluted with water (7 mL) while being rapidly stirred. The pH of the solution was adjusted to 7.5 with 0.05M aqueous NaOH before Alcalase® [2.4L extract from Novo Nordisk Industrials] (300 mg) was added. During incubation pH was stabilized with NaOH and a pH stat was set up to monitor the addition of the NaOH solution. After 40 h the mixture was diluted with EtOAc and $H_2O$ (with 5 mL sat. $NaHCO_3$) and the phases separated. The aqueous phase was acidified with 10% aqueous HCl and extracted with EtOAc, dried ($MgSO_4$), filtered and concentrated to give acid 9a (48.5 mg). The absolute stereochemistry was determined using the correlation described in Examples 7 and 8.

b) Treatment of an aliquot of acid 10a with diazomethane in $Et_2O$ to give the methyl ester followed by analysis by HPLC using a chiral column [Chiralcel® OD-H, 2.5% Isopropanol/hexane, isocratic] showed a 51:1 ratio of the (1S,2R) isomer.

a') The organic phase was dried ($MgSO_4$), filtered and concentrated to give the unhydrolyzed esters (0.248 g). This material was re-subjected to the above enzyme protocol until the pH remained stable (98 h). After extraction as before, 0.146 mg (100%) of unhydrolyzed ester was recovered. Analysis by HPLC using a chiral column showed a ratio of >50:1 in favor of the (1R,2R) isomer.

b') The aqueous phase was acidified with 10% aqueous HCl and extracted with EtOAc, dried ($MgSO_4$), filtered and concentrated to give the acid analog (82 mg). A portion of this material was treated with diazomethane and then analyzed by HPLC using a chiral column as before which showed a ratio of 65:1 of the (1S,2R) derivative.

Example 11

Synthesis of (1R,2)/(1S,2S) 1-amino-2-ethylcyclopropyl carboxylic acid:

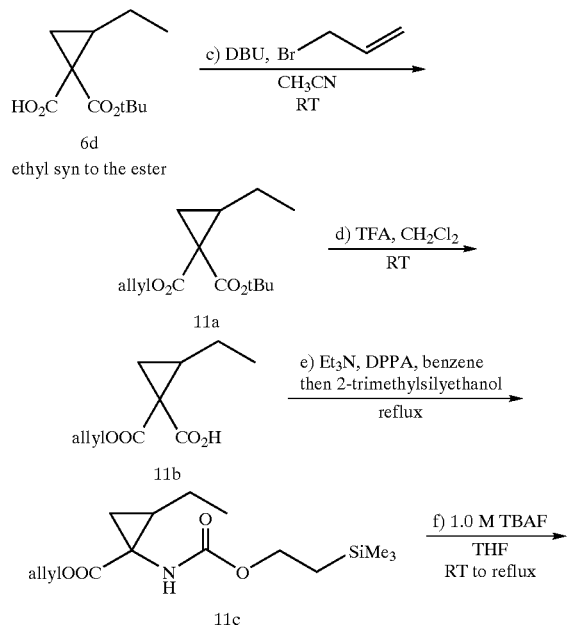

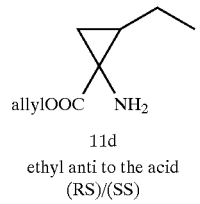

11d
ethyl anti to the acid
(RS)/(SS)

Starting from acid 6d described in Example 6:

c) To 6d (1.023 g, 4.77 mmol) in $CH_3CN$ (25 mL) were successively added DBU (860 µL, 5.75 mmol, 1.2 eq.) and allyl bromide (620 µL, 7.16 mmol, 1.5 eq.). The reaction mixture was stirred for 4 h at RT and then concentrated. The residue was diluted with $Et_2O$ and successively washed with a 10% aq. citric acid solution (2×), $H_2O$, saturated aqueous $NaHCO_3$, $H_2O$ (2×) and brine. After the usual treatment ($MgSO_4$, filtration and concentration) the desired ester 11a was isolated (1.106 g, 3.35 mmol, 91% yield) as a colorless oil. MS (FAB) 255 ($MH^+$); $^1H$ NMR ($CDCl_3$) δ 5.96–5.86 (m, 1H), 5.37–5.22 (m, 2H), 4.70–4.65 (m, 1H), 4.57–4.52 (m, 1H), 1.87–1.79 (m, 1H), 1.47 (s, 9H), 1.45–1.40 (m, 1H), 1.33–1.24 (m, 3H), 1.03 (t, J=7.3 Hz, 3H).

d) To ester 11a (1.106 g, 4.349 mmol) in dry $CH_2Cl_2$ (5 mL) at RT was added TFA (5 mL). The reaction mixture was stirred for 1.5 h and then concentrated to afford 11b (854 mg, 4.308 mmol, 99% yield). MS (FAB) 199 ($MH^+$); $^1H$ NMR ($CDCl_3$) δ 5.99–5.79 (m, 1H), 5.40–5.30 (m, 2H), 4.71–4.62 (m, 2H), 2.22–2.00 (m, 2H), 1.95–1.88 (m, 1H), 1.84–1.57 (m, 2H), 0.98 (t, J=7.3 Hz, 3H).

e) To acid 11b (853 mg, 4.30 mmol) in dry benzene (14.8 mL) were successively added $Et_3N$ (684 µL, 4.91 mmol, 1.14 eq.) and DPPA (992 µL, 4.60 mmol, 1.07 eq.). The reaction mixture was refluxed for 4.5 h then 2-trimethylsilylethanol (1.23 mL, 8.58 mmol, 2.0 eq.) was added. The reflux was maintained overnight then the reaction mixture was diluted with $Et_2O$ and successively washed with a 10% aqueous citric acid solution, water, saturated aq. $NaHCO_3$, water (2×) and brine. After the usual treatment ($MgSO_4$, filtration, concentration) the residue was flash chromatographed (5 cm, 10 to 15% AcOEt-hexane) to afford carbamate 11c (1.212 g, 3.866 mmol, 90% yield) as a pale yellow oil. MS (FAB) 314 ($MH^+$); $^1H$ NMR ($CDCl_3$) δ 5.93–5.84 (m, 1H), 5.32–5.20 (m, 2H), 5.05 (bs, 1H), 4.60–4.56 (m, 2H), 4.20–4.11 (m, 2H), 1.71–1.60 (m, 3H), 1.39–1.22 (m, 1H), 1.03 (t, J=7.6 Hz, 3H), 0.96–0.86 (m, 1H), 0.04 (s, 9H).

f) To carbamate 11c (267 mg, 0.810 mmol) was added a 1.0 M TBAF solution in THF (1.62 mL, 1.62 mmol, 2.0 eq.). The reaction mixture was stirred overnight at RT, refluxed for 30 min and then diluted with AcOEt. The solution was successively washed with water (2×) and brine. After the usual treatment ($MgSO_4$, filtration and concentration) the desired amine 11d was isolated (122 mg, 0.721 mmol, 89% yield) as a pale yellow liquid. $^1H$ NMR ($CDCl_3$) δ 5.94–5.86 (m, 1H), 5.31–5.22 (m, 2H), 4.58 (d, J=5.7 Hz, 2H), 1.75 (bs, 2H), 1.61–1.53 (m, 2H), 1.51–1.42 (m, 2H), 1.00 (t, J=7.3 Hz, 3H), 0.70–0.62 (m, 1H).

Example 12
Synthesis of ethyl-(1R,2S)/(1S,2S)-1-amino-2-vinylcyclopropyl carboxylate:

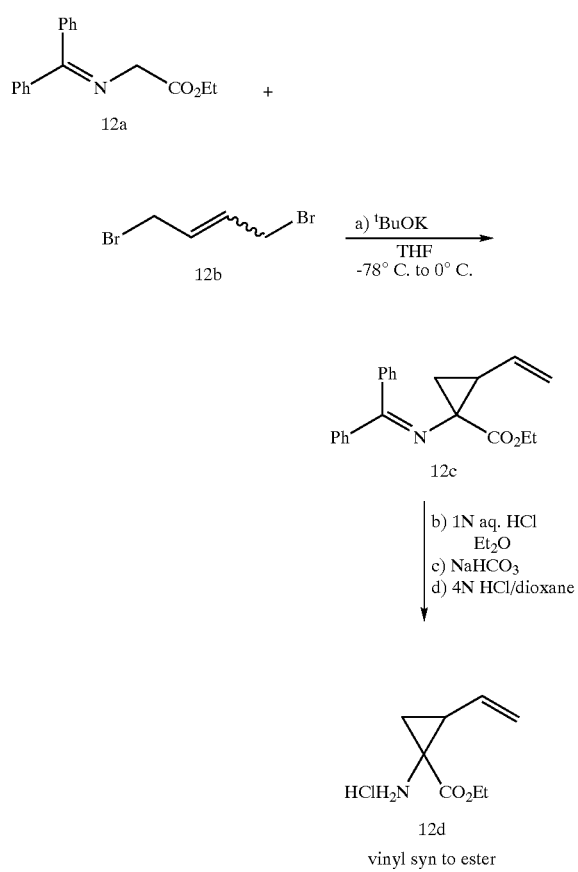

a) To a THF solution (180 mL) of potassium tert-butoxide (4.62 g, 41.17 mmol, 1.1 eq.) at −78° C. was added commercially available imine 12a (10.0 g, 37.41 mmol) in THF (45 mL). The reaction mixture was warmed to 0° C. and stirred at this temperature for 40 min. The mixture was then cooled back to −78° C. for the addition of 1,4-dibromobutene 12b (8.0 g, 37.40 mmol) and then stirred at 0° C. for 1 h and cooled back to −78° C. for the addition of potassium tert-butoxide (4.62 g, 41.17 mmol, 1.1 eq.). The reaction mixture was finally stirred one more hour at 0° C. and concentrated to yield compound 12c.

b, c, d) 12c was taken up in $Et_2O$ (265 mL) and treated with a 1 N aq. HCl solution (106 mL). After 3.5 h at RT, the layers were separated and the aqueous layer was washed with $Et_2O$ (2×) and basified with a saturated aq. $NaHCO_3$ solution. The desired amine was extracted with $Et_2O$ (3×) and the combined organic extract was washed with brine. After the usual treatment ($MgSO_4$, filtration and concentration) the residue was treated with a 4N HCl solution in dioxane (187 mL, 748 mmol). After concentration, hydrochloride salt 12d was isolated as a brown solid (2.467 g, 12.87 mmol, 34% yield). $^1H$ NMR ($CDCl_3$) δ 9.17 (bs, 3H), 5.75–5.66 (m, 1H), 5.39 (d, J=17.2 Hz, 1H), 5.21 (d, J=10.2 Hz, 1H), 4.35–4.21 (m, 2H), 2.77–2.70 (m, 1H), 2.05 (dd, J=6.4, 10.2 Hz, 1H), 1.75 (dd, J=6.4, 8.3 Hz, 1H), 1.33 (t, J=7.0 Hz, 3H).

Example 13
Preparation of (1R,2S/1S,2S)-1-Boc-amino-2-vinylcyclopropyl carboxylic acid ethyl ester:

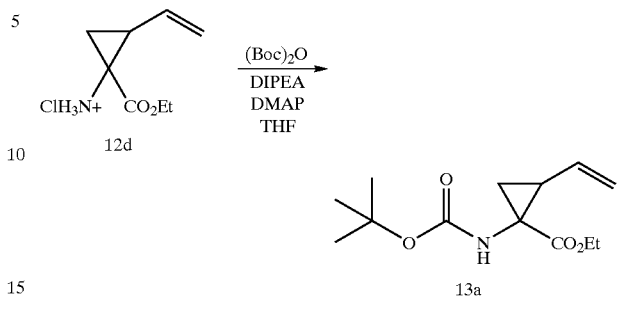

The hydrochloride salt 12d (1.0 g, 5.2 mmol) and $(Boc)_2O$ (1.2 g, 5.7 mmol) were dissolved in THF (30 mL) and treated with DMAP (0.13 g, 1.04 mmol, 0.2 equiv.) and diisopropylethylamine (2.8 mL, 15.6 mmol). The reaction mixture was stirred 24 h before being diluted with EtOAc (40 mL) and washed successively with sat. $NaHCO_3$ (aq). 5% aqueous HCl, and sat. brine. The organic phase was dried ($MgSO_4$), filtered and concentrated to give after purification by flash chromatography (15% EtOAc/hexane), 13a (0.29 g, 23%). $^1H$ NMR ($CDCl_3$) δ 5.80–5.72 (m, 1H), 5.29–5.25 (dd, J=17.2, 17.2 Hz, 1H), 5.24–5.1 (bs, 1H), 5.10 (dd, J=9.2, 9.2 Hz, 1H), 4.22–4.13 (m, 2H), 2.15–2.04 (m, 1H), 1.85–1.73 (bs, 1H), 1.55–1.5 (m, 1H), 1.49 (s, 9H), 1.26 (t, J=7.3 Hz, 3H).

Example 14
Enzymatic Resolution of ethyl (1R,2S)/(1S,2S) 1-amino-2-vinylcyclopropyl carboxylate:

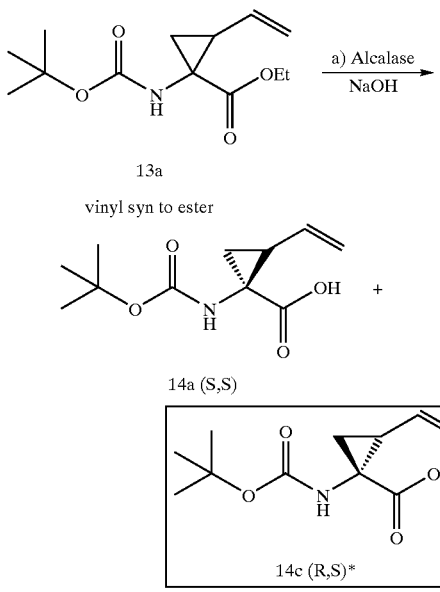

*Analysis by HPLC using Chiralce® OD-H column a) Racemic derivative 13a (0.29 g, 1.14 mmol) was dissolved in acetone (5 mL) and diluted with $H_2O$ (10 mL). The pH was adjusted with 0.2N aqueous NaOH to 7.2 before Alcalase® was added (300 mg). To keep the pH constant during incubation, a NaOH solution was added by a pH stat titrator over 9 days until the theoretical amount of base had been added. Following acid/base extraction as described in Example 10, the unhydrolyzed ester (0.15 g, 100%) and the hydrolyzed material (0.139 g, 95%) were isolated. Analysis of the unhydrolyzed ester by HPLC using a chiral column showed a ratio of 43:1 of the desired compound 14c that was assigned the (1R,2S) stereochemistry based on chemical correlation as described in Examples 7 and 8.

Following acid/base extraction as described in Example 10, the unhydrolyzed ester (0.15 g, 100%) and the hydrolyzed material (0.139 g, 95%) were isolated. Analysis of the unhydrolyzed ester by HPLC using a chiral column showed a ratio of 43:1 of the desired compound 14c. Compound 606 (wherein $R_1$ is vinyl, Table 6) was hydrogenated (10.8 mg, 0.015 mmol in 1 mL of EtOH with about 1 mL of 20% Pd(OH)$_2$ under 1 atm of H$_2$ for 45 min) to yield compound 214 (wherein $R_1$ is ethyl. Table 6). Compound 614 had been assigned the (1R,2R) stereochemistry based on chemical correlation as described in Examples 7 and 8 indicating that compound 606 ($R_1$=vinyl) has the same absolute configuration as represented by 14c (albeit 1R,2S because $R_1$=vinyl).

Conditions for HPLC analysis: Chiralcel® OD-H (4.6 mm×25 cm), isocratic conditions using a mobile phase of 2.5% isopropanol/hexane.

Example 15
Resolution of (1R,2S)/(1S,2S) 1-amino-2-vinylcyclopropyl carboxylate by Crystallization With dibenzoyl-D-tartaric acid

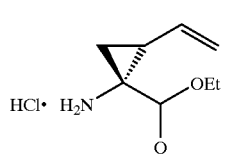

(15)

To a solution of crude racemic (1R,2S and 1S,2S) ethyl 1-amino-2-vinylcyclopropyl carboxylate [obtained from N-(diphenylmethylene)glycine ethyl ester (25.0 g, 93.5 mol) as described in Example 13] in EtOAc (800 mL) was added dibenzoyl-D-tartaric acid (33.5 g, 93.5 mol). The mixture was heated to reflux, left at RT for 15 min then cooled to 0° C. A white solid was obtained after 30 min. The solid was filtered, washed with EtOAc (100 mL) and air-dried. The solid was suspended in acetone (70 mL), sonicated and filtered (3×). The solid was next recrystallized twice in hot acetone (crop A). The mother liquors were concentrated and the residue was recrystallized three times in hot acetone (crop B). The two crops of the amorphous white solids of dibenzoyl-D-tartaric acid salt were combined (5.53 g) and suspended in a mixture of Et$_2$O (250 mL) and saturated NaHCO$_3$ solution (150 mL). The organic layer was washed with brine, dried (MgSO$_4$) and filtered. The filtrate was diluted with 1 N HCl/Et$_2$O (100 mL) and concentrated under reduced pressure. The oily residue was evaporated with CCl$_4$ to afford ethyl 1(R)-amino-2(S)-vinyl cyclopropanecarboxylate hydrochloride (940 mg, 11% yield) as a white hygroscopic solid for which absolute stereochemistry was assigned by correlation with compound 14c of Example 14.

$[\alpha]_D^{25}$+39.5° C. (c 1.14 MeOH); $[\alpha]_{365}^{25}$+88.5° C. (c 1.14 MeOH); $^1$H NMR (DMSO-d$_6$) δ 9.07 (broad s, 2H), 5.64 (ddd, J=17.2, 10.4, 8.7 Hz, 1H), 5.36 (dd, J=17.2, 1.6 Hz, 1H), 5.19 (dd, J=10.4, 1.6 Hz, 1H), 4.24–4.16 (m, 2H), 2.51–2.45 (m, peaks hindered by DMSO, 1H), 1.84 (dd, J=10.0, 6.0 Hz, 1H), 1.64 (dd, J=8.3, 6.0 Hz, 1H), 1.23 (t, J=7.1 Hz, 3H); MS (ESI) m/z 156 (MH)$^+$: the enantiomeric purity was determined to be 91% ee by HPLC analysis (CHIRALPAK AS® column, Hex:i-PrOH) of the Boc derivative. (Example 14)

P4-P2 BUILDING BLOCKS

Example 16

Synthesis of Segment: Ac-Chg-Chg-Pro (4(R)-naphthalen-1-ylmethoxy)-OH (16g)

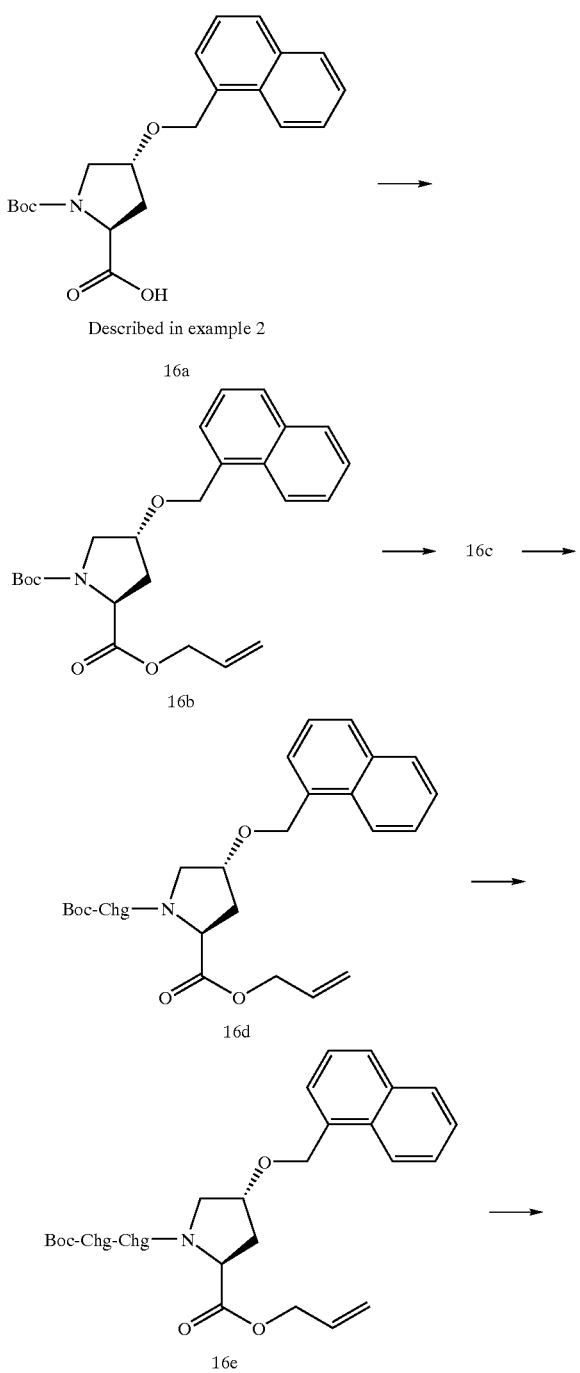

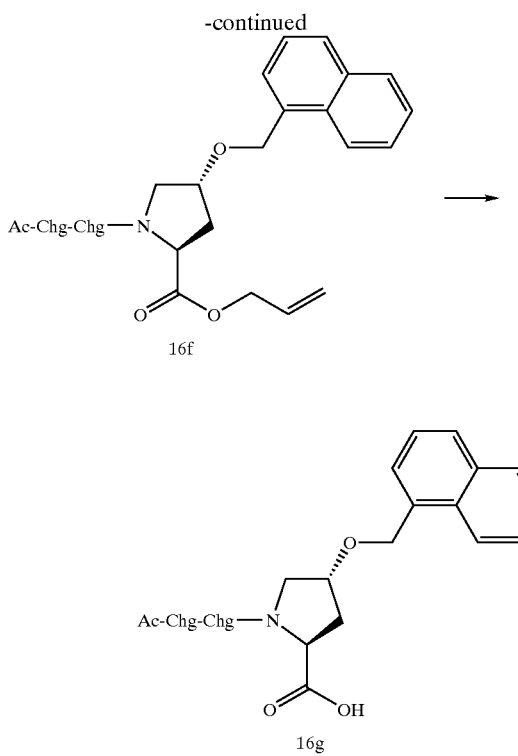

16f

16g

Compound 16a (same as compound 3 from Example 3)(4.45 g, 11.98 mmol) was dissolved in anhydrous $CH_3CN$ (60 mL), DBU (2.2 mL, 14.38 mmol) and allyl bromide (1.1 mL, 13.18 mmol) were added successively and the reaction mixture was stirred 24 h at RT. The mixture was concentrated, the resulting oil was diluted with EtOAc and water and successively washed with water (2×) and brine (1×). The EtOAc layer was dried ($MgSO_4$), filtered and evaporated to dryness. The yellow oil was purified by flash chromatography (eluent:hexane:EtOAc; 90:10 to 85:15) to provide the product 16b as a yellow oil (2, 4.17 g; 85% yield). MS (FAB) 412 $MH^+$ $^1H$ NMR ($CDCl_3$), mixture of rotamers ca.1:2, δ (d, J=8 Hz, 1H), 7.87 (d, J=8 Hz, 1H), 7.82 (d, J=8 Hz, 1H), 7.55–7.41 (m, 4H), 5.95–5.85 (m, 1H), 5.34–5.21 (m, 2H), 5.03–4.88 (m, 2H), 4.70–4.56 (m, 2H), 4.48 & 4.39 (t, J=8, 15 Hz, 1H), 4.28–4.23 (m, 1H), 3.81–3.55 (m, 2H), 2.46–2.36 (m, 1H), 2.13–2.05 (m, 1H), 1.44 & 1.41 (s, 9H).

Compound 16b (2.08 g, 5.05 mmol) was treated for 30 min at RT with 4N HCl/dioxane. Evaporation to dryness provided the corresponding amine-HCl as an oil. The amine-HCl 16c was dissolved in anhydrous DCM (25 mL) and NMM (2.2 mL, 20.22 mmol), Boc-Chg-OH.$H_2O$ (1.53 g, 5.56 mmol) and TBTU (1.95 g, 6.07 mmol) were added successively. The reaction mixture was stirred at RT overnight, then, diluted with EtOAc and successively washed with 10% aqueous citric acid (2×), saturated aqueous $NaHCO_3$ (2×), water (2×), and brine (1×). The EtOAc layer was dried ($MgSO_4$), filtered and evaporated to dryness to provide the crude product 16d as a yellowish-white foam (ca 2.78 g, 100% yield). MS (FAB) 551.4 $MH^+$. $^1H$ NMR ($CDCl_3$) δ 8.03 (d, J=8 Hz, 1H), 7.86 (bd, J=8.5 Hz, 1H), 7.84 (d, J=8 Hz, 1H), 7.56–7.40 (m, 4H), 5.92–5.85 (m, 1H), 5.31 (dd, J=1, 17 Hz, 1H), 5.22 (dd, J=1, 10 Hz, 1H), 5.17 (d, J=9 Hz, 1H), 5.05 (d, J=12 Hz, 1H), 4.91 (d, J=12 Hz, 1H), 4.67–4.60 (m, 3H), 4.31–4.27 (m, 2H), 4.16 (bd, J=11 Hz, 1H), 3.71 (dd, J=4, 11 Hz, 1H), 2.47–2.41 (m, 1H), 2.08–1.99 (m, 1H), 1.85–1.63 (m, 5H), 1.44–1.40 (m, 1H), 1.36 (s, 9H), 1.28–1.00 (m, 5H).

The crude dipeptide 16d (ca.5.05 mmol) was treated with 4N HCl/dioxane (25 mL) as described for the synthesis of compound 16c. The crude hydrochloride salt was coupled to Boc-Chg-OH.$H_2O$ (1.53 g, 5.55 mmol) with NMM (2.22 mL, 20.22 mmol) and TBTU (1.95 g, 6.07 mmol) in DCM (25 mL) as described for the synthesis of compound 16d to yield crude tripeptide 16e as a yellow-oil foam. The crude material was purified by flash chromatography (eluent:hexane:EtOAc; 80:20 to 75:25) to provide the tripeptide 16e as a white foam (2.75 g; 79% yield over 2 steps). MS (FAB) 690.5 $MH^+$. $^1H$ NMR ($CDCl_3$), mainly one rotamer, δ 8.06 (d, J=8 Hz, 1H), 7.87 (bd, J=8.5 Hz, 1H), 7.82 (d, J=8 Hz, 1H), 7.57–7.40 (m, 4H), 6.41 (d, J=8.5 Hz, 1H), 5.92–5.84 (m, 1H), 5.31 (dd, J=1, 17 Hz, 1H), 5.23 (dd, J=t, 10.5 Hz, 1H), 5.04 (d, J=12 Hz, 1H), 4.98 (bd, J=7 Hz, 1H), 4.93 (d, J=(2 Hz, 1H), 4.63–4.58 (m, 4H), 4.29–4.25 (m, 1H), 4.10–4.07 (m, 1H), 3.90–3.84 (m, 1H), 3.72 (dd, J=4, 11 Hz, 1H), 2.48–2.40 (m, 1H), 2.07–1.99 (m, 1H), 1.83–1.55 (m, 12H), 1.43 (s, 9H). 1.23–0.89 (m, 10H).

The tripeptide 16e (2.75 g, 3.99 mmol) was treated with 4N HCl/dioxane (20 mL) as described for the synthesis of compound 16c. The crude hydrochloride salt was dissolved in anhydrous DCM (20 mL). NMM (1.75 mL, 15.94 mmol) and acetic anhydride (752 μl, 7.97 mmol) were added successively. The reaction mixture was stirred overnight at RT, then diluted with EtOAc. The organic layer was washed successively with 10% aqueous citric acid (2×), saturated aqueous $NaHCO_3$ (2×), water (2×) and brine (1×), dried ($MgSO_4$), filtered, and evaporated to dryness to provide the crude tripeptide 16f as a white foam (2.48 g, 98% yield).

MS (FAB) 632.4 $MH^{+1}$. $^1H$ NMR ($CDCl_3$), mainly one rotamer, δ 8.06 (bd, J=8 Hz, 1H), 7.87 (bd, J=8 Hz, 1H), 7.83 (d, J=8 Hz, 1H), 7.58–7.40 (m, 4H), 6.36 (d, J=9 Hz, 1H), 6.01 (d, J=9 Hz, 1H), 5.94–5.83 (m, 1H), 5.34–5.28 (m, 1H), 5.25–5.21 (m, 1H), 5.05 (d, J=12 Hz, 1H), 4.94 (d, J=12 Hz, 1H), 4.64–4.57 (m, 4H), 4.30–4.23 (m, 2H), 4.12–4.08 (m, 1H), 3.73 (dd, J=4, 11 Hz, 1H), 2.49–2.42(m, 1H), 2.08–2.01 (m, 1H), 1.99 (s, 3H), 1.85–1.53 (m, 11H), 1.25–0.88 (m, 11H).

The crude tripeptide 16f (2.48 g, 3.93 mmol)was dissolved in an anhydrous mixture of $CH_3CN$: DCM (20 mL). Triphenylphosphine (53.5 mg, 0.200 mmol) and tetrakis (triphenylphosphine)-palladium (0) catalyst (117.9 mg, 0.102 mmol) were added successively, followed by pyrrolidine (353.9 μL, 4.24 mmol). The reaction mixture was stirred at RT for 18 h. Thereafter, the solvent was evaporated. The residue was dissolved in EtOAc and 10% aqueous citric acid, then, further washed twice more with 10%, aqueous citric acid, water (2×), and brine (1×). The organic layer was dried ($MgSO_4$), filtered and evaporated. The crude product was triturated in $Et_2O$: DCM (85:15) to provide after filtration the tripeptide 16g as a white solid (2.099, 90% yield). MS (FAB) 592.4 $MH^+$ 614.3 $(M+Na)^+$. $^1H$ NMR ($CDCl_3$), mainly one rotamer, δ 8.08 (d, J=8 Hz, 1H), 7.93 (bd, J=9 Hz, 1H), 7.88 (bd, J=8 Hz, 1H), 7.82 (d, J=8 Hz, 1H), 7.57–7.41 (m, 4H), 6.47 (d, J=8.5 Hz, 1H), 5.05 (d, J=12.5 Hz, 1H), 4.94 (d, J=12.5 Hz, 1H), 4.73 (t, J=9.5, 19 Hz, 1H), 4.44–4.35 (m, 2H), 4.26 (bs, 1H), 4.19 (d, J=11.5 Hz, 1H), 3.75 (dd, J=4, 11 Hz, 1H), 2.47 (bdd, J=7.5, 13.5 Hz, 1H), 2.20–2.11 (m, 1H), 2.04 (s, 3H), 1.88–1.41 (m, 11H), 1.30–0.80 (11H).

Example 17

Synthesis of Segment Ac-Chg-Val-Pro(4(R)-naphthalen-1-ylmethoxy)-OH (17e)

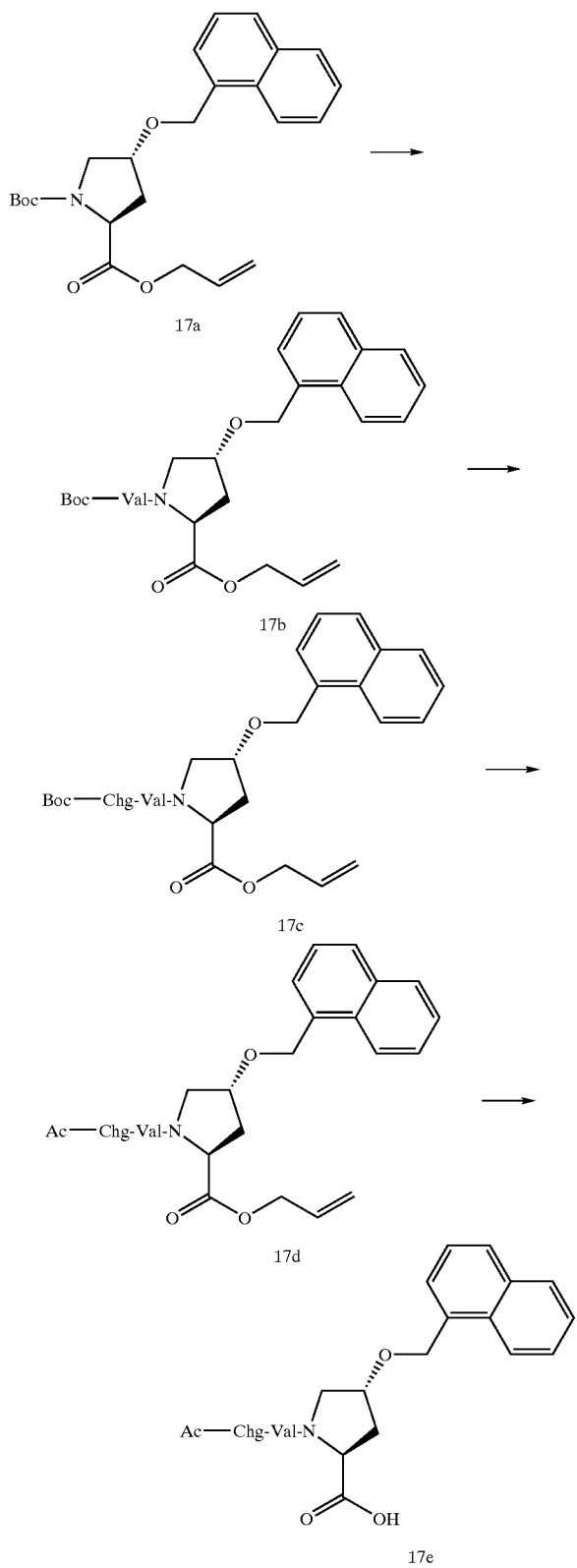

Compound 17a (2.89 g, 7.02 mmol) was treated with 4N HCl/dioxane (30 mL) as described for the synthesis of compound 16c. The crude hydrochloride salt was coupled to Boc-Val-OH (1.53 g, 7.73 mmol) with NMM (3.1 mL, 28.09 mmol) and TBTU (2.71 g, 8.43 mmol) in DCM (35 mL) for 3½ h as described for the synthesis of compound 16d to provide the crude dipeptide 17b as an ivory oil-foam (ca.3.60 g, 100% yield). MS (FAB) 509.3 MH⁻ 511.3 MH⁺ 533.2 (M+Na)⁺. ¹H NMR (CDCl₃) δ 8.04 (bd, J=8 Hz, 1H), 7.87 (bd, J=7 Hz, 1H), 7.82 (d, J=8 Hz, 1H), 7.56–7.40 (m, 4H), 5.93–5.85 (m, 1H), 5.34–5.28 (m, 1H), 5.24–5.19 (m, 2H), 5.04 (d, J=12 Hz, 1H), 4.92 (d, J=12 Hz, 1H), 4.67–4.60 (m, 3H), 4.31–4.26 (m, 2H), 4.11–4.09 (m, 1H), 3.72 (dd, J=4, 11 Hz, 1H), 2.48–2.41 (m, 1H), 2.07–1.99 (m, 1H), 1.44–1.36 (m, 1H), 1.37 (s, 9H), 1.01 (d, J=7 Hz, 3H), 0.93 (d, J=7 Hz, 3H).

The crude dipeptide 17b (ca.7.02 mmol) was treated with 4N HCl/dioxane (30 mL) as described for the synthesis of compound 16c. The crude hydrochloride salt was coupled to Boc-Chg-OH.H₂O (2.13 g, 7.73 mmol) with NMM (3.1 mL, 28.09 mmol) and TBTU (2.71 g, 8.43 mmol) in CH₂Cl₂ (35 mL) as described for the synthesis of compound 16d to provide the crude tripeptide 17c as an ivory foam (ca.4.6 g, 100% yield). MS (FAB) 648.5 MH⁻ 672.4 (M+Na)⁺. ¹H NMR (CDCl₃) δ 8.06 (bd, J=8 Hz, 1H), 7.87 (bd, J=7.5 Hz, 1H), 7.82 (bd, J=8 Hz, 1H), 7.57–7.40 (m, 4H), 6.46 (bd, J=8.5 Hz, 1H), 5.94–5.84 (m, 1H), 5.31 (dd, J=1, 17 Hz, 1H), 5.23 (dd, J=1, 10.5 Hz, 1H), 5.03 (d, J=12 Hz, 1H), 5.00–4.97 (m, 1H), 4.93 (d, J=, 12 Hz, 1H), 4.63–4.59 (m, 4H), 4.29–4.27 (m, 1H), 4.10–4.07 (m, 1H), 3.92–3.86 (m, 1H), 3.72 (dd, J=5, 11 Hz, 1H), 2.48–2.41 (m, 1H), 2.10–1.99 (m, 1H), 1.76–1.57 (m, 6H), 1.43 (s, 9H), 1.20–0.92 (m, 6H), 1.00 (d, J=7 Hz, 3H), 0.93 (d, J=7 Hz, 3H).

The crude tripeptide 17c (ca.7.02 mmol) was treated with 4N HCl/dioxane (30 mL) as described for the synthesis of compound 16c. The crude hydrochloride salt was further treated with acetic anhydride (1.33 mL, 14.05 mmol) and NMM (3.1 mL, 28.09 mmol) in CH₂Cl₂ (35 mL) as described for the synthesis of compound 16d. The crude product was flash purified (eluent:hexane:EtOAc; 30:70) to provide the acetylated protected tripeptide 17d as a white foam (3.39 g, 81% yield over 3 steps).

MS (FAB) 590.3 MH⁻ 592.4 MH⁺ 614.4 (M+Na)⁺; ¹H NMR (CDCl₃), mainly one rotamer, δ 8.06 (d, J=8 Hz, 1H), 7.88 (bd, J=8 Hz, 1H), 7.83 (d, J=8 Hz, 1H), 7.58–7.41 (m, 4H), 6.37 (d, J=9 Hz, 1H), 5.97 (d, J=8.5 Hz, 1H), 5.94–5.84 (m, 1H), 5.31 (dd, J=1, 17 Hz, 1H), 5.24 (dd, J=1, 10.5 Hz, 1H), 5.05 (d, J=12 Hz, 1H), 4.94 (d, J=12 Hz, 1H), 4.66–4.57 (m, 4H), 4.31–4.22 (m, 2H), 4.11–4.05 (m, 1H), 3.73 (dd, J=4.5, 11 Hz, 1H), 2.50–2.43 (m, 1H), 2.09–2.01 (m, 2H), 2.00 (s, 3H), 1.68–1.55 (m, 5H), 1.15–0.89 (m, 6H), 0.99 (d, J=7 Hz, 3H), 0.91 (d, J=7 Hz, 3H).

The acetylated tripeptide 17d (3.39 g, 5.73 mmol) was deprotected by tetrakis(triphenylphosphine)-palladium (0) catalyst (172.1 mg, 0.149 mmol) with triphenylphosphine (78.1 mg, 0.298 mmol) and pyrrolidine (516 μL, 6.19 mmol) in a 1:1 mixture of anhydrous CH₃CN: DCM (30 mL) as described for the synthesis of compound 16g. The crude light yellow foam product was triturated in Et₂O: DCM (85:15) to provide after filtration the tripeptide 17e as an off-white solid (3.0 g: 95% yield). MS (FAB) 550.3 MH⁻.

¹H NMR (CDCl₃) δ 8.08 (d, J=8 Hz, 1H), 8.04 (bd, J=9 Hz, 1H), 7.88 (bd, J=7.5 Hz, 1H), 7.82 (d, J=8 Hz, 1H), 7.58–7.37 (m, 5H), 5.05 (d, J=12 Hz, 1H), 4.94 (d, J=12 Hz, 1H), 4.61 (t, J=9.5, 19.5 Hz, 1H), 4.46–4.37 (m, 2H), 4.27 (bs, 1H), 4.17 (d, J=11 Hz, 1H), 3.74 (dd, J=4, 11 Hz, 1H), 2.49 (bdd, J=7.5, 13 Hz, 1H), 2.17–2.09 (m, 1H), 2.04 (s, 3H), 2.03–1.94 (m, 1H), 1.79 (bd, J=12.5 Hz, 1H), 1.62–1.43 (m, 5H), 1.08–0.85 (m, 5H), 1.00 (d, J=7 Hz, 3H), 0.90 (d, J=7 Hz, 3H).

COMPOUNDS OF TABLES 1 TO 10

Example 18
Synthesis of Polymer-bound Compound #246 of Table 2

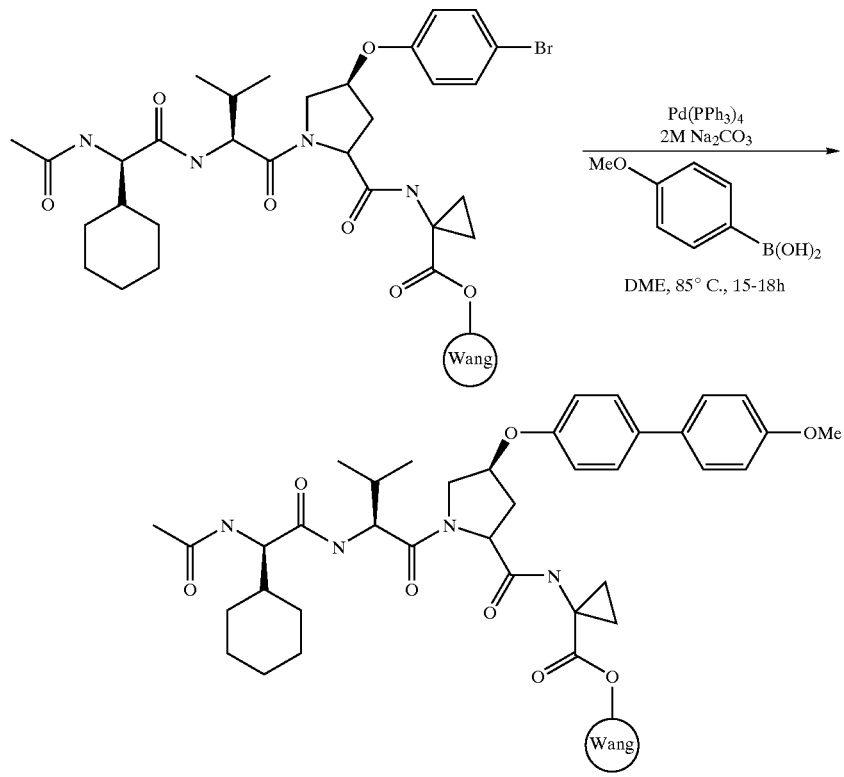

The precursor, aromatic bromide compound 238 of Table 2, was first synthesized from the polymer-bound tetrapeptide having a cis-hydroxyproline at the P2 position and 4-bromophenol using the Mitsunobu protocol described in Example A The synthesis of compound 246 was done according to the application of a biaryl synthesis via Suzuki coupling on a solid support (cf. R. Frenette and R. W. Friesen, Tetrahedron Lett. (1994), 35, 9177) (Example B).

Compound 246:

ES-MS m/z 675.3 [(M–H)–]: ~95% pure by C18 reversed phase HPLC; Mixture of two rotamers in a ratio of ~1:3 based on $^1$H NMR.

$^1$H NMR of major rotamer (400 MHz, DMSO): δ 8.44 (s, 1H), 7.84 (d, J=8.6 Hz, 1H), 7.82 (d, J=~8.6 Hz, 1H), 7.54 (bd, J=8.3 Hz, 4H), 6.99 (d, J=8.9 Hz, 2H), 6.98 (d, J=8.9 Hz, 2H), 5.11 (bs, 1H), 4.29–4.34 (m, 2H), 4.21 (bt, J=7.8 Hz, 1H), 3.94–4.02 (m, 2H), 3.78 (s, 3H), 2.29–2.33 (m, 2H), 2.15–2.21 (m, 1H), 1.95–1.99 (m, 1H), 1.83 (s, 3H), 1.45–1.70 (m, 8H), 1.33–1.40 (m, 1H), 1.20–1.28 (m, 1H), 1.02–1.18 (m, 2H), ~0.9–1.02 (m, 2H), 0.90 (d, J=6.7 Hz, 3H) 0.84 (d, J=6.7 Hz, 3H).

Example 19
Synthesis of Compound 210 (Table 2)

Using the experimental protocol described in Example 16 and starting with Fmoc-Cys(Trityl)-Wang resin, the above compound was obtained as a white solid (15.7 mg). MS (FAB) 849.2 (MH$^+$), $^1$H NMR (DMSO-d$_6$) δ 12.8 (broad s, 1H), 12.1 (broad s, 2H), 8.27 (d, J=8 Hz, 1H), 8.17 (d, J=7.5 Hz, 1H), 8.07 (d, J=8 Hz, 1H), 8.00 (d, J=8.4 Hz, 1H), 7.75 (d, J=8.9 Hz, 1H), 7.34–7.27 (m, 5H), 4.54–4.39 (m, 5H), 4.31–4.18 (m, 4H), 4.10 (d, J=11 Hz, 1H), 3.68 (dd, J=3.9 Hz, J'=10.8 Hz, 1H), 2.90–2.82 (m, 1H), 2.78–2.70 (m, 1H), 2.67–2.42 (m, 4H), 2.21–2.17 (m, 3H), 2.00–1.85 (m, 3H), 1.83 (s, 3H), 1.80–1.67 (m, 1H), 1.67–1.42 (m, 6H), 1.15–0.95 (m, 4H), 0.88 (dd, J=6.9 Hz, J'=8.9 Hz, 6H).

Example 20
Synthesis of Compound 215 (Table 2)
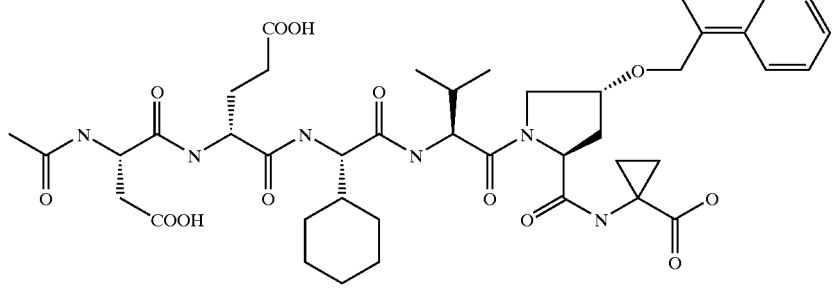
The synthesis was carried out as shown below:
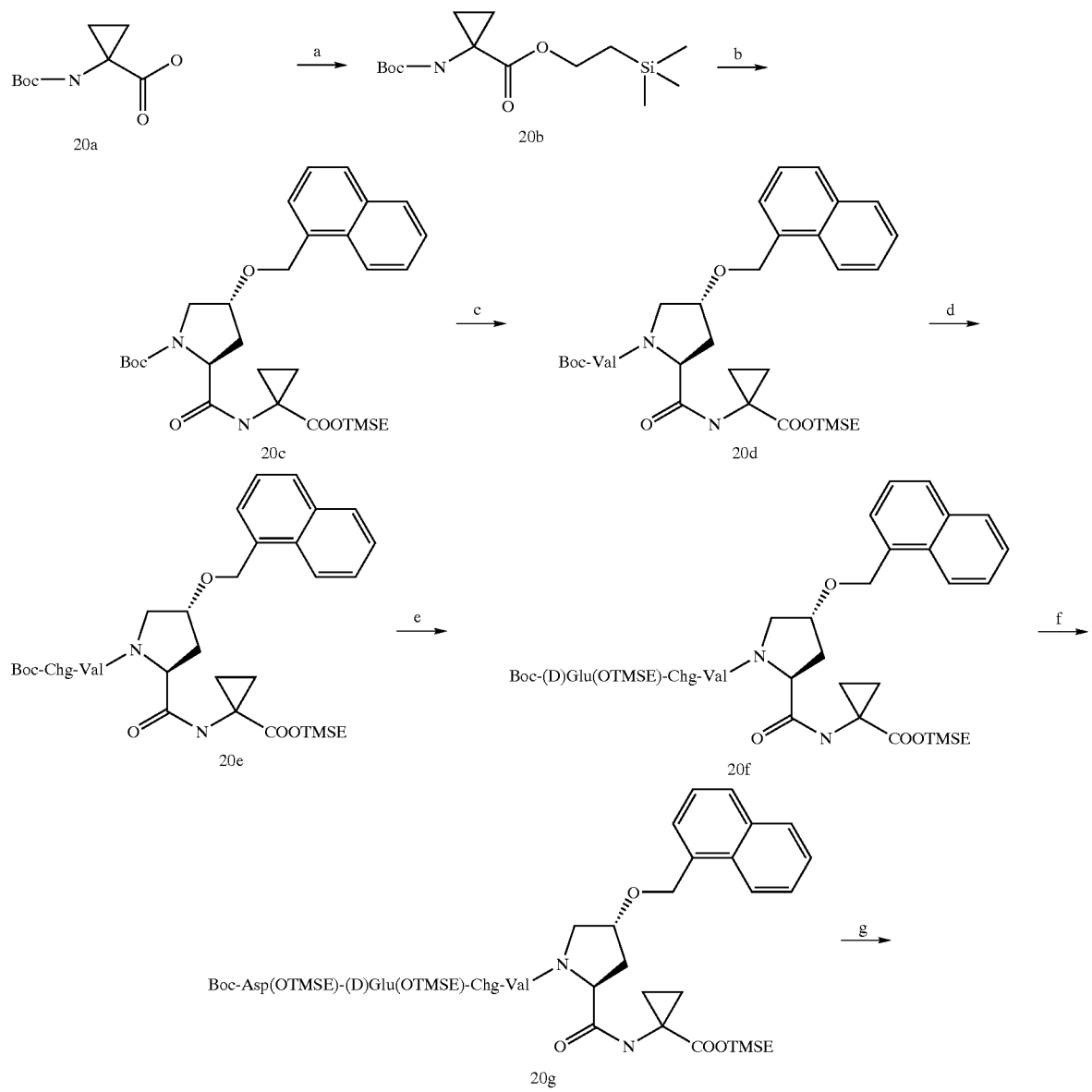

-continued

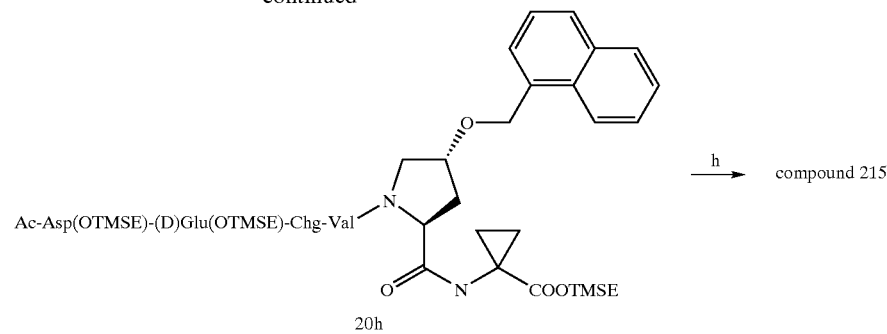

20h a) Synthesis of Compound 20b:

1-(N-t-Boc-amino)cyclopropanecarboxylic acid (20a) (997 mg, 4.96 mmol) was dissolved in a mixture of anhydrous $CH_2Cl_2$ (25 mL) and THF (10 mL). The solution was cooled to 0° C. 2-trimethylsilylethanol (0.852 mL, 5.95 mmol), DMAP (121.1 mg, 0.991 mmol) and a $DCC/CH_2Cl_2$ solution (3.65 M: 1.63 mL, 5.95 mmol) were added successively. The reaction mixture was stirred at 0° C. for ca.4 h then at RT overnight. The white suspension was filtered through a diatomaceous earth pad. The pad was and rinsed with $CH_2Cl_2$. Filtrate and washing were evaporated to dryness. The residue was diluted with EtOAc and sequentially washed with 10% aqueous citric acid (2×), saturated $NaHCO_3$ (2×), water (2×) and brine (1×). The organic layer was dried ($MgSO_4$), filtered, and evaporated to provide ester 20b as an oil (ca.1.5 g, 100%). $^1H$ NMR ($CDCl_3$) δ 5.08 (s, 1H), 4.20–4.16 (m, 2H), 1.57–1.43 (m, 2H), 1.45 (s, 9H), 1.17–1.12 (m, 2H), 1.00–0.94 (m, 2H), 0.04 (s, 9H).

b) Synthesis of Compound 20c:

Ester 20b (ca.700 mg, 2.33 mmol) was treated for 40 min at RT with 4N HCl/dioxane (11 mL). The solution was concentrated to dryness to provide the amine hydrochloride as a white solid which was then subjected to the reaction conditions described in Example A. The crude hydrochloride salt (950 mg, 2.55 mmol) and Boc-4(R)(naphthalen-1-ylmethoxy)proline (3) were dissolved in anhydrous $CH_2Cl_2$. NMM (1.02 mL, 9.30 mmol) and HATU (1.06 g, 2.79 mmol) were added successively and the mixture was stirred at RT. After 1.75 h, the reaction mixture was diluted with EtOAc and washed sequentially with 10% aq. citric acid (2×), saturated aq. $NaHCO_3$ (2×), water (2×), and brine(1×). The EtOAc layer was dried ($MgSO_4$), filtered and concentrated to dryness to provide the crude dipeptide 20c as an off-white foam (1.22 g) MS (FAB) 555.4 ($MH^+$). $^1H$ NMR ($CDCl_3$); mixture of rotamers, δ 8.06–8.04 (m, 1H), 7.87–7.80 (m, 2H), 7.55–7.41 (m, 5H), 4.99–4.93 (m, 2H), 4.45–4.21 (m, 2H), 4.16–4.11 (m, 2H), 3.97–3.45 (m, 2H), 2.70–1.80 (m, 2H), 1.73–1.40 (m, 2H), 1.53 (s, (6/9) 9H), 1.44 (s, (3/9) 9H), 1.20–1.05 (m, 2H), 0.97–0.93 (m, 2H), 0.02 (s, 9H).

c) Synthesis of Compound 20d:

The crude dipeptide 20d (ca. 2.20 mmol) was treated with 4N HCl/dioxane (11 mL) 40 min, RT and the resulting hydrochloride salt was coupled to Boc-Val-OH (525 mg, 2.42 mmol) with NMM (968 mL, 8.80 mmol) and HATU (1.00 g, 2.64 mmol) as described for compound 20c (with the modification of 2.5 h coupling time). The crude tripeptide 20d was obtained as an off-white foam (1.5 g). MS (FAB) 654.4 ($MH^+$). $^1H$ NMR ($CDCl_3$) δ 8.05–8.02 (m, 1H), 7.87–7.80 (m, 2H), 7.55–7.40 (m, 5H), 7.30–7.28 (m, 1H), 5.19–4.62 (m, 4H), 4.41–3.70 (m, 1H), 4.35–4.27 (m, 1H), 4.09–3.95 (m 1H) 3.73–3.62 (m, 2H), 2.69–2.60 (m, 1H), 2.14–1.94 (m, 2H), 1.55–1.38 (m, 2H), 1,39 (s, 9H), 1.22–1.18 (m, 1H), 1.11–1.07 (m, 1H), 0.98–0.90 (m, 8H), 0.02 (s, 9H).

d) Synthesis of Compound 20e:

The crude tripeptide 20d (ca. 2.20 mmol) was treated with 4N HCl/dioxane (11 mL) 40 min, RT and the resulting hydrochloride salt was coupled to Boc-Chg-OH (622 mg, 2.42 mmol) with NMM (968 mL, 8.80 mmol) and TBTU (847 mg, 2.64 mmol) as described for compound 20c (with the modifications of using TBTU as a coupling agent and stirring at RT for ca. 64 h prior to work-up). The foam-like residue was purified by flash chromatography (eluent:hexane:EtOAc; 6:4) to provide the tetrapeptide 20e as a white foam (710.8 mg; 41% yield over 3 steps). MS (FAB) 793.4 ($MH^+$). $^1H$ NMR ($CDCl_3$) δ 8.07–8.05 (m, 1H), 7.87–7.80 (m, 2H), 7.57–7.41 (m, 4H), 7.35 (s, 1H), 6.72–6.64 (m, 1H), 5.02–4.95 (m, 3H), 4.68–4.62 (m, 2H), 4.43–4.40 (m, 1H), 4.15–4.00 (m, 2H), 3.96–3.93 (m, 2H), 3.68 (dd, J=11, J'=5 Hz, 1H), 2.62–2.56 (m, 1H), 2.16–2.00 (m, 2H), 1.70–1.54 (m, 6H), 1.49–1.42 (m, 2H), 1.43 (s, 9H), 1.14–1.02 (m, 5H), 0.95–0.88 (m, 10H), 0.02 (s, 9H).

e) Synthesis of Compound 20f:

Tetrapeptide 20e (168.1 mg, 0.212 mmol) was treated with 4N HCl/dioxane solution (2 mL) and the resulting hydrochloride salt was coupled to Boc-(D)Glu(OTMSE)-OH (81.0 mg, 0.233 mmol) with NMM (94 mL, 0.848 mmol) and TBTU (81.7 mg, 0.254 mmol) as described for compound 20e (with the modification of 17 h coupling time). The crude pentapeptide 20f was obtained as an off-white foam (220 mg, 0.212 mmol). MS (FAB) 1022.8 ($MH^+$) 1044.8 ($MNa^+$). $^1H$ NMR ($CDCl_3$) δ 8.07–8.05 (m, 1H), 7.88–7.81 (m, 2H), 7.57–7.41 (m, 4H), 7.29 (s, 1H), 6.70–6.55 (m, 2H), 5.45–5.35 (m, 1H), 4.99–4.98 (m, 2H), 4.66–4.57 (m, 2H), 4.44–4.40 (m, 1H), 4.30–4.01 (m, 5H), 3.91 (dd, J=11, J'=4 Hz, 1H), 3.76–3.62 (m, 2H), 2.62–2.56 (m, 1H), 2.50–2.30 (m, 3H), 2.18–2.09 (m, 2H), 2.06–1.90 (m, 2H), 1.67–1.53 (m, 4H), 1.50–1.42 (m, 4H), 1.43 (s, 9H), 1.14–0.86 (m, 10H), 0.93 (d, J=7 Hz, 3H), 0.87 (d, J=7 Hz, 3H), 0.04 (s, 9H), 6.02 (s, 9H).

f) Synthesis of Compound 20g:

The crude pentapeptide 20f (ca. 0.212 mmol) was treated with 4N HCl/dioxane solution (2.5 mL) 40 min, RT and the resulting hydrochloride salt was coupled to Boc-Asp (OTMSE)-OH (77.8 mg, 0.233 mmol) with NMM (93 mL, 0.848 mmol) and TBTU (81.7 mg, 0.254 mmol) as described for compound 20e (with the modification of 2.5 h coupling time). The crude hexapeptide 20g was obtained as an ivory foam (278 mg, 0.212 mmol). MS (FAB) 1237.5 ($MH^+$) 1259($MNa^+$).

g) Synthesis of Compound 20h:

The crude hexapeptide 20g (ca. 0.2 mmol) was treated for 40 min at RT with 2.5 mL 4N HCl/dioxane solution. Concentration to dryness provided the amine hydrochloride as a white solid. The crude hydrochloride salt was dissolved in anhydrous DMF (2.5 mL) and treated successively with pyridine (377 µL, 4.66 mmol) and acetic anhydride (378 µL, 4.01 mmol). The reaction mixture was stirred overnight at RT then poured into brine and extracted with EtOAc (3×). The combined organic layer was washed successively with 10% aqueous citric acid (2×), saturated NaHCO$_3$ (2×), water (2×), and brine (1×). The organic layer was dried (MgSO$_4$), filtered and evaporated to dryness. The foamy residue was purified by flash chromatography (eluent:hexane:EtOAc; 3:7) to provide the acetylated hexapeptide 20h as an off-white foam (78.5 mg, 31% yield over 3 steps). MS (FAB) 1179.6 (MH$^+$) 1201.5 (MNa$^+$). $^1$H NMR (CDCl$_3$) δ 8.11–8.09 (m, 1H), 7.86–7.79 (m, 2H), 7.55–7.41 (m, 5H), 7.28 (s, 1H), 7.02–6.96 (m, 2H), 6.70–6.68 (m, 1H), 5.13–5.10 (m, 1H), 4.96–4.91 (m, 2H), 4.58–4.41 (m, 4H), 4.22–4.08 (m, 8H), 3.77 (dd, J=10.5, J'=5 Hz, 1H), 3.09 (dd, J=18, J'=4 Hz, 1H), 2.76 (dd, J=17.5, J'=8 Hz, 1H), 2.51–2.20 (m, 3H), 2.12–2.08 (m, 2H), 2.09 (s, 3H), 1.73–1.53 (m, 8H), 1.27–1.09 (m, 7H), 1.01–0.85 (m, 8H), 0.98 (d, J=6.5 Hz, 3H), 0.97(d, J=6 Hz, 3H), 0.04 (s, 9H), 0.03 (s, 9H), 0.01 (s, 9H).

h) Synthesis of Compound 215:

The acetylated hexapeptide 20h (76.5 mg, 0.065 mmol) was dissolved in anhydrous THF (2 mL), a TBAF solution (1M in THF; 389 µL, 0.389 mmol) was added and the mixture was stirred at RT for 16 h. The solution was concentrated under vacuum and the residue was dissolved in glacial acetic acid, filtered through a Millipore®: Millex®-HV 0.45 µm filter unit and injected onto an equilibrated Whatman Partisil® 10-ODS-3 (2.2×50 cm) C18 reverse phase column. Purification program: Linear Gradient at 15 mL/min, λ 230 nm, program at 5% A for 10 min, 5–30% A in 10 min, at 30% A for 10 min, 30–60% A in 90 min A:0.06% TFA/CH$_3$CN; B:0.06% TFA/H$_2$O. Fractions were analyzed by analytical HPLC. The product collected was lyophilized to provide the hexapeptide acid 215 as a white amorphous solid (26.9 mg; contains 41% by weight of tetrabutylammonium salts, 28% yield). MS (FAB) 879.4 (MH$^+$) 901.3 (MNa$^+$). In order to remove the tetrabutylammonium salt, the above product (ca.18 mg) was dissolved in EtOAc and washed with 10% HCl (2×). The EtOAc layer was evaporated, then lyophilized with water to provide the salt-free product as a white amorphous solid (3.8 mg, 36% yield). $^1$H NMR (DMSO-d$_6$) δ 8.39 (s, 1H), 8.10–7.81 (m, 7H), 7.57–7.45 (m, 4H), 5.07–4.87 (m, 2H), 4.55–4.00 (m, 7H), 3.76–3.71 (m, 1H), 2.67–2.62 (m, 1H), 2.33–2.10 (m, 3H), 2.05–1.42 (m, 8H), 1.79 (s, 3H), 1.38–0.71 (m, 1H), 0.89 (d, J=6.68 Hz, 3H), 0.86 (d, J=6.36 Hz, 3H).

Example 21

Synthesis of Compound 214 (Table 2)

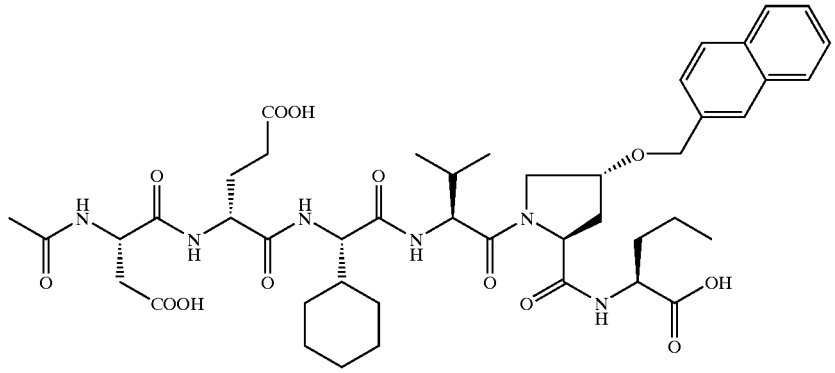

214

For the synthesis of compound 214 the procedure described in Example 20 was followed, using Boc-4(R)-(naphthalen-2-ylmethoxy)proline for the introduction of the P2 fragment and with different protecting groups at the side chain carboxylic acid residues.

The synthesis is described below:

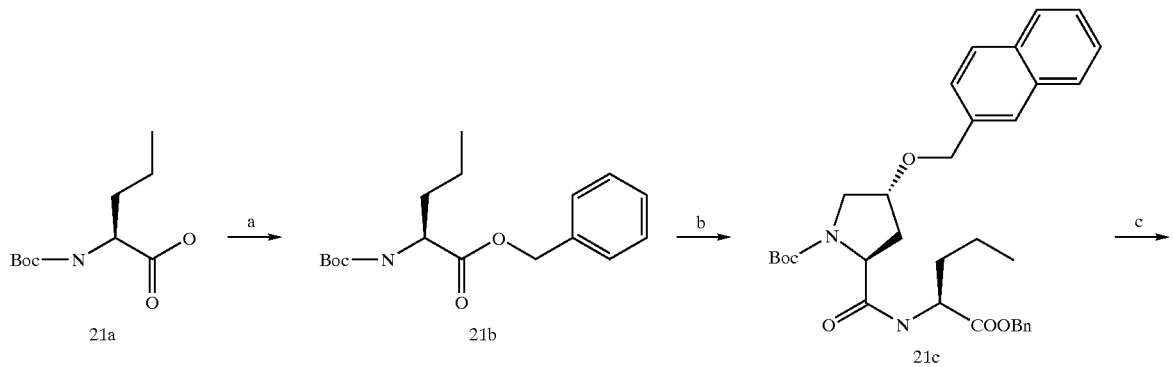

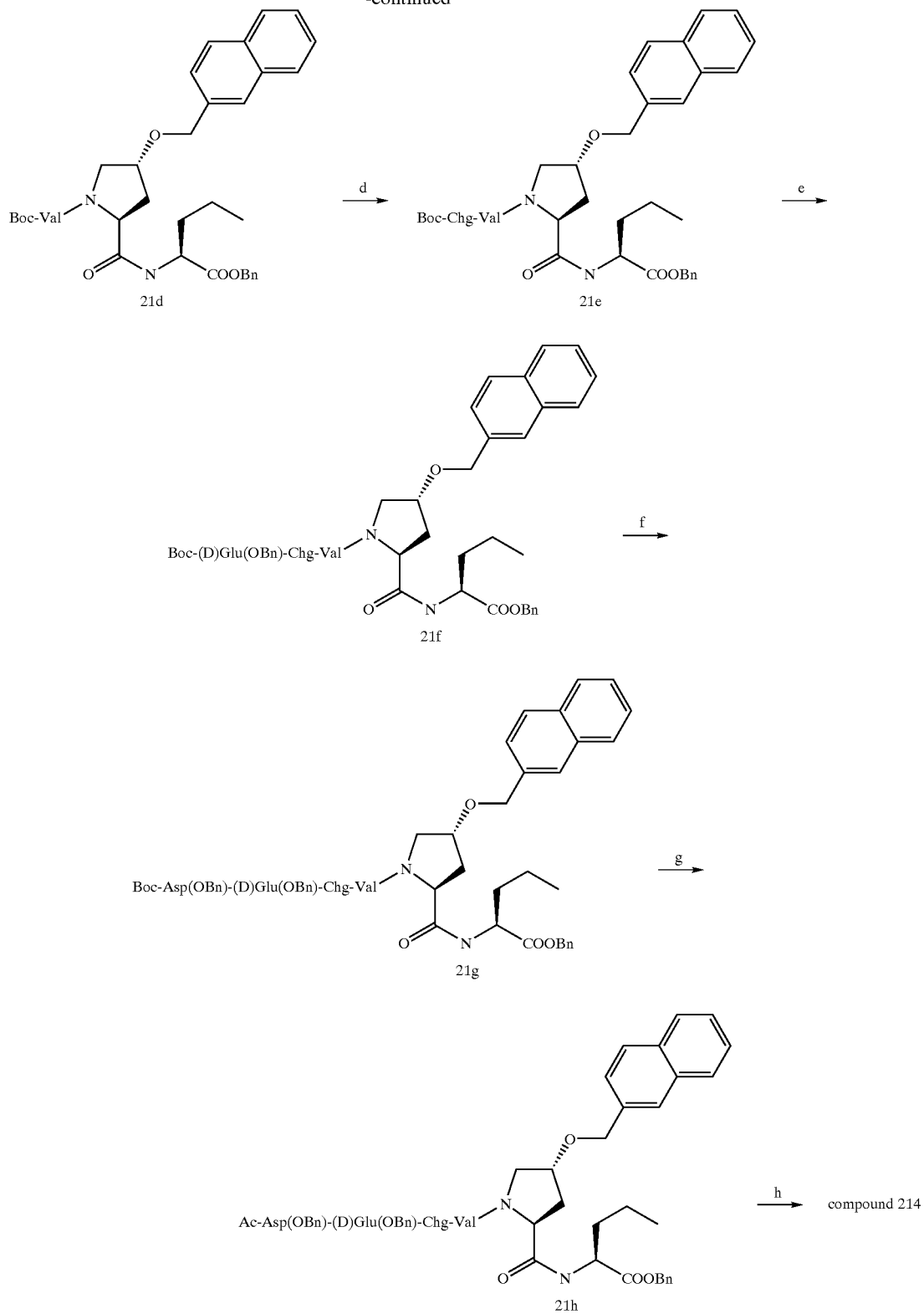

a) Synthesis of Compound 21b:

At 0° C. benzyl bromide (5.74 mL, 48.3 mmol) was added to a mixture of Boc-norvaline (21a) (10.0 g, 46.0 mmol) and DBU (7.57 mL, 50.6 mmol) in acetonitrile (200 mL). After stirring at RT for 20 h, the solution was concentrated and the residue dissolved in ether. The organic solution was washed sequentially with 10% aqueous citric acid (2×), saturated aqueous. NaHCO$_3$ (2×) and brine (1×), dried (MgSO$_4$), filtered and concentrated to give the desired benzyl ester 21b as a colorless oil (13.7 g, 97% yield). $^1$H NMR (CDCl$_3$) δ

7.40–7.32 (m, 5H), 5.16 (dd, J=26.7, J'=12.4 Hz, 2H), 4.99 (d, J=7.9 Hz, 1H), 4.35–4.32 (m, 1H), 1.82–1.73 (m, 1H), 1.66–1.57 (m, 1H), 1.43 (s, 9H), 1.41–1.32 (m, 2H), 0.90 (t, J=7.3 Hz, 3H). b, c, d, e, f, g) Synthesis of compound 21h:

The above Boc-Nva benzyl ester (121 mg, 0.48 mmol) was subjected to the same sequence of reactions as described in Example B. However, for the introduction of P2 (step b) Boc-4(R)-(naphthalen-2-ylmethoxy)proline was used. Also, for the introduction of P5 (step e) and P6 (step f) the corresponding Boc-D-Glu-OH and Boc-Asp-OH residues were protected as benzyl esters at the carboxylic acid side chain.

h) Synthesis of Compound 214:

To a solution of hexapeptide 21h (ca. 0.210 mmol) in ethanol (3 mL) was added 10% palladium on charcoal (10 mg) and ammonium acetate (10 mg). The mixture was stirred under an atmosphere of hydrogen for 5 h, then filtered through a Millipore®: Millex®-HV 0.45 μm filter unit and injected onto an equilibrated Whatman Partisil® 10-ODS-3 (2.2×50 cm) C18 reverse phase column. Purification program: Linear Gradient at 15 mL/min, λ 230 nm, at 5% to 50% A in 60 min A: 0.06% TFA/CH$_3$CN; B: 0.06% TFA/H$_2$O. Fractions were analyzed by HPLC. The collected product was lyophilized to provide 214 as a white solid (20 mg, 0.02 mmol). MS (FAB) 895.5 (MH$^+$). $^1$H NMR (CDCl$_3$) δ 8.16 (d, J=7.6 Hz, 1H), 8.11 (d, J=8 Hz, 1H), 8.09 (d, J=8 Hz, 1H), 7.98 (d, J=9 Hz, 1H), 7.91–7.88 (m, 3H), 7.85 (s, 1H), 7.77 (d, J=9 Hz, 1H), 7.51–7.46 (m, 3H), 4.70 (d, J=12 Hz, 1H), 4.60 (d, J=12 Hz, 1H), 4.53–4.45 (m, 2H), 4.33–4.10 (m, 6H), 3.69 (dd, J=19, J'=4.4 Hz, 1H), 2.66–2.60 (m, 1H), 2.49–2.43 (m, 1H), 2.21–2.18 (m, 3H), 2.07–1.94 (m, 3H), 1.82 (s, 3H), 1.76–1.33 (m, 10H), 1.04–0.86 (m, 15H).

Example 22
Synthesis of Compound 221 (Table 2)

221

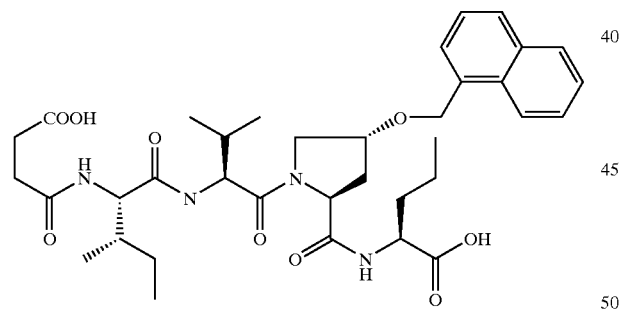

Mono-benzylsuccinic acid (prepared as described in: Bischoff, V. et al., Chem.Ber. (1902), 35, 4078) (27 mg, 0.134 mmol) was stirred in acetonitrile (2 mL) with TBTU (52 mg, 0.160 mmol) and NMM (47 mg, 0.469 mmol) for 5 min. To this mixture, the hydrochloride salt of the appropriate tetrapeptide (prepared as described for compound 21e but using isoleucine instead of cyclohexylglycine and 4(R)-(naphthalen-1-ylmethoxy)proline instead of a 4(R)-(naphthalen-2-ylmethoxy)proline (97.0 mg, 0 134 mmol) was added. The mixture was stirred at RT for 2.5 h. Ethyl acetate was added and the mixture was washed with 10% aqueous citric acid (2×), with saturated aqueous NaHCO$_3$ (2×) and brine (1×), dried (MgSO$_4$), filtered and concentrated to afford the protected tetrapeptide as a yellow oil.

The above compound (ca. 0.134 mmol) was dissolved in ethanol (3 mL) and ammonium acetate (10 mg) and 20% palladium hydroxide on activated carbon (30 mg) were added. The mixture was stirred under 1 atmosphere of hydrogen for 18 h, then filtered through a Millipore®: Millex®-HV 0.45 μm filter unit and injected onto an equilibrated Whatman Partisil 10-ODS-3 (2.2×50 cm) C18 reverse phase column. Purification program: Linear Gradient at 15 mL/min, λ 230 nm, 5% A for 10 min, 5–60% A in 60 min (A: 0.06% TFA/CH$_3$CN; B: 0.06% TFA/H$_2$O). Fractions were analyzed by HPLC. The collected product was lyophilized to provide 221 as a white solid (21 mg). MS (FAB) 683 (MH$^+$). $^1$H NMR (DMSO-d$_6$) δ 8.12 (d, J=7.6 Hz, 1H), 8.07–8.03 (m, 1H), 7.96–7.81 (m, 4H), 7.59–7.51 (m, 3H), 7.55 (t, J=8.0 Hz, 1H), 4.90 (d, J=8 Hz, 1H), 4.82 (d, J=8 Hz, 1H), 4.45 (t, J=8.0 Hz, 1H), 4.36–4.31 (m, 2H), 4.24–4.12 (m, 3H), 3.74–3.68 (m, 1H), 2.43–2.31 (m, 4H), 2.24–2.18 (m, 1H), 2.01–1.92 (m, 2H), 1.67–1.51 (m, 3H), 1.42–1.32 (m, 3H), 1.14–0.96 (m, 1H), 0.93–0.67 (m, 15H).

Example 23

Preparation of Compound 413 (Table 4)

The following description is an example of a compounds of formula I wherein. Q is CH$_2$.

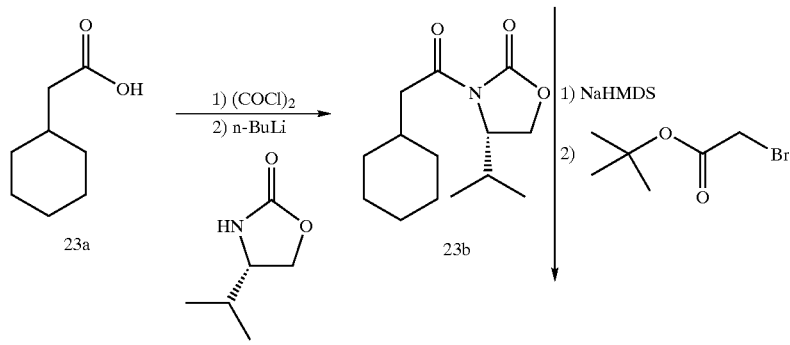

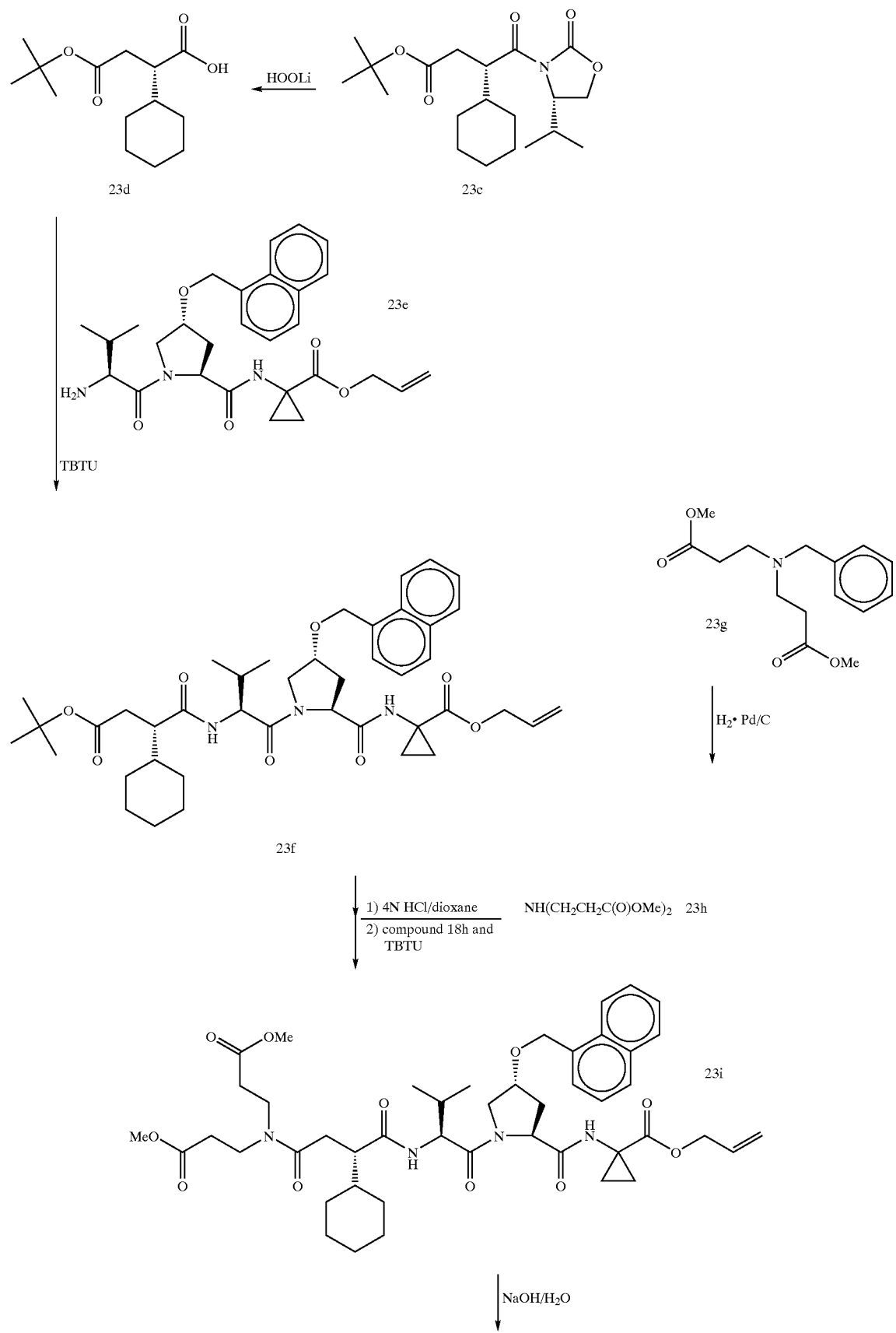

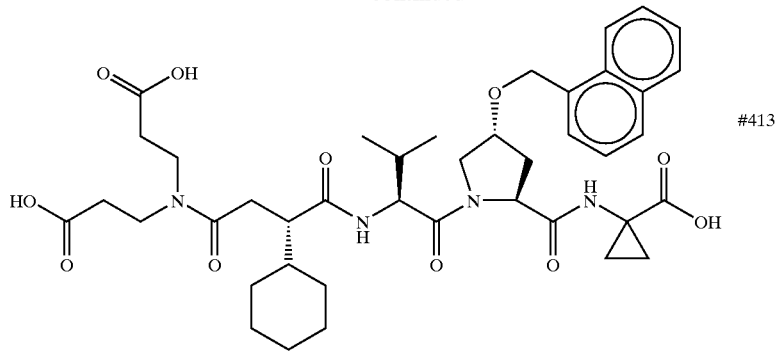

413

Compound 23b

1) To cyclohexylacetic acid (23a) (89, 56.25 mmol) in DCM (160 mL) at room temperature was added the oxalyl chloride (6.4 mL, 73.14 mmol) and 2 drops of DMF. The reaction mixture was stirred at room temperature for 1 h, then concentrated under reduced pressure to give cyclohexylacetyl chloride.

2) The chiral auxiliary, (4S)-(−)-4-isopropyl-2-oxazolidinone, (7.63 g, 59.06 mmol) was dissolved in THF (200 mL) and cooled to −78° C. N-butyllithium (1.6M) in hexane (36.9 mL, 59.06 mmol) was added slowly (over a 10 min period). The mixture was stirred at −78° C. for 30 min (formed a gel). The aforementioned cyclohexylacetyl chloride was added in THF (50 mL) at −78° C. The reaction mixture was stirred at −78° C. for 30 min and then at 0° C. for 1 h. The reaction was quenched by adding an aqueous solution of $NH_4Cl$ (16 mL). The reaction mixture was concentrated under reduced pressure. $Et_2O$ (300 mL) was added. The organic phase was separated and washed with a 10% aqueous solution of citric acid (2×200 mL), a saturated aqueous solution of $NaHCO_3$ (2×200 mL) and brine (200 mL), dried, filtered and concentrated under reduced pressure. The residue was purified by flash chromatography (silica gel, 40–60μ, 60×100 mm, 9/1→8/→2, hexane/EtOAc) to give compound 23b as a colorless oil (11.3 g, 79% yield).

$^1$H NMR ($CDCl_3$) δ 4.40–4.36 (m, 1H), 4.20 (dd, J=8.3 Hz, J=9.1 Hz, 1H), 4.13 (dd, J=2.9 Hz, 9.1 Hz, 1H), 2.86 (dd, J=6.4 Hz, 15.7 Hz, 1H), 2.65 (dd, J=7.1 Hz, 15.7 Hz, 1H), 2.35–2.27 (m, 1H), 1.83–1.76 (m, 1H), 1.70–1.57 (m, 5H), 1.26–0.90 (m, 5H), 0.85 (d, J=7.0 Hz, 3H), 0.81 (d, J=6.7 Hz, 3H).

Compound 23c

To a solution of compound 23b (11.3 g, 44.68 mmol) in THF (125 mL) at −78° C. was added a NaHMDS solution (1M in THF, 49.2 mL, 49.15 mmol). The reaction mixture was stirred at −78° C. for 1.5 h. A solution of tert-butyl bromoacetate (8.67 mL, 53.62 mmol) in THF (25 mL) was added at −78° C. The mixture was stirred at that temperature for 3h. A saturated aqueous solution of $NH_4Cl$ solution (33 mL) was added slowly. The cold bath was removed and the mixture was stirred at room temperature for 10 min. The THF was removed. EtOAc was added (200 mL). The organic phase was separated, washed serially with a saturated aqueous solution of $NaHCO_3$ (200 mL), $H_2O$ (200 mL), aqueous 1N HCl solution (200 mL) and brine (200 mL), dried ($MgSO_4$), filtered and concentrated under reduced pressure. The residue was purified by trituration with $Et_2O$ giving compound 23c as a white solid (12.65 g, 77% yield).

$^1$H NMR (DMSO-$d_6$) δ 4.61–4.53 (m, 3H), 4.27–4.25 (m, 1H), 2.84–2.66 (m, 2H), 2.55–2.41 (m, 1H), 1.89–1.76 (m, 6H), 1.58 (s, 9H), 1.35–1.31 (m, 4H), 1.14–1.04 (m, 7H).

Compound 23d

To an ice-cold solution of compound 23c (12.2 g, 33.28 mmol) in a mixture of THF/$H_2O$ (3/1 mixture, 495 mL/165 mL) was added $H_2O_2$ (30%, 15.1 mL, 133.1 mmol), followed by a slow addition of LiOH—$H_2O$ (2.79 g, 66.56 mmol). The reaction mixture was stirred at 0° C. for 1 h, then at RT overnight. The mixture was cooled to 0° C. and a 1.5N aqueous solution of $Na_2SO_3$ was added slowly to decompose excess peroxide (monitored by KI paper). The mixture was concentrated under reduced pressure, the residual aqueous solution was washed with DCM (2×150 mL). The aqueous layer was made acidic with a 10% aqueous solution of citric acid. The mixture was extracted with EtOAc (3×200 mL). The combined organic phase were washed with brine (200 mL), dried ($MgSO_4$), filtered and concentrated under reduced pressure. Compound 23d was obtained as a colorless oil (8.38 g, 98% yield).

$^1$H NMR ($CDCl_3$) δ 2.71–2.66 (m, 1H), 2.59 (dd, J=10.8 Hz, 16.0 Hz, 1H), 2.36 (dd, J=3.8 Hz, 16.0 Hz, 1H), 1.78–1.57 (m, 6H), 1.41 (s, 9H), 1.30–0.98 (m, 5H).

Compound 23f

1) The corresponding Boc derivative of compound 23e (1.63 g, 2.74 mmol) was treated with HCl 4N/dioxane (14 mL, 54.91 mmol) at RT for 1 h. The reaction mixture was concentrated under reduced pressure. A 5% aqueous solution of $Na_2CO_3$ (25 mL) was added to the residue and the resulting solution was stirred vigorously for 5 min. EtOAc was added (75 mL). The two resulting phases were separated. The organic phase was washed with brine (50 mL), dried ($MgSO_4$), filtered and concentrated under reduced pressure to give 23e which was used as such for the next step.

2) To the amino tripeptide in DMF (5 mL) at RT was added compound 23d (739 mg, 288 mmol) in DMF (5 mL), followed by DIPEA (1.43 mL, 8.24 mmol) and TBTU (502 mg, 2.88 mmol). The reaction mixture was stirred at RT overnight. EtOAc was added (125 mL). The organic phase was separated, washed with a saturated aqueous solution of $NaHCO_3$ (100 mL), $H_2O$ (100 mL) and brine (100 mL), dried ($MgSO_4$), filtered and concentrated under reduced pressure. The residue was purified by flash chromatography (silica gel, 40–60μ, 40×125 mm, 6/4→5/5 hexane/EtOAc) to give the tert-butyl ester compound 23f as a white foam (1.18 g, 59% yield).

$^1$H NMR ($CDCl_3$) δ 8,06 (d, J=8.3 Hz, 1H), 7 86 (d, J=7.6 Hz, 1H), 7.81 (d, J=8.3 Hz, 1H), 7.55–7.40 (m, 4H), 7.35 (s, 1H), 6.28 (d, J=8.9 Hz, 1H), 5.86–5.79 (m, 1H), 5.24 (dd, J=1.6 Hz, 17.2 Hz, 1H), 5.17 (dd, J=1.3 Hz, J=10.5 Hz, 1H), 4.98 (ABq, Δv=18.7 Hz, J=12.1 Hz, 2H), 4.67–4.51 (m, 4H), 4.41–4.38 (m, 1H), 3.99 (dd, J=3.8 Hz, 10.8 Hz, 1H), 2.64–2.59 (m, 2H), 2.42–2.38 (m, 2H), 2.10–1.95 (m, 2H), 1.68–1.53 (m, 9H), 1.43–1.41 (m, 1H), 1.42 (s, 9H), 1.15–1.04 (m, 4H), 0.97–0.91 (m, 8H).

Compound 23h

To the commercially available 3-[benzyl-2-methoxycarbonylethyl)amino]propionic acid methyl ester (23g) (2 g, 7.16 mmol) in MeOH (24 mL), was added the palladium catalyst (Pd/C 10%, 500 mg, 25% w/w). The reaction mixture was stirred under a nitrogen atmosphere (balloon) for 18 h. The mixture was filtered through diatomaceous ester and the filter pad was washed with MeOH (20 mL). The MeOH (filtrate plus washing) was evaporated to give 1.2 g (89% yield) of compound 23h as a pale yellow oil. This product was used as such for the next step.

Compound 23I

1) The t-butyl ester compound 23f, (1.18 g, 1.62 mmol) was treated with 4N HCl in dioxane (8.5 mL, 32.4 mol) at RT for 6 h. The mixture was concentrated under reduced pressure, and then co-evaporated with benzene/Et$_2$O to give 1.04 g of the corresponding acid as a beige foam (95% yield).

2) To the latter acid (200 mg, 0.29 mmol) in DMF (1 mL) at RT was added the amine (compound 23h, 59 mg, 0.31 mmol) in DMF (2 mL), followed by DIPEA (154 µL, 0.89 mmol) and TBTU (100 mg, 0.31 mmol). The reaction mixture was stirred at RT for 72 h. EtOAc (125 mL) was added. The organic phase was separated, washed with a saturated aqueous solution of NaHCO$_3$ (75 mL), H$_2$O (75 mL) and brine (75 mL), dried (MgSO$_4$), filtered and concentrated under reduced pressure. The product was purified by flash chromatography (silica gel, 40–60µ, 20×100 mm, 8/2 EtOAc/hexane to give compound 23i as a yellow oil (82 mg, 33% yield).

MS (ESI) 869.3 (M+Na)$^+$, 845.4 (M−H)$^+$.

Compound 413

An aqueous 1M solution of NaOH (774 µL, 0.774 mmol) was added to a solution of compound 23i (82 mg, 0.097 mmol) in a mixture of THF/MeOH (1/1, 1 mL each). The reaction mixture was stirred at RT for 18 h. H$_2$O was added (15 mL). The aqueous phase was separated and washed with DCM (3×15 mL). The aqueous phase was made acidic (pH 3) by adding an aqueous solution of 1N HCl. The mixture was extracted with EtOAc (3×15 mL). The organic phase was washed with brine (25 mL), dried (MgSO$_4$), filtered and concentrated under reduced pressure. The residue was purified by preparative HPLC (5%→53% MeCN in 60 min) to give compound 413 as a white lyophilized solid (31 mg, 41% yield).

MS (ESI) 779.3 (M+H)$^+$, 801.3 (M+Na)$^+$, 777.3 (M−H)$^+$.
$^1$H NMR (DMSO-d$_6$) δ 8.38 (S, 1H), 8.06 (d, J=8.3 Hz, 1H), 7.93 (d, J=7.6 Hz, 1H), 7.86 (d, J=8.3 Hz, 1H), 7.74 (d, J=8.6 Hz, 1H), 7.57–7.44 (m, 5H), 5.01 (d, J=12.1 Hz, 1H), 4.89 (d, J=12.1 Hz, 1H), 4.35–4.31 (m, 2H), 4.25 (dd, J=7.9 Hz, 8.3 Hz, 1H), 4.18 (d, J=11.1 Hz, 1H), 3.80–3.49 (m, 3H), 3.37–3.34 (m, 2H), 2.63–2.61 (m, 1H), 2.56–2.52 (m, 1H), 2.39–2.35 (m, 2H), 2.25–2.20 (m, 2H), 2.05–1.91 (m, 2H), 1.62–1.59 (m, 1H), 1.41–1.22 (m, 5H), 0.96–0.73 (m, 16H).

Example 24

Synthesis of Compound 505 of Table 5

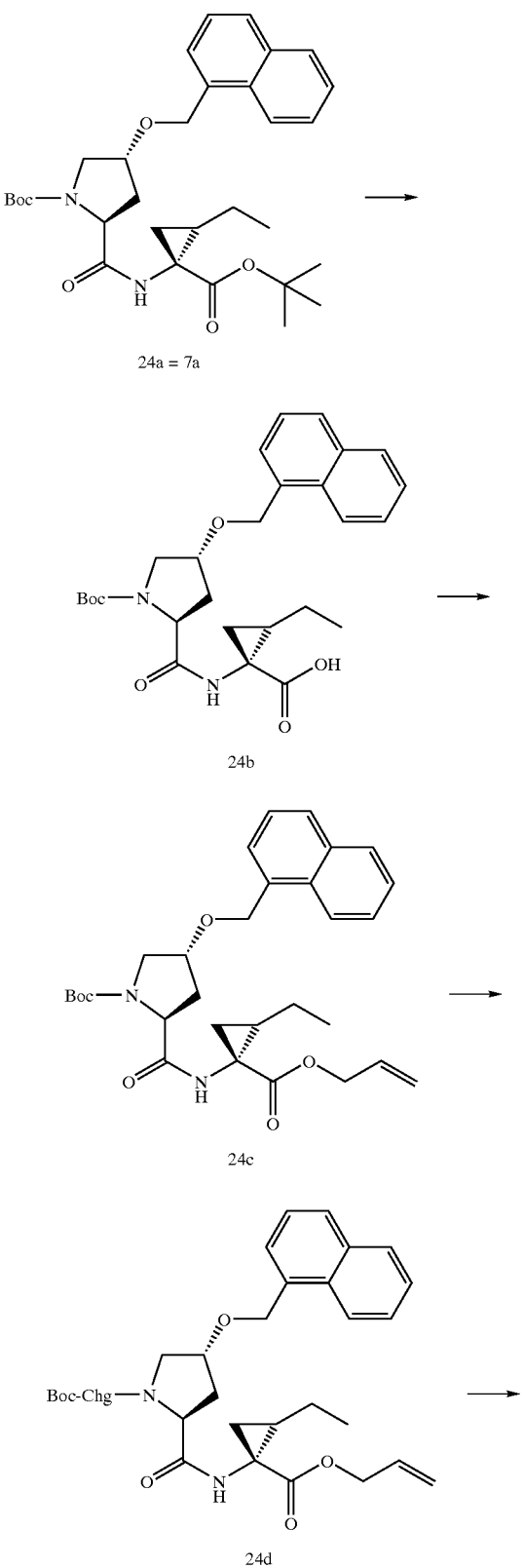

24a = 7a

24b

24c

24d

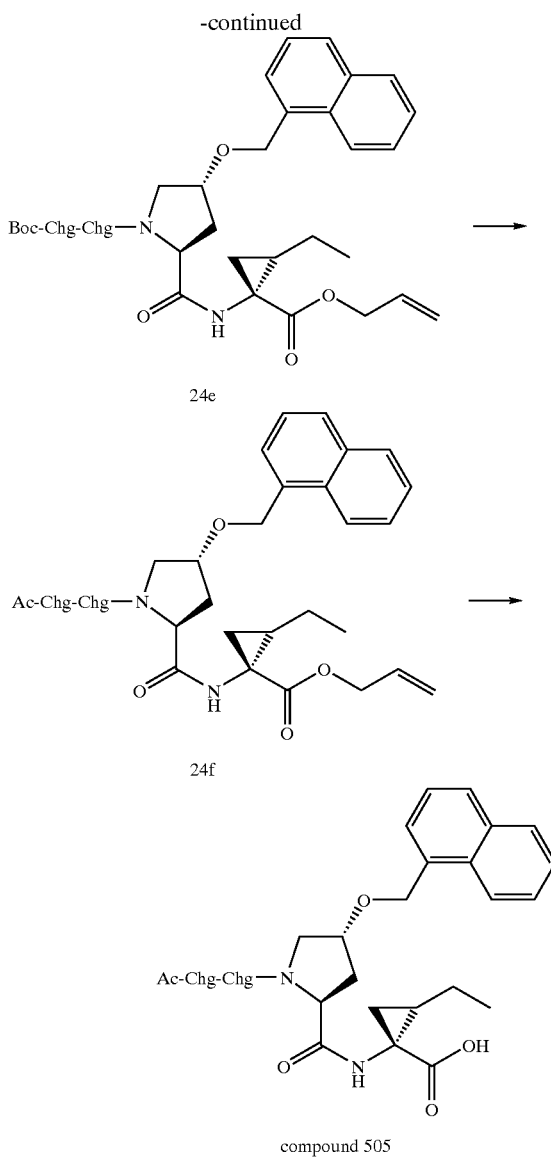

compound 505

Compound 24a (4.27 g, 7.93 mmol, described as compound 7a in Example 7) was treated with 4N HCl/dioxane (40 mL) for 5 h as described for compound 20c. The crude hydrochloride salt was dissolved in THF (10 mL) and a solution of NaOH (348.7 mg, 8.72 mmol) in $H_2O$ (5 mL) was added, followed by a dropwise addition of $(Boc)_2O$ (1.73 g, 7.93 mmol) dissolved in THF (13 mL). The pH was maintained at 8 by the addition of 10% aqueous NaOH as required. The reaction mixture was stirred vigorously, then diluted with $Et_2O$ and $H_2O$ and extracted one time more with $Et_2O$. The water layer was acidified to pH 3 with 10% aqueous citric acid. The mixture was extracted with EtOAc (3×). The combined EtOAc extracts were washed with $H_2O$ (2×), brine(1×), dried ($MgSO_4$), filtered and evaporated to dryness to provide crude compound 24b as an ivory foam (ca.7.93 mmol). MS (FAB) 481.3 $MH^{-1}$ H NMR ($CDCl_3$), ca.1:1 mixture of rotamers, δ 8.04 (bd, J=7.5 Hz, 1H), 7.87 (bd, J=7.5 Hz, 1H), 7.82 (d, J=7.5 Hz, 1H), 7.56–7.40 (m, 5H), 4.96 (bs, 2H), 4.33 (t, J=7.5, 14.5 Hz, 1H), 4.21–4.09 (m, 0.5H), 3.99–3.84 (m, 0.5H), 3.78–3.75 (m, 0.5H), 3.68–3.62 (m, 0.5H), 3.61–3.42 (m, 1H), 2.55–2.41 (m, 1H), 2.22–2.11 (m, 1H), 1.61–1.52 (m, 3H), 1.43 (s, 9H), 1.40–1.31 (m, 1H), 1.25–1.19 (m, 1H), 0.99 (t, J=7.5, 14.5 Hz, 3H).

Compound 24b (ca.7.93 mmol) was treated with DBU (1.18 mL, 93 mmol) and allylbromide (4.12 mL, 47.61 mmol) in anhydrous CH3CN (40 mL) for 48 h as described for compound 20b to provide the allylated dipeptide 24c as an ivory foam (3.54 g: 86% yield over 2 steps). MS (FAB) 521.3 MH– 545.2 (M+Na)+. 1H NMR (CDCl3), ca.1:1 mixture of rotamers, δ 8.05 (bd, J=8 Hz, 1H), 7.86 (bd, J=7.5 Hz, 1H), 7.82 (d, J=8 Hz, 1H), 7.55–7.40 (m, 5H), 5.88–5.79 (m, 1H), 5.27 (bd, J=17.5 Hz, 1H), 5.18 (bd, J=10 Hz, 1H), 5.03–4.89 (m, 2H), 4.63–4.50 (m, 2), 4.44–4.19 (m, 2H), 4.00–3.40 (m, 2H), 2.70–2.02 (m, 2H), 1.66–1.35 (m, 5H), 1.44 (s, 9H), 0.95 (t, J=7.5, 14.5 Hz, 3H).

The crude dipeptide 24c (1.18 g, 2.26 mmol) was treated with 4N HCl/dioxane (35 mL) as described for compound 20c. The crude hydrochloride salt was coupled to Boc-Chg-OH.$H_2O$ (684 mg, 2.48 mmol) with NMM (993 μL, 9.03 mmol) and TBTU (870 mg, 2.71 mmol) in DCM (11 mL) as described for compound 20d to provide the crude tripeptide 24d as an ivory foam (1.41 g; 95%). MS (FAB) 660.4 MH⁻ 662.3 MH⁺. ¹H NMR (CDCl₃), mainly one rotamer, δ 8.03 (bd, J=8 Hz, 1H), 7.85 (bd, J=8 Hz, 1H), 7.81 (d, J=8 Hz, 1H), 7.56–7.39 (m, 5H), 5.88–5.77 (m, 1H), 5.26 (dd, J=1.5, 17 Hz, 1H), 5.15 (dd, J=1.5, 10.5 Hz, 1H), 5.12 (s, 1H), 5.02–4.92 (m, 2H), 4.72–4.59 (m, 1H), 4.57–4.46 (m, 1H), 4.42–4.35 (m, 1H), 4.33–4.20 (m, 1H), 4.02–3.90 (m, 1H), 3.78–3.70 (m, 1H), 3.67–3.51 (m, 1H), 2.71–2.61 (m, 1H), 2.12–2.02 (m, 1H), 1.79–1.48 (m, 10H), 1.45–1.39 (m, 1H), 1.38 (s, 9H), 1.25–1.01 (m, 5H), 0.94 (t, J=7.5, 14 Hz, 3H).

The crude tripeptide 24d (265 mg, 0.400 mmol) was treated with 4N HCl/dioxane (3 mL) as described for compound 20c. The crude hydrochloride salt was coupled to Boc-Chg-OH $H_2O$ (143.3 mg, 0.521 mmol) with NMM (176 μL, 1.60 mmol) and TBTU (154.3 mg, 0.481 mmol) in DCM (3 mL) as described for compound 20d to provide crude tetrapeptide 24e as an ivory foam (ca.0.400 mmol; 100%). MS (FAB) 799.5 MH⁻ 801.5 MH⁺ 823 (M+Na)⁺. ¹H NMR (CDCl₃), ca. 1:1 mixture of rotamers, δ 8.05 (bd, J=8.5 Hz, 1H), 7.87 (bd, J=7.5 Hz, 1H), 7.81 (d, J=8.5 Hz, 1H), 7.55–7.40 (m, 4H), 7.37 (s, 1H), 6.58–6.41 (m, 1H), 5.89–5.78 (m, 1H), 5.26 (bdd, J=1.5, 17 Hz, 1H), 5.16 (bdd, J=1.5, 10.5 Hz, 1H), 5.20–4.92 (m, 3H), 4.68–4.58 (m, 2H), 4.57–4.47 (m, 1H), 4.43–4.26 (m, 1H), 3.99–3.81 (m, 2H), 3.78–3.60 (m, 2H), 2.67–2.60 (m, 1H), 2.11–2.02 (m, 1H), 1.78–1.42 (m, 14H), 1.44 & 1.43 (s, 9H), 1.25–0.91 (m, 13H), 0.95 (t, J=7.5, 15 Hz, 3H).

The crude tetrapeptide 24e (ca.0.400 mmol) was treated with 4N HCl/dioxane (3 mL) as described for compound 20c. The crude hydrochloride salt was further treated with acetic anhydride (83 μL, 0.884 mmol) and NMM (194 μL, 1.77 mmol) in DCM (3 mL) as described for compound 20f to provide the crude acetylated tetrapeptide 24f as an ivory foam (ca.0.400 mmol).

MS (FAB) 741.5 MH 743.4 MH⁻ 765.4 (M+Na)⁺. ¹H NMR (CDCl₃) δ 8.05 (bd, J=8.5 Hz, 1H), 7.87 (bd, J=7.5 Hz, 1H), 7.82 (d, J=8.5 Hz, 1H), 7.55–7.41 (m, 4H), 7.39 (s, 1H), 6.63–6.48 (m, 1H), 6.01 (d, J=8.5 Hz, 1H), 5.90–5.79 (m, 1H), 5.27 (bdd, J=1.5, 17 Hz, 1H), 5.16 (bdd, J=1.5, 10.5 Hz, 1H), 5.01 (d, J=12 Hz, 1H), 4.96 (d, J=12 Hz, 1H), 4.69–4.48 (m, 3H), 4.44–4.37 (m, 1H), 4.36–4.22 (m, 1H), 3.96 (dd, J=4, 11 Hz, 1H), 3.78–3.60 (m, 2H), 2.67–2.59 (m, 1H), 2.10–2.00 (m, 1H), 2.01 (s, 3H), 1.78–1.48 (m, 13H), 1.45–1.35 (m, 1H), 1.26–0.89 (m, 13H), 0.95 (t, J=7.5, 15 Hz, 3H).

The acetylated tetrapeptide 24f (ca.0.400 mmol) was deprotected by tetrakis(triphenylphosphine)-palladium (0) catalyst (11.3 mg, 0.010 mmol) with triphenylphosphine (5.12 mg, 0.020 mmol) and pyrrolidine (34 μL, 0.406 mmol)

in a 1:1 mixture of anhydrous CH₃CN: DCM (2 mL) as described for compound 20g. The crude product was purified by flash chromatography (eluent-1$^{st}$ EtOAc, then, 2$^{nd}$ 1.92% HOAc, 3.85% MeOH in DCM) to provide, after lyophilization, the tetrapeptide compound 505 of Table 5 as an off-white amorphous solid (193.1 mg; 73% yield over 5 steps).

MS (FAB) 701.4 MH 703.4 MH⁻ 725.4 (M+Na)⁺. $^1$H NMR (DMSO), ca.1:5 mixture of rotamers, δ 8.57 & 8.32 (s, 1H), 8.04 (d, J=7.5 Hz, 1H), 7.94 (bd, J=7.5 Hz, 1H), 7.88 (d, J=8 Hz, 1H), 7.83–7.78 (m, 2H), 7.58–7.30 (m, 4H), 4.99 (d, J=12 Hz, 1H), 4.90 (d, J=12 Hz, 1H), 4.44–4.29 (m, 2H), 4.29–4.05 (m, 3H), 3.87–3.73 (m, 1H), 2.23–2.13 (m, 1H), 2.05–1.95 (m, 1H), 1.91 & 1.84 (s, 3H), 1.75–1.40 (m, 15H), 1.29–0.84 (m, 12H), 0.91 (t, J=7.5, 14.5 Hz, 3H).

Example 25
The Synthesis of Compound 506 of Table 5

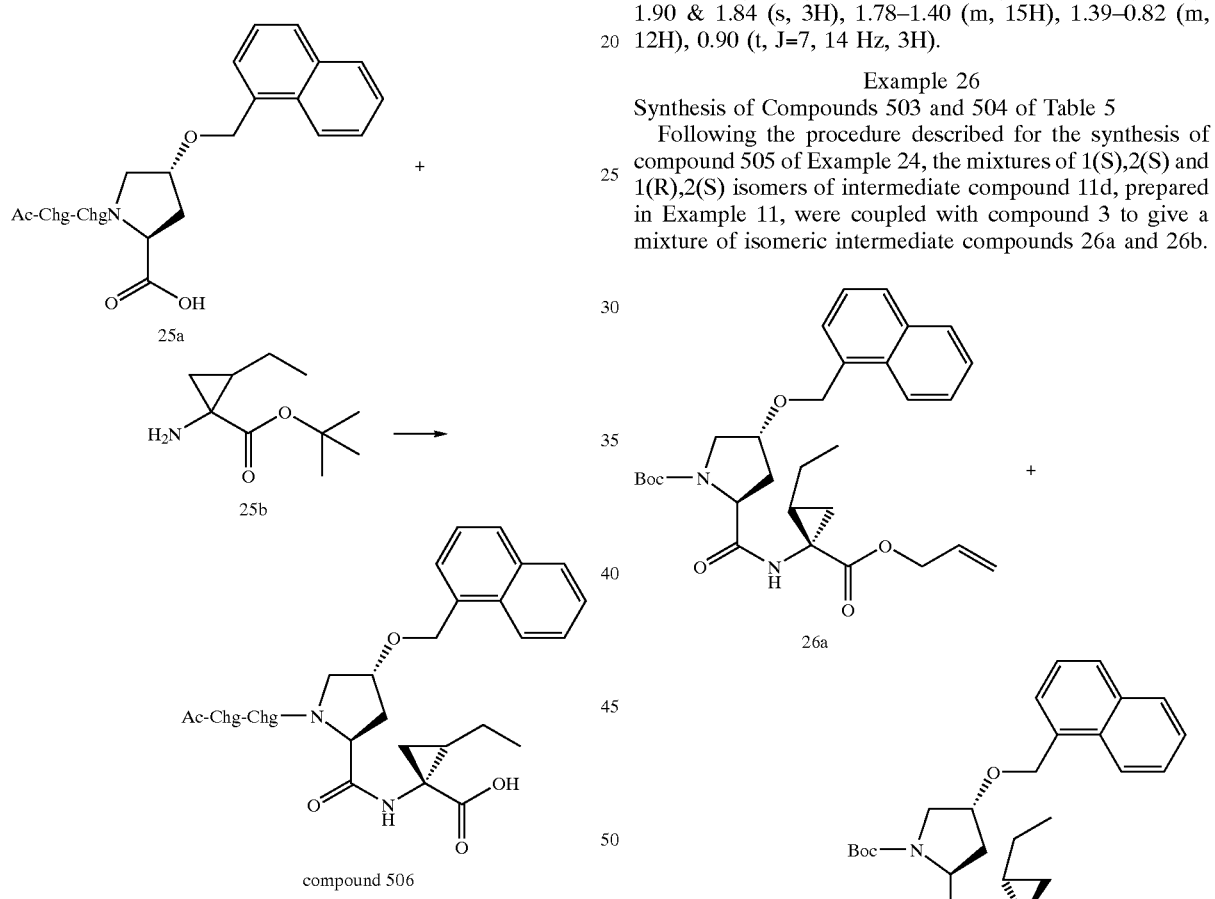

compound 506

Compound 25b, i.e. corresponding to compound 6f of Example 6, was coupled to the preformed tripeptide 25a described previously in Example 15. More specifically, compound 25b (ca.0.521 mmol) was combined with compound 25a (323.6 mg, 0.547 mmol) in DCM (3 mL) and NMM (172 μL, 1.562 mmol), followed by the addition of HATU (237.6 mg, 0.625 mmol). The reaction mixture was stirred at RT for 18 h, after which it was worked up as described for compound 20d to give the crude tetrapeptide as a racemic mixture at P1. Both isomers were partially separated by flash chromatography (eluent-toluene:EtOAc; 40:60). Combination of the first eluting fractions gave a 9:1 mixture in which analogous tert-butyl ester of 24f was the major component (58 mg). The middle fractions contain different ratios of the corresponding tert-butyl esters of 24f and compound 506 t-butyl ester (163 mg). The latter eluting fractions provided the corresponding tert-butyl ester of compound 506 as the major isomer (75.8 mg).

The latter ester (74 mg, 0.0975 mmol) was dissolved in 4N HCl/dioxane (2 mL), stirred at RT for 5.5 h then evaporated to dryness to give an oil. Purification by flash chromatography (eluent-1$^{st}$ EtOAc, then 2$^{nd}$ 1.92% HOAc, 3.85% MeOH, in DCM) yielded, after lyophilization, compound 603 as a white-amorphous solid (38.7 mg, 56% yield). HPLC analysis indicated a 3:1 ratio of compound 506 and compound 505. MS and NMR data for compound 603: MS (FAB) 701.5 MH⁻ 703.5 MH⁺ 725.6 (M+Na)⁺. $^1$H NMR (DMSO), ca.1:2.5 mixture of rotamers, δ 8.76 & 8.34 (s, 1H), 8.05 (bd, J=7.5 Hz, 1H), 7.94 (bd, J=8 Hz, 1H), 7.88 (d, J=8.5 Hz, 1H), 7.85–7.78 (m, 2H), 7.59–7.43 (m, 4H), 4.99 (d, J=12 Hz, 1H), 4.89 (d, J=12 Hz, 1H), 4.41–4.05 (m, 5H), 3.82–3.66 (m, 1H), 2.25–2.11 (m, 1H), 2.11–1.98 (m, 1H), 1.90 & 1.84 (s, 3H), 1.78–1.40 (m, 15H), 1.39–0.82 (m, 12H), 0.90 (t, J=7, 14 Hz, 3H).

Example 26
Synthesis of Compounds 503 and 504 of Table 5

Following the procedure described for the synthesis of compound 505 of Example 24, the mixtures of 1(S),2(S) and 1(R),2(S) isomers of intermediate compound 11d, prepared in Example 11, were coupled with compound 3 to give a mixture of isomeric intermediate compounds 26a and 26b.

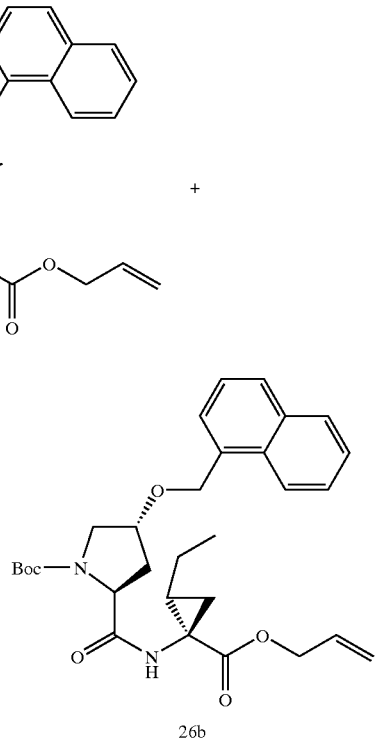

Following the procedures of Example 25, isomeric compounds 26a and 26b were separated and transformed into their corresponding compound of formula I; namely, the corresponding compound 503 and 504 of Table 5.

Spectral data:
Compound 503 of Table 5: Rotamer population by NMR ca. (1:8.7):
MS (FAB) m/z: 703 (MH+): 1H-NMR (DMSO-d₆) δ 8.21–8.09 (bs, 1H), 8.05 (bd, J=7.63 Hz, 1H), 7.94 (bd, J=7.0 Hz, 1H), 7.91–7.83 (m, 2H), 7.83–7.76 (m, 1H), 7.59–7.5 (m, 3H), 7.5–7.43 (m, 1H), 4.99 (d, J=11.8 Hz, 1H), 4.89 (d, J=11.8 Hz, 1H), 4.43–4.30 (m, 3H), 4.23–4.16 (m, 1H), 4.13 (bd, J=10.8 Hz, 1H), 3.71 (dd, J=11.1, 4 Hz, 1H), 2.2–2.02 (m, 2H), 1.87 and 1.84 (2×s, 3H), 1.81–1.71 (m, 2H), 1.70–1.40 (m, 12H), 1.26–1.06 (m, 4H), 1.04–0.83 (m, 11H), 0.59 (m, 1H).

Compound 504 of Table 5: Rotamer population by NMR ca. (1:9.5):

MS (FAB) m/z: 703 (MH$^+$); $^1$H-NMR (DMSO-d$_6$) δ 8.11–8.03 (m, 2H), 7.94 (bd, J=7.31 Hz, 1H), 7.90–7.83 (m, 2H), 7.79 (d, J=8.9 Hz, 1H), 7.59–7.50 (m, 3H), 7.50–7.44 (m, 1H), 4.99 (d, J=12.1 Hz, 1H), 4.91 (d, J=12.1 Hz, 1H), 4.41–4.30 (m, 3H), 4.23–4.16 (m, 1H), 4.15–4.09 (m, 1H), 3.77 (dd, J=3.8 Hz, 1H), 2.27–2.17 (m, 1H), 2.11–2.02 (m, 1H), 1.90 and 1.84 (2×s, 3H), 1.76–1.41 (m, 12H), 1.40–1.34 (m, 1H), 1.20–1.06 (m, 5H), 1.03–0.84 (m, 11H), 0.64–0.58 (m, 1H).

Example 27

Synthesis of Compound 509 of Table 5

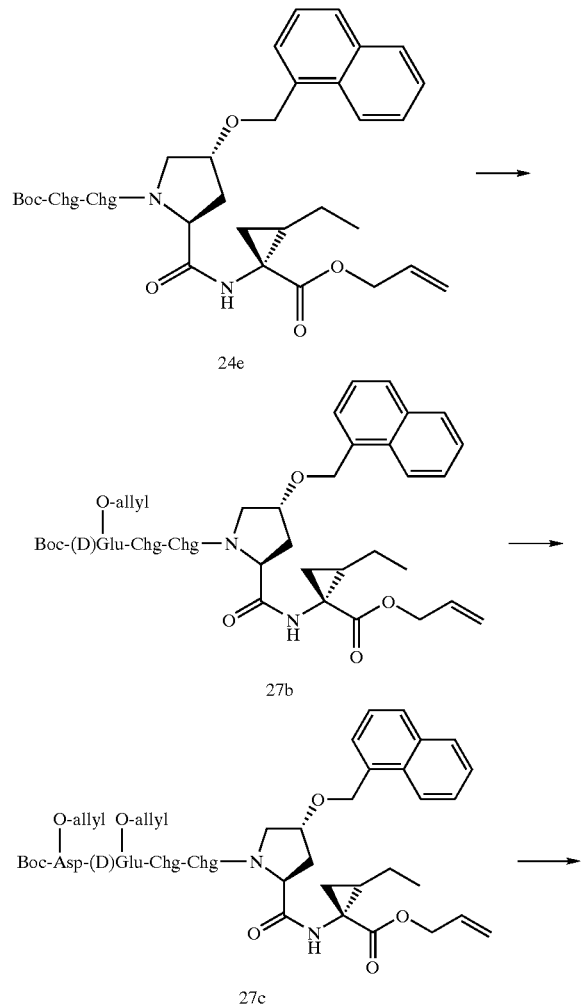

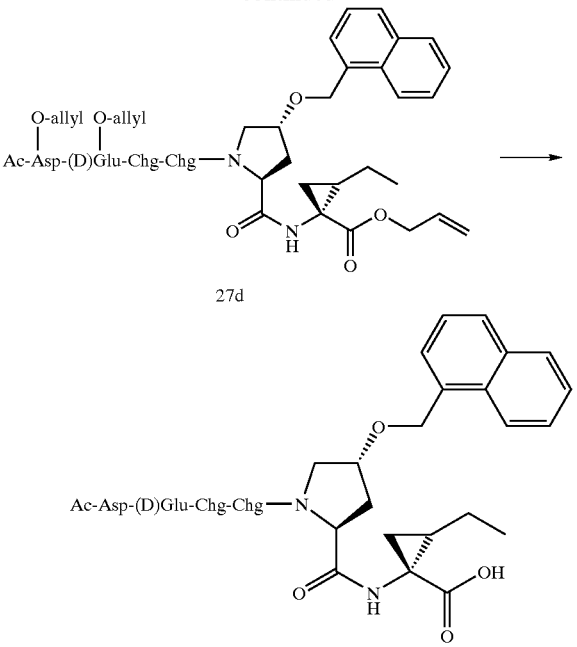

Compound 509

The crude tetrapeptide 24e from Example 24 (ca.0.963 mmol) was treated with 4N HCl/dioxane solution (5 mL) as described for compound 20c. The crude hydrochloride salt was coupled to Boc-(D)Glu(O-allyl)-OH (331.9 mg, 1.155 mmol) with NMM (423 μl, 3.850 mmol) and TBTU (370.8 mg, 1.155 mmol) in DCM (5 mL) for 3 h at RT as described for compound 20d. The crude pentapeptide 27b was obtained as an ivory foam (ca.933.9 mg, 0.963 mmol). MS (FAB) 968.6 MH$^-$ 970.6 MH$^+$ 992.5 (M+Na).

$^1$H NMR (CDCl$_3$), ca.1:4 mixture of rotamers. δ 8.05 (d, J=8.5 Hz, 1H), 7.87 (bd, J=7.5 Hz, 1H), 7.81 (d, J=8.5 Hz, 1H), 7.58–7.34 (m, 5H), 6.77–6.25 (m, 2H), 5.98–5.77 (m, 2H), 5.38–5.21 (m, 4H), 5.16 (dd, J=1.5, 10.5 Hz, 1H), 5.06–4.89 (m, 2H), 4.68–4.13 (m, 7H), 3.96–3.52 (m, 4H), 2.69–2.38 (m, 3H), 2.23–1.87 (m, 2H), 1.78–1.37 (m, 17H), 1.46 & 1.44 (s, 9H), 1.22–0.87 (m, 11H), 0.95 (t, J=7, 14.5 Hz, 3H).

The crude pentapeptide 27b (ca.0.963 mmol) was treated with 4N HCl/dioxane solution (5 mL) as described for compound 20c. The crude hydrochloride salt was coupled to Boc-Asp(O-allyl)-OH (315.6 mg, 1.155 mmol) with NMM (423 μl, 3.85 mmol) and TBTU (370.8 mg, 1.155 mmol) in DCM (5 mL) as described for compound 20d. The crude hexapeptide 27c was obtained as an ivory foam (ca.1.083 g, 0.963 mmol). MS (FAB) 1147.6 (M+Na)$^+$. $^1$H NMR (CDCl$_3$), ca.1:1 mixture of rotamers, δ 8.06 (bd, J=8 Hz, 1H), 7.86 (d, J=8 Hz, 1H), 7.81 (d, J=8 Hz, 1H), 7.59–7.39 (m, 5H), 7.39–6.34 (m, 4H), 5.98–5.76 (m, 3H), 5.38–5.10 (m, 6H), 5.10–4.89 (m, 2H), 4.66–4.05 (m, 10H), 3.87–3.58 (m, 4H), 3.30–2.65 (m, 2H), 2.65–1.89 (m 3H), 1.79–1.33 (m, 19H), 1.47 & 1.45 (s, 9H), 1.33–0.86 (m, 14H). The crude hexapeptide 27c (ca.0.963 mmol) was treated with 4N HCl/dioxane solution (5 mL) as described for compound 20c. The crude hydrochloride was acetylated with acetic anhydride (182 μl, 1.193 mmol) and NMM (423.5 μL, 3.850 mmol) in DCM (5 mL) as described for compound 20f to provide the crude acetylated tetrapeptide. The foam residue was purified by flash chromatography (eluent: 1$^{st}$ hexane:EtOAc 20:80 to 10:90 and 2$^{nd}$ pure EtOAc) to provide the acetylated hexapeptide 27d as an ivory foam (528 mg, 51% yield over 4 steps). MS (FAB) 1067.6 (MH⁺) 1089.6 (M+Na).

The acetylated hexapeptide 27d (528 mg, 0.495 mmol) was dissolved in DCM (3 mL) and treated with a premixed, 15 min stirred solution of tetrakis(triphenylphosphine)-palladium (0) catalyst (90 mg, 0.078 mmol) and pyrrolidine (134 μL, 1.603 mmol) in DCM (3 mL). The reaction mixture was stirred at RT for 48 h after which the solvent was evaporated. The crude product was purified partially by trituration in Et₂O: DCM (85:15), then, purified in two bathes by preparatory HPLC. Half of the partially purified material was dissolved in glacial HOAc (5 mL), filtered through a Millipore®: Millex®-HV 0.45 μm filter and injected onto an equilibrated Whatman Partisil® 10-ODS-3 (2.2×50 cm) C₁₈ reverse phase column. Purification program linear gradient at 15 mL/min, 230 μm, injected at 5% A; once all HOAc had eluted the program was begun—at 5% A for 10 min, 5–58%A in 70 min: A: 0.06%TFA/CH₃CN; B: 0.06%/TFA/H₂O. Fractions were analyzed by analytical HPLC, appropriate fractions from both HPLC purifications were collected and lyophilized to provide the desired hexapeptide compound 509 of Table 5, as a white amorphous solid (218.3 mg, 47% yield).

MS (FAB) 945.5 MH⁻ 947.4 MH⁺ 969.5 (M+Na)⁺ 985.4 (M+K)⁺. ¹H NMR (DMSO), ca.1:9 mixture of rotamers, δ 8.55 & 8.31 (s, 1H), 8.16 (d, J=7.5 Hz, 1H), 8.11 (d, J=8 Hz, 1H), 8.05 (d, J=8.5 Hz, 1H), 7.97–7.85 (m, 2H), 7.88 (d, J=8.5 Hz, 1H), 7.75 (d, J=9 Hz, 1H), 7.59–7.39 (m, 4H), 4.99 (d, J=12 Hz, 1H), 4.89 (d, J=12 Hz, 1H), 4.53 (dd, J=7, 14 Hz, 1H), 4.08–4.45 (m, 6H), 3.77 (bdd, J=4, 11 Hz, 1H), 2.64 (dd, J=6.5, 16.5 Hz, 1H), 2.48–2.41 (m, 1H), 2.25–2.12 (m, 3H), 2.07 & 1.82 (s, 3H), 2.04–1.86 (m, 2H), 1.80–1.35 (m, 14H), 1.32–0.80 (m, 14H), 0.91 (t, J=7.5, 14.5 Hz, 3H).

Example 28

Synthesis of Compound 701 of Table 7

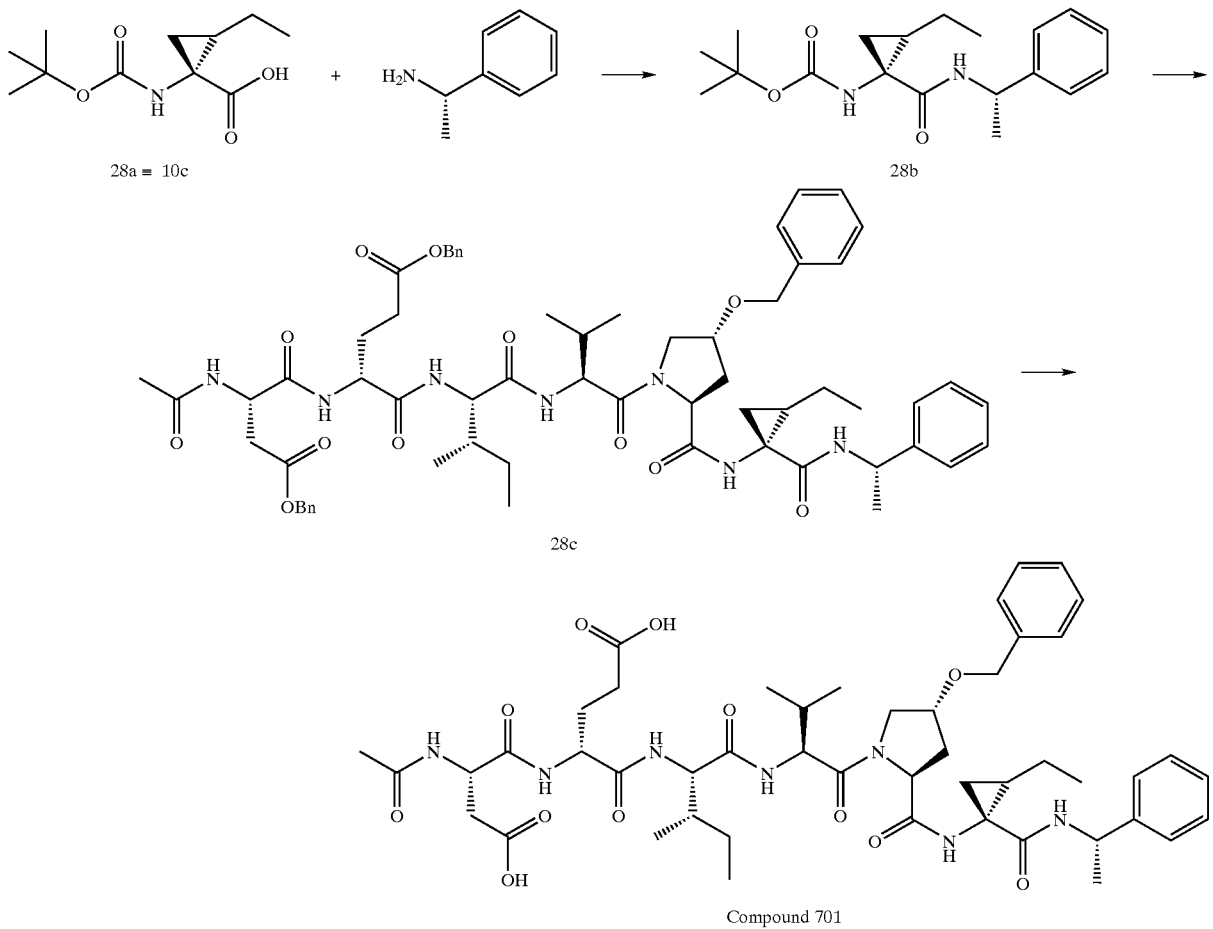

A solution of lithium hydroxide monohydrate (23 mg, 0.56 mmol) in H₂O (4 mL) was added to a solution of the ester compound 28a (45 mg, 0.185 mmol, described previously as the (R,R) isomer 10c) in MeOH (3.5 mL) and THF (3.5 mL). The resulting solution was stirred vigorously for 16 h and then partitioned between EtOAc (60 mL) and 10% aqueous HCl (20 mL). The organic phase was separated, dried (MgSO₄), filtered and concentrated to give the corresponding acid in quantitative yield.

This material (ca. 0.185 mmol) was combined with (S)-(−)-α-methylbenzylamine (27 mg, 0.22 mmol), HATU (77 mg. 0.20 mmol), and DIPEA (0.11 mL, 0.65 mmol) in DMF (5 mL). After 20 h. the reaction was concentrated. The residue dissolved in EtOAc and the solution was washed sequentially with saturated aqueous NaHCO₃, 10% aqueous HCl, and brine before being dried (MgSO₄), filtered and concentrated in vacua. Purification by flash chromatography (eluent: 35% EtOAc/hexane) gave 11 mg (28%) of the coupled product 28b. This material (11 mg, 0.033 mmol) was treated with 4N HCl/dioxane for 35 min. The reaction mixture thereafter was concentrated to dryness to give the hydrochloride salt of the corresponding amine.

The latter product was coupled with:

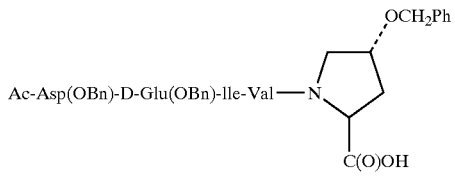

(33 mg, 0.036 mmol, prepared by procedures analogous to those of Example 20 and 27), HATU (14 mg, 0.036 mmol) and DIPEA (0.116 mL, 0.02 mmol) in DMF (4 mL). After the reaction mixture has been stirred 16 h, the mixture was concentrated. The residue was dissolved in EtOAc. The solution was washed sequentially with saturated aqueous NaHCO$_3$, 10% aqueous HCl and brine, dried (MgSO$_4$), filtered and concentrated in vacuo to give a white solid. This material (ca. 0.033) was dissolved in EtOH (6 mL) and treated with ammonium acetate (7 mg, 0.09 mmol) and 10% Pd/C (10 mg) under an atmosphere of hydrogen gas. After 3 h, the reaction mixture was filtered through diatomaceous earth. The filtrate was concentrated to dryness. The residue was then dissolved in DMSO and purified by preparative HPLC to give a white solid after lyophilization (17.6 mg, 57% yield over two steps).

Spectral data: MS (FAB) ES$^-$ 932.6 (M–H)$^-$, 954.5 (M–Na)$^-$; HRMS calcd for C$_{48}$H$_{67}$N$_7$O$_{12}$ (MH$^+$) 934.49261, found: 934.49010; $^1$H-NMR (DMSO, d$_6$) δ 8.90 (s, 1H), 8.24 (d, J=7.95 Hz, 1H), 8.14 (d, J=7.63 Hz, 1H), 7.99 (d, J=8.26 Hz, 1H), 7.79 (d, J=8.9 Hz, 1H), 7.75 (d, J=8.26 Hz, 1H), 7.42–7.17 (m, 10H), 5.00 (quintet, J=7.63 Hz, 1H), 4.7 (m, 1H), 4.52 (d, J=11.76 Hz, 1H), 4.43 (d, J=11.4 Hz, 1H), 4.33–4.2 (m, 6H), 3.70 (dd, J=11.4 and 11.1 Hz, 2H), 2.63 (dd, J=5.7 and 5.7 Hz, 1H), 2.45 (dd, J=7.95 and 7.95 Hz, 1H), 2.21–2.11 (m, 3H), 2.07–1.97 (m, 1H), 1.93–1.83 (m, 2H), 1.81 (s, 3H), 1.78–1.63 (m, 2H), 1.54–1.41 (m, 2), 1.39 (d, J=7.0 Hz, 3H), 1.29 (dd, J=7.94 and 7.63 Hz, 1H), 1.15 (quintet, J=7.0 Hz, 1H), 1.05 (m, 1H), 0.90 (d, J=6.36 Hz, 6H), 0.88–0.83 (m, 1H), 0.71 (m, 9H), Example 29

Compound 508 of Table 5 was synthesized according to the protocol described in Example 24.

Rotamer population by NMR (1:7.6)

MS (FAB) m/z: 675 (MH+); $^1$H-NMR (DMSO-d$_6$) δ 8.35–8.19 (bs, 1H), 8.04 (d, J=7.63 Hz, 1H), 7.93 (bd, J=7.31 Hz, 1H), 7.88 (d, J=8.27 Hz, 1H), 7.86–7.79 )m, 2H), 7.59–7.49 (m, 3H), 7.46 (dd, J=7.95, 7.95 Hz, 1H), 4.98 (d, J=11.8 Hz, 1H), 4.89 (d, J=11.8 Hz, 1H), 4.40–4.34 (m, 1H), 4.32 (bs, 1H), 4.29–4.24 (m, 1H), 4.22–4.15 (m, 1H), 4.09 (d, J=11.8 Hz, 1H), 3.74 (dd, J=11.1, 4 Hz, 1H), 2.20–2.12 (m, 1H), 2.05–1.94 (m, 2H), 1.84 (s, 3H), 1.72–1.42 (m, 7H), 1.20–1.13 (m, 1H), 1.08–0.87 (m, 13H), 0.85 (d, J=6.68 Hz, 6H),

Example 30

Compound 515 of Table 5 was synthesized according to the protocol described in Example 24.

Rotamer population by NMR (1:7.5):

MS (FAB) m/z: 747 (M+Na+); $^1$H-NMR (DMSO-d$_6$) δ 8.40–8.24 (bs, 1H), 8.07–8.01 (m, 1H), 7.96–7.91 (m, 1H), 7.87 (d J=8.26 Hz, 1H), 7.85–7.78 (m, 2H), 7.58–7.49 (m, 3H), 7.46 (dd, J=7.95, 7.95 Hz, 1H), 7.30–7.21 (m, 4H), 7.20–7.14 (m, 1H), 4.98 (d, J=11.8 Hz, 1H), 4.89 (d, J=11.8 Hz, 1H), 4.40–4.34 (m, 1H), 4.34–4.29 (m, 1H), 4.29–4.25 (m, 1H), 4.22–4.15 (m, 1H), 4.09 (d, J=11.8 Hz, 1H), 3.74 (dd, J=11.1, 4 Hz, 1H), 2.95–2.79 (m, 2H), 2.21–2.11 (m, 1H), 2.05–1.94 (m, 2H), 1.89–1.83 (2×s, 3H), 1.63–1.41 (m, 7H), 1.38–1.30 (m, 1H), 1.27–1.22 (m, 1H), 1.12–0.94 (m, 5H), 0.89 (d, J=6.4 Hz, 3H), 0.84 (d, J=6.4 Hz, 3H).

Example 31

Compound 519 of Table 5 was synthesized according to the protocol described in Example 24.

Rotamer population by NMR ca. (1:6.3):

MS (FAB) m/z: 677.4 (MH+); $^1$H-NMR (DMSO-d$_6$) δ 8.58 and 8.38 (2×bs, 1H), 8.04 (d, J=7.63 Hz, 1H), 7.93 (d, J=7.63 Hz, 1H), 7.91–7.81 (m, 3H), 7.59–7.49 (m, 3H), 7.49–7.43 (m, 1H), 4.98 (d, J=12.1 Hz, 1H), 4.89 (d, J=12.1 Hz, 1H), 4.41–4.29 (m, 2H), 4.29–4.14 (m, 2H), 4.1 (d, J=10.8 Hz, 1H), 3.74 (bd, J=7.63 Hz, 1H), 2.21–2.12 (m, 1H), 2.04–1.92 (m, 2H), 1.90 and 1.84 (2×s, 3H), 1.63–1.41 (m, 9H), 1.39–1.26 (m, 3H), 1.21–1.15 (m, 1H), 1.06–0.92 (m, 5H), 0.92–0.80 (m, 9H).

Example 32

Compound 517 of Table 5 was synthesized according to the protocol described in Example 24.

$^1$H NMR (DMSO-d$_6$) δ 8.36 (s, 1H), 8.14 (d, J=8 Hz, 1H), 8.04 (d, J=8 Hz, 1H), 7.99 (d, J=9 Hz, 1H), 7.79 (d, J=9 Hz, 1H), 7.33–7.26 (m, 5H), 4.54–4.42 (m, 3H), 4.30–4.21 (m, 5H), 4.06 (d, J=11 Hz, 1H), 3.69 (dd, J=Hz, 1H), 2.62 (dd, J=16, 10 Hz, 1H), 2.47–2.42 (m, 1H), 2.18–2.14 (m, 3H), 2.02–1.87 (m, 2H), 1.82 (s, 3H), 1.74–1.66 (m, 2H), 1.54–1.47 (m, 2H), 1.38–1.27 (m, 2H), 1.21–1.18 (m, 1H), 0.97–0.85 (m, 11H), 0.80–0.70 (m, 7H),

Example 33

Compound 522 of Table 5 was synthesized according to the protocol described in Example 24.

$^1$H NMR (DMSO-d$_6$) δ 9.12 (d, J=6 Hz, 1H), 8.64 (s, 1H), 8.30 (d, J=8 Hz, 1H), 8.12 (d, J=9 Hz, 1H), 8.05 (dd, J=8, 7 Hz, 1H), 7.97 (d, J=8 Hz, 1H), 7.80 (dd, J=8, 7 Hz, 1H), 7.66 (d, J=9 Hz, 1H), 7.54 (d, J=6 Hz, 1H), 5.70–5.61 (m, 2H), 5.26 (d, J=17 Hz, 1H), 5.07 (d, J=12 Hz, 1H), 4.52 (d, J=12 Hz, 1H), 4.39 (dd, J=9, 8 Hz, 1H), 4.23–4.12 (m, 2H), 4.03–3.99 (m, 1H), 2.66–2.54 (m, 1H), 2.5–2.28 (m, 1H), 2.08 (dd, J=9, 17 Hz, 1H), 2.01–1.93 (m, 1H), 1.83 (s, 3H), 1.65–1.46 (m, 5H), 1.41–1.38 (m, 1H), 1.24–1.20 (dd, J=9, 5 Hz, 1H), 01.05–0.78 (m, 12H),

Example 34

C compound 605 of Table 5 was synthesized according to the protocol described in Example 24.

$^1$H NMR (DMSO-d$_6$) δ 9.14 (d, J=6 Hz, 1H), 8.60 (s, 1H), 8.32 (d, J=8 Hz, 1H), 8.14–8.06 (m, 2H), 7.98 (d, J=8 Hz, 1H), 7.82 (dd, J=8, 7 Hz, 1H), 7.66 (d, J=9 Hz, 1H), 7.55 (d, J=8 Hz, 1H), 5.75–5.66 (m, 2H), 5.22 (d, J=17 Hz, 1H), 5.07 (d, J=10 Hz, 1H), 4.50 (d, J=12 Hz, 1H), 4.39 (dd, J=9, 9 Hz, 1H), 4.23–4.08 (m, 3H), 2.56–2.50 (m, 1H), 2.36–2.28 (m, 1H), 2.04–1.97 (m, 1H), 1.82 (s, 3H), 1.62–1.41 (m, 7H), 1.24 (dd, J=5, 4 Hz, 1H), 0.94–0.75 (m, 12H).

Example 35

Compound 518 of Table 5 was synthesized according to the protocol described in Example 27.

$^1$H NMR (DMSO-d$_6$) δ 8.36 (s, 1H), 8.17 (d, J=8 Hz, 1H), 8.09 (d, J=8 Hz, 1H), 8.04 (d, J=8 Hz, 1H), 7.96–7.92 (m, 2H), 7.87 (d, J=8 Hz, 1H), 7.77 (d, J=9 Hz, 1H), 7.56–7.45 (m, 4H), 4.99 (d, J=12 Hz, 1H), 4.89 (d, J=12 Hz, 1H), 4.52 (dd, J=14, 7 Hz, 1H), 4.37–4.12 (m, 6H), 3.78–3.73 (m, 1H), 2.63 (dd, J=17, 6 Hz, 1H), 2.47–2.42 (m, 1H), 2.22–2.16 (m, 3H), 2.04–1.86 (m, 2H), 1.82 (s, 3H), 1.77–171 (m, 1H), 1.69–1.42 (m, 8H), 1.30 (quint., J=8 Hz, 1H), 1.20 (dd, J=12, 8 Hz, 1H), 1.10–0.85 (m, 15H), 0.76–0.72 (m, 1H),

Example 36

Compound 521 of Table 5 was synthesized according to the protocol described in Example 27.

$^1$H NMR (DMSO-d$_6$) δ 8.34 (s, 1H), 8.12 (d, J=8 Hz, 1H), 8.05 (d, J=8 Hz, 1H), 7.95–7.87 (m, 3H), 7.81 (d, J=9 Hz, 1H), 7.64–7.52 (m, 4H), 7.46 (dd, J=8, 7 Hz, 1H), 4.99 (d, J=12 Hz, 1H), 4.89 (d, J=12 Hz, 1H), 4.63 (dd, J=14, 7 Hz, 1H), 4.37–4.14 (m, 4H), 3.74 (dd, J=11, 4 Hz, 1H), 3.41–3.35 (m, 2H), 2.61 (dd, J=16, 7 Hz, 1H), 2.44 (dd, J=16, 8 Hz, 1H), 2.20–2.15 (m, 1H), 2.04–1.96 (m, 3H), 1.82 (s, 3H), 1.70–1.64 (m, 1H), 1.56–1.43 (m, 7H), 1.30 (quint., J=8 Hz, 1H), 1.20 (dd, J=8, 5 Hz, 1H), 0.99–0.72 (m, 21H),

Example 37

Cloning, Expression and Purification of the Recombinant HCV NS3 Protease type 1b.

Serum from an HCV-infected patient was obtained through an external collaboration (Bernard Willems MD, Hôpital St-Luc. Montréal. Canada and Dr. Donald Murphy, Laboratoire de Santé Publique du Québec, Ste-Anne de Bellevue, Canada). An engineered full-length cDNA template of the HCV genome was constructed from DNA fragments obtained by reverse transcription-PCR (RT-PCR) of serum RNA and using specific primers selected on the basis of homology between other genotype 1b strains. From the determination of the entire genomic sequence, a genotype 1b was assigned to the HCV isolate according to the classification of Simmonds et al. (J. Clin. Microbiol., (1993), 31, p.1493–1503). The amino acid sequence of the non-structural region, NS2-NS4B, was shown to be greater than 93% identical to HCV genotype 1b (BK, JK and 483 isolates) and 88% identical to HCV genotype 1a (HCV-1 isolate). A DNA fragment encoding the polyprotein precursor (NS3/NS4A/NS4B/NS5A/NS5B) was generated by PCR and introduced into eukaryotic expression vectors. After transient transfection, the polyprotein processing mediated by the HCV NS3 protease was demonstrated by the presence of the mature NS3 protein using Western blot analysis. The mature NS3 protein was not observed with expression of a polyprotein precursor containing the mutation S1165A, which inactivates the NS3 protease, confirming the functionality of the HCV NS3 protease.

The DNA fragment encoding the recombinant HCV NS3 protease (amino acid 1027 to 1206) was cloned in the pET11d bacterial expression vector. The NS3 protease expression in E. coli BL21(DE3)pLysS was induced by incubation with 1 mM IPTG for 3 h at 22° C. A typical fermentation (18 L) yielded approximately 100 g of wet cell paste. The cells were resuspended in lysis buffer (3.0 mL/g) consisting of 25 mM sodium phosphate, pH 7.5, 10% glycerol (v/v), 1 mM EDTA, 0.01% NP-40 and stored at −80° C. Cells were thawed and homogenized following the addition of 5 mM DTT. Magnesium chloride and DNase were then added to the homogenate at final concentrations of 20 mM and 20 μg/mL respectively. After a 25 min incubation at 4° C., the homogenate was sonicated and centrifuged at 15000×g for 30 min at 4° C. The pH of the supernatant was then adjusted to 6.5 using a 1 M sodium phosphate solution.

An additional gel filtration chromatography step was added to the 2 step purification procedure described in WO 95/22985 (incorporated herein by reference). Briefly, the supernatant from the bacterial extract was loaded on a SP HiTrap column (Pharmacia) previously equilibrated at a flow rate of 2 mL/min in buffer A (50 mM sodium phosphate. pH 6.5, 100% glycerol, 1 mM EDTA, 5 mM DTT, 0.01% NP-40). The column was then washed with buffer A containing 0.15 M NaCl and the protease eluted by applying 10 column volumes of a linear 0.15 to 0.3 M NaCl gradient. NS3 protease-containing fractions were pooled and diluted to a final NaCl concentration of 0.1 M. The enzyme was further purified on a HiTrap Heparin column (Pharmacia) equilibrated in buffer B (25 mM sodium phosphate, pH 7.5, 10% glycerol, 5 mM DTT, 0.01% NP-40). The sample was loaded at a flow rate of 3 mL/min. The column was then washed with buffer B containing 0.15 M NaCl at a flow rate of 1.5 mL/min. Two step washes were performed in the presence of buffer B containing 0.3 or 1 M NaCl. The protease was recovered in the 0.3M NaCl wash, diluted 3-fold with buffer B, reapplied on the HiTrap Heparin column and eluted with buffer B containing 0.4 M NaCl. Finally, the NS3 protease-containing fractions were applied on a Superdex 75 HiLoad 16/60 column (Pharmacia) equilibrated in buffer B containing 0.3 M NaCl. The purity of the HCV NS3 protease obtained from the pooled tractions was judged to be greater than 95% by SDS-PAGE followed by densitometry analysis.

The enzyme was stored at −80° C. and was thawed on ice and diluted just prior to use.

Example 38

Recombinant HCV NS3 Protease Radiometric Assay

The substrate used for the HCV NS3 protease radiometric assay, DDIVPC-SMSYTW [SEQ. ID NO. 2], is cleaved between the cysteine and the serine residues by the enzyme. The sequence DDIVPC-SMSYTW [SEQ. ID NO. 2] corresponds to the NS5A/NS5B natural cleavage site in which the cysteine residue in P2 has been substituted for a proline. The peptide substrate DDIVPC-SMSYTW [SEQ. ID NO. 2] and the tracer biotin-DDIVPC-SMS[ $^{125}$I-YW [SEQ. ID NO. 3] were incubated with the recombinant NS3 protease in the absence or in the presence of inhibitors. The separation of substrate from products was performed by adding avidin-coated agarose beads to the assay mixture followed by filtration. The amount of SMS[$^{125}$I-Y]TW [SEQ. ID NO. 4] product found in the filtrate (with or without inhibitor) allowed for the calculation of the percentage of substrate conversion and of the percentage of inhibition.

A. Reagents

Tris and Tris-HCl (UltraPure) were obtained from Life Technologies, Glycerol (UltraPure), MES and BSA were purchased from Sigma®. TCEP was obtained from Pierce, DMSO from Aldrich® and NaOH from Anachemia®. Assay buffer, 50 mM Tris-HCl, pH 7.5, 30% (w/v) glycerol, 2% (w/v) CHAPS, 1 mg/mL BSA, 1 mM TCEP (TCEP added just prior to use from a 1 M stock solution in water).

Substrate: DDIVPC-SMSYTW [SEQ. ID NO. 2], 25 μM final concentration (from a 2 mM stock solution in DMSO stored at −20° C. to avoid oxidation).

Tracer: reduced mono-iodinated substrate(biotin-DDIVPC-SMS[$^{125}$I-Y]TW) [SEQ. ID NO. 3](≈1 nM final concentration).

HCV NS3 protease type 1b, 25 nM final concentration (from a stock solution in 50 mM sodium phosphate, pH 7.5, 10% glycerol, 300 mM NaCl, 5 mM DTT, 0.01% NP-40).

B. Protocol

The assay was performed in a 96-well polypropylene plate. Each well contained:

20 µL substrate/tracer in assay buffer;

10 µL±inhibitor in 20% DMSO/assay buffer;

10 µL NS3 protease 1b.

Blank (no inhibitor and no enzyme) and control (no inhibitor) were also prepared on the same assay plate.

The enzymatic reaction was initiated by the addition of the enzyme solution and the assay mixture was incubated for 60 min at 23° C. under gentle agitation. Twenty (20) µL of 0.025 N NaOH were added to quench the enzymatic reaction. Twenty (20) µL of avidin-coated agarose beads (purchased from Pierce®) were added in a Millipore® MADP N65 filtration plate. The quenched assay mixture was transferred to the filtration plate, and incubated for 60 min at 23° C. under gentle agitation.

The plates were filtered using a Millipore® MultiScreen Vacuum Manifold Filtration apparatus, and 40 µL of the filtrate was transferred to an opaque 96-well plate containing 60 µL of scintillation fluid per well.

The filtrates were counted on a Packard® TopCount instrument using a $^{125}$I-liquid protocol for 1 minute.

The %inhibition was calculated with the following equation:

$$100-[(\text{counts}_{inh}-\text{counts}_{blank})/(\text{counts}_{ctl}-\text{counts}_{blank}) \times 100]$$

A non-linear curve fit with the Hill model was applied to the inhibition-concentration data, and the 50% effective concentration (IC$_{50}$) was calculated by the use of SAS software (Statistical Software System; SAS Institute, Inc. Cary, N.C.).

Example 39

Recombinant HCV NS3 Protease/NS4A Cofactor Peptide Radiometric Assay.

The enzyme was cloned, expressed and prepared according to the protocol described in Example 37. The enzyme was stored at –80° C., thawed on ice and diluted just prior to use in the assay buffer containing the NS4A cofactor peptide.

The substrate used for the NS3 protease/NS4A cofactor peptide radiometric assay, DDIVPC-SMSYTW [SEQ. ID NO. 2], is cleaved between the cysteine and the serine residues by the enzyme. The sequence DDIVPC-SMSYTW [SEQ. ID NO. 2] corresponds to the NS5A/NS5B natural cleavage site in which the cysteine residue in P2 has been substituted for a proline. The peptide substrate DDIVPC-SMSYTW [SEQ. ID NO. 2] and the tracer biotin-DDIVPC-SMS[$^{125}$I-Y]TW [SEQ. ID NO. 3] are incubated with the recombinant NS3 protease and the NS4A peptide cofactor KKGSVVIVGRIILSGRK [SEQ. ID NO. 5] (molar ratio enzyme: cofactor 1:100) in the absence or presence of inhibitors. The separation of substrate from products is performed by adding avidin-coated agarose beads to the assay mixture followed by filtration. The amount of SMS[$^{125}$I-Y]TW [SEQ. ID NO. 4] product found in the filtrate allows for the calculation of the percentage of substrate conversion and of the percentage of inhibition.

A. Reagents

Tris and Tris-HCl (UltraPure) were obtained from Gibco-BRL. Glycerol (UltraPure), MES and BSA were purchased from Sigma. TCEP was obtained from Pierce, DMSO from Aldrich and NaOH from Anachemia.

Assay buffer: 50 mM Tris HCl, pH 7.5, 30% (w/v) glycerol, 1 mg/mL BSA, 1 mM TCEP (TCEP added just prior to use from a 1 M stock solution in water).

Substrate: DDIVPCSMSYTW [SEQ. ID NO. 2], 25 µM final concentration (from a 2 mM stock solution in DMSO stored at –20° C. to avoid oxidation).

Tracer: reduced mono iodinated substrate biotin DDIVPC SMS[$^{125}$I Y]TW [SEQ. ID NO. 3] (~1 nM final concentration).

HCV NS3 protease type 1b, 25 nM final concentration (from a stock solution in 50 mM sodium phosphate. pH 7.5, 10% glycerol, 300 mM NaCl, 5 mM DTT, 0.01% NP-40).

NS4A Cofactor peptide: KKGSVVIVGRIILSGRK [SEQ. ID NO. 5], 2.5 µM final concentration (from a 2 mM stock solution in DMSO stored at –20° C.).

B. Protocol

The assay was performed in a 96-well polypropylene plate from Costar. Each well contained:

20 µL substrate/tracer in assay buffer;

10 µL±inhibitor in 20% DMSO/assay buffer;

10 µL NS3 protease 1b/NS4 cofactor peptide (molar ratio 1:100).

Blank (no inhibitor and no enzyme) and control (no inhibitor) were also prepared on the same assay plate.

The enzymatic reaction was initiated by the addition of the enzyme/NS4A peptide solution and the assay mixture was incubated for 40 min at 23° C. under gentle agitation. Ten (10) µL of 0.5N NaOH were added and 10 µL 1 M MES, pH 5.8 were added to quench the enzymatic reaction.

Twenty (20) µL of avidin-coated agarose beads (purchased from Pierce) were added in a Millipore MADP N65 filtration plate. The quenched assay mixture was transferred to the filtration plate, and incubated for 60 min at 23° C. under gentle agitation.

The plates were filtered using a Millipore MultiScreen Vacuum Manifold Filtration apparatus, and 40 µL of the filtrate was transferred in an opaque 96-well plate containing 60 µL of scintillation fluid per well.

The filtrates were counted on a Packard TopCount instrument using a $^{125}$I-liquid protocol for 1 minute.

The % inhibition was calculated with the following equation:

$$100-[(\text{counts}_{inh}-\text{counts}_{blank})/(\text{counts}_{ctl}-\text{counts}_{blank}) \times 100]$$

A non-linear curve fit with the Hill model was applied to the inhibition-concentration data, and the 50% effective concentration (IC$_{50}$) was calculated by the use of SAS software (Statistical Software System; SAS Institute, Inc. Cary, N.C.).

Example 40

Full-length NS3-NS4A Heterodimer Protein Assay

The NS2-NS5B-3' non coding region was cloned by RT-PCR into the pCR®3 vector (Invitrogen) using RNA extracted from the serum of an HCV genotype 1b infected individual (provided by Dr. Bernard Willems, Hôpital St-Luc, Montréal, Québec, Canada). The NS3-NS4A DNA region was then subcloned by PCR into the pFastBac™ HTa baculovirus expression vector (Gibco/BRL). The vector sequence includes a region encoding a 28-residue N-terminal sequence which contains a hexahistidine tag.

The Bac-to-Bac™ baculovirus expression system (Gibco/BRL) was used to produce the recombinant baculovirus. The full length mature NS3 and NS4A heterodimer protein (His-NS3-NS4AFL) was expressed by infecting $10^6$ Sf21 cells/mL with the recombinant baculovirus at a multiplicity of infection of 0.1–0.2 at 27° C. The infected culture was harvested 48 to 64 h later by centrifugation at 4° C. The cell pellet was homogenized in 50 mM $NaPO_4$, pH 7.5, 40% glycerol (w/v), 2 mM β-mercaptoethanol, in presence of a cocktail of protease inhibitors. His-NS3-NS4AFL was then extracted from the cell lysate with 1.5% NP-40, 0.5% Triton X-100, 0.5M NaCl, and a DNase treatment. After ultracentrifugation, the soluble extract was diluted 4-fold and bound on a Pharmacia Hi-Trap Ni-chelating column. The His-NS3-NS4AFL was eluted in a >90% pure form (as judged by SDS-PAGE), using a 50 to 400 mM imidazole gradient. The His-NS3-NS4AFL was stored at −80° C. in 50 mM sodium phosphate, pH 7.5, 10% (w/v) glycerol, 0.5 M NaCl, 0.25 M imidazole, 0.1% NP-40. It was thawed on ice and diluted just prior to use. The protease activity of His-NS3-NS4AFL was assayed in 50 mM Tris-HCl, pH 8.0, 0.25 M sodium citrate, 0.01% (w/v) n-dodecyl-β-D-maltoside, 1 mM TCEP. Five (5) $\mu$M of the internally quenched substrate antiranilyl-DDIVPAbu[C(O)—O]-AMY(3-$NO_2$)TW-OH (SEQ. ID NO. 6] in presence of various concentrations of inhibitor were incubated with 1.5 nM of His-NS3-NS4AFL for 45 min at 23° C. The final DMSO concentration did not exceed 5.25%. The reaction was terminated with the addition of 1 M MES, pH 5.8. Fluorescence of the N-terminal product was monitored on a Perkin-Elmer LS-50B fluorometer equipped with a 96-well plate reader (excitation wavelength: 325 nm; emission wavelength: 423 nm). A non-linear curve fit using the Hill model was then applied to the % inhibition-concentration data and 50% effective concentration ($IC_{50}$) was calculated through the use of SAS (Statistical Software System, SAS Institute Inc., Cary. N.C.).

Example 41
NS3 Protease Cell-based Assay

This assay was done with Huh-7 cells, a human cell line derived from a hepatoma, co-transfected with 2 DNA constructs:

one expressing a polyprotein comprising the HCV non-structural proteins fused to tTA in the following order: NS3-NS4A-NS4B-NS5A-tTA (called NS3);

the other expressing the reporter protein, secreted alkaline phosphatase, under the control of tTA (called SEAP).

The polyprotein must be cleaved by the NS3 protease for the mature proteins to be released. Upon release of the mature proteins, it is believed that the viral proteins will form a complex at the membrane of the endoplasmic reticulum while tTA will migrate to the nucleus and transactivate the SEAP gene. Therefore, reduction of NS3 proteolytic activity should lead to reduction of mature tTA levels and concomitant decrease in SEAP activity.

To control for other effects of the compounds, a parallel transfection was done where a construct expressing tTA alone (called tTA) was co-transfected with the SEAP construct such that SEAP activity is independent of NS3 proteolytic activity. Protocol of the assay: Huh-7 cells, grown in CHO-SFMII+10% FCS (fetal calf serum), were co-transfected with either NS3 and SEAP or tTA and SEAP, using the FuGene protocol (Boehringer Mannheim). After 5 h at 37°, the cells were washed, trypsinized and plated (at 80 000 cells/well) in 96-well plates containing a range of concentrations of the compounds to be tested. After a 24-h incubation period, an aliquot of the medium was drawn and the SEAP activity in this aliquot was measured with the Phospha-Light kit (Tropix).

Analysis of the percent inhibition of SEAP activity with respect to compound concentration was performed with the SAS software to obtain the $EC_{50}$.

The toxicity of the compound ($TC_{50}$) was then assessed using the MTT assay as follows:

20 $\mu$L of a MTT solution (5 mg/ml medium) was added per well and incubated at 37° for 4 hrs;

the medium was removed and 50 $\mu$l of 0.01N HCl+10% Triton X-100 was added; after shaking at RT for at least 1 hr, the OD of each well was read at 595 nm wavelength.

The $TC_{50}$ was calculated in the same way as the $EC_{50}$.

Example 42
Specificity Assays

The specificity of the compounds was determined against a variety of serine proteases: human leukocyte elastase, porcine pancreatic elastase and bovine pancreatic α-chymotrypsin and one cysteine protease: human liver cathepsin B. In all cases a 96-well plate format protocol using a colorimetric p-nitroaniline (pNA) substrate specific for each enzyme was used. Each assay included a 1 h enzyme-inhibitor pre-incubation at 30° C. followed by addition of substrate and hydrolysis to ≈30% conversion as measured on a UV Thermomax® microplate reader. Substrate concentrations were kept as low as possible compared to $K_M$ to reduce substrate competition. Compound concentrations varied from 300 to 0.06 $\mu$M depending on their potency. The final conditions for each assay were as follows:

50 mM Tris-HCl pH 8, 0.5 M $Na_2SO_4$, 50 mM NaCl, 0.1 mM EDTA, 3% DMSO, 0.01% Tween-20 with;

[100 $\mu$M Succ-AAPF-pNA [SEQ. ID NO. 7] and 250 pM α-chymotrypsin], [133 $\mu$M Succ-AAA-pNA and 8 nM porcine elastase], [133 $\mu$M Succ-AAV-pNA and 8 nM leukocyte elastase]; or

[100 mM $NaHPO_4$ pH 6, 0.1 mM EDTA, 3% DMSO, 1 mM TCEP, 0.01% Tween-20, 30 $\mu$M Z-FR-pNA and 5 nM cathepsin B (tile stock enzyme was activated in buffer containing 20 mM TCEP before use)].

A representative example is summarized below for porcine pancreatic elastase: In a polystyrene flat-bottom 96-well plate were added using a Biomek liquid handler (Beckman):

40 $\mu$L of assay buffer (50 mM Tris-HCl pH 8, 50 mM NaCl, 0.1 mM EDTA);

20 $\mu$L of enzyme solution (50 mM Tris-HCl pH 8, 50 mM NaCl, 0.1 mM EDTA, 0.02% Tween-20, 40 nM porcine pancreatic elastase); and 20 $\mu$L of inhibitor solution (50 mM Tris-HCl, pH 8, 50 mM NaCl, 0.1 mM EDTA, 0.02% Tween-20, 1.5 mM-0.3 $\mu$M inhibitor, 15% v/v DMSO).

After 60 min pre-incubation at 30° C., 20 $\mu$L of substrate solution (50 mM Tris/HCl, pH 8, 0.5 M $Na_2SO_4$, 50 mM NaCl, 0.1 mM EDTA, 665 $\mu$M Succ-AAA-pNA) were added to each well and the reaction was further incubated at 30° C. for 60 min after which time the absorbance was read on the UV Thermomax® plate reader. Rows of wells were allocated for controls (no inhibitor) and for blanks (no inhibitor and no enzyme). The sequential 2-fold dilutions of the inhibitor solution were performed on a separate plate by the liquid handler using 50 mM Tris-HCl pH 8, 50 mM NaCl, 0.1 mM EDTA, 0.02% Tween-20, 15% DMSO. All other specificity assays were performed in a similar fashion.

The percentage of inhibition was calculated using the formula:

$$[1-((UV_{inn}-UV_{blank})/(UV_{ctr}-UV_{blank}))]\times 100$$

A non-linear curve fit with the Hill model was applied to the inhibition-concentration data, and the 50% effective concentration ($IC_{50}$) was calculated by the use of SAS software (Statistical Software System; SAS Institute, Inc., Cary, N.C.).

TABLES OF COMPOUNDS

The following tables list $IC_{50}$ values of compounds representative of the invention.

The results presented in Tables 1 to 10 indicate that this family of compounds is highly specific for the NS3 protease.

The following abbreviations are used:

$IC_{50}$: The concentration required to obtain 50% inhibition in the NS3 protease/NS4A cofactor peptide radiometric assay according to Example 38; the results marked with an * indicate an $IC_{50}$ value obtained in the recombinant HCV NS3 protease radiometric assay according to Example 37; the results marked with ** indicate an $IC_{50}$ value obtained in the full-length protein assay of Example 39.

HLE: The concentration required to obtain 50% inhibition in the human leukocyte elastase assay; PPE: The concentration required to obtain 50% inhibition in the porcine pancreatic elastase assay; Other figures unmarked indicate the concentration required to obtain 50% inhibition in the bovine pancreatic α-chymotrypsin assay; figures marked with ** indicate the concentration required to obtain 50% inhibition in the human liver cathepsiri B assay; MS: Mass spectrometric data ($MH^+$ from FAB); AAA: amino acid analysis data expressed in % peptide recovery; Acca: 1-amino-cyclopropylcarboxylic acid; Acpe: 1-amino-cyclopentylcarboxylic acid; Abu: 2-aminobutyric acid; Chg: cyclohexylglycine (2-amino-2-cyclohexyl-acetic acid); Hyp: 4(R)-hydroxyproline; Hyp(4-Bn): 4(R)-benzyloxyproline; Pip: pipecolic acid (i.e. homoprolyl); Tbg: tert-butylglycine; Ac: acetyl; Bn: benzyl; O—Bn: benzyloxy; DAD: 3-carboxypropionyl; and DAE: 4-carboxybutyryl; AlGly: allylglycine (2-amino-4-pentenoic acid); thioxolle: L-thionoisoleucine; Ph: phenyl; 3I—Ph: 3-iodophenyl; 4I—Ph: 4-iodophenyl; 2Br—Ph: 2-bromophenyl; 3Br—Ph: 3-bromophenyl; 4Br—Ph: 4-bromophenyl; 1-$NpCH_2O$: naphthalen-1-ylmethoxy; 2-$NpCH_2O$: naphthalen-2-ylmethoxy 3,5-$Br_2Ph$: 3,5-dibromophenyl.

TABLE 1

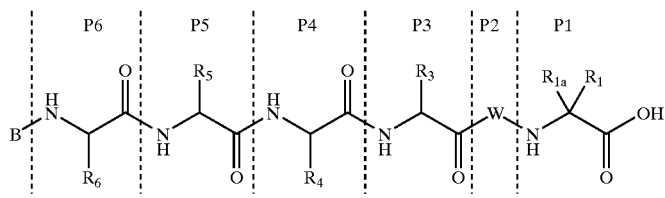

| Tab. 1 Comp. # | B | P6 | P5 | P4 | P3 | W | P1 | $IC_{50}$ (μM) | HLE (μM) | PPE (μM) | Other (μM) | MS ($MH^+$) | AAA (%) | SEQ ID NO. |
|---|---|---|---|---|---|---|---|---|---|---|---|---|---|---|
| 101 | Ac | Asp | Asp | Ile | Val | Pro | Cys | 46 | | | | 703 | 113 | 8 |
| 102 | Ac | Glu | Asp | Ile | Val | Pro | Cys | 59 | | | | 717 | 85.4 ± 1.6 | 9 |
| 103 | DAD | — | Asp | Ile | Val | Pro | Cys | 26 | | | | 646 | 100.3 ± 1.8 | 10 |
| 104 | Ac | Asp | D-Asp | Ile | Val | Pro | Cys | 8.5 | | | | 703 | 113.85 ± 4.9 | — |
| 105 | Ac | Asp | D-Glu | Ile | Val | Pro | Cys | 1.5 | | | | 717 | 95.8 ± 0.8 | — |
| 106 | Ac | Asp | Glu | Ile | Val | Pro | Cys | 16* | | | | 717 | 98.8 ± 2.6 | 11 |
| 107 | Ac | Asp | Val | Ile | Val | Pro | Cys | 85* | | | | 687 | 85.9 ± 1.1 | 12 |
| 108 | Ac | Asp | Tbg | Ile | Val | Pro | Cys | 31 | | | | 701 | 101.15 ± 1.65 | 13 |
| 109 | Ac | Asp | Asp | Val | Val | Pro | Cys | 80* | | | | 689 | 99.2 ± 5 | 14 |
| 110 | Ac | Asp | Asp | Chg | Val | Pro | Cys | 24* | | | | 729 | 102.95 ± 3.65 | 15 |
| 111 | Ac | Asp | Asp | Tbg | Val | Pro | Cys | 79 | | | | 703 | | 16 |
| 112 | Ac | Asp | Asp | Leu | Val | Pro | Cys | 92* | | | | 703 | 109.7 ± 6.9 | 17 |
| 113 | Ac | Asp | Asp | Ile | Ile | Pro | Cys | 56* | | | | 717 | 72.4 ± 2.4 | 18 |
| 114 | Ac | Asp | Asp | Ile | Chg | Pro | Cys | 50* | | | | 743 | 103.65 ± 3.8 | 19 |
| 115 | Ac | Asp | Asp | Ile | Val | Abu | Cys | 58* | | | | 691 | 59.4 ± 2.85 | 20 |
| 116 | Ac | Asp | Asp | Ile | Val | Leu | Cys | 16* | | | | 719 | 95.4 ± 1.5 | 21 |
| 117 | Ac | Asp | Asp | Ile | Val | Phe | Cys | 25* | | | | 753 | 99.6 | 22 |
| 118 | Ac | Asp | Asp | Ile | Val | Val | Cys | 133* | | | | 705 | 96.8 ± 1 | 23 |
| 119 | Ac | Asp | Asp | Ile | Val | Ile | Cys | 90 | | | | 719 | 87.0 ± 3.0 | 24 |
| 120 | Ac | Asp | Asp | Ile | Val | Ala | Cys | 76* | | | | 677 | N.S. | 25 |
| 121 | Ac | Asp | Asp | Ile | Val | Hyp(4-Bn) | Cys | 1.7 | | | | 809 | 101 | 26 |
| 122 | Ac | Asp | Asp | Ile | Val | Pro | Abu | 315 | | | | 685 | 91.0 ± 4.5 | 27 |
| 123 | Ac | Asp | Asp | Ile | Val | Pro | Nva | 220 | >300 | >300 | | 699 | 107.6 | 28 |
| 124 | Ac | Asp | Asp | Ile | Val | Pro | AlGly | 210 | | | | 697 | 106.3 ± 8.2 | 29 |
| 125 | Ac | Asp | Asp | Ile | Val | Pro | Acpe | 210 | | | | 711 | 94.02 ± 3.19 | 30 |
| 126 | Ac | Asp | Asp | Ile | Val | Pro | Acca | 45 | | | | 683 | 100.2 | 31 |
| 127 | Ac | Asp | Asp | Ile | Val | Pip | Nva | 605* | | | | 713 | 107 | 32 |
| 128 | Ac | Asp | D-Glu | Ile | Val | Pro | Nva | 7.4 | | | | 713 | 100.9 ± 3.6 | — |
| 129 | Ac | Asp | Tbg | Ile | Val | Pro | Nva | 270* | | | | 697 | 99.8 ± 0.6 | 33 |
| 130 | DAD | — | Asp | Ile | Val | Pro | Nva | 123 | | | | 642 | 107 | 34 |
| 131 | Ac | Asp | Glu | Chg | Glu | Glu | Cys | 24 | | | | | | 35 |
| 132 | Ac | Asp | D-Glu | Chg | Glu | Glu | Acca | 36 | | | | | | — |
| 133 | Ac | Asp | Glu | Chg | Val | Glu(OBn) | Acca | 39 | | | | | | 36 |

TABLE 2

| Tab. 2 Comp | B | P6 | P5 | P4 | P3 | R13 |
|---|---|---|---|---|---|---|
| 201 | Ac | Asp | Asp | Ile | Val | O-Bn |
| 202 | Ac | Asp | D-Val | Ile | Val | O-Bn |
| 203 | Ac | Asp | D-Glu | Ile | Val | O-Bn |
| 204 | Ac | Asp | Asp | Ile | Val | o-tolyl-methoxy |
| 205 | Ac | Asp | Asp | Ile | Val | m-tolyl-methoxy |
| 206 | Ac | Asp | Asp | Ile | Val | p-tolyl-methoxy |
| 207 | Ac | Asp | Asp | Ile | Val | 1-NpCH$_2$O |
| 208 | Ac | Asp | Asp | Ile | Val | 2-NpCH$_2$O |
| 209 | Ac | Asp | Asp | Ile | Val | 4-tert-butyl-phenyl)-methoxy |
| 210 | Ac | Asp | D-Glu | Chg | Val | O-Bn |
| 211 | Ac | Asp | D-Glu | Chg | Val | O-Bn |
| 212 | Ac | Asp | D-Glu | Ile | Val | O-Bn |
| 213 | Ac | Asp | D-Glu | Ile | Val | 2-NpCH$_2$O |
| 214 | Ac | Asp | D-Glu | Chg | Val | 2-NpCH$_2$O |
| 215 | Ac | Asp | D-Glu | Chg | Val | 1-NpCH$_2$O |
| 216 | Ac | Asp | Asp | Ile | Val | Bn |
| 217 | Ac | Asp | Asp | Ile | Val | Ph(CH$_2$)$_3$ |
| 218 | Ac | Asp | D-Glu | Ile | Val | O-Bn |
| 219 | Ac | — | Asp | Ile | Val | 1-NpCH$_2$O |
| 220 | DAD | — | — | N(Me)Ile | Val | 1-NpCH$_2$O |
| 221 | DAD | — | — | Ile | Val | 1-NpCH$_2$O |
| 222 | DAE | — | — | Ile | Val | 1-NpCH$_2$O |
| 223 | (structure) | — | — | Ile | Val | 1-NpCH$_2$O |
| 224 | (structure) | — | — | Ile | Val | 1-NpCH$_2$O |
| 225 | Ac | — | — | Ile | Val | 1-NpCH$_2$O |
| 226 | DAE | — | — | Chg | Val | 1-NpCH$_2$O |
| 227 | Ac | — | — | Chg | Val | 1-NpCH$_2$O |
| 228 | Ac | — | — | Chg | Val | O-Bn |
| 230 | Ac | Asp | Asp | Ile | Val | Ph(CH$_2$)$_3$ |
| 231 | Ac | — | — | Chg | Chg | 1-NpCH$_2$O |
| 232 | AcOCH$_2$—C(O) | — | — | Chg | Chg | 1-NpCH$_2$O |
| 233 | Ac | Asp | Glu | Ile | Val | (3I-Ph)CH$_2$O |
| 234 | Ac | — | — | Chg | Chg | O-Bn |
| 235 | Boc | — | — | Chg | Chg | 1-NpCH$_2$O |
| 236 | Ac | — | Gly | thioxo-Ile | Val | 1-NpCH$_2$O |
| 237 | DAE | — | — | Ile | Val | 1-NpCH$_2$O |
| 238 | Ac | — | — | Chg | Val | (4Br-Ph)O |
| 239 | Ac | — | — | Chg | Val | (2Br-Ph)O |
| 240 | Ac | — | — | Chg | Val | (3Br-Ph)O |

TABLE 2-continued

| | P6 | P5 | P4 | P3 | P2 | P1 |
|---|---|---|---|---|---|---|
| 241 | Ac | — | — | Chg | Val | benzothiazol-2-yl-S |
| 242 | Ac | — | — | Chg | Val | (4Br-Ph)S |
| 243 | Ac | — | — | Chg | Val | 2-Br-pyridin-3-yl-O |
| 244 | Ac | — | — | Chg | Val | 7-CF₃-quinolin-4-yl-S |
| 245 | Ac | — | — | Chg | Val | 7-CF₃-quinolin-4-yl-O |
| 246 | Ac | — | — | Chg | Val | 4'-MeO-biphenyl-4-yl-O |
| 247 | Ac | Asp | Asp | Ile | Val | Ph(CH$_2$)$_2$ |
| 248 | Ac | — | — | Chg | Chg | quinolin-8-yl-CH$_2$O |
| 249 | Ac | — | — | Chg | Val | (4I-Ph)O |
| 250 | Ac | — | — | Chg | Val | quinolin-4-yl-O |
| 251 | Ac | — | — | Chg | Val | 3-HO-quinoxalin-2-yl-C(O)O |
| 252 | Ac | — | — | Chg | Val | 1-NpCH$_2$O |

TABLE 2-continued
| | P6 | P5 | P4 | P3 | P2 | P1 |
|---|---|---|---|---|---|---|
| 253 | Ac | — | — | Chg | Val | 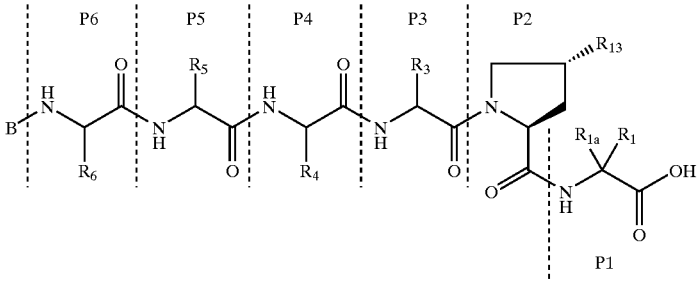 |
| 254 | Ac | — | — | Chg | Val | 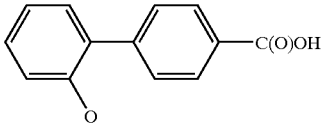 |
| 255 | Ac | — | — | Chg | Val | 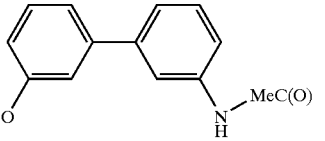 |
| 256 | Ac | — | — | Chg | Val | 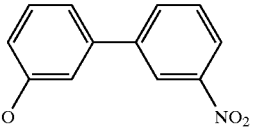 |
| 257 | Ac | — | — | Chg | Val | 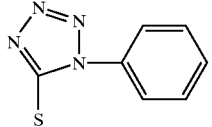 |
| 258 | Ac | — | — | Chg | Val | 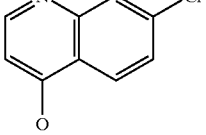 |
| 259 | Ac | — | — | Chg | Val | 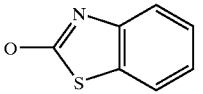 |
| 260 | Ac | Asp | D-Glu | Ile | Val | O-Bn |
| 261 | Ac | — | — | Chg | Val | O-Bn |
| 262 | Ac | — | — | Ile | Val | 1-NpCH$_2$O |
| 263 | 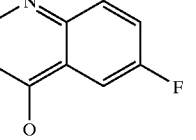 | — | — | Ile | Val | 1-NpCH$_2$O |

TABLE 2-continued
| | P6 | P5 | P4 | P3 | P2 | P1 |
|---|---|---|---|---|---|---|
| 264 | 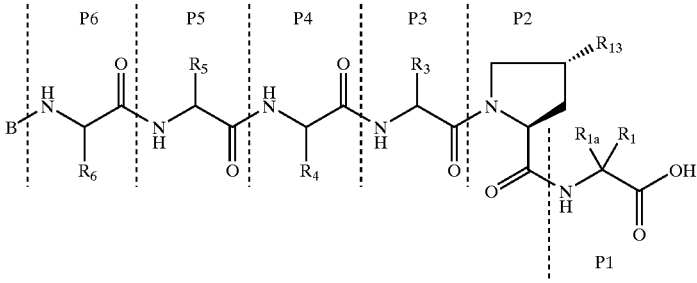 | — | — | Ile | Val | 1-NpCH$_2$O |
| 265 | 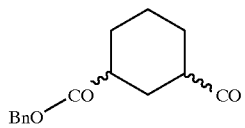 | — | — | Ile | Val | 1-NpCH$_2$O |
| 266 | 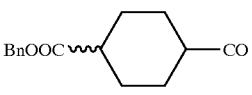 | — | — | Ile | Val | 1-NpCH$_2$O |
| 267 | 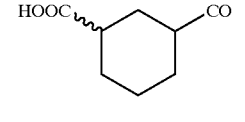 | — | — | Ile | Val | 1-NpCH$_2$O |
| 268 | Ac | — | — | Chg | Val | (3Br-Ph)CH$_2$O |
| 269 | 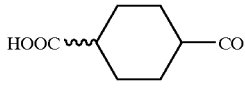 | — | — | Chg | Val | 1-NpCH$_2$O |
| 270 | 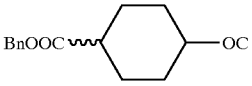 | — | — | Chg | Val | 1-NpCH$_2$O |
| 271 | 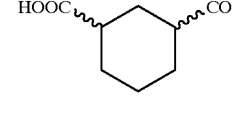 | — | — | Chg | Val | 1-NpCH$_2$O |
| 272 | Ac | — | — | Chg | Val | (3,5-Br$_2$-Ph)CH$_2$O |
| 273 | Ac | Asp | Asp | Ile | Val | H |
| 274 | Ac | Asp | D-Val | Ile | Val | H |
| 275 | Ac | — | — | Chg | Val | 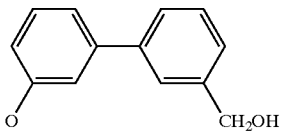 |

TABLE 2-continued
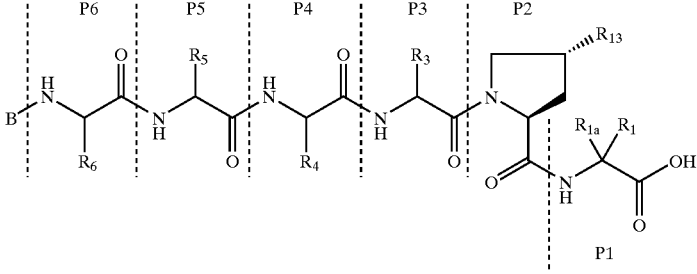
| Tab. 2 Comp | P1 | IC$_{50}$ ($\mu$M) | HLE ($\mu$M) | PPE ($\mu$M) | Other ($\mu$M) | MS (MH$^+$) | AAA (%) | SEQ ID NO. |
|---|---|---|---|---|---|---|---|---|
| 201 | Nva | 7.2 | | | | 805 | 107 | 37 |
| 202 | Nva | 0.93 | | | | 789 | 103 | — |
| 203 | Nva | 0.6 | >300 | >300 | >300** | 819 | 96.3 ± 1.7 | — |
| 204 | Nva | 9.4* | | | | 819 | 95 | 38 |
| 205 | Nva | 6.7* | | | | 819 | 98.7 | 39 |
| 206 | Nva | 6.4* | | | | 819 | 101.9 | 40 |
| 207 | Nva | 0.39 | | | | 855 | 112 | 41 |
| 208 | Nva | 0.71 | | | | 855 | 104 | 42 |
| 209 | Nva | 2.6 | | | | 861 | 114 | 43 |
| 210 | Cys | 0.033 | >300 | >300 | >300 | 849 | 101.7 ± 5.4 | — |
| 211 | Nva | 0.12 | | | | 845 | 93.4 ± 2 | — |
| 212 | Acca | 0.21 | >300 | >300 | | 803 | 99.4 ± 2 | — |
| 213 | Nva | 0.036 | | | | 869 | 101.8 | — |
| 214 | Nva | 0.028 | >300 | >300 | >300 >300** | 895 | 104.1 | — |
| 215 | Acca | 0.014 | | | | 879 | — | — |
| 216 | Nva | 60 | | | | 789 | 100.6 ± 0.8 | 44 |
| 217 | Nva | 3 | | | | 818 | 94.6 ± 3 | 45 |
| 218 | Nva | 0.49 | | | | 910 | 111.2 | — |
| 219 | Nva | 2.3 | | | | 740 | 95.7 | 46 |
| 220 | Nva | 31 | | | | 697 | — | — |
| 221 | Nva | 22 | | | | 683 | | — |
| 222 | Nva | 20 | | | | 698 | N.S. | — |
| 223 | Nva | 51 | | | | 737 | N.S. | — |
| 224 | Nva | 56 | | | | 737 | N.S. | — |
| 225 | Nva | 45 | | | | 929 | — | — |
| 226 | Acca | 0.76 | | | | 707 | — | — |
| 227 | Acca | 3 | >600 | | | 635 | | — |
| 228 |  | 35 | >600 | | | 613.4 | | — |
| 230 | Nva | 3.3 | | | | 818 | | 47 |
| 231 | Acca | 2.6 | | | | 675.4 | | — |
| 232 | Acca | 1.4 | | | | | | — |
| 233 | Acca | 0.14 | | | | 929.2 | | 48 |
| 234 | Acca | 41 | | | | | | — |
| 235 | Acca | 12 | | | | | | — |
| 236 | Nva | 4.0 | | | | 720 (M + Na) | | — |
| 237 | Acca | 5.5 | | | | 598 (M + Na) | | — |
| 238 | Acca | 27 | 195 | | | | | — |
| 239 | Acca | 27 | | | | | | — |
| 240 | Acca | 42 | | | | | | — |
| 241 | Acca | 18 | | | | | | — |
| 242 | Acca | 36 | | | | | | — |
| 243 | Acca | 35 | | | | | | — |
| 244 | Acca | 10 | | | | | | — |
| 245 | Acca | 5.0 | | | | | | — |
| 246 | Acca | 33 | | | | | | — |
| 247 | Nva | 10 | | | | 803.6 | 119 ± 1 | 49 |
| 248 | Acca | 3.6 | | | | | | — |
| 249 | Acca | 9.7 | | | | | | — |

TABLE 2-continued
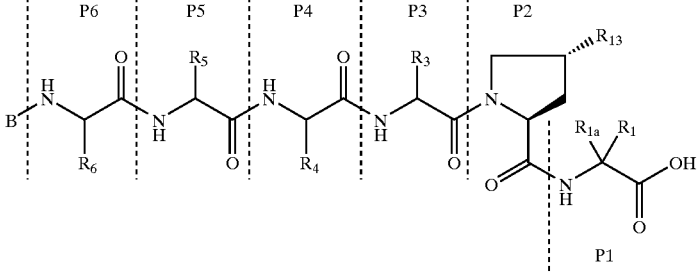
| Cpd # | P6 | IC$_{50}$ (μM) | HLE (μM) | PPE (μM) | Other (μM) | MS (MH$^+$) | AAA (%) | SEQ ID NO. |
|---|---|---|---|---|---|---|---|---|
| 250 | Acca | 4.5 | | | | | | — |
| 251 | Acca | 13 | | | | | | — |
| 252 | Nva | 20 | | | | 651.4 | 91 ± 1 | — |
| 253 | Acca | 28 | | | | | | — |
| 254 | Acca | 5.1 | | | | | | — |
| 255 | Acca | 4.5 | | | | | | — |
| 256 | Acca | 11 | | | | | | — |
| 257 | Acca | 2.2 | >300 | | | | | — |
| 258 | Acca | 16 | | | | | | — |
| 259 | Acca | 28 | | | | | | — |
| 260 | Cys | 0.18 | | | | | | — |
| 261 | Cys | 28 | | | | | | — |
| 262 | Acca | 40 | | | | 631 (M + Na) | | — |
| 263 | Acca | 17 | | | | 771 (M + Na) | | — |
| 264 | Acca | 6.4 | | | | 811 | | — |
| 265 | Acca | 10 | | | | 811 | | — |
| 266 | Acca | 9.7 | | | | 721.4 | | — |
| 267 | Acca | 12 | | | | 721.4 | | — |
| 268 | Acca | 24 | | | | 665.1 | | — |
| 269 | Acca | 2.2 | | | | 835.5 (M − H) | | — |
| 270 | Acca | 2.0 | | | | 745 (M − H) | | — |
| 271 | Acca | 3.8 | | | | | | — |
| 272 | Acca | 27 | | | | | | — |
| 273 | Nva | 17.5 | | | | | | 50 |
| 274 | Cys | 7.6 | | | | | | — |
| 275 | Acca | 6.2 | | | | | | — |
TABLE 3
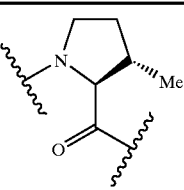
| TAB 3 Cpd # | B | P6 | P5 | P4 | P3 | W | P1 | IC$_{50}$ (μM) | HLE (μM) | PPE (μM) | Other (μM) | MS (MH$^+$) | AAA (%) | SEQ ID NO. |
|---|---|---|---|---|---|---|---|---|---|---|---|---|---|---|
| 301 | Ac | Asp | Asp | Ile | Val | | Nva | 98* | | | | 713 | 99.8 | 51 |

TABLE 3-continued
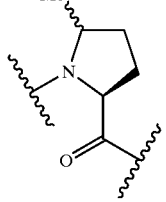
| TAB 3 Cpd # | B | P6 | P5 | P4 | P3 | W | P1 | IC₅₀ (μM) | HLE (μM) | PPE (μM) | Other (μM) | MS (MH⁺) | AAA (%) | SEQ ID NO. |
|---|---|---|---|---|---|---|---|---|---|---|---|---|---|---|
| 302 | Ac | Asp | Asp | Ile | Val | 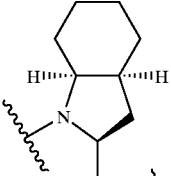 | Nva | 89* | | | | 713 | 102 | 52 |
| 303 | Ac | Asp | Asp | Ile | Val | 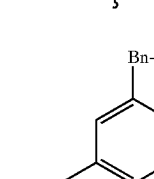 | Nva | 44* | | | | 753 | 104.4 | 53 |
| 304 | Ac | — | — | Chg | Val |  | Acc | 1.1 | | | | | | — |
TABLE 4
| TAB 4 Comp. | B | R⁴ | P3 | R₁₃ | P1 | IC₅₀ (μM) | HLE (μM) | PPE (μM) | MS (MH⁺) | AAA (%) |
|---|---|---|---|---|---|---|---|---|---|---|
| 401 | HOCO-piperidine-Ac | cyclohexyl | Val | 1-NpCH₂O | Acca | 37 | | | 747 | |

TABLE 4-continued

| TAB 4 Comp. | B | R⁴ | P3 | R₁₃ | P1 | IC₅₀ (μM) | HLE (μM) | PPE (μM) | MS (MH⁺) | AAA (%) |
|---|---|---|---|---|---|---|---|---|---|---|
| 402 | MeOCO—piperidine-N-acetyl | cyclohexyl | Val | 1-NpCH₂O | Acca | 28 | | | 761 | |
| 403 | methyl-dihydrobenzoxazine-COOH | cyclohexyl | Val | 1-NpCH₂O | Acca | 9.6 | | | 783 | |
| 404 | N-methyl-N-acetyl-benzyl-COOMe | cyclohexyl | Val | 1-NpCH₂O | Acca | 10 | | | 797 | |
| 405 | HOOC—CH₂CH₂—N(Me)C(O)— | cyclohexyl | Val | 1-NpCH₂O | Acca | 1.6 | | | 721 | |
| 406 | MeOOC—CH₂—CH₂—N(Me)c(O)— | cyclohexyl | Val | 1-NpCH₂O | Acca | 25 | | | 735 | |
| 407 | HOOC—CH₂CH₂—N(Me)₂—C(O)— | cyclohexyl | Val | 1-NpCH₂O | Acca | 1.5 | | | 749 | |
| 408 | MeOOC—(CH₂)₂—N(Me)₂—C(O)— | cyclohexyl | Val | 1-NpCH₂O | Acca | 11 | | | 763 | |
| 409 | HOOC—CH₂—N(Me)—C(O)— | cyclohexyl | Val | 1-NpCH₂O | Acca | 24 | | | 735 | |
| 410 | EtOOC—CH—N(Me)₂—C(O)— | cyclohexyl | Val | 1-NpCH₂O | Acca | 32 | | | 763 | |
| 411 | [HOOC—(CH₂)₂]₂—NH—CH₂— | cyclohexyl | Val | 1-NpCH₂O | Acca | 0.36 | | | 779 | |
| 412 | [HOOC—CH₂]₂—NC(O)— | cyclohexyl | Val | 1-NpCH₂O | Acca | 0.8 | | | 751 | |
| 413 | [HOOC—(CH₂)₂]₂—NC(O)— | cyclohexyl | Val | 1-NpCH₂O | Acca | 0.12 | | | 779 | |
| 414 | HOOC-CH₂CH₂-N(CH₂-cyclopropyl)-acetyl | cyclohexyl | Val | 1-NpCH₂O | Acca | 0.5 | | | 761 | |

TABLE 4-continued

| TAB 4 Comp. | B | R⁴ | P3 | R₁₃ | P1 | IC₅₀ (μM) | HLE (μM) | PPE (μM) | MS (MH⁺) | AAA (%) |
|---|---|---|---|---|---|---|---|---|---|---|
| 415 | HOOC-CH₂CH₂-N(CH₂-cyclohexyl)-C(O)CH₃ | cyclohexyl | Val | 1-NpCH₂O | Acca | 0.89 | | | 803 | |
| 416 | HOOC-CH₂CH₂-N(CH₂-tetrahydrofuran-2-yl)-C(O)CH₃ | cyclohexyl | Val | 1-NpCH₂O | Acca | 0.58 | | | 791 | |
| 417 | HOOC-CH₂CH₂-N(iBu)-C(O)CH₃ | cyclohexyl | Val | 1-NpCH₂O | Acca | 0.59 | | | 763 | |
| 418 | HOOC-CH₂CH₂-N(Bn)-C(O)CH₃ | cyclohexyl | Val | 1-NpCH₂O | Acca | 0.63 | | | 797 | |
| 419 | HOOC-CH₂CH₂-N(CH₂CH₂C(CH₃)₃)-C(O)CH₃ | cyclohexyl | Val | 1-NpCH₂O | Acca | 1.4 | | | 775 (M − H) | |
| 420 | HOOC-CH₂CH₂-N(CH₂CHPh₂)-C(O)CH₃ | cyclohexyl | Val | 1-NpCH₂O | Acca | 0.52 | | | 925 (M + K)⁺ | |

TABLE 4-continued

| TAB 4 Comp. | B | R⁴ | P3 | R₁₃ | P1 | IC₅₀ ($\mu$M) | HLE ($\mu$M) | PPE ($\mu$M) | MS (MH⁺) | AAA (%) |
|---|---|---|---|---|---|---|---|---|---|---|
| 421 | (HOOC-CH₂CH₂-N(Ac)-CH₂-2-thienyl) | cyclohexyl | Val | 1-NpCH₂O | Acca | 1.7 | | | 841 (M + K)⁺ | |

TABLE 5

| Tab. 5 Cpd | B | P6 | P5 | P4 | P3 | R₁₃ | R₁₄ | P1 C₁–C₂ | MS (MH⁺) | IC₅₀ ($\mu$M) (HLE) |
|---|---|---|---|---|---|---|---|---|---|---|
| 501 | Ac | — | — | Chg | Val | OBn | Et | 1R, 2R | 613.4 | 17.1 |
| 502 | Ac | — | — | Chg | Val | OBn | Et | 1R, 2? | 613.4 | 12.6 |
| 503 | Ac | — | — | Chg | Chg | 1-NpCH₂O | Et | 1R, 2? | 703 | 1.35 |
| | | | | | | | | | | 250 |
| 504 | Ac | — | — | Chg | Chg | 1-NpCH₂O | Et | 1R, 2? | 703 | 9.53 |
| 505 | Ac | — | — | Chg | Chg | 1-NpCH₂O | Et | 1R, 2R | 703.4 | 0.55 |
| 506 | Ac | — | — | Chg | Chg | 1-NpCH₂O | Et | 1S, 2S | 703.5 | 4.85 |
| | | | | | | | | | | >400 |
| 507 | Ac | — | — | Chg | Val | 1-NpCH₂O | Me | 1R, 2? | 649.5 | 5.10 |
| 508 | Ac | — | — | Chg | Val | 1-NpCH₂O | CHMe₂ | 1R, 2? | M + Na 699 | 4.15 |
| 509 | Ac | Asp | D-Glu | Chg | Chg | 1-NpCH₂O | Et | 1R, 2R | 947.4 | 0.015 |
| | | | | | | | | | | >300 |
| 510 | Ac | — | — | Chg | Val | 1-NpCH₂O | CH₂OCH₂Ph | 1R, 2? | M + Na 777.4 | 15.5 |
| 511 | Ac | — | — | Chg | Val | 1-NpCH₂O | CH₂OCH₂Ph | 1R, 2? | M + Na 777.4 | 32.5 |
| 512 | Ac | — | — | Chg | Val | 1-NpCH₂O | (CH₂)₂Ph | 1R, 2? | M + Na 761 | 19.5 |
| 513 | Ac | — | — | Chg | Val | 1-NpCH₂O | Et | 1R, 2R | M + Na 685 | 1.66 |
| | | | | | | | | | | >300 |
| 514 | Ac | — | — | Chg | Val | 1-NpCH₂O | Et | 1S, 2S | M + Na 685 | 27.5 |
| 515 | Ac | — | — | Chg | Val | 1-NpCH₂O | Bz | 1R, 2? | M + Na 747 | 9.2 |
| 516 | Ac | — | — | Chg | Val | 1-NpCH₂O | Bz | 1R, 2? | M + Na 747 | 46.5 |
| 517 | Ac | Asp | D-Glu | Ile | Val | OBn | Et | 1R, 2R | | 0.075 |
| 518 | Ac | Asp | D-Glu | Ile | Val | 1-NpCH₂O | Et | 1R, 2R | M + Na 929.4 | 0.011 |
| | | | | | | | | | | >300 |
| 519 | Ac | — | — | Chg | Val | 1-NpCH₂O | Pr | 1R, 2? | 677.4 | 3.45 |
| 520 | Ac | — | — | Chg | Val | 1-NpCH₂O | Pr | 1R, 2? | 677.4 | 22.5 |

TABLE 5-continued

| Tab. 5 Cpd | B | P6 | P5 | P4 | P3 | R$_{13}$ | R$_{14}$ | P1 C$_1$–C$_2$ | MS (MH$^+$) | IC$_{50}$ ($\mu$M) (HLE) |
|---|---|---|---|---|---|---|---|---|---|---|
| 521 | Ac | Asp | D-Val | Chg | Val | 1-NpCH$_2$O | Et | 1R, 2R | M + Na 899.5 | 0.024 >300 |
| 522 | Ac | — | — | Chg | Val | quinolin-4-yloxy | vinyl | 1S, 2R | 648.3 | 2.5 |
| 523 | Ac | — | — | Chg | Val | 2-(cyclohex-2-enyl)quinolin-4-yloxy | ethyl | 1R, 2S | 726.6 | 0.072 |
| 524 | Ac | — | — | Chg | Val | 2-(cyclohex-2-enyl)quinolin-4-yloxy | propyl | 1R, 2R | 740.3 | 0.185 |

TABLE 6

| Tab 6 Cpd# | P6 | P5 | P4 | P3 | R$_{13}$ | R$_{14}$ | MS (MH$^+$) | IC$_{50}$ ($\mu$M) |
|---|---|---|---|---|---|---|---|---|
| 601 | — | — | Chg | Val | OBn | CH=CH$_2$ | 611.3 | 3.61 |
| 602 | — | — | Chg | Chg | 1-NpCH$_2$O | CH=CH$_2$ | 701.3 | 0.13 |
| 603 | — | — | Chg | Val | 1-NpCH$_2$O | CH=CH$_2$ | 661.1 | 0.36 |
| 604 | — | — | Chg | Val | OBn | CH=CHBr* | 687.4 | 2.55 |

TABLE 6-continued
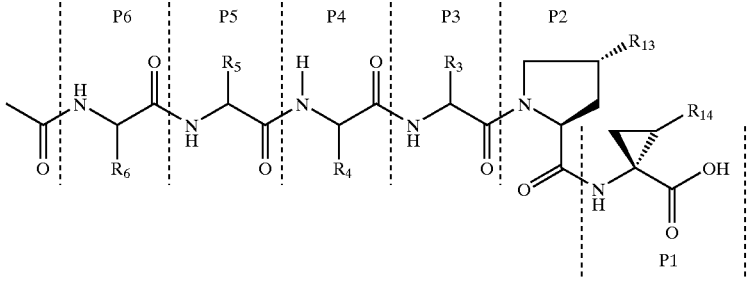
| Tab 6 Cpd# | P6 | P5 | P4 | P3 | R13 | R14 | MS (MH+) | IC50 (μM) |
|---|---|---|---|---|---|---|---|---|
| 605 | — | — | Chg | Val | 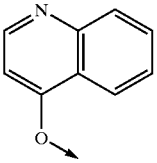 | CH=CH2 | 648.4 | 0.22 |
| 606 | — | — | Chg | Val | 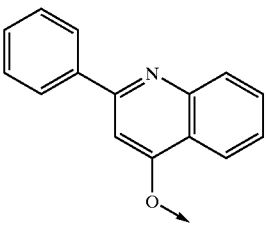 | CH=CH2 | 724.4 | 0.015** |
| 607 | — | — | Chg | Tbg | 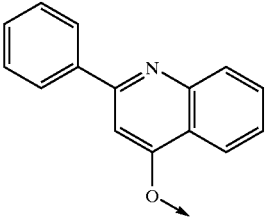 | CH=CH2 | 738.4 | 0.003** |
| 608 | — | — | Chg | Val | 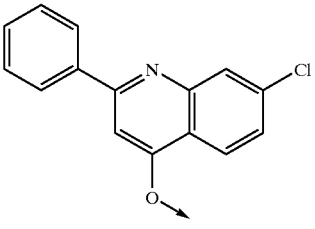 | CH=CH2 | 758.5 | 0.013** |
| 609 | — | — | Chg | Val | 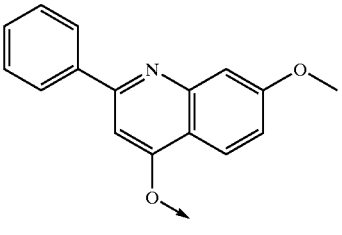 | CH=CH2 | 754.5 | 0.002** |

TABLE 6-continued

| Tab 6 Cpd# | P6 | P5 | P4 | P3 | R13 | R14 | MS (MH+) | IC50 (μM) |
|---|---|---|---|---|---|---|---|---|
| 610 | — | — | Chg | Val | 2-phenyl-6-methoxy-quinolin-4-yloxy | CH=CH2 | 754.3 | 0.026** |
| 611 | — | — | Chg | Val | 2-phenyl-8-methoxy-quinolin-4-yloxy | CH=CH2 | 754.3 | 0.003** |
| 612 | Asp | D-Glu | Chg | Val | 2-phenyl-quinolin-4-yloxy | CH=CH2 | 968.4 | 0.001** |
| 613 | — | — | Chg | Val | 2-(N,N-dimethylcarbamoyl)-quinolin-4-yloxy | CH=CH2 | 719.3 | 1.5 |
| 614 | — | — | Chg | Val | 2-phenyl-quinolin-4-yloxy | ethyl | 726.4 | 0.07 |

TABLE 6-continued

| Tab 6 Cpd# | P6 | P5 | P4 | P3 | R13 | R14 | MS (MH+) | IC50 (µM) |
|---|---|---|---|---|---|---|---|---|
| 615 | — | — | Val | Chg | 4-quinolinyloxy | CH=CH2 | 648.3 | 0.31 |
| 616 | — | — | Chg | Val | 2-(N-benzylcarboxamide)-4-quinolinyloxy | CH=CH2 | 781.6 | 0.022 |
| 617 | — | — | Chg | Val | 2-(pyridin-4-yl)-4-quinolinyloxy | CH=CH2 | 690.6 | 0.68 |
| 618 | — | — | Chg | Val | 2-(N-morpholinylcarboxamide)-4-quinolinyloxy | CH=CH2 | 776.4 | 0.32 |
| 619 | — | — | Chg | Val | 2-(N-tetrazolylcarboxamide)-4-quinolinyloxy | CH=CH2 | 759.3 | 0.091 |

TABLE 6-continued
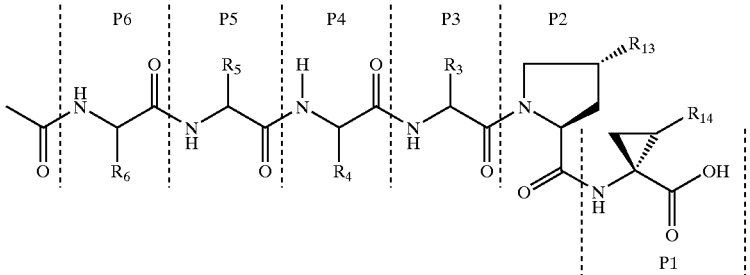
| Tab 6 Cpd# | P6 | P5 | P4 | P3 | R13 | R14 | MS (MH+) | IC50 (μM) |
|---|---|---|---|---|---|---|---|---|
| 620 | — | — | Chg | Val | 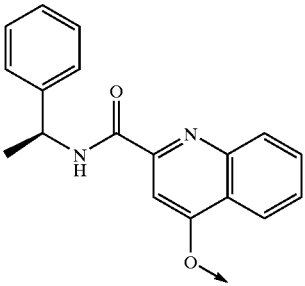 | CH=CH2 | 795.3 | 0.048 |
| 621 | — | — | Chg | Val | 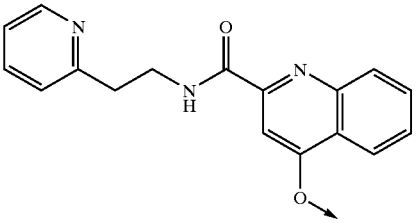 | CH=CH2 | 796.3 | 0.025 |
| 622 | Asp | D-Glu | Chg | Tbg | 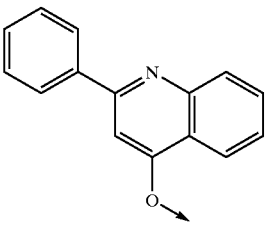 | CH=CH2 | 982.4 | 0.001** |
| 623 | — | — | Chg | Val | 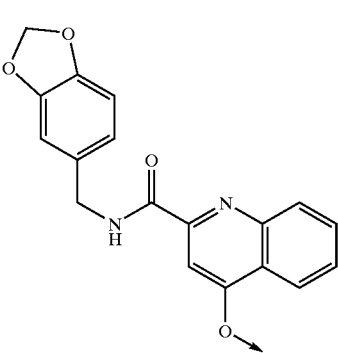 | CH=CH2 | 825.3 | 0.042 |

TABLE 6-continued
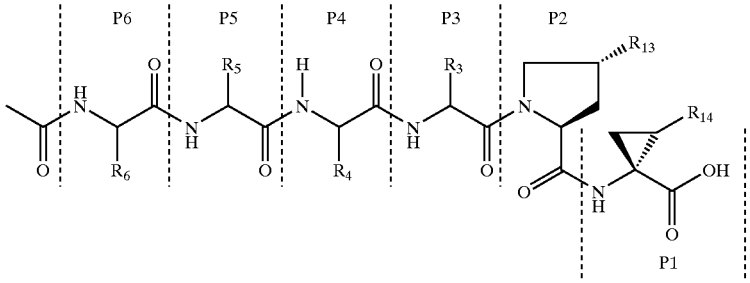
| Tab 6 Cpd# | P6 | P5 | P4 | P3 | R13 | R14 | MS (MH+) | IC50 (μM) |
|---|---|---|---|---|---|---|---|---|
| 624 | — | — | Chg | Tbg | 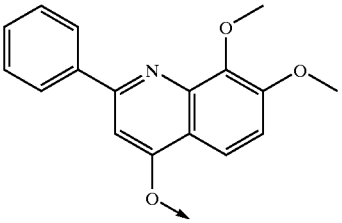 | CH=CH2 | 798.3 | 0.004** |
| 625 | — | — | Chg | Val | 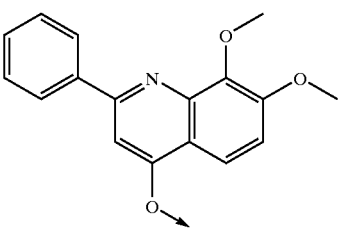 | CH=CH2 | 784.2 | 0.007 |
| 626 | — | — | Chg | Val | 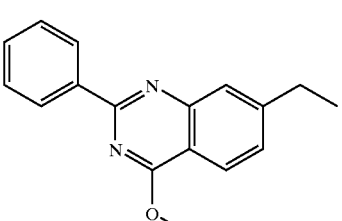 | CH=CH2 | 752.2 | 0.007 |
| 627 | — | — | Chg | Val | 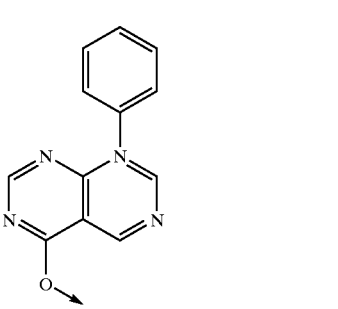 | CH=CH2 | 715.4 | 1.7 |
| 628 | — | — | Chg | Tbg | 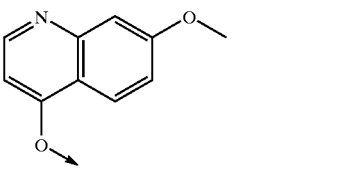 | CH=CH2 | 692.2 | 0.004** |

TABLE 6-continued
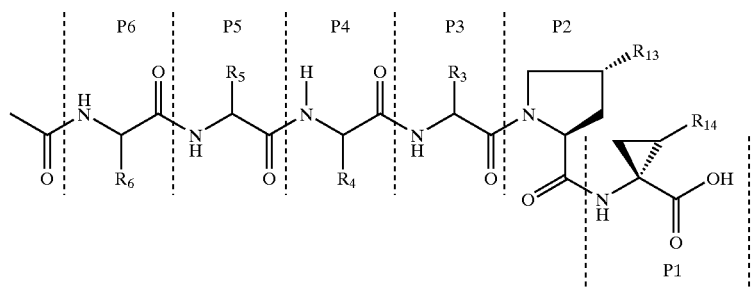
| Tab 6 Cpd# | P6 | P5 | P4 | P3 | R₁₃ | R₁₄ | MS (MH⁺) | IC₅₀ (μM) |
|---|---|---|---|---|---|---|---|---|
| 629 | — | — | Chg | Val | (2-chloro-6,7-dimethoxyquinolin-4-yloxy) | CH=CH₂ | 743.2 | 0.27 |
| 630 | — | — | Chg | Val | (2-(tetrazol-5-yl)quinolin-4-yloxy) | CH=CH₂ | 716.3 | 0.16 |
| 631 | — | — | Chg | Tbg | (7-phenylquinolin-4-yloxy) | CH=CH₂ | 738.3 | 0.005** |
| 632 | — | — | Chg | Tbg | (2-phenyl-7-isopropoxyquinolin-4-yloxy) | CH=CH₂ | 796.4 | 0.002 |
| 633 | — | — | Chg | Tbg | (2-phenyl-7-methoxyquinolin-4-yloxy) | CH=CH₂ | 768.3 | 0.001** |

TABLE 6-continued
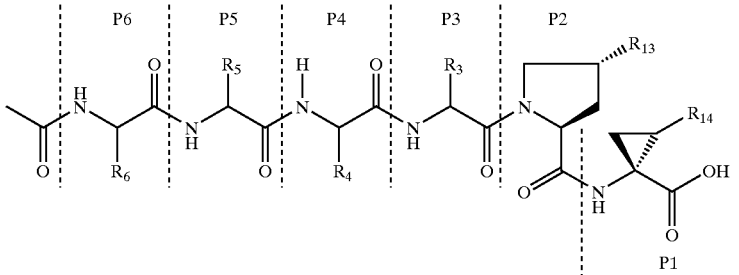
| Cpd# | P6 | P5 | P4 | P3 | R₁₃ | R₁₄ | MS (MH⁺) | IC₅₀ (μM) |
|---|---|---|---|---|---|---|---|---|
| 634 | — | — | Chg | Tbg | 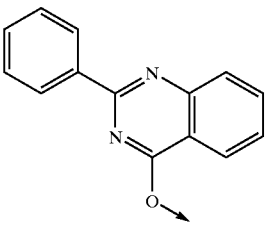 | CH=CH₂ | 739.4 | 0.005** |
| 635 | — | — | Chg | Val | 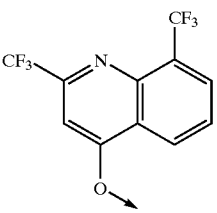 | vinyl | 782.2 | 0.19 |
| 636 | Asp | D-Glu | Ile | Val | O—Bn | vinyl | 829.3 | 0.47 |
| 637 | — | — | Chg | Val | 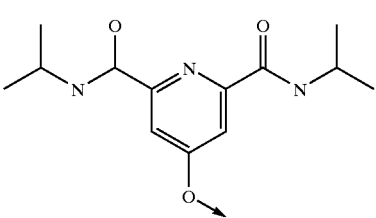 | vinyl | 768.4 | 0.76 |
| 638 | Asp | D-Glu | Chg | Tbg | 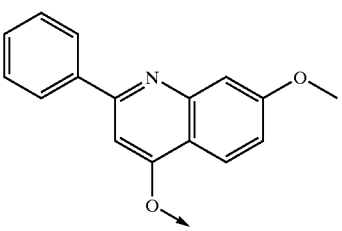 | vinyl | 1012.6 | 0.001 |
*Br isomer ratio 5.5:2

TABLE 7
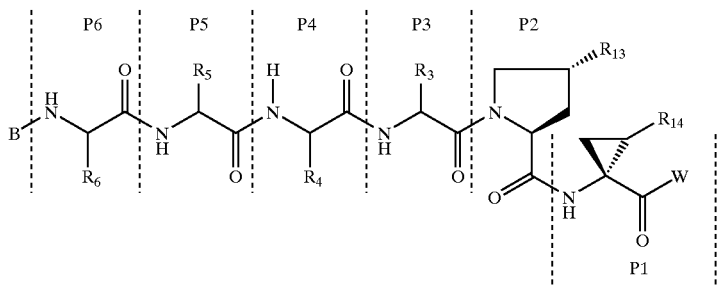
| Tab. 7 Cpd# | B | P6 | P5 | P4 | P3 | R₁₃ | R₁₄ | W | MS (M − H) | IC₅₀ (μM) | HLE (μM) |
|---|---|---|---|---|---|---|---|---|---|---|---|
| 701 | Ac | Asp | D-Glu | Ile | Val | OBn | Et | NH—(S)—CHMePh | 932.6 | 0.082 | 191 |
| 702 | Dnl | Asp | D-Glu | Chg | Tbg | 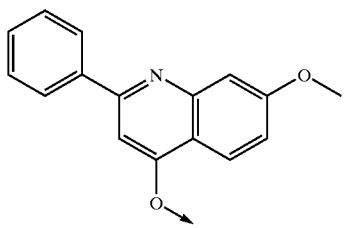 | vinyl | OH | 1203.5 | 0.001 | |
TABLE 8
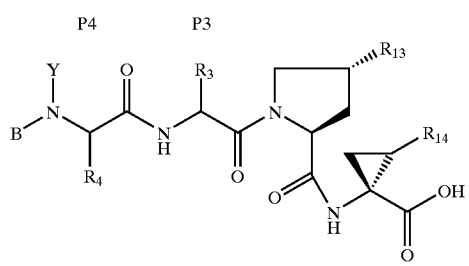
| Tab 8 Cpd# | B | Y | P4 | P3 | R₁₃ | R₁₄ | MS (MH⁺) | IC₅₀ (μM) |
|---|---|---|---|---|---|---|---|---|
| 801 | Ac | Me | Chg | Tbg | 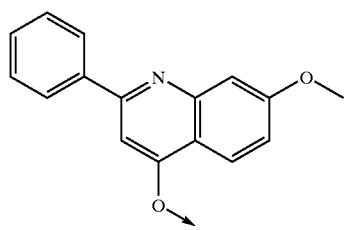 | vinyl | 782.3 | 0.002 |

TABLE 9
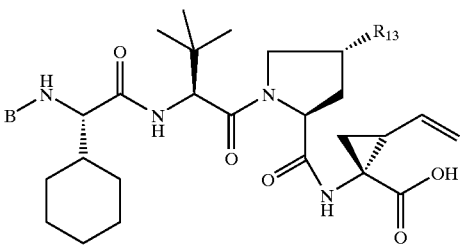
| Tab 9 cpd# | B | R13 | MS | IC50 |
|---|---|---|---|---|
| 901 | 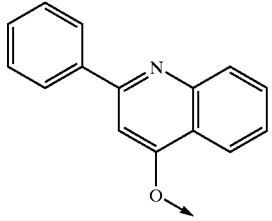 | 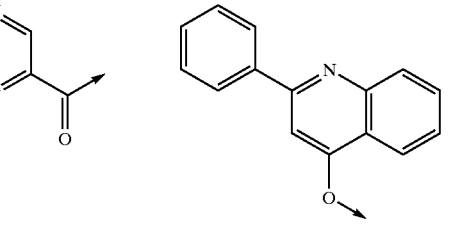 | 802.4 | 0.003 |
| 902 | 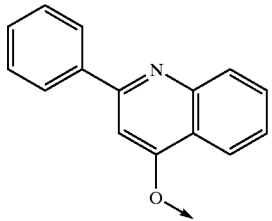 | 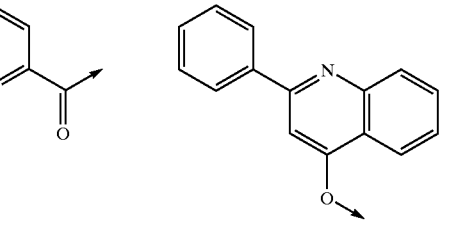 | 852.4 | 0.013 |
| 903 | 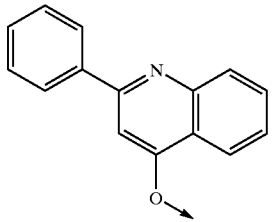 | 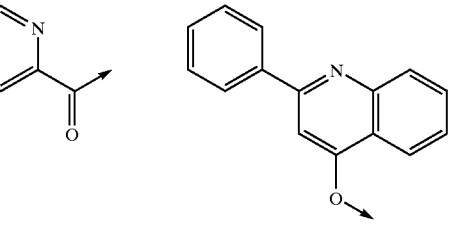 | 851.3 | 0.037 |
| 904 | 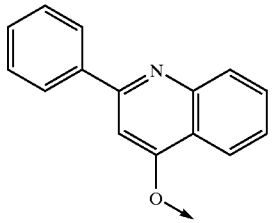 | | 851.3 | 0.085 |

TABLE 9-continued
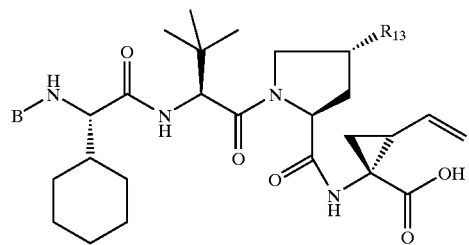
| Tab 9 cpd# | B | R13 | MS | IC50 |
|---|---|---|---|---|
| 905 | 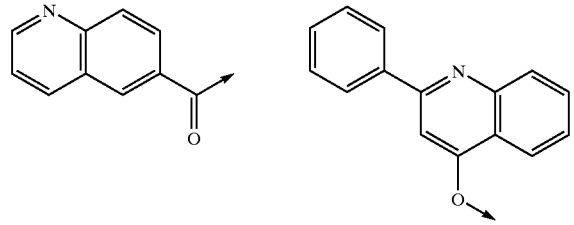 | | 851.3 | 0.007 |
| 906 | H | | 696.3 | 0.068 |
| 907 | 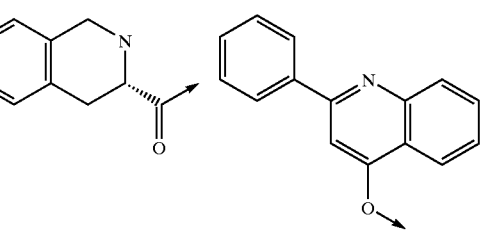 | | 871.4 | ? |
| 908 | 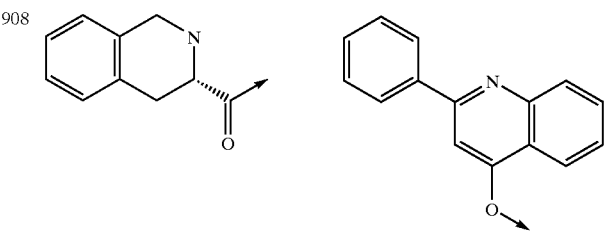 | | 855.4 | 0.003 |
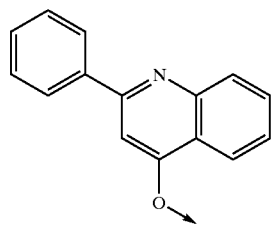

TABLE 9-continued

| Tab 9 cpd# | B | R₁₃ | MS | IC₅₀ |
|---|---|---|---|---|
| 909 | H | 2-phenyl-7-methoxyquinolin-4-yloxy | 726.7 | 0.018 |
| 910 | (S)-1,2,3,4-tetrahydroisoquinoline-3-carbonyl | 2-phenyl-7-methoxyquinolin-4-yloxy | 901.7 | 0.001 |
| 911 | Dnl | 2-phenyl-7-methoxyquinolin-4-yloxy | 959.4 | 0.01 |

TABLE 10

| Tab. 10 Comp. | B | P6 | P5 | P4 | P3 | R₁₃ | R₁₄ | P1 C₁–C₂ | A | IC₅₀ (μM) | HLE (μM) | MS (MH⁺) |
|---|---|---|---|---|---|---|---|---|---|---|---|---|
| 1001 | Ac | Asp | D-Glu | Ile | Val | OBn | Et | 1S, 2S | NH—(S)—CHMePh | 2.00 | | 934.5 |
| 1002 | Ac | Asp | D-Glu | Ile | Val | OBn | Et | 1S, 2S | NH—(R)—CHMePh | 49.0 | | 934.4 |

What is claimed is:

1. A compound of formula I or a racemate, a diastereoisomer or an optical isomer thereof:

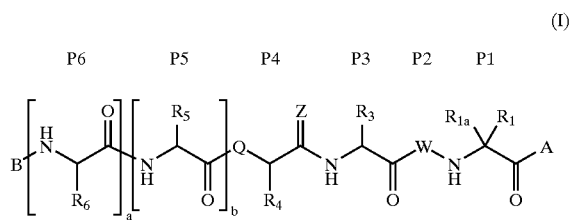

(I)

wherein Q is $CH_2$ or N—Y wherein Y is H or $C_{1-6}$ alkyl;

a) when Q is $CH_2$, a is 0, b is 0, and B is an amide derivative of formula $R_{11a}N(R_{11b})$—C(O)— wherein $R_{11a}$ is H; $C_{1-10}$ alkyl; $C_6$ aryl; $C_{7-10}$ alkylaryl; $C_{3-7}$ cycloalkyl or $C_{4-8}$ (alkylcycloalkyl) oplionally substituted with carboxyl; or heterocycle-$C_{1-6}$ alkyl;

and $R_{11b}$ is $C_{1-6}$ alkyl substituted with carboxyl, ($C_{1-6}$ alkoxy)carbonyl or phenylmethoxycarbonyl; or $C_{7-16}$ aralkyl substituted on the aromatic portion with carboxyl, ($C_{1-6}$ alkoxy)carbonyl or phenylmethoxycarbonyl;

or $R_{11a}$ and $R_{11b}$ are joined to form a 3 to 7-membered nitrogen-containing ring optionally substituted with carboxyl or ($C_{1-6}$ allcoxy)carbonyl; or b) when Q is N—Y, a is 0 or 1, b is 0 or 1, and B is an acyl derivative of formula $R_{11}$—C(O)— or a sulfonyl of formula $R_{11}$—$SO_2$ wherein $R_{11}$ is (i) $C_{1-10}$ alkyl optionally substituted with carboxyl or $C_{1-6}$ alkanoyloxy; $C_{1-6}$ alkoxy; or carboxyl substituted with 1 to 3 $C_{1-6}$ alkyl substituents;

(ii) $C_{3-7}$ cycloalkyl or $C_{4-10}$ alkylcycloalkyl, both optionally substituted with carboxyl, ($C_{1-6}$ alkoxy)carbonyl or phenylmethoxycarbonyl;

(iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or (iv) Het optionally substituted with $C_{1-6}$ alkyl, hydroxy, amino optionally substituted with $C_{1-6}$ alkyl, or amido optionally substituted with $C_{1-6}$ alkyl,

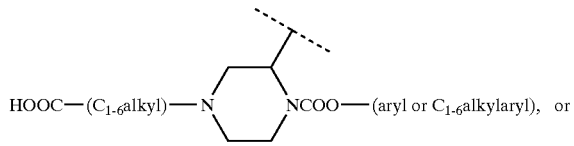

HOOC—($C_{1-6}$alkyl)—N  NCOO—(aryl or $C_{1-6}$alkylaryl), or $R_6$, when present, is $C_{1-6}$ alkyl substituted with carboxyl;

$R_5$, when present, is $C_{1-6}$ alkyl optionally substituted with carboxyl; and c) when Q is either $CH_2$ or N—Y, then $R_4$ is $C_{1-10}$ alkyl, $C_{3-7}$ cycloalkyl or $C_{4-10}$ (alkylcycloalkyl);

z is oxo or thioxo;

$R_3$ is $C_{1-10}$ alkyl optionally substituted with carboxyl, $C_{3-7}$ cycloalkyl or $C_{4-10}$ (alkylcycloalkyl);

W is a group of formula II:

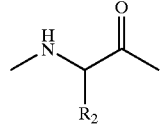

Formula II wherein $R_2$ is $C_{1-10}$ alkyl or $C_{3-10}$ cycloalkyl optionally substituted with carboxyl or an ester or amide thereof; $C_6$ or $C_{10}$ aryl or $C_{7-16}$ aralkyl; or W is a group of formula IIa:

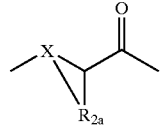

Formula IIa wherein X is CH or N; and $R_{2a}$ is a divalent $C_{3-4}$ alkylene which together with X and the carbon atom to which X and $R_{2a}$ are attached form a 5- or 6-membered ring, said ring optionally substituted with OH;

SH; $NH_2$; carboxyl; $R_{12}$; $CH_2$—$R_{12}$, $OR_{12}$, $C(O)OR_{12}$, $SR_{12}$, $NHR_{12}$ or $NR_{12}R_{12a}$;

wherein $R_{12}$ and $R_{12a}$ are independently a saturated or unsaturated $C_{3-7}$ cycloalkyl or $C_{4-10}$ (alkyl cycloalkyl) being optionally mono-, di- or tri-substituted with $R_{15}$, or each of $R_{12}$ and $R_{12a}$ is a $C_6$ or $C_{10}$ aryl or $C_{7-16}$ aralkyl optionally mono-, di- or tri-substituted with $R_{15}$, or each of $R_{12}$ and $R_{12a}$ is Het or (lower alkyl)-Het optionally mono-, di- or tri-substituted with $R_{15}$, wherein each $R_{15}$ is independently $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{16}$;

wherein $R_{16}$ is $C_{1-6}$ alkyl; $C_{1-6}$ alkoxy; amino optionally mono- or di-substituted with $C_{1-6}$ alkyl; sulfonyl; $NO_2$; OH; SH; halo; haloalkyl; carboxyl; amide; or (lower alkyl)amide;

or X is CH or N; and $R_{2a}$ is a divalent $C_{3-4}$ alkylene which together with X and the carbon atom to which X and $R_{2a}$ are attached form a 5- or 6-membered ring which in turn is fused with a second 5-, 6- or 7-membered ring to form a bicyclic system wherein the second ring is substituted with $OR_{12a'}$ wherein $R_{12a}$ is $C_{7-16}$ aralkyl;

$R_{1a}$ is hydrogen, and $R_1$ is the side chain of an amino acid selected from the group consisting of cysteine (Cys), aminobutyric acid (Abu), norvaline (Nva) and allylglycine (AlGly); or $R_{1a}$ and $R_1$ together form a 3- to 6-membered ring optionally substituted with $R_{14}$ wherein $R_{14}$ is $C_{1-6}$ alkyl, $C_{3-5}$ cycloalkyl, $C_{2-6}$ alkenyl, $C_{2-6}$ alkynyl, $C_6$ aryl or $C_{7-10}$ aralkyl all optionally substituted with halo; and A is hydroxy; or $C_{1-6}$ alkylamino, di($C_{1-6}$ alkyl)amino or phenyl-$C_{1-6}$ alkylamino;

wherein Het is a five-, six-, or seven-membered saturated or unsaturated, aromatic or non-aromatic, heterocycle containing from one to four heteroatoms selected from nitrogen, oxygen and sulfur, which heterocycle is optionally fused to a benzene ring;

or a non-toxic salt or ester thereof.

2. The compound of formula I according to claim 1, wherein B is an acyl derivative of formula $R_{11}C(O)$— wherein $R_{11}$ is $C_{1-6}$ alkyl optionally substituted with carboxyl, $C_{1-6}$ alkanoyloxy or $C_{1-6}$ alkoxy;

$C_{3-7}$ cycloalkyl optionally substituted with carboxyl, MeOC(O), EtOC(O) or BnOC(O);

3-carboxypropionyl (DAD); 4-carboxybutyryl (DAE); or

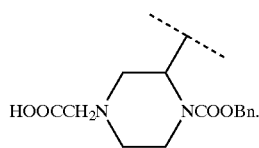

3. The compound of formula I according to claim 2, wherein B is acetyl, 3-carboxypropionyl (DAD), 4-carboxylbutyryl (DAE),

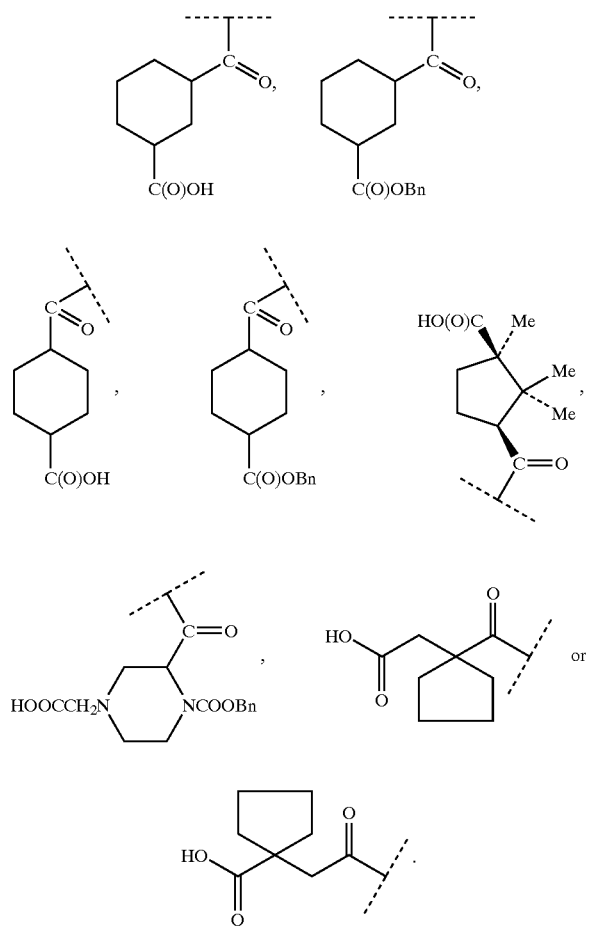

4. The compound of formula I according to claim 3, wherein B is acetyl, DAD, DAE,

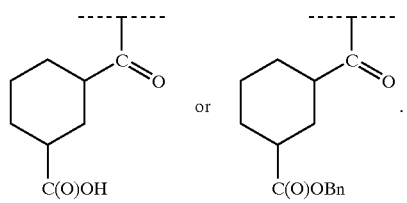

5. The compound of formula I according to claim 4, wherein B is acetyl.

6. The compound of formula I according to claim 1, wherein $R_6$, when present, is the side chain of Asp or Glu.

7. The compound of formula I according to claim 6, wherein $R_6$, when present, is the side chain of Asp.

8. The compound of formula I according to claim 7, wherein a is 0 and then $R_6$ is absent.

9. The compound of formula I according to claim 1, wherein $R_5$, when present, is the side chain of an amino acid selected from the group consisting of: aspartic acid, glutamic acid, valine and tert-butylglycine, and wherein the carbon bearing $R_5$ is in the D or L configuration.

10. The compound of formula I according to claim 9, wherein $R_5$, when present, is the side chain of aspartic acid, valine or glutamic acid, and wherein the carbon bearing $R_5$ is in the D configuration.

11. The compound of formula I according to claim 10, wherein $R_5$, when present, is the side chain of glutamic acid wherein the carbon bearing $R_5$ is in the D configuration.

12. The compound of formula I according to claim 1, wherein a is 0 and b is 0, and then both $R_6$ and $R_5$ are absent.

13. The compound of formula I according to claim 1, wherein $R_4$ is isopropyl, cyclohexyl, 1-methylpropyl, 2-methylpropyl or tert-butyl.

14. The compound of formula I according to claim 13, wherein $R_4$ is cyclohexyl or 1-methylpropyl.

15. The compound of formula I according to claim 14, wherein $R_4$ is cyclohexyl.

16. The compound of formula I according to claim 1, wherein z is oxo.

17. The compound of formula I according to claim 1, wherein $R_3$ is the side chain of an amino acid selected from the group consisting of: Ile, allo-Ile, Chg, cyclohexylalanine (Cha), Val, Tbg or Glu.

18. The compound of formula I according to claim 17, wherein $R_3$ is the side chain of Val, Tbg or Chg.

19. The compound of formula I according to claim 18, wherein $R_3$ is the side chain of Val.

20. The compound of formula I according to claim 1, wherein W is a group of formula II:

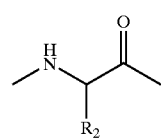

II wherein $R_2$ is $C_{1-8}$ alkyl; $C_{1-8}$ alkyl substituted with carboxyl, $C_{1-6}$ alkoxycarbonyl, benzyloxycarbonyl or benzylaminocarhonyl; $C_{3-7}$ cycloalkyl or benzyl.

21. The compound of formula I according to claim 20, wherein $R_2$ is the side of chain of aminobutyric acid (Abu), Leu, Phe, Cha, Val, Ala, Asp, Glu, Glu(OBn), or Glu(NHBn).

22. The compound of formula I according to claim 21, wherein $R_2$ is the side chain of Asp, Abu or Val.

23. The compound of formula I according to claim 1, wherein W is a group of formula IIa:

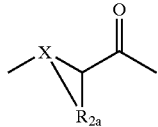
(IIa)

wherein X is CH or N, and $R_{2a}$ is a $C_3$ or $C_4$ alkylene that joins X to form a 5- or 6-membered ring of formula III:

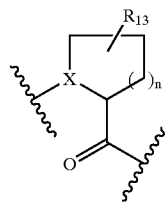
(III)

$R_{2a}$ being optionally substituted at any position with $R_{13}$, wherein X is CH or N; n is 1 or 2, and $R_{13}$ is S—$R_{12}$ or O—$R_{12}$ wherein $R_{12}$ is a $C_6$ or $C_{10}$ aryl, $C_{7-16}$ aralkyl, Het or —$CH_2$—Het, all optionally mono-, di- or tri-substituted with $R_{15}$,
  wherein $R_{15}$ is $C_{1-6}$ alkyl; $C_{1-6}$ alkoxy; amino; mono- or di-(lower alkyl)amino; amido optionally mono-substituted with $C_{1-6}$ alkyl, $C_6$ or $C_{10}$ aryl, $C_{7-16}$ aralkyl, Het or (lower alkyl)-Het; $NO_2$; OH; halo; trifluoromethyl; carboxyl; $C_6$ or $C_{10}$ aryl, $C_{7-16}$ aralkyl, or Het, said aryl, aralkyl or Het being optionally substituted with $R_{16}$, and
    wherein $R_{16}$ is $C_{1-6}$ alkyl; $C_{1-6}$ alkoxy; amino; mono- or di-(lower alkyl)amino; (lower alkyl)amide; $NO_2$; OH; halo; trifluoromethyl; or carboxyl.

24. The compound of formula I according to claim 23, wherein $R_{2a}$ is propyl joined to X wherein X is nitrogen to form a proline substituted with $R_{13}$ as defined in claim 23.

25. The compound of formula I according to claim 24, wherein $R_{2a}$ is the side chain of proline substituted at the 3-, 4-, or 5-position with $R_{13}$, wherein $R_{13}$ is as defined in claim 24.

26. The compound of formula I according to claim 25, wherein $R_{2a}$ is the side chain of proline substituted with $R_{13}$ at the 4-position with the stereochemistry shown in formula IIIa:

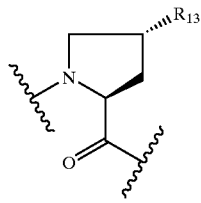
(IIIa)

wherein $R_{13}$ is S—$R_{12}$ or O—$R_{12}$ wherein $R_{12}$ is a $C_6$ or $C_{10}$ aryl, $C_{7-16}$ aralkyl, Het or —$CH_2$—Het, all optionally mono-, di- or tri-substituted with $R_{15}$,
  wherein $R_{15}$ is $C_{1-6}$ alkyl; $C_{1-6}$ alkoxy; amino; di(lower alkyl)amino; (lower alkyl)amide; $C_6$ or $C_{10}$ aryl, or Het, said aryl or Het being optionally substituted with $R_{16}$, and $R_{16}$ is $C_{1-6}$ alkoxy; amino; di(lower alkyl)amino; (lower alkyl)amide; halo; or trifluoromethyl.

27. A compound of formula I:

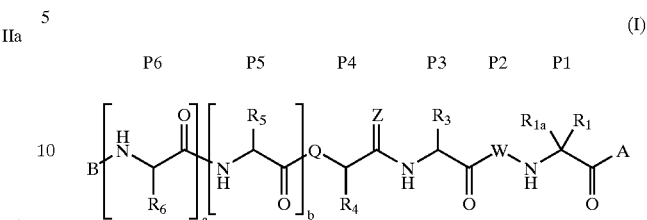
(I)

wherein Q is $CH_2$ or N—Y wherein Y is H or $C_{1-6}$ alkyl;

a) when Q is $CH_2$, a is 0, b is 0, and B is an amide derivative of formula $R_{11a}N(R_{11b})$—C(O)— wherein $R_{11a}$ is H; $C_{1-10}$ alkyl; $C_6$ aryl; $C_{7-10}$ alkylaryl; $C_{3-7}$ cycloalkyl or $C_{4-8}$ (alkylcycloalkyl) optionally substituted with carboxyl; or heterocycle-$C_{1-6}$ alkyl;

and $R_{11b}$ is $C_{1-6}$ alkyl substituted with carboxyl, ($C_{1-6}$ alkoxy)carbonyl or phenylmethoxycarbonyl; or $C_{7-16}$ aralkyl substituted on the aromatic portion with carboxyl, ($C_{1-6}$ alkoxy)carbonyl or phenylmethoxycarbonyl;

or $R_{11a}$ and $R_{11b}$ are joined to form a 3 to 7-membered nitrogen-containing ring optionally substituted with carboxyl or ($C_{1-6}$ alkoxy) carbonyl; or b) when Q is N—Y, a is 0 or 1, b is 0 or 1, and B is an acyl derivative of formula $R_{11}$—C(O)— or a sulfonyl of formula $R_{11}$—$SO_2$ wherein
  $R_{11}$ is (i) $C_{1-10}$ alkyl optionally substituted with carboxyl or $C_{1-6}$ alkanoyloxy; $C_{1-6}$ alkoxy; or carboxyl substituted with 1 to 3 $C_{1-6}$ alkyl substituents;
  (ii) $C_{3-7}$ cycloalkyl or $C_{4-10}$ alkylcycloalkyl, both optionally substituted with carboxyl, ($C_{1-6}$ alkoxy) carbonyl or phenylmethoxycarbonyl;
  (iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or
  (iv) Het optionally substituted with $C_{1-6}$ alkyl, hydroxy, amino optionally substituted with $C_{1-6}$ alkyl, or amido optionally substituted with $C_{1-6}$ alkyl,

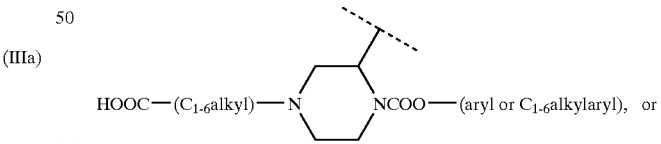

$R_6$ when present, is $C_{1-6}$ alkyl substituted with carboxyl;

$R_5$, when present, is $C_{1-6}$ alkyl optionally substituted with carboxyl; and c) when Q is either $CH_2$ or N—Y, then $R_4$ is $C_{1-10}$ alkyl, $C_{3-7}$ cycloalkyl or $C_{4-10}$ (alkylcycloalkyl);

z is oxo or thioxo;

$R_3$ is $C_{1-10}$ alkyl optionally substituted with carboxyl, $C_{3-7}$ cycloalkyl or $C_{4-10}$ (alkylcycloalkyl);

W is a group of formula IIIa:

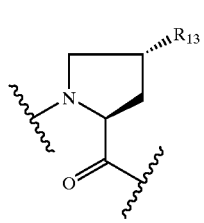

(IIIa)

wherein $R_{13}$ is o-tolylmethoxy; m-tolylmethoxy; p-tolylmethoxy; (4-tert-butyl)methoxy; (3I—Ph)CH$_2$O; (4Br—Ph)O; (2Br—Ph)O; (3Br—Ph)O; (4I—Ph)O; (3Br—Ph)CH$_2$O; (3,5-Br$_2$—Ph)CH$_2$O; or $R_{13}$ is $OR_{12}$ or $SR_{12}$ wherein $R_{12}$ is $C_6$ or $C_{10}$ aryl, $C_{7-16}$ aralkyl or Het, all optionally substituted with $C_{1-6}$ alkyl, $C_{3-7}$ cycloalkyl, $C_{1-6}$ alkoxy, acetylamido, nitro, $CF_3$, $NH_2$, OH, SH, halo, carboxyl, carboxy(lower)alkyl or a second aryl or aralkyl;

$R_{1a}$ is hydrogen, and $R_1$ is the side chain of an amino acid selected from the group consisting of cysteine (Cys), aminobutyric acid (Abu), norvaline (Nva) and allylglycine (AlGly); or $R_{1a}$ and $R_1$ together form a 3- to 6-membered ring optionally substituted with $R_{14}$ wherein $R_{14}$ is $C_{1-6}$ alkyl, $C_{3-5}$ cycloalkyl, $C_{2-6}$ alkenyl, $C_{2-6}$ alkynyl, $C_6$ aryl or $C_{7-10}$ aralkyl all optionally substituted with halo; and A is hydroxy; or $C_{1-6}$ alkylamino, di($C_{1-6}$ alkyl)amino or phenyl-$C_{1-6}$ alkylamino; wherein Het is a five-, six-, or seven-membered saturated or unsaturated, including aromatic, heterocycle containing from one to four heteroatoms selected from nitrogen, oxygen and sulfur, which heterocycle is optionally fused to a benzene ring; or a non-toxic salt or thereof.

28. The compound of formula I according to claim 27, wherein $R_{13}$ is 1-naphthyloxy; 2-naphthyloxy; 1-naphthylmethoxy; 2-naphthylmethoxy;

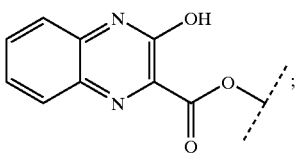

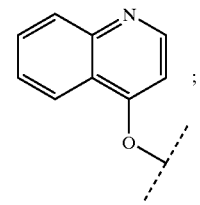

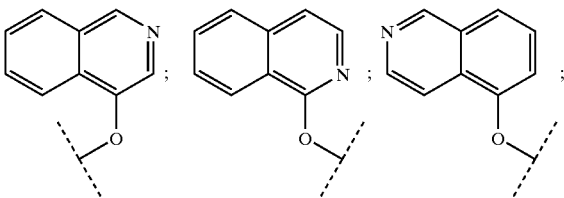

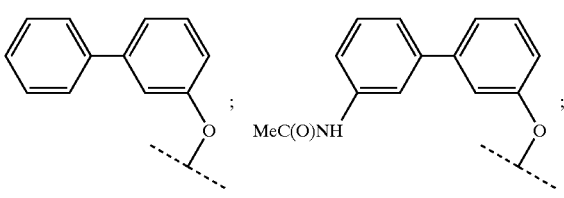

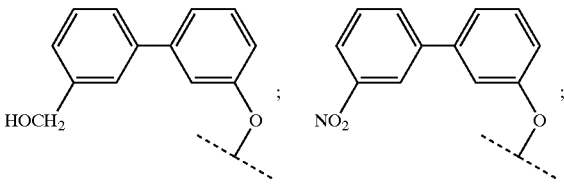

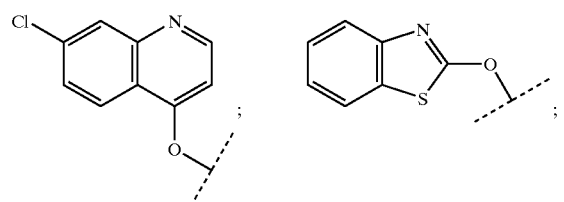

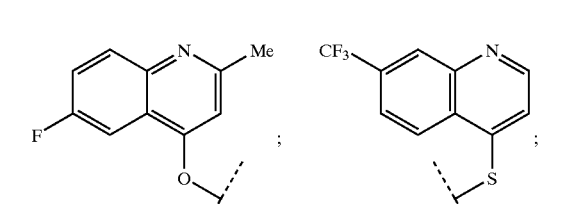

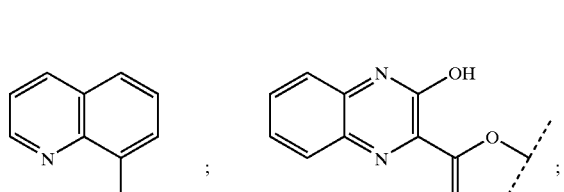

183

-continued

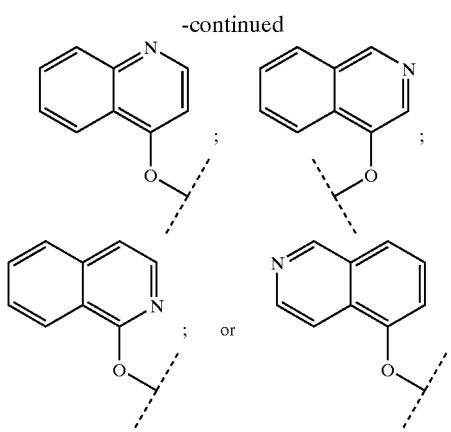

29. The compound of formula I according to claim 1, wherein $R_{1a}$ is hydrogen and $R_1$ is the side chain of the amino acid selected from the group consisting of: cysteine (Cys), aminobutyric acid (Abu), norvaline (Nva), and allylglycine (AlGly).

30. The compound of formula I according to claim 29, wherein $R_{1a}$ is H and $R_1$ is propyl.

31. The compound of formula I according to claim 1, wherein $R_{1a}$ and $R_1$ together form a 3- to 6-membered ring, said ring being optionally substituted with $R_{14}$, wherein $R_{14}$ is methyl, ethyl, propyl, vinyl, allyl, benzyl, phenylethyl or phenylpropyl, each of which is optionally substituted with halo.

32. The compound of formula I according to claim 31, wherein $R_{1a}$ and $R_1$ together form a cyclopropyl optionally substituted with $R_{14}$ as defined in claim 31.

33. The compound of formula I according to claim 32, wherein $R_{14}$ is ethyl, propyl, vinyl, bromovinyl or allyl.

34. The compound of formula I according to claim 33, wherein $R_{14}$ is ethyl, vinyl or bromovinyl.

35. The compound of formula I according to claim 1, wherein A is hydroxy, or $N(R_{17a})R_{17b}$ wherein $R_{17a}$ and $R_{17b}$ are independently H, aryl or $C_{1-6}$ alkyl optionally substituted with hydroxy or aryl.

36. The compound of formula I according to claim 35, wherein A is OH, NH-benzyl or NH—CH(Me)Ph.

37. The compound of formula I according to claim 36, wherein A is OH or NH—CH(Me)-phenyl.

38. A compound of formula (IA) or a racemate, a diastereoisomer or an optical isomer thereof:

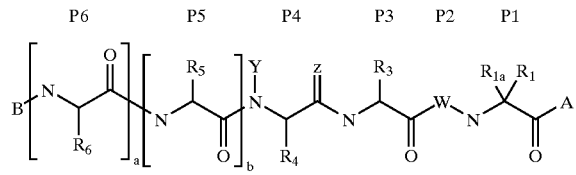

(IA)

wherein Y is H or $C_{1-6}$ alkyl;
a is 0 or 1;
b is 0 or 1;
B is as defined in claim 1, paragraph b);
$R_6$, $R_5$, $R_4$, z, $R_3$, W, $R_1$, $R_{1a}$ and A are as defined in claim 1.

39. The compound of formula IA according to claim 38, wherein B is an acyl derivative of formula $R_{11}C(O)$— wherein $R_{11}$ is $C_{1-6}$ alkyl optionally substituted with carboxyl, $C_{1-6}$ alkanoyloxy or $C_{1-6}$ alkoxy;

184

$C_{3-7}$ cycloalkyl optionally substituted with carboxyl, MeOC(O), EtOC(O) or BnOC(O); 3-carboxypropionyl (DAD); 4-carboxybutyryl (DAE); or

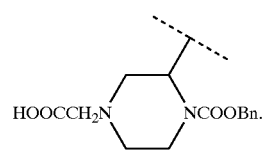

40. The compound of formula IA according to claim 39, wherein B is acetyl, 3-carboxypropionyl (DAD), 4-carboxylbutyryl (DAE),

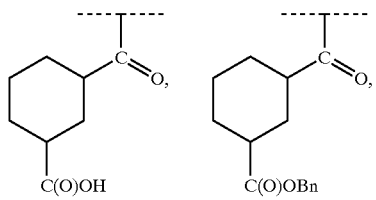

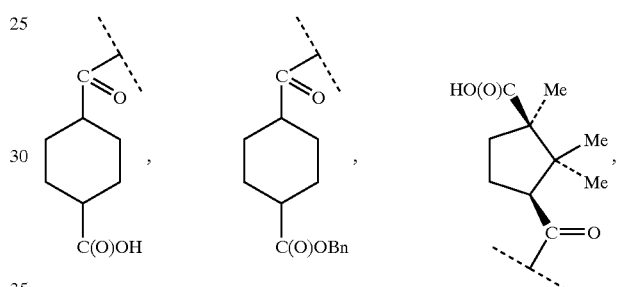

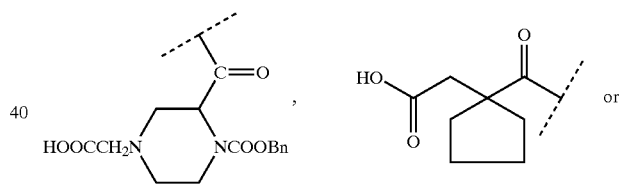

41. The compound of formula IA according to claim 40, wherein B is acetyl, DAD, DAE,

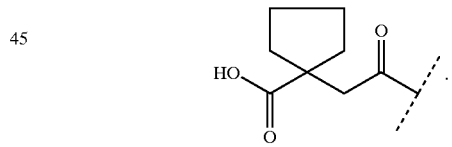

42. The compound of formula IA according to claim 41, wherein B is acetyl.

43. A compound of formula IB, or a or a racemate, a diastereoisomer or an optical isomer thereof:

(IB)

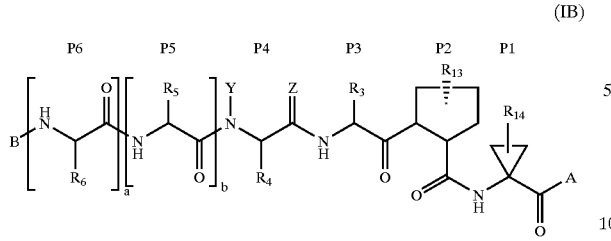

wherein
B, a, b, $R_6$, $R_5$, Y, $R_4$, Z, $R_3$, and A are as defined in claim 1,
$R_{13}$ is $R_{12}$, $OR_{12}$, $C(O)OR_{12}$, $SR_{12}$, $NHR_{12}$ or $NR_{12}R_{12a}$ wherein $R_{12}$ and $R_{12a}$ are as defined in claim 1; and
$R_{14}$ is $C_{1-6}$ alkyl, $C_{2-6}$ alkenyl optionally substituted with halogen; $C_{6-10}$ aryl or $C_{7-10}$ aralkyl optionally substituted with halogen; or a non-toxic salt or ester thereof.

44. The compound of formula IB according to claim 43, wherein B is $R_{11}$—$SO_2$ wherein $R_{11}$ is $C_6$ or $C_{10}$ aryl, a $C_{7-16}$ aralkyl or Het all optionally substituted with $C_{1-6}$ alkyl.

45. A compound of formula IB:

(IB)

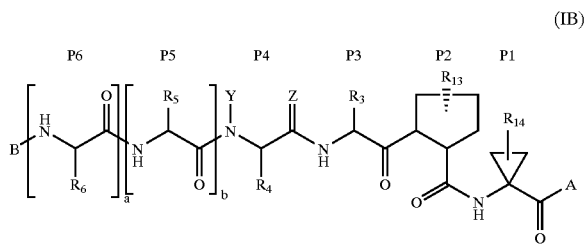

wherein B is an acyl derivative of formula $R_{11}C(O)$— wherein $R_{11}$ is $C_{1-6}$ alkyl; $C_{1-6}$ alkoxy; $C_{3-7}$ cycloalkyl optionally substituted with hydroxy; amido optionally substituted with $C_{1-6}$ alkyl or Het; $C_6$ or $C_{10}$ aryl, $C_{7-16}$ aralkyl or Het all optionally substituted with $C_{1-6}$ alkyl or hydroxy;
a, b, $R_6$, $R_5$, Y, $R_4$, Z, $R_3$, and A are as defined in claim 1,
$R_{13}$ is $R_{12}$, $OR_{12}$, $C(O)OR_{12}$, $SR_{12}$, $NHR_{12}$ or $NR_{12}R_{12a}$ wherein $R_{12}$ and $R_{12a}$ are as defined in claim 1; and
$R_{14}$ is $C_{1-6}$ alkyl, $C_{2-6}$ alkenyl optionally substituted with halogen; $C_{6-10}$ aryl or $C_{7-10}$ aralkyl optionally substituted with halogen; or a non-toxic salt or ester thereof.

46. The compound of formula IB according to claim 45, wherein B is $R_{11}C(O)$— wherein $R_{11}$ is $C_{1-6}$ alkyl,

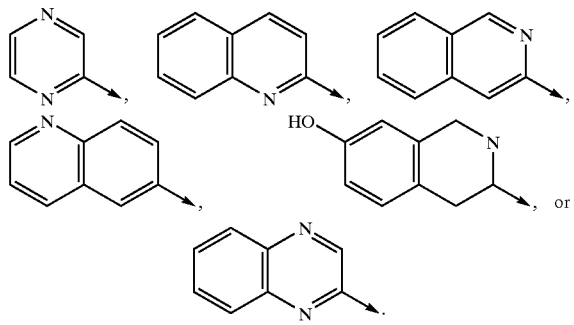

47. The compound of formula IB according to claim 46, wherein

B is acetyl;

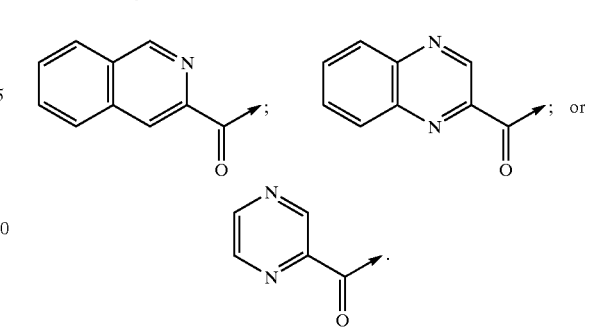

48. The compound of formula IB according to claim 43, wherein $R_{13}$ is o-tolylmethoxy; m-tolylmethoxy; p-tolylmethoxy; (4-tert-butyl)methoxy; (3I—Ph)CH$_2$O; (4Br—Ph)O; (2Br—Ph)O; (3Br—Ph)O; (4I—Ph)O; (3Br—Ph)CH$_2$O; (3,5-Br$_2$—Ph)CH$_2$O; or $R_{13}$ is $OR_{12}$ or $SR_{12}$ wherein $R_{12}$ is $C_6$ or $C_{10}$ aryl, $C_{7-16}$ aralkyl or Het, all optionally substituted with $C_{1-6}$ alkyl, $C_{3-7}$ cycloalkyl, $C_{1-6}$ alkoxy, acetylamido, nitro, $CF_3$, $NH_2$, OH, SH, halo, carboxyl, carboxy(lower)alkyl or a second aryl or aralkyl.

49. The compound of formula IB according to claim 48, wherein $R_{13}$ is 1-naphthyloxy; 2-naphthyloxy; 1-naphthylmethoxy; 2-naphthylmethoxy; 2-, 3-, 4-, or 6-quinolinoxy, all optionally substituted.

50. The compound of formula IB according to claim 49, wherein $R_{13}$ is 1-naphthyloxy; 2-naphthyloxy; 1-naphthylmethoxy; 2-naphthylmethoxy; or substituted 4-quinolinoxy.

51. The compound of formula IB according to claim 50, wherein $R_{13}$ is 1-naphthylmethoxy; 2-naphthylmethoxy; benzyloxy, 1-naphthyloxy; 2-naphthyloxy; or quinolinoxy unsubstituted, mono- or di-substituted with $R_{15}$ wherein $R_{15}$ is $C_{1-6}$ alkyl; $C_{1-6}$ alkoxy; amino; mono- or di-(lower alkyl)amino; amido optionally mono-substituted with $C_{1-6}$ alkyl, $C_6$ or $C_{10}$ aryl, $C_{7-16}$ aralkyl, Het or (lower alkyl)-Het; NO$_2$; OH; halo; trifluoromethyl; carboxyl; $C_6$ or $C_{10}$ aryl, $C_{7-16}$ aralkyl, or Het, said aryl, aralkyl or Het being optionally substituted with $R_{16}$, wherein $R_{16}$ is $C_{1-6}$ alkyl; $C_{1-6}$ alkoxy; amino; mono- or di-(lower alkyl)amino; (lower alkyl)amide; NO$_2$; OH; halo; trifluoromethyl; or carboxyl.

52. The compound of formula IB according to claim 51, wherein $R_{13}$ is 1-naphthylmethoxy; or quinolinoxy unsubstituted, mono- or di-substituted with $R_{15}$ as defined in claim 51.

53. The compound of formula IB according to claim 52, wherein $R_{13}$ is:

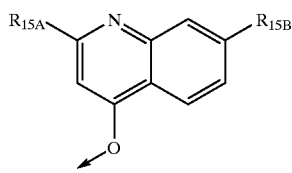

wherein $R_{15A}$ is amido optionally mono-substituted with $C_{1-6}$ alkyl, $C_6$ or $C_{10}$ aryl, $C_{7-16}$ aralkyl or Het; or $C_6$ or $C_{10}$ aryl or Het optionally substituted with $R_{16}$, $R_{15B}$ is $C_{1-6}$ alkyl; $C_{1-6}$ alkoxy; amino; di(lower alkyl)amino; (lower alkyl)amide; NO$_2$; OH; halo; trifluoromethyl; or carboxyl, and $R_{16}$ is amino; di(lower alkyl)amino; or (lower alkyl) amide.

54. The compound of formula IB according to claim 53, wherein $R_{15A}$ is $C_6$ or $C_{10}$ aryl or Het, all optionally substituted with $R_{16}$, $R_{15B}$ is $C_{1-6}$ alkoxy; or di(lower alkyl)amino, and $R_{16}$ is as defined in claim 53.

55. The compound of formula IB according to claim 54, wherein $R_{15A}$ is $C_6$ or $C_{10}$ aryl or Het, all unsubstituted, $R_{15B}$ is methoxy, and $R_{16}$ is amino; dimethylamino; or acetamido.

56. The compound of formula IB according to claim 43, wherein P1 is a cyclopropyl ring system of formula:

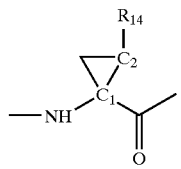

wherein $R_{14}$ is as defined in claim 43.

57. The compound of formula IB according to claim 56, wherein P1 exists as a racemic mixture of two stereoisomers wherein $R_{14}$ at position 2 is orientated syn to the carbonyl at position 1, represented by the radical:

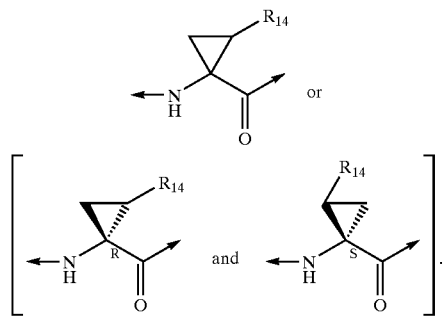

58. The compound of formula IB according to claim 56, wherein P1 exists as a racemic mixture of two stereoisomers wherein $R_{14}$ at position 2 is orientated anti to the carbonyl at position 1, represented by the radical:

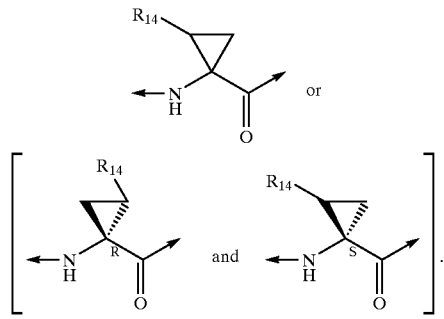

59. The compound of formula IB according to claim 56, wherein the $C_1$ carbon atom has the R configuration:

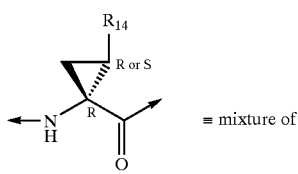

≡ mixture of

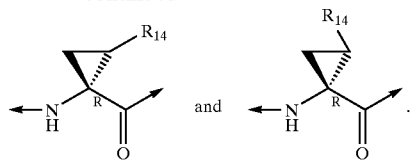

60. The compound of formula IB according to claim 59, wherein said $R_{14}$ substituent and said carbonyl are in syn orientation in the following absolute configuration:

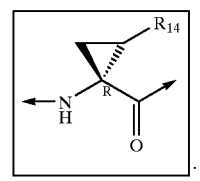

61. The compound of formula IB according to claim 59, wherein said $R_{14}$ is methyl, ethyl, propyl, vinyl, allyl, benzyl, phenylethyl or phenylpropyl, each of which is optionally substituted with halo.

62. The compound of formula IB according to claim 59, wherein $R_{14}$ is ethyl, propyl, vinyl, bromovinyl or allyl.

63. The compound of formula IB according to claim 62, wherein $R_{14}$ is ethyl, vinyl or bromovinyl.

64. The compound of formula IB according to claim 59, wherein P1 is

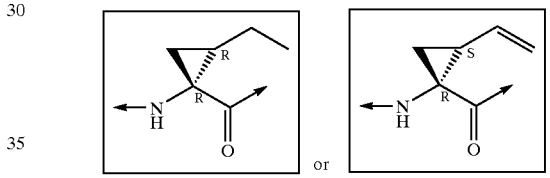

65. A compound of formula IC or a racemate, a diastereoisomer or an optical isomer thereof:

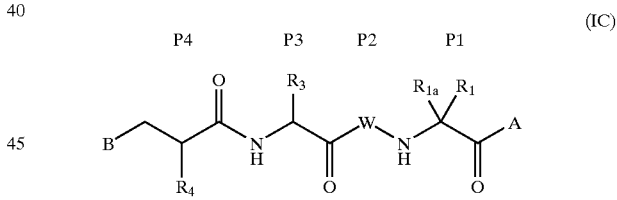

(IC)

wherein B is as defined in claim 1, paragraph a);
$R_4$, $R_3$, W, $R_{1a}$, $R_1$, and A are as defined in claim 1.

66. A compound of formula IC:

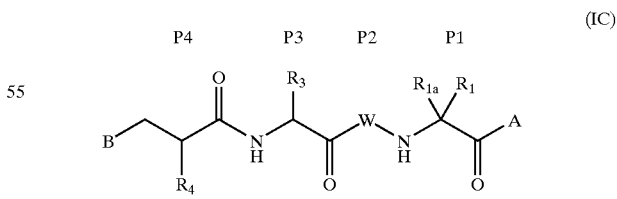

(IC)

wherein B is an amide of formula $R_{11a}N(R_{11b})C(O)$— wherein $R_{11a}$ is $C_{1-6}$ alkyl; $C_{3-6}$ cycloalkyl; $C_{3-7}$ (alkylcycloalkyl) optionally substituted with carboxy; $C_{1-3}$ carboxyalkyl;

$C_6$ aryl; $C_{7-10}$ arylalkyl; 2-tetrahydrofuranylmethyl; or 2-thiazolidylmethyl; and $R_{11b}$ is $C_{1-4}$ alkyl substituted with carboxyl;

$R_4$, $R_3$, W, $R_{1a}$, $R_1$, and A are as defined in claim 1.

67. The compound of formula (IC) according to claim 66, wherein $R_{11a}$ is cyclopropylmethyl, isopropyl, carboxyethyl, benzylmethyl, benzyl, or 2-tetrahydrofuranylmethyl.

68. The compound of formula (IC) according to claim 67, wherein $R_{11b}$ is $C_{1-4}$ alkyl substituted with carboxyl.

69. The compound of formula (IC) according to claim 68, wherein $R_{11b}$ is ethyl carboxyl.

70. A compound of formula (I):

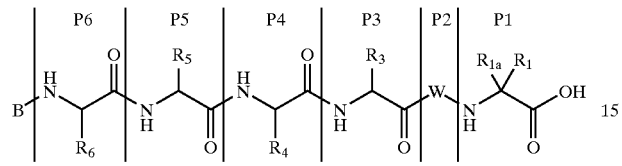

(I)

wherein B, P6, P5, P4, P3, W and P1 are as defined below, said compound selected from the group consisting of:

71. A compound of formula (I):

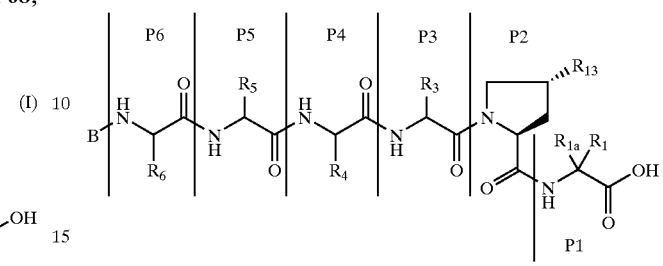

(I)

wherein B, P6, P5, P4, P3, $R_{13}$ and P1 are as defined below, said compound selected from the group consisting of:

| Comp | B | P6 | P5 | P4 | P3 | W | P1 | SEQ ID NO. |
|---|---|---|---|---|---|---|---|---|
| 101 | Ac | Asp | Asp | Ile | Val | Pro | Cys; | 8 |
| 102 | Ac | Glu | Asp | Ile | Val | Pro | Cys; | 9 |
| 103 | DAD | — | Asp | Ile | Val | Pro | Cys; | 10 |
| 104 | Ac | Asp | D-Asp | Ile | Val | Pro | Cys; | — |
| 105 | Ac | Asp | D-Glu | Ile | Val | Pro | Cys; | — |
| 106 | Ac | Asp | Glu | Ile | Val | Pro | Cys; | 11 |
| 107 | Ac | Asp | Val | Ile | Val | Pro | Cys; | 12 |
| 108 | Ac | Asp | Tbg | Ile | Val | Pro | Cys; | 13 |
| 109 | Ac | Asp | Asp | Val | Val | Pro | Cys; | 14 |
| 110 | Ac | Asp | Asp | Chg | Val | Pro | Cys; | 15 |
| 111 | Ac | Asp | Asp | Tbg | Val | Pro | Cys; | 16 |
| 112 | Ac | Asp | Asp | Leu | Val | Pro | Cys; | 17 |
| 113 | Ac | Asp | Asp | Ile | Ile | Pro | Cys; | 18 |
| 114 | Ac | Asp | Asp | Ile | Chg | Pro | Cys; | 19 |
| 115 | Ac | Asp | Asp | Ile | Val | Abu | Cys; | 20 |
| 116 | Ac | Asp | Asp | Ile | Val | Leu | Cys; | 21 |
| 117 | Ac | Asp | Asp | Ile | Val | Phe | Cys; | 22 |
| 118 | Ac | Asp | Asp | Ile | Val | Val | Cys; | 23 |
| 119 | Ac | Asp | Asp | Ile | Val | Ile | Cys; | 24 |
| 120 | Ac | Asp | Asp | Ile | Val | Ala | Cys; | 25 |
| 121 | Ac | Asp | Asp | Ile | Val | Hyp(4-Bn) | Cys; | 26 |
| 122 | Ac | Asp | Asp | Ile | Val | Pro | Abu; | 27 |
| 123 | Ac | Asp | Asp | Ile | Val | Pro | Nva; | 28 |
| 124 | Ac | Asp | Asp | Ile | Val | Pro | AlGly; | 29 |
| 125 | Ac | Asp | Asp | Ile | Val | Pro | Acpe; | 30 |
| 126 | Ac | Asp | Asp | Ile | Val | Pro | Acca; | 31 |
| 127 | Ac | Asp | Asp | Ile | Val | Pip | Nva; | 32 |
| 128 | Ac | Asp | D-Glu | Ile | Val | Pro | Nva; | — |
| 129 | Ac | Asp | Tbg | Ile | Val | Pro | Nva; | 33 |
| 130 | DAD | — | Asp | Ile | Val | Pro | Nva; | 34 |
| 131 | Ac | Asp | Glu | Chg | Glu | Glu | Cys; | 35 |
| 132 | Ac | Asp | D-Glu | Chg | Glu | Glu | Acca; | — |
| and | | | | | | | | 36 |
| 133 | Ac | Asp | Glu | Chg | Val | Glu(OBn) | Acca. | |

| Comp. | B | P6 | P5 | P4 | P3 | R13 | P1 | SEQ ID NO. |
|---|---|---|---|---|---|---|---|---|
| 201 | Ac | Asp | Asp | Ile | Val | O-Bn | Nva; | 37 |
| 202 | Ac | Asp | D-Val | Ile | Val | O-Bn | Nva; | — |
| 203 | Ac | Asp | D-Glu | Ile | Val | O-Bn | Nva; | — |
| 204 | Ac | Asp | Asp | Ile | Val | o-tolyl-methoxy | Nva; | 38 |
| 205 | Ac | Asp | Asp | Ile | Val | m-tolyl-methoxy | Nva; | 39 |
| 206 | Ac | Asp | Asp | Ile | Val | p-tolyl-methoxy | Nva; | 40 |
| 207 | Ac | Asp | Asp | Ile | Val | 1-NpCH$_2$O | Nva; | 41 |
| 208 | Ac | Asp | Asp | Ile | Val | 2-NpCH$_2$O | Nva; | 42 |
| 209 | Ac | Asp | Asp | Ile | Val | 4-tert-butyl-phenyl)-methoxy | Nva; | 43 |
| 210 | Ac | Asp | D-Glu | Chg | Val | O-Bn | Cys; | — |
| 211 | Ac | Asp | D-Glu | Chg | Val | O-Bn | Nva; | — |
| 212 | Ac | Asp | D-Glu | Ile | Val | O-Bn | Acca; | — |
| 213 | Ac | Asp | D-Glu | Ile | Val | 2-NpCH$_2$O | Nva; | — |
| 214 | Ac | Asp | D-Glu | Chg | Val | 2-NpCH$_2$O | Nva; | — |
| 215 | Ac | Asp | D-Glu | Chg | Val | 1-NpCH$_2$O | Acca; | — |
| 216 | Ac | Asp | Asp | Ile | Val | Bn | Nva; | 44 |
| 217 | Ac | Asp | Asp | Ile | Val | Ph(CH$_2$)$_3$ | Nva; | 45 |
| 218 | Ac | Asp | D-Glu | Ile | Val | O-Bn | Nva; | — |
| 219 | Ac | — | Asp | Ile | Val | 1-NpCH$_2$O | Nva; | 46 |
| 220 | DAD | — | — | N(Me)Ile | Val | 1-NpCH$_2$O | Nva; | — |
| 221 | DAD | — | — | Ile | Val | 1-NpCH$_2$O | Nva; | — |
| 222 | DAE | — | — | Ile | Val | 1-NpCH$_2$O | Nva; | — |
| 223 | [HOOC-CH$_2$-C(cyclopentyl)-C(O)-] | — | — | Ile | Val | 1-NpCH$_2$O | Nva; | — |
| 224 | [HOOC-C(cyclopentyl)-CH$_2$-C(O)CH$_3$] | — | — | Ile | Val | 1-NpCH$_2$O | Nva; | — |
| 225 | Ac | — | — | Ile | Val | 1-NpCH$_2$O | Nva; | — |
| 226 | DAE | — | — | Chg | Val | 1-NpCH$_2$O | Acca; | — |
| 227 | Ac | — | — | Chg | Val | 1-NpCH$_2$O | Acca; | — |
| 228 | Ac | — | — | Chg | Val | O-Bn | [ethyl-cyclopropyl-N(H)-acetyl group] | — |
| 230 | Ac | Asp | Asp | Ile | Val | Ph(CH$_2$)$_3$ | Nva; | 47 |
| 231 | Ac | — | — | Chg | Chg | 1-NpCH$_2$O | Acca; | — |
| 232 | AcOCH$_2$—C(O) | — | — | Chg | Chg | 1-NpCH$_2$O | Acca; | — |
| 233 | Ac | Asp | Glu | Ile | Val | (3I—Ph)CH$_2$O | Acca; | 48 |
| 234 | Ac | — | — | Chg | Chg | O—Bn | Acca; | — |
| 235 | Boc | — | — | Chg | Chg | 1-NpCH$_2$O | Acca; | — |
| 236 | Ac | — | Gly | thioxo-Ile | Val | 1-NpCH$_2$O | Nva; | — |
| 237 | DAE | — | — | Ile | Val | 1-NpCH$_2$O | Acca; | — |
| 238 | Ac | — | — | Chg | Val | (4Br—Ph)O | Acca; | — |
| 239 | Ac | — | — | Chg | Val | (2Br—Ph)O | Acca; | — |
| 240 | Ac | — | — | Chg | Val | (3Br—Ph)O | Acca; | — |
| 241 | Ac | — | — | Chg | Val | benzothiazol-2-yl-S | Acca; | — |
| 242 | Ac | — | — | Chg | Val | (4Br—Ph)S | Acca; | — |

-continued
| Comp. | B | P6 | P5 | P4 | P3 | R13 | P1 | SEQ ID NO. |
|---|---|---|---|---|---|---|---|---|
| 243 | Ac | — | — | Chg | Val | 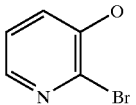 | Acca; | — |
| 244 | Ac | — | — | Chg | Val | 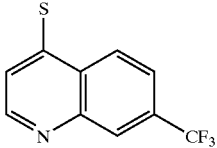 | Acca; | — |
| 245 | Ac | — | — | Chg | Val | 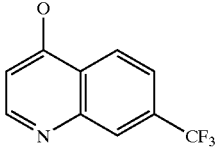 | Acca; | — |
| 246 | Ac | — | — | Chg | Val | 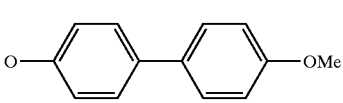 | Acca; | — |
| 247 | Ac | Asp | Asp | Ile | Val | Ph(CH$_2$)$_2$ | Nva; | 49 |
| 248 | Ac | — | — | Chg | Chg | 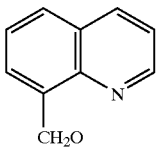 | Acca; | — |
| 249 | Ac | — | — | Chg | Val | (4I—Ph)O | Acca; | — |
| 250 | Ac | — | — | Chg | Val | 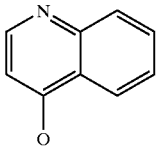 | Acca; | — |
| 251 | Ac | — | — | Chg | Val | 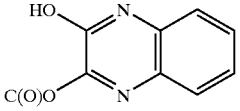 | Acca; | — |
| 252 | Ac | — | — | Chg | Val | 1-NpCH$_2$O | Nva; | — |
| 253 | Ac | — | — | Chg | Val | 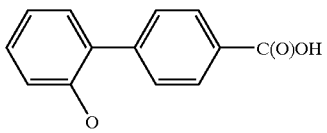 | Acca; | — |
| 254 | Ac | — | — | Chg | Val | 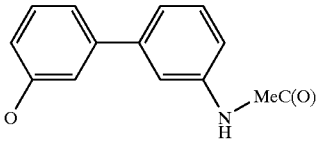 | Acca; | — |

-continued
| Comp. | B | P6 | P5 | P4 | P3 | R13 | P1 | SEQ ID NO. |
|---|---|---|---|---|---|---|---|---|
| 255 | Ac | — | — | Chg | Val | 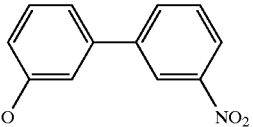 | Acca; | — |
| 256 | Ac | — | — | Chg | Val | 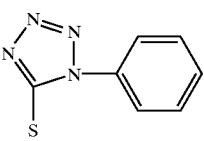 | Acca; | — |
| 257 | Ac | — | — | Chg | Val | 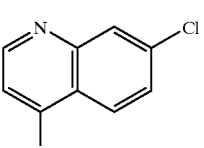 | Acca; | — |
| 258 | Ac | — | — | Chg | Val | 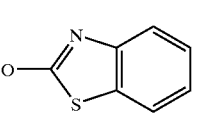 | Acca; | — |
| 259 | Ac | — | — | Chg | Val | 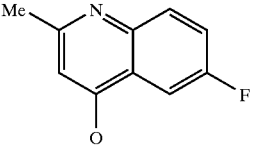 | Acca; | — |
| 260 | Ac | Asp | D-Glu | Ile | Val | O—Bn | Cys; | — |
| 261 | Ac | — | — | Chg | Val | O—Bn | Cys; | — |
| 262 | Ac | — | — | Ile | Val | 1-NpCH$_2$O | Acca; | — |
| 263 | 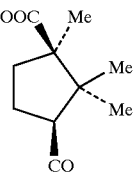 | — | — | Ile | Val | 1-NpCH$_2$O | Acca; | — |
| 264 | 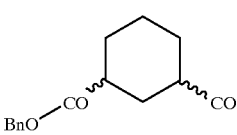 | — | — | Ile | Val | 1-NpCH$_2$O | Acca; | — |
| 265 | 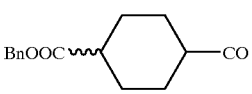 | — | — | Ile | Val | 1-NpCH$_2$O | Acca; | — |
| 266 | 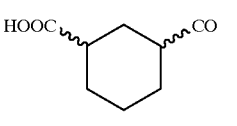 | — | — | Ile | Val | 1-NpCH$_2$O | Acca; | — |
| 267 | 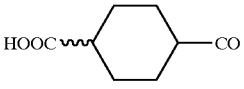 | — | — | Ile | Val | 1-NpCH$_2$O | Acca; | — |
| 268 | Ac | — | — | Chg | Val | (3Br—Ph)CH$_2$O | Acca; | — |

-continued

| Comp. | B | P6 | P5 | P4 | P3 | R13 | P1 | SEQ ID NO. |
|---|---|---|---|---|---|---|---|---|
| 269 | BnOOC-cyclohexyl-CO | — | — | Chg | Val | 1-NpCH$_2$O | Acca; | — |
| 270 | HOOC-cyclohexyl-CO | — | — | Chg | Val | 1-NpCH$_2$O | Acca; | — |
| 271 | piperazine-CH$_2$COOH, N-CO-OBn | — | — | Chg | Val | 1-NpCH$_2$O | Acca; | — |
| 272 | Ac | — | — | Chg | Val | (3,5-Br$_2$—Ph)CH$_2$O | Acca; | — |
| 273 | Ac | Asp | Asp | Ile | Val | H | Nva; | 50 |
| 274 | Ac | Asp | D-Val | Ile | Val | H | Cys; | — |
| and 275 | Ac | — | — | Chg | Val | 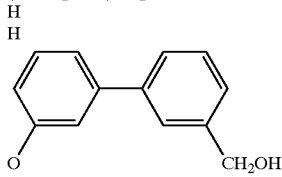 | Acca. | — |

72. A compound of formula (I):

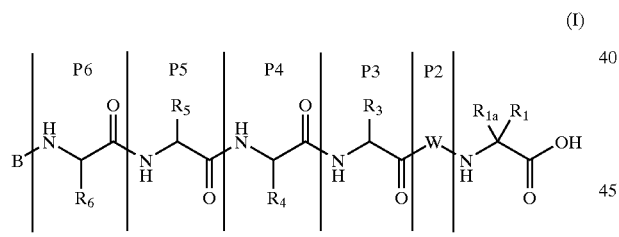

(I)

wherein B, P6, P5, P4, P3, W and P1 are as defined below, said compound selected from the group consisting of:

| Comp | B | P6 | P5 | P4 | P3 | W | P1 | SEQ ID NO. |
|---|---|---|---|---|---|---|---|---|
| 301 | Ac | Asp | Asp | Ile | Val | (pyrrolidine with Me) | Nva; | 51 |

-continued
| Comp | B | P6 | P5 | P4 | P3 | W | P1 | SEQ ID NO. |
|---|---|---|---|---|---|---|---|---|
| 302 | Ac | Asp | Asp | Ile | Val | 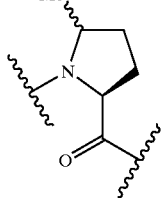 | Nva; | 52 |
| 303 | Ac | Asp | Asp | Ile | Val | 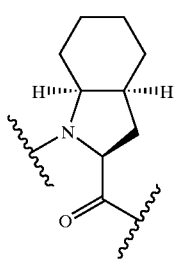 | Nva; | 53 |
| and 304 | Ac | — | — | Chg | Val | 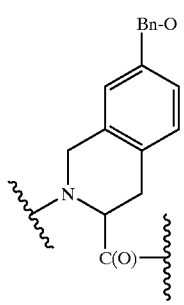 | Acca. | — |
73. A compound of formula (I):
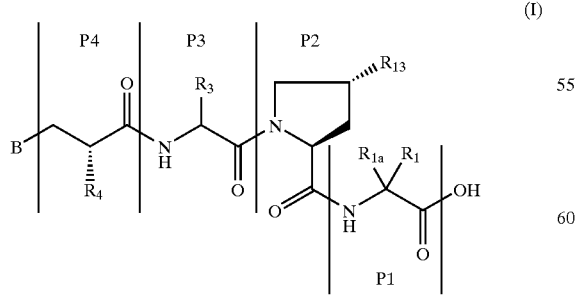
wherein B, $R_4$ P3, $R_{13}$, P1 are as defined below, said compound selected from the group consisting of:

| Comp. | B | R⁴ | P3 | $R_{13}$ | P1 |
|---|---|---|---|---|---|
| 401 | 4-(HOCO)-piperidin-1-yl-C(O)CH₃ (1-acetyl-4-carboxypiperidine) | cyclohexyl | Val | 1-NpCH₂O | Acca; |
| 402 | 4-(MeOCO)-piperidin-1-yl-C(O)CH₃ (1-acetyl-4-methoxycarbonylpiperidine) | cyclohexyl | Val | 1-NpCH₂O | Acca; |
| 403 | 4-(HOOC)-C₆H₄-CH₂-N(Me)-C(O)-CH₃ | cyclohexyl | Val | 1-NpCH₂O | Acca; |
| 404 | 4-(MeOOC)-C₆H₄-CH₂-N(Me)-C(O)-CH₃ | cyclohexyl | Val | 1-NpCH₂O | Acca; |
| 405 | HOOC—CH₂CH₂—N(Me)C(O)— | cyclohexyl | Val | 1-NpCH₂O | Acca; |
| 406 | MeOOC—CH₂—CH₂—N(Me)c(O)— | cyclohexyl | Val | 1-NpCH₂O | Acca; |
| 407 | HOOC—CH₂CH₂—N(Me)₂—C(O)— | cyclohexyl | Val | 1-NpCH₂O | Acca; |
| 408 | MeOOC—(CH₂)₂—N(Me)₂—C(O)— | cyclohexyl | Val | 1-NpCH₂O | Acca; |
| 409 | HOOC—CH₂—N(Me)₂—C(O)— | cyclohexyl | Val | 1-NpCH₂O | Acca; |
| 410 | EtOOC—CH₂—N(Me)₂—C(O)— | cyclohexyl | Val | 1-NpCH₂O | Acca; |
| 411 | [HOOC—(CH₂)₂]₂—NH—CH₂— | cyclohexyl | Val | 1-NpCH₂O | Acca; |
| 412 | [HOOC—CH₂]₂—NC(O)— | cyclohexyl | Val | 1-NpCH₂O | Acca; |
| 413 | [HOOC—(CH₂)₂]₂—NC(O)— | cyclohexyl | Val | 1-NpCH₂O | Acca; |
| 414 | HO-C(O)-CH₂CH₂-N(CH₂-cyclopropyl)-C(O)-CH₃ | cyclohexyl | Val | 1-NpCH₂O | Acca; |

-continued

| Comp. | B | R⁴ | P3 | R₁₃ | P1 |
|---|---|---|---|---|---|
| 415 | (3-(N-(cyclohexylmethyl)acetamido)propanoic acid structure) | cyclohexyl | Val | 1-NpCH₂O | Acca; |
| 416 | (3-(N-((tetrahydrofuran-2-yl)methyl)acetamido)propanoic acid structure) | cyclohexyl | Val | 1-NpCH₂O | Acca; |
| 417 | (3-(N-isobutylacetamido)propanoic acid structure) | cyclohexyl | Val | 1-NpCH₂O | Acca; |
| 418 | (3-(N-benzylacetamido)propanoic acid structure, Bn) | cyclohexyl | Val | 1-NpCH₂O | Acca; |
| 419 | (3-(N-(3,3-dimethylbutyl)acetamido)propanoic acid structure) | cyclohexyl | Val | 1-NpCH₂O | Acca; |
| 420 | (3-(N-(2,2-diphenylethyl)acetamido)propanoic acid structure, Ph₂CHCH₂) | cyclohexyl | Val | 1-NpCH₂O | Acca; |
| and 421 | (3-(N-(thiophen-2-ylmethyl)acetamido)propanoic acid structure) | cyclohexyl | Val | 1-NpCH₂O | Acca. |

74. A compound of formula (I):

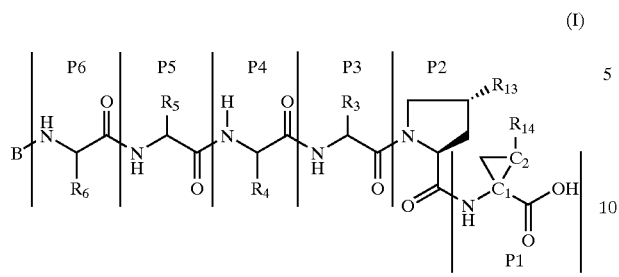

wherein B, B6, P5, P4, P3, $R_{13}$, $R_{14}$ and P1 are as defined below, said compound selected from the group consisting of:

| Tab 5 Cpd | B | P6 | P5 | P4 | P3 | $R_{13}$ | $R_{14}$ | P1 $C_1$–$C_2$ |
|---|---|---|---|---|---|---|---|---|
| 501 | Ac | — | — | Chg | Val | OBn | Et | 1R, 2R |
| 502 | Ac | — | — | Chg | Val | OBn | Et | 1R, 2? |
| 503 | Ac | — | — | Chg | Chg | 1-NpCH$_2$O | Et | 1R, 2? |
| 504 | Ac | — | — | Chg | Chg | 1-NpCH$_2$O | Et | 1R, 2? |
| 505 | Ac | — | — | Chg | Chg | 1-NpCH$_2$O | Et | 1R, 2R |
| 506 | Ac | — | — | Chg | Chg | 1-NpCH$_2$O | Et | 1S, 2S |
| 507 | Ac | — | — | Chg | Val | 1-NpCH$_2$O | Me | 1R, 2? |
| 508 | Ac | — | — | Chg | Val | 1-NpCH$_2$O | CHMe$_2$ | 1R, 2? |
| 509 | Ac | Asp | D-Glu | Chg | Chg | 1-NpCH$_2$O | Et | 1R, 2R |
| 510 | Ac | — | — | Chg | Val | 1-NpCH$_2$O | CH$_2$OCH$_2$Ph | 1R, 2? |
| 511 | Ac | — | — | Chg | Val | 1-NpCH$_2$O | CH$_2$OCH$_2$Ph | 1R, 2? |
| 512 | Ac | — | — | Chg | Val | 1-NpCH$_2$O | (CH$_2$)$_2$Ph | 1R, 2? |
| 513 | Ac | — | — | Chg | Val | 1-NpCH$_2$O | Et | 1R, 2R |
| 514 | Ac | — | — | Chg | Val | 1-NpCH$_2$O | Et | 1S, 2S |
| 515 | Ac | — | — | Chg | Val | 1-NpCH$_2$O | Bz | 1R, 2? |
| 516 | Ac | — | — | Chg | Val | 1-NpCH$_2$O | Bz | 1R, 2? |
| 517 | Ac | Asp | D-Glu | Ile | Val | OBn | Et | 1R, 2R |
| 518 | Ac | Asp | D-Glu | Chg | Val | 1-NpCH$_2$O | Et | 1R, 2R |
| 519 | Ac | — | — | Chg | Val | 1-NpCH$_2$O | Pr | 1R, 2? |
| 520 | Ac | — | — | Chg | Val | 1-NpCH$_2$O | Pr | 1R, 2? |
| 521 | Ac | Asp | D-Val | Chg | Val | 1-NpCH$_2$O | Et | 1R, 2R |
| 522 | Ac | — | — | Chg | Val | 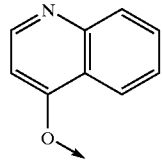 | vinyl | 1S, 2R |
| 523 | Ac | — | — | Chg | Val | 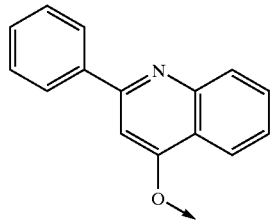 | ethyl | 1R, 2S |
| 524 | Ac | — | — | Chg | Val | 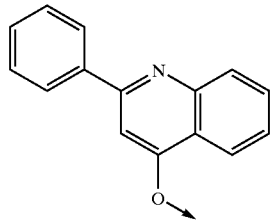 | propyl | 1R, 2R. |

75. A compound of formula (I):

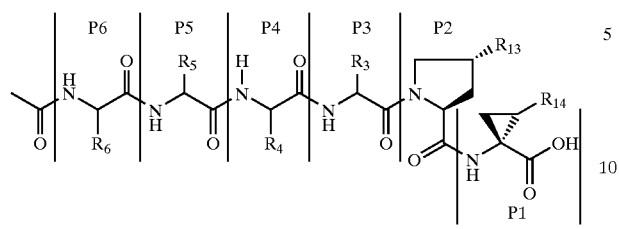

wherein P6, P5, P4, P3, $R_{13}$, and $R_{14}$ are as defined below, said compound selected from the group consisting of:

| Tab 6 Cpd # | P6 | P5 | P4 | P3 | $R_{13}$ | $R_1$ |
|---|---|---|---|---|---|---|
| 601 | — | — | Chg | Val | OBn | CH=CH$_2$ |
| 602 | — | — | Chg | Chg | 1-NpCH$_2$O | CH=CH$_2$ |
| 603 | — | — | Chg | Val | 1-NpCH$_2$O | CH=CH$_2$ |
| 604 | — | — | Chg | Val | OBn | CH=CHBr* |
| 605 | — | — | Chg | Val | quinolin-4-yloxy | CH=CH$_2$ |
| 606 | — | — | Chg | Val | 2-phenylquinolin-4-yloxy | CH=CH$_2$ |
| 607 | — | — | Chg | Tbg | 2-(pyridin-2-yl)quinolin-4-yloxy | CH=CH$_2$ |
| 608 | — | — | Chg | Val | 7-chloro-2-phenylquinolin-4-yloxy | CH=CH$_2$ |

| Tab 6 Cpd # | P6 | P5 | P4 | P3 | R13 | R1 |
|---|---|---|---|---|---|---|
| 609 | — | — | Chg | Val | 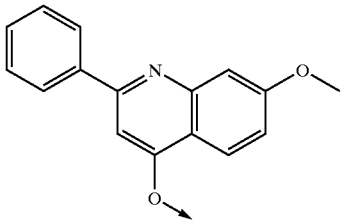 | CH=CH2 |
| 610 | — | — | Chg | Val | 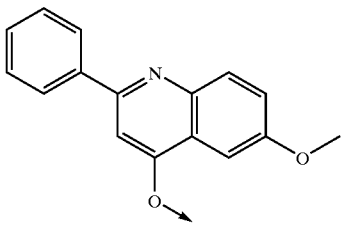 | CH=CH2 |
| 611 | — | — | Chg | Val | 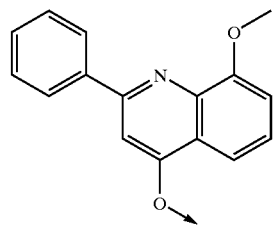 | CH=CH2 |
| 612 | Asp | D-Glu | Chg | Val | 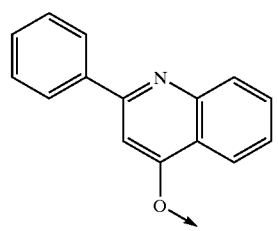 | CH=CH2 |
| 613 | — | — | Chg | Val | 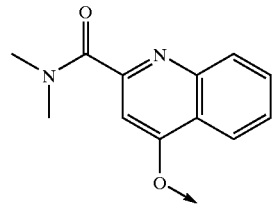 | CH=CH2 |
| 614 | — | — | Chg | Val | 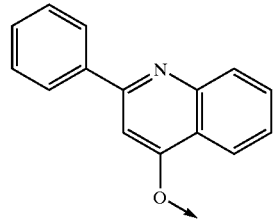 | ethyl |

-continued
| Tab 6 Cpd # | P6 | P5 | P4 | P3 | R₁₃ | R₁ |
|---|---|---|---|---|---|---|
| 615 | — | — | Val | Chg | 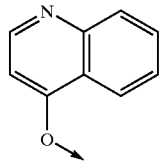 | CH=CH₂ |
| 616 | — | — | Chg | Val | 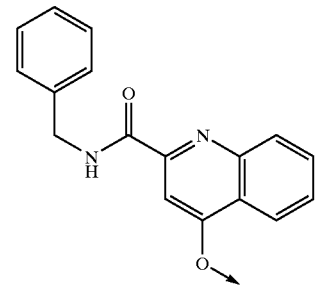 | CH=CH₂ |
| 617 | — | — | Chg | Val | 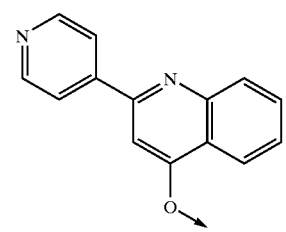 | CH=CH₂ |
| 618 | — | — | Chg | Val | 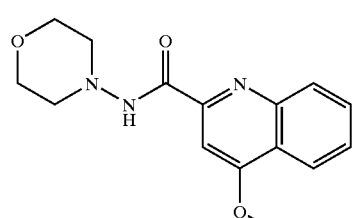 | CH=CH₂ |
| 619 | — | — | Chg | Val | 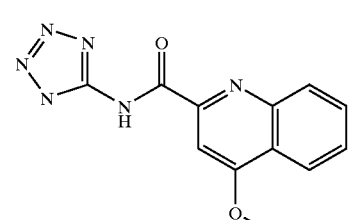 | CH=CH₂ |
| 620 | — | — | Chg | Val | 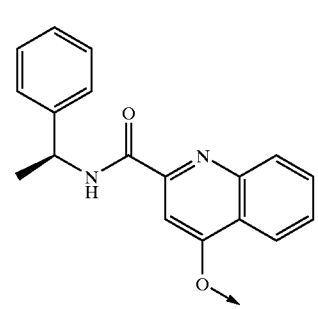 | CH=CH₂ |

-continued

| Tab 6 Cpd # | P6 | P5 | P4 | P3 | R₁₃ | R₁ |
|---|---|---|---|---|---|---|
| 621 | — | — | Chg | Val | (2-pyridylethyl)aminocarbonyl-quinoline-4-yloxy | CH=CH₂ |
| 622 | Asp | D-Glu | Chg | Tbg | 2-phenyl-quinolin-4-yloxy | CH=CH₂ |
| 623 | — | — | Chg | Val | (benzo[1,3]dioxol-5-ylmethyl)aminocarbonyl-quinolin-4-yloxy | CH=CH₂ |
| 624 | — | — | Chg | Tbg | 7,8-dimethoxy-2-phenyl-quinolin-4-yloxy | CH=CH₂ |
| 625 | — | — | Chg | Val | 7,8-dimethoxy-2-(pyridin-2-yl)-quinolin-4-yloxy | CH=CH₂ |
| 626 | — | — | Chg | Val | 7-ethyl-2-phenyl-quinazolin-4-yloxy | CH=CH₂ |

-continued
| Tab 6 Cpd # | P6 | P5 | P4 | P3 | R13 | R1 |
|---|---|---|---|---|---|---|
| 627 | — | — | Chg | Val | 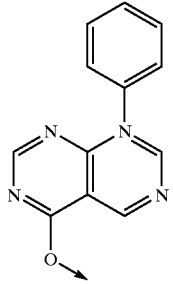 | CH=CH2 |
| 628 | — | — | Chg | Tbg | 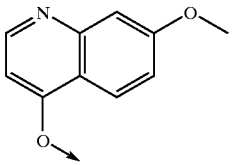 | CH=CH2 |
| 629 | — | — | Chg | Val | 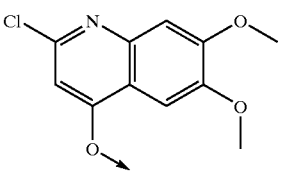 | CH=CH2 |
| 630 | — | — | Chg | Val | 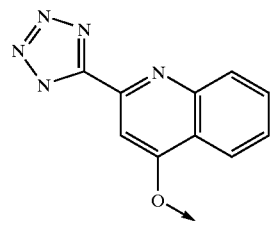 | CH=CH2 |
| 631 | — | — | Chg | Tbg | 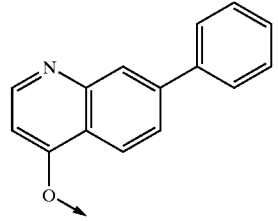 | CH=CH2 |
| 632 | — | — | Chg | Tbg | 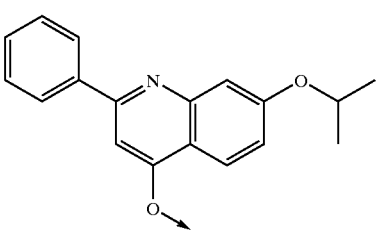 | CH=CH2 |

-continued
| Tab 6 Cpd # | P6 | P5 | P4 | P3 | R13 | R1 |
|---|---|---|---|---|---|---|
| 633 | — | — | Chg | Tbg | 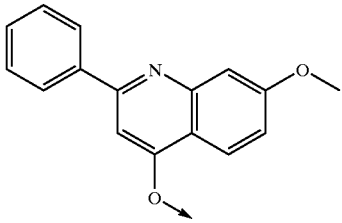 | CH=CH2 |
| 634 | — | — | Chg | Tbg | 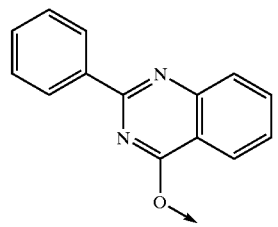 | CH=CH2 |
| 635 | — | — | Chg | Val | 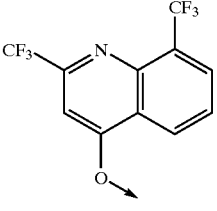 | vinyl |
| 636 | Asp | D-Glu | Ile | Val | O-Bn | vinyl |
| 637 | — | — | Chg | Val | 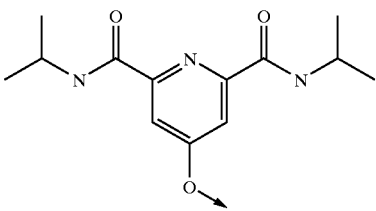 | vinyl |
| 638 | Asp | D-Glu | Chg | Tbg | 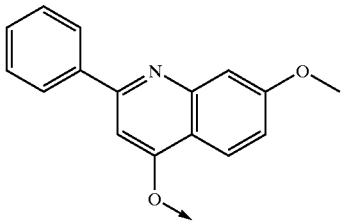 | vinyl |
*Br isomer ratio 5.5:2.

76. A compound of formula (I):
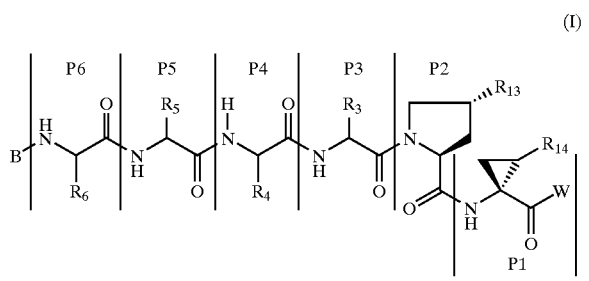
wherein B, P6, P5, P4, P3, $R_{13}$, and $R_{14}$ are as defined below:
| Tab 7 Cpd # | B | P6 | P5 | P4 | P3 | $R_{13}$ | $R_{14}$ | W |
|---|---|---|---|---|---|---|---|---|
| 701 | Ac | Asp | D-Glu | Ile | Val | OBn | Et | NH—(S)—CHMePh. |
77. A compound of formula (I):
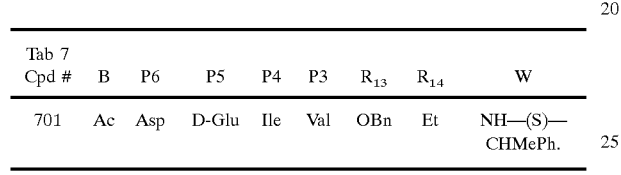
wherein B, Y, P4, P3, $R_{13}$, and $R_{14}$ are as defined below:
| Tab 8 Cpd # | B | Y | P4 | P3 | $R_{13}$ | $R_{14}$ |
|---|---|---|---|---|---|---|
| 801 | Ac | Me | Chg | Tbg | 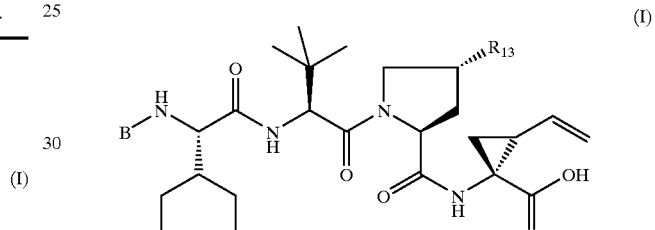 | vinyl. |
78. A compound of formula (I):
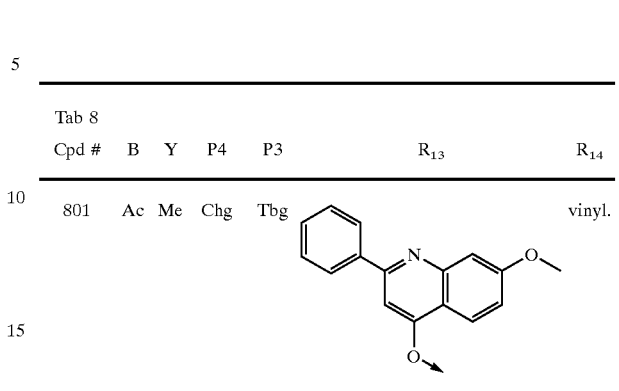
wherein B, and $R_{13}$ are as defined below, said compound selected from the group consisting of:
| Tab 9 cpd # | B | $R_{13}$ |
|---|---|---|
| 901 | | |
| 902 | | |
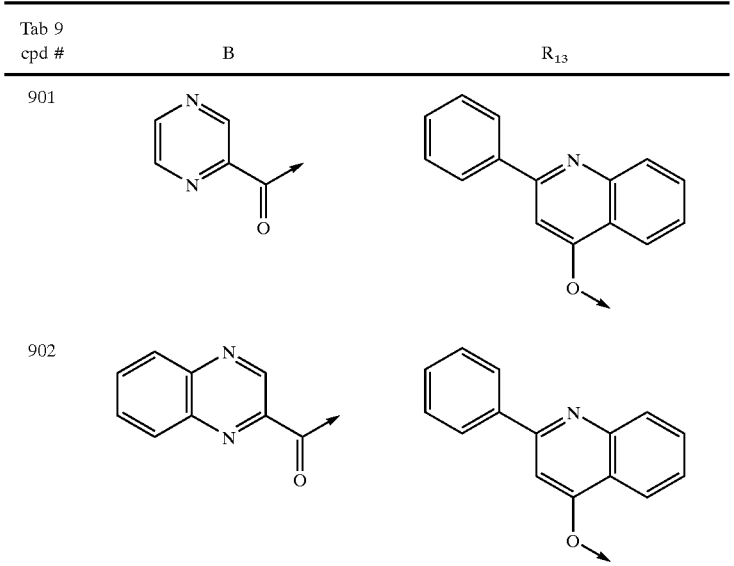

-continued
| Tab 9 cpd # | B | R$_{13}$ |
|---|---|---|
| 903 | 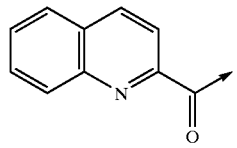 | 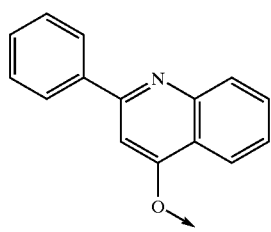 |
| 904 | 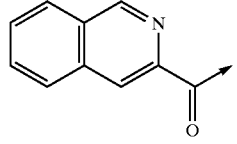 | 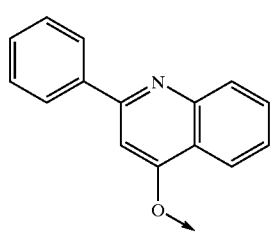 |
| 905 | 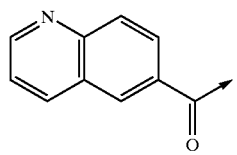 | 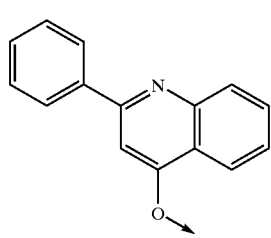 |
| 906 | H | 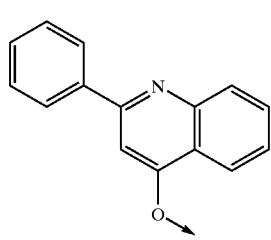 |
| 907 | 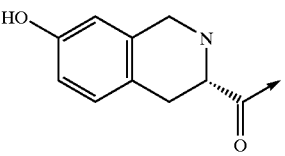 | 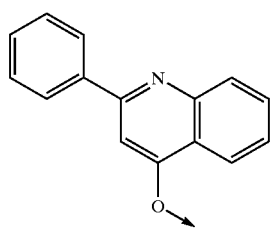 |
| 908 | 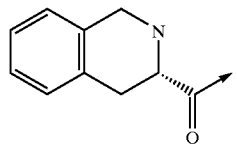 | 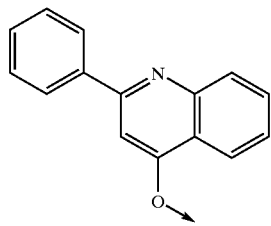 |

-continued

| Tab 9 cpd # | B | R$_{13}$ |
|---|---|---|
| 909 | H | 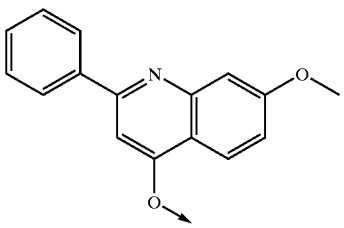 |
| 910 | 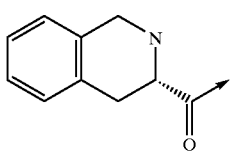 | 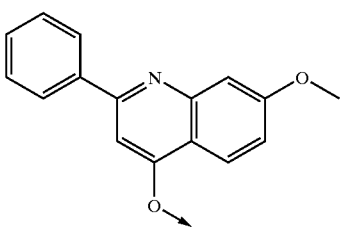 |

79. A compound of formula (I):

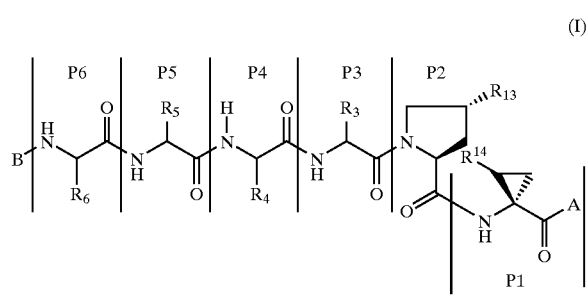

wherein B, P6, P5, P4, P3, R$_{13}$, R$_{14}$, P1 and A are as defined below, said compound selected from the group consisting of:

| Tab. 10 Comp. | B | P6 | P5 | P4 | P3 | R$_{13}$ | R$_{14}$ | P1 C$_1$–C$_2$ | A |
|---|---|---|---|---|---|---|---|---|---|
| 1001 | Ac | Asp | D-Glu | Ile | Val | OBn | Et | 1S,2S | NH-(S)-CHMePh |
| 1002 | Ac | Asp | D-Glu | Ile | Val | OBn | Et | 1S,2S | NH-(R)-CHMePh. |

80. A hexapeptide of formula I according to claim 74, selected from the group consisting of compound #:508; 516; 517; and 520.

81. A hexapeptide of formula I according to claim 75, selected from the group consisting of compound #: 612; 622; 636; and 638.

82. A hexapeptide of formula I according to claim 76, selected from the group consisting of compound #: 701 and 702.

83. A tetrapeptide of formula I according to claim 74 selected from the group consisting of compound #: 522; and 523.

84. A tetrapeptide of formula I according to claim 75, selected from the group consisting of compound #: 602; 603; 605; 606; 607; 608; 609; 610; 611; 614; 615; 616; 618; 619; 620; 621; 623; 624; 625; 626; 628; 629; 630; 631; 632; 633; 634 and 635.

85. A tetrapeptide of formula I according to claim 77, selected from the group consisting of compound #: 801.

86. A tetrapeptide of formula I according to claim 78, selected from the group consisting of compound #: 901; 902; 903; 904; 905; 906; 907; 908; 909; 910; and 911.

87. A composition comprising an anti-hepatitis C virally effective amount of a compound of formula I according to claim I, or a non-toxic salt or ester thereof, in admixture with a non-toxic carrier medium or auxiliary agent.

88. A combination comprising a compound of formula I according to claim 1, or a non-toxic salt or ester thereof, and an interferon in admixture with a non-toxic carrier medium or auxiliary agent.

89. The compound of formula I according to claim 1, wherein R$_{11a}$ is

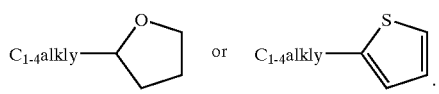

90. The compound of formula I according to claim 1, wherein R$_{11}$ is AcOCH$_2$— or tert-butyloxy.

91. The compound of formula I according to claim 1, wherein R$_{11}$ is

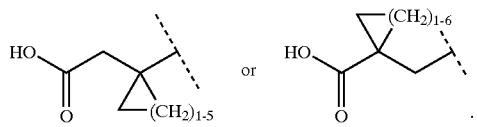

92. A process for the preparation of a peptide compound of formula (I) according to claim 1, wherein P1 is a substituted aminocyclopropyl carboxylic acid residue, comprising the steps of:

(1) coupling a peptide of the formula: APG-P6-P5-P4-P3-P2-OH with a P1 intermediate of formula:

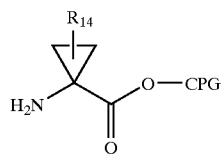

wherein $R_{14}$ is $C_{1-6}$ alkyl or $C_{2-6}$ alkenyl optionally substituted with halogen, APG is an amino protecting group, CPG is a carboxyl protecting group and P6 to P2 are as defined below:

P6:

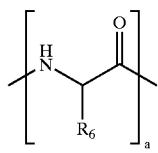

P5:

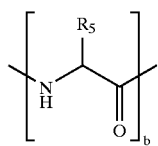

P4:

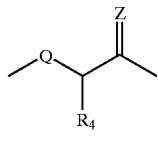

P3:

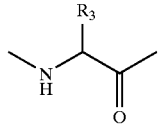

P2:

wherein W, $R_3$, $R_4$, Z, Q, $R_5$, $R_6$, a and b are as defined in claim 1, to obtain a compound of the following formula:

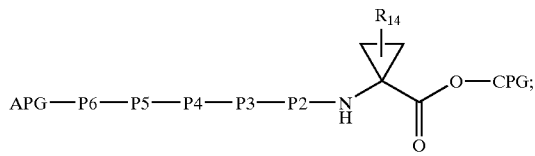

(2) cleaving the APG in the compound obtained in step (1) and reacting the resulting unprotected product with a compound of the formula B—Cl wherein B is as defined in claim 1 to obtain a compound of the following formula:

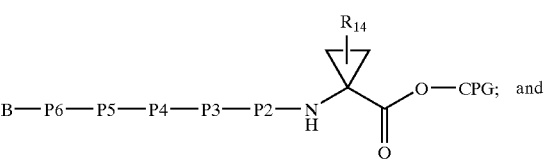

(3) cleaving the CPG in the compound obtained in step (2) and isolating a compound of formula (I) according to claim 1 having the following formula:

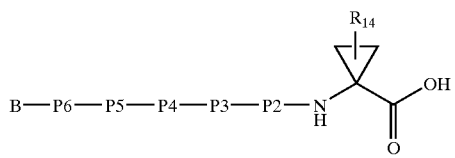

and wherein one or more of the side-chain functionalities in groups P2, P3, P4, P5 and P6 may be protected and deprotected as is necessary during the process.

93. A process for the preparation of a peptide compound of formula (I) according to claim 1, wherein P1 is a substituted aminocyclopropyl carboxylic acid residue, comprising the steps of:

(1) coupling a peptide of the formula: APG-P6-P5-P4-P3-P2-OH with a P1 intermediate of formula:

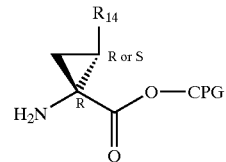

wherein $R_{14}$ is ethyl, vinyl or bromovinyl, APG is an amino protecting group, CPG is a carboxyl protecting group and P6 to P2 are as defined below:

P6:

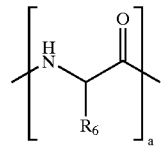

-continued

P5:
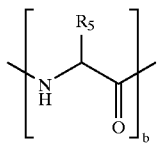

P4:
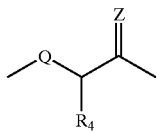

P3:
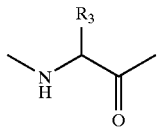

P2:

wherein W, $R_3$, $R_4$, Z, Q, $R_5$, $R_6$, a and b are as defined in claim 1, to obtain a compound of the following formula:

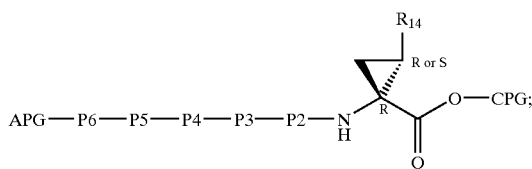

(2) cleaving the APG in the compound obtained in step (1) and reacting the resulting unprotected product with a compound of the formula B—Cl wherein B is as defined in claim 1 to obtain a compound of the following formula:

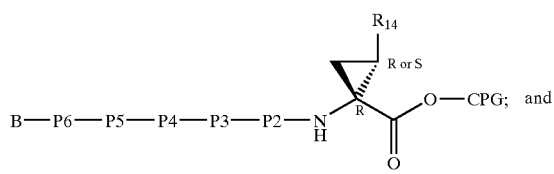

(3) cleaving the CPG in the compound obtained in step (2) and isolating a compound of formula (I) according to claim 1 having the following formula:

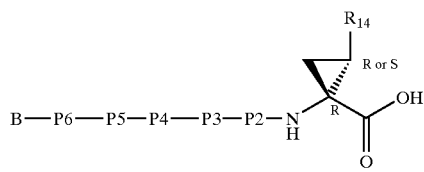

and wherein one or more of the side-chain functionalities in groups P2, P3, P4, P5 and P6 may be protected and deprotected as is necessary during the process.

94. A process for the preparation of a peptide compound of formula (I) according to claim 1, wherein P1 is a substituted aminocyclopropyl carboxylic acid residue, comprising the steps of:

(1) coupling a peptide of the formula: APG-P6-P5-P4-P3-P2-OH with a P1 intermediate of formula:

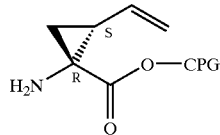

wherein APG is an amino protecting group, CPG is a carboxyl protecting group and P6 to P2 are as defined below:

P6:
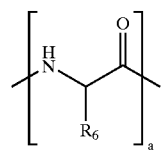

P5:
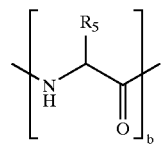

P4:
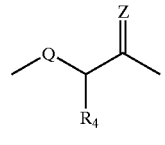

P3:
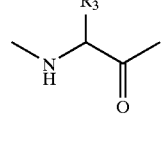

P2:
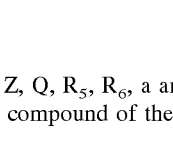

wherein W, $R_3$, $R_4$, Z, Q, $R_5$, $R_6$, a and b are as defined in claim 1, to obtain a compound of the following formula:

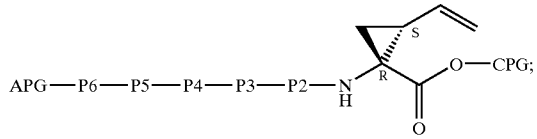

(2) cleaving the APG in the compound obtained in step (1) and reacting the resulting unprotected product with a compound of the formula B—Cl wherein B is as defined in claim 1 to obtain a compound of the following formula:

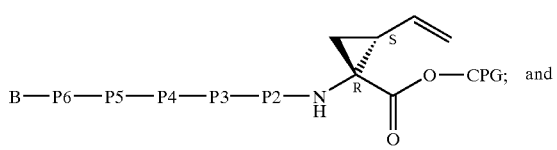

(3) cleaving the CPG in the compound obtained in step (2) and isolating a compound of formula (I) according to claim 1 having the following formula:

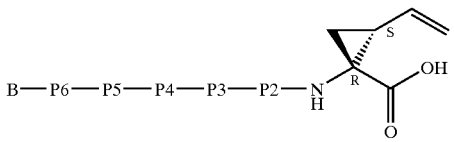

and wherein one or more of the side-chain functionalities in groups P2, P3, P4, P5 and P6 may be protected and deprotected as is necessary during the process.

95. The process according to any one of claims 92 to 94 wherein said carboxyl protecting group (CPG) is selected from the group consisting of: alkyl, aralkyl, and groups being cleavable by mild base treatment or mild reductive means.

96. A method inhibiting hepatitis C nonstructural protein-3 protease (HCV NS3 protease) comprising contacting HCV NS3 protease with a compound of claim 1 for a time and under conditions effective to inhibit HCV NS3 protease.

97. A method of inhibiting hepatitis C nonstructural protein-3 protease (HCV NS3 protease) in a cell comprising contacting a cell containing HCV NS3 protease with a compound of claim 1 for a time and under conditions effective to inhibit HCV NS3 protease.

98. A method of inhibiting hepatitis C nonstructural protein-3 protease (HCV NS3 protease) in a mammal infected with hepatitis C virus comprising administering a compound of claim 1 to said mammal for a time and under conditions effective to inhibit HCV NS3 protease.

99. A method of inhibiting hepatitis C nonstructural protein-3 (HCV NS3 protease) in a human infected with hepatitis C virus comprising administering a compound of claim 1 to said human for a time and under conditions effective to inhibit HCV NS3 protease.

100. A method of inhibiting replication of hepatitis C virus comprising contacting hepatitis C virus with a compound of claim 1 for a time and under conditions effective to inhibit hepatitis C nonstructural protein-3 (HCV NS3) protease.

101. A method of inhibiting replication of hepatitis C virus in a mammal infected with hepatitis C virus comprising administering a compound of claim 1 to said mammal for a time and under conditions effective to inhibit hepatitis C nonstructural protein-3 (HCV NS3) protease.

102. A method of inhibiting replication of hepatitis C virus in a human infected with hepatitis C virus comprising administering a compound of claim 1 to said human for a time and under conditions effective to inhibit hepatitis C nonstructural protein-3 (HCV NS3) protease.

103. A combination according to claim 88, further comprising ribavirin (1-β-D-ribofuranosyl-1H-1,2,4-triazole-3-carboxamide).

104. A combination comprising a compound of formula I according to claim 1, or a non-toxic salt or ester thereof, and ribavirin in admixture with a non-toxic carrier medium or auxiliary agent.

\* \* \* \* \*

UNITED STATES PATENT AND TRADEMARK OFFICE
CERTIFICATE OF CORRECTION

PATENT NO. : 6,767,991 B1  Page 1 of 1
APPLICATION NO. : 09/368670
DATED : July 27, 2004
INVENTOR(S) : Montse Llinas-Brunet et al.

It is certified that error appears in the above-identified patent and that said Letters Patent is hereby corrected as shown below:

On the front page under "Related U.S. Application Data", Section (63), delete "Continuation of application No. 09/219,939" and replace with: --Continuation-in-part of Application No. 09/219,939--.

In column 1, line 3, delete "continuation" and replace with -- CIP --.

In column 1, line 4, delete "and" and replace with -- which is --.

In column 221, (in Claim 78) delete

" 906   H   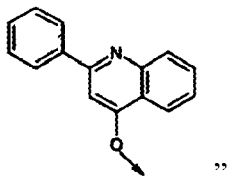   "

Signed and Sealed this

Twenty-first Day of November, 2006

JON W. DUDAS
*Director of the United States Patent and Trademark Office*